US009315811B2

(12) United States Patent
Bhattacharjee et al.

(10) Patent No.: US 9,315,811 B2
(45) Date of Patent: Apr. 19, 2016

(54) METHODS FOR MODULATING KALLIKREIN (KLKB1) EXPRESSION

(75) Inventors: Gourab Bhattacharjee, San Diego, CA (US); Alexey Revenko, San Diego, CA (US); Robert A. MacLeod, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 135 days.

(21) Appl. No.: 14/124,630

(22) PCT Filed: Jun. 8, 2012

(86) PCT No.: PCT/US2012/041743
§ 371 (c)(1), (2), (4) Date: Mar. 5, 2014

(87) PCT Pub. No.: WO2012/170945
PCT Pub. Date: Dec. 13, 2012

(65) Prior Publication Data

US 2014/0213631 A1 Jul. 31, 2014

Related U.S. Application Data

(60) Provisional application No. 61/495,945, filed on Jun. 10, 2011, provisional application No. 61/496,462, filed on Jun. 13, 2011.

(51) Int. Cl.

| | |
|---|---|
| ***A61K 31/70*** | (2006.01) |
| ***C07H 21/02*** | (2006.01) |
| ***C07H 21/04*** | (2006.01) |
| ***C12N 15/113*** | (2010.01) |
| ***A61K 31/7125*** | (2006.01) |
| *C12N 5/00* | (2006.01) |

(52) U.S. Cl.
CPC .......... *C12N 15/113* (2013.01); *A61K 31/7125* (2013.01); *C12N 15/1137* (2013.01); *C12N 2310/11* (2013.01); *C12N 2310/315* (2013.01); *C12N 2310/3231* (2013.01); *C12N 2310/3341* (2013.01); *C12N 2310/341* (2013.01); *C12N 2750/14143* (2013.01); *C12Y 304/21034* (2013.01)

(58) Field of Classification Search
None
See application file for complete search history.

(56) References Cited

U.S. PATENT DOCUMENTS

| | | | |
|---|---|---|---|
| 4,153,687 | A | 5/1979 | Schnabel et al. |
| 4,973,668 | A | 11/1990 | Jallat et al. |
| 4,981,957 | A | 1/1991 | Lebleu et al. |
| 5,034,506 | A | 7/1991 | Summerton et al. |
| 5,118,800 | A | 6/1992 | Smith et al. |
| 5,166,315 | A | 11/1992 | Summerton et al. |
| 5,185,444 | A | 2/1993 | Summerton et al. |
| 5,319,080 | A | 6/1994 | Leumann |
| 5,359,044 | A | 10/1994 | Cook et al. |
| 5,393,878 | A | 2/1995 | Leumann |
| 5,446,137 | A | 8/1995 | Maag et al. |
| 5,466,786 | A | 11/1995 | Buhr et al. |
| 5,514,785 | A | 5/1996 | Van Ness et al. |
| 5,519,134 | A | 5/1996 | Acevedo et al. |
| 5,567,811 | A | 10/1996 | Misiura et al. |
| 5,576,427 | A | 11/1996 | Cook et al. |
| 5,591,722 | A | 1/1997 | Montgomery et al. |
| 5,597,909 | A | 1/1997 | Urdea et al. |
| 5,610,300 | A | 3/1997 | Altmann et al. |
| 5,627,053 | A | 5/1997 | Usman et al. |
| 5,639,873 | A | 6/1997 | Barascut et al. |
| 5,646,265 | A | 7/1997 | McGee |
| 5,670,633 | A | 9/1997 | Cook et al. |
| 5,698,685 | A | 12/1997 | Summerton et al. |
| 5,700,920 | A | 12/1997 | Altmann et al. |
| 5,786,328 | A | 7/1998 | Dennis et al. |
| 5,792,847 | A | 8/1998 | Buhr et al. |
| 5,801,154 | A | 9/1998 | Baracchini et al. |
| 6,268,490 | B1 | 7/2001 | Imanishi et al. |
| 6,525,191 | B1 | 2/2003 | Ramasamy |
| 6,582,908 | B2 | 6/2003 | Fodor et al. |
| 6,600,032 | B1 | 7/2003 | Manoharan et al. |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 7,034,133 | B2 | 4/2006 | Wengel et al. |
| 7,053,207 | B2 | 5/2006 | Wengel |
| 7,235,530 | B2 | 6/2007 | Blair et al. |
| 7,399,845 | B2 | 7/2008 | Seth et al. |
| 7,427,672 | B2 | 9/2008 | Imanishi et al. |
| 7,547,684 | B2 | 6/2009 | Seth et al. |
| 7,696,345 | B2 | 4/2010 | Allerson et al. |
| 2001/0053519 | A1 | 12/2001 | Fodor et al. |

(Continued)

FOREIGN PATENT DOCUMENTS

| | | |
|---|---|---|
| WO | WO 98/03665 | 1/1998 |
| WO | WO 98/39352 | 9/1998 |

(Continued)

OTHER PUBLICATIONS

Albaek et al., "Analogues of a Locked Nucleic Acid with Three-Carbon 2',4'—Linkages: Synthesis by Ring-Closing Metathesis and Influence of Nucleic Acid Duplex Stability" J. Org. Chem. (2006) 71:7731-7740.

(Continued)

*Primary Examiner* — Sean McGarry
(74) *Attorney, Agent, or Firm* — Knobbe, Martens, Olson & Bear, LLP

(57) ABSTRACT

Disclosed herein are methods for decreasing kallikrein and treating or preventing inflammatory conditions in an individual in need thereof. Examples of disease conditions that can be ameliorated with the administration of antisense compounds targeted to kallikrein include hereditary angioedema (HAE). Methods for inhibiting kallikrein can also be used as a prophylactic treatment to prevent individuals at risk for developing an inflammatory condition, such as, hereditary angioedema.

22 Claims, 2 Drawing Sheets

(56) References Cited

U.S. PATENT DOCUMENTS

| | | | | |
|---|---|---|---|---|
| 2003/0228597 | A1 | 12/2003 | Cowsert et al. | |
| 2004/0171570 | A1 | 9/2004 | Allerson et al. | |
| 2005/0089893 | A1 | 4/2005 | Lopez et al. | |
| 2005/0130923 | A1 | 6/2005 | Bhat et al. | |
| 2005/0245475 | A1 | 11/2005 | Khvorova et al. | |
| 2005/0246794 | A1 | 11/2005 | Khvorova et al. | |
| 2005/0255487 | A1 | 11/2005 | Khvorova et al. | |
| 2006/0069020 | A1 | 3/2006 | Blair et al. | |
| 2006/0185027 | A1 | 8/2006 | Bartel et al. | |
| 2006/0264603 | A1* | 11/2006 | Markland et al. | 530/300 |
| 2007/0031844 | A1 | 2/2007 | Khvorova et al. | |
| 2007/0039072 | A1 | 2/2007 | Khvorova et al. | |
| 2007/0191296 | A1 | 8/2007 | Golz et al. | |
| 2007/0207974 | A1 | 9/2007 | Khvorova et al. | |
| 2007/0253949 | A1 | 11/2007 | Golz et al. | |
| 2008/0039618 | A1 | 2/2008 | Allerson et al. | |
| 2008/0188409 | A1 | 8/2008 | Blair et al. | |
| 2008/0221031 | A1 | 9/2008 | Blair et al. | |
| 2008/0280811 | A1 | 11/2008 | Feener et al. | |
| 2009/0012281 | A1 | 1/2009 | Swayze et al. | |
| 2009/0075887 | A1 | 3/2009 | McPherson | |
| 2009/0105142 | A1 | 4/2009 | Moscicki | |
| 2009/0221480 | A1 | 9/2009 | Blair et al. | |
| 2009/0227494 | A1 | 9/2009 | Blair et al. | |
| 2009/0227495 | A1 | 9/2009 | Blair et al. | |
| 2009/0233852 | A1 | 9/2009 | Blair et al. | |
| 2009/0234009 | A1 | 9/2009 | Blair et al. | |
| 2009/0247453 | A1 | 10/2009 | Blair et al. | |
| 2009/0264350 | A1 | 10/2009 | Blair et al. | |
| 2010/0029003 | A1 | 2/2010 | Bartel et al. | |
| 2010/0183625 | A1 | 7/2010 | Sternlicht | |
| 2011/0200611 | A1* | 8/2011 | Sexton | 424/158.1 |
| 2011/0301215 | A1 | 12/2011 | Sinha et al. | |

FOREIGN PATENT DOCUMENTS

| | | |
|---|---|---|
| WO | WO 99/14226 | 3/1999 |
| WO | WO 01/49687 | 7/2001 |
| WO | WO 03/004602 | 1/2003 |
| WO | WO 03/103475 | 12/2003 |
| WO | WO 2004/106356 | 12/2004 |
| WO | WO 2005/021570 | 3/2005 |
| WO | WO 2005/075665 | 8/2005 |
| WO | WO 2005/083110 | 9/2005 |
| WO | WO 2005/121371 | 12/2005 |
| WO | WO 2006/008002 | 1/2006 |
| WO | WO 2006/036860 | 4/2006 |
| WO | WO 2006/047842 | 5/2006 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2010/036696 | 4/2010 |
| WO | WO 2011/075684 | 6/2011 |
| WO | WO 2012/170945 | 12/2012 |
| WO | WO 2012/170947 | 12/2012 |
| WO | WO 2013/003808 | 1/2013 |

OTHER PUBLICATIONS

Altmann et al., "Second-generation antisense oligonucleoties: structure-activity relationships and the design of improved signal-transduction inhibitors" Biochem. Soc. Trans. (1996) 24: 630-637.

Altmann et al., "Second Generation of Antisense Oligonucleotides: From Nuclease Resistance to Biological Efficacy in Animals" Chimia (1996) 50: 168-176.

Altmann et al., "Second Generation Antisense Oligonucleotides—Inhibition of PKC-a and c-RAF Kinase Expression by Chimeric Oligonucleotides Incorporating 5'-Substituted Carbocyclic Nucleosides and 2'-O-Ethylene Glycol Substituted Ribonucleosides" Nucleosides Nucleotides (1997) 16(7-9): 917-926.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18): 11944-12000.

Braasch et al., "Novel Antisense and Peptide Nucleic Acid Strategies for Controlling Gene Expression" Biochemistry (2002) 41(14): 4503-4510.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Chao et al., "Novel roles of kallistatin, a specific tissue kallikrein inhibitor, in vascular remodeling." Biol Chem (2001) 382(1): 15-21.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Cichon et al., "Increased activity of coagulation factor XII (Hageman factor) causes hereditary angioedema type III." Am. J. Hum. Genet. (2006) 79: 1098-1104.

Crooke et al., "Basic Principles of Antisense Therapeutics" Antisense Research and Application (1998) Chapter 1:1-50.

Cruz-Silva et al., "A proteinase inhibitor from Caesalpinia echinata (pau-brasil) seeds for plasma kallikrein, plasmin and factor XIIa." Biol Chem (2004) 385(11): 1083-1086.

Dowd, "Concomitant antiplatelet and anticoagulation therapy: Indications, controversies and practical advice" Plenary Sessions/ Thrombosis Research (2008) 123, Supplement 1: S11-S15.

Elayadi et al., "Applications of PNA and LNA oligomers to chemotherapy" Curr. Opinion Invest. Drugs (2001) 2:558-561.

Evans et al., "Selective inhibitors of plasma kallikrein" Immunopharmacology (1996) 32(1-3): 115-116.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Gautschi et al., "Activity of a Novel bcl-2/bcl-xL-Bispecific Antisense Oligonucleotide Against Tumors of Diverse Histologic Origins" J. Natl. Cancer Inst. (2001) 93(6):463-471.

Gigli et al., "Interaction of plasma kallikrein with the C1 inhibitor." J. Immunol. (1970) 104:574-581.

Gonzalez et al., "Purification and preliminary characterization of a plasma kallikrein inhibitor isolated from sea hares Aplysia dactylomela Rang, 1828" Toxicon (2004) 43(2): 219-223.

Gu et al., "Base Pairing Properties of D- and L-Cyclohexene Nucleic Acids (CeNA)" Oligonucleotides (2003) 13(6): 479-489.

Gu et al., "Synthesis of enantiomeric-pure cyclohexenyl nucleoside building blocks for oligonucleotide synthesis" Tetrahedron (2004) 60(9): 2111-2123.

Gu et al., "Enzymatic Resolution and Base Pairing Properties of D- and L-Cyclohexenyl Nucleic Acids (CeNA)" Nucleosides, Nucleotides & Nucleic Acids (2005) 24(5-7): 993-998.

Han et al., "Increased vascular permeability in C1 inhibitor-deficient mice mediated by the bradykinin type 2 receptor." J. Clin. Invest. (2002) 109: 1057-1063.

Horvath et al., "Stereoselective synthesis of (−)-ara-cyclohexenyl-adenine" Tetrahedron Letters (2007) 48: 3621-3623.

Ikarugi et al., "Synergistic antithrombotic effect of a combination of NO donor and plasma kallikrein inhibitor." Thromb Res (2005) 116: 403-408.

Kaplan et al., "Pathways for bradykinin formation and inflammatory disease." J. Allergy Clin. Immunol. (2002) 109(2): 195-209.

Kim et al., "Pretreatment with nafamostat mesilate, a kallikrein inhibitor, to decrease withdrawal response associated with rocuronium." J. Anesth. (2010) 24(4): 549-552.

Koshkin et al., "LNA (Locked Nucleic Acids): Synthesis of the Adenine, Cytosine, Guanine, 5-Methylcytosine, Thymine and Uracil Biocyclonucleoside Monomers, Oligomerisation, and Unprecedented Nucleic Acid Recognition" Tetrahedron (1998) 54:3607-3630.

(56) References Cited

OTHER PUBLICATIONS

Kubitza et al., "Rivaroxaban (BAY 59-7939)—an oral, direct Factor Xa inhibitor—has no clinically relevant interaction with naproxen" Br. J. Clin. Pharmacol. (2006) 63(4): 469-476.
Kumar et al., "The First Analogues of LNA (Locked Nucleic Acids): Phosphorothioate-LNA and 2'-Thio-LNA" Bioorg. Med. Chem. Lett. (1998) 8:2219-2222.
Leumann, "DNA Analogues: From Supramolecular Principles to Biological Properties" Bioorganic & Medicinal Chemistry (2002) 10:841-854.
MacKenzie et al., "Plasma prekallikrein levels are positively associated with circulating lipid levels and the metabolic syndrome in children." Appl. Physiol. Nutr. Metab. (2010) 35: 518-525.
Maher et al., "Comparative hybrid arrest by tandem antisense oligodeoxyribonucleotides or oligodeoxyribonucleoside methylphosphonates in a cell-free system" Nuc. Acid. Res. (1988) 16:3341-3358.
Martin, "Ein neuer Zugang zu 2'-O-Alkylribonucleosiden and Eigenschaften eren Oligonucleotide" Helv. Chim. Acta (1995) 78: 486-504.
Nakane et al., "Nafamostat mesilate, a kallikrein inhibitor, prevents pain on injection with propofol." Br. J. Aneaesth. (1998) 81(6): 963-964.
Heinis et al., "Phage-encoded combinatorial chemical libraries based on bicyclic peptides." Nat Chem Biol (2009) 5(7): 502-507.
Nauwelaerts et al., "Structural characterization and biological evaluation of small interfering RNAs containing cyclohexenyl nucleosides." J. Am. Chem. Soc. (2007) 129(30): 9340-9348.
Nauwelaerts et al., "Cyclohexenyl nucleic acids: conformationally flexible oligonucleotides" Nucleic Acids Research (2005) 33(8): 2452-2463.
New England Biolabs 1998/99 Catalog (cover page and pp. 121 and 284).
Orum et al., "Locked nucleic acids: A promising molecular family for gene-function analysis and antisense drug development" Curr. Opinion Mol. Ther. (2001) 3(3):239-243.
Ravindran et al., "Inhibition of plasma kallikrein by C1-inhibitor: role of endothelial cells and the amino-terminal domain of C1-inhibitor." Thromb Haemost (2004) 92: 1277-1283.
Reynolds et al., "Rational siRNA design for RNA interference" Nature Biotechnology (2004) 22(3):326-330.
Riedl et al., "Response time for ecallantide treatment of acute hereditary angioedema attacks." Ann Allergy Asthma Immunol (2010) 105(6): 430-436.e2.
Robeyns et al., "Oligonucleotides with cyclohexene-nucleoside building blocks: crystallization and preliminary X-ray studies of a left-handed sequence GTGTACAC" Acta Crystallographica, Section F: Structural Biology and Crystallization Communications (2005) F61(6): 585-586.
Robeyns et al., "Structure of the Fully Modified Left-Handed Cyclohexene Nucleic Acid Sequence GTGTACAC" J. Am. Chem. Soc. (2008) 130(6): 1979-1984.
Sanghvi et al., "Heterocyclic Base Modifications in Nucleic Acids and Their Applications in Antisense Oligonucleotides" Antisense Research and Applications (1993) pp. 273-288.
Schneider et al., "Critical role of kalikrein in hereditary angioedema pathogenesis: a clinical trial of escallantide, a novel kallikrein inhibitor" J. Allery Clin. Immunol. (2007) 120(2):416-422.
Scott et al., "Alpha-1-antitrypsin-Pittsburgh. A potent inhibitor of human plasma factor XIa, kallikrein, and factor XIIf." J Clin Invest (1986) 77(2): 631-634.
Sexton et al., "Specific inhibition of tissue kallikrein 1 with a human monoclonal antibody reveals a potential role in airway diseases" Biochem. J. (2009) 422: 383-392.
Singh et al., "LNA (locked nucleic acids): synthesis and high-affinity nucleic acid recognition" Chem. Commun. (1998) 4:455-456.
Singh et al., "Synthesis of 2'-Amino-LNA: A Novel Conformationally Restricted High-Affinity Oligonucleotide Analogue with a Handle" J. Org. Chem. (1998) 63:10035-10039.
Srivastava et al., "Five- and Six-Membered Conformationally Locked 2',4'-Carbocyclic ribo-Thymidines: Synthesis, Structure, and Biochemical Studies" J. Am. Che,. Soc. (2007) 129:8362-8379.
Stolz et al., "Ecallantide: a plasma kallikrein inhibitor for the treatment of acute attacks of hereditary angioedema." Drugs Today (2010) 46(8): 547-555.
Stoop et al., "Analysis of an engineered plasma kallikrein inhibitor and its effect on contact activation" Biol Chem 2010; 391(4): 425-433.
Verbeure et al., "RNase H mediated cleavage of RNA by cyclohexene nucleic acid (CeNA)" Nucleic Acids Research (2001) 29(24): 4941-4947.
Wahlestedt et al., "Potent and nontoxic antisense oligonucleoties containing locked nucleic acids" PNAS (2000) 97(10):5633-5638.
Wang et al., "Cyclohexene Nucleic Acids (CeNA): Serum Stable Oligonucleotides that Activate RNase H and Increase Duplex Stability with Complementary RNA" J. Am. Chem. (2000) 122: 8595-8602.
Wang et al., "A Straightforward Stereoselective Synthesis of D- and L-5-Hydroxy-4-hydroxymethy1-2-cyclohexenylguanine" J. Org. Chem. (2001) 66: 8478-8482.
Wang et al., "Stereocontrolled Synthesis of Ara-Type Cyclohexenyl Nucleosides" J. Org. Chem. (2003) 68: 4499-4505.
Wang et al., "Cyclohexene Nucleic Acids (CeNA) Form Stable Duplexes With RNA and Induce RNASE H Activity" Nucleosides, Nucleotides & Nucleic Acids (2001) 20(4-7), 785-788.
Wong et al. "Arterial antithrombotic and bleeding time effects of apixaban, a direct factor Xa inhibitor, in combination with antiplatelet therapy in rabbits" Journal of Thrombosis and Haemostasis (2008) 6: 1736-1741.
Wolf et al., "A synthetic tissue kallikrein inhibitor suppresses cancer cell invasiveness." Am J Pathol (2001) 159: 1797-1805.
Woolf et al., "Specificity of antisense oligonucleotides in vivo" PNAS (1992) 89:7305-7309.
Wulf et al., "CU-2010—A Novel Small Molecule Protease Inhibitor with Antifibrinolytic and Anticoagulant Properties" Anesthesiology (2009) 110(1): 123-130.
Zhou et al., "Kallistatin: a novel human tissue kallikrein inhibitor. Purification, characterization, and reactive center sequence." J. Biol. Chem. (1992) 267(36): 25873-25880.
Zhou et al., "Fine Tuning of Electrostatics around the Internucleoside Phosphate through Incorporation of Modified 2',4'-Carbocylic-LNAs and -ENAs Leads to Significant Modulation of Antisense Properties" J. Org. Chem. (2009) 74: 118-134.
Zuraw, "Hereditary Angioedema" N. Engl. J. Med. (2008) 359: 1027-36.
International Search Report for application PCT/US12/45105 dated Sep. 25, 2012.
International Search Report for application PCT/US12/41743 dated Nov. 20, 2012.
Bhattacharjee et al., "Inhibition of Vascular Permeability by Antisense-Mediated Inhibition of Plasma Kallikrein and Coagulation Factor 12" Nucleic Acid Therapeutics (2013) 23(3): 175-187.
European Search Report for application EP 12796547.3 dated Nov. 14, 2014.

* cited by examiner

METHODS FOR MODULATING KALLIKREIN (KLKB1) EXPRESSION

CROSS REFERENCED TO RELATED APPLICATIONS

This application is a U.S. National Phase filing under 35 U.S.C. §371 claiming priority to International Serial No. PCT/US2012/041743 filed Jun. 8, 2012, which claims priority to U.S. Provisional Application 61/495,945, filed Jun. 10, 2011 and U.S. Provisional Application 61/496,462, filed Jun. 13, 2011, each of which is incorporated herein by reference in its entirety.

SEQUENCE LISTING

The present application is being filed along with a Sequence Listing in electronic format. The Sequence Listing is provided as a file entitled BIOL0155USASEQ.txt, created Nov. 8, 2013, which is 220 Kb in size. The information in the electronic format of the sequence listing is incorporated herein by reference in its entirety.

FIELD

Provided are methods for reducing expression of kallikrein mRNA and protein in an animal. Such methods are useful to treat, prevent, or ameliorate inflammatory conditions, including hereditary angioedema (HAE).

BACKGROUND

Inflammation

Inflammation is a complex biological process of the body in response to an injury or abnormal stimulation caused by a physical, chemical, or biological stimulus. Inflammation is a protective process by which the body attempts to remove the injury or stimulus and begins to heal affected tissue in the body.

The inflammatory response to injury or stimulus is characterized by clinical signs of increased redness (rubor), temperature (calor), swelling (tumor), pain (dolor) and/or loss of function (functio laesa) in a tissue. Increased redness and temperature is caused by vasodilation leading to increased blood supply at core body temperature to the inflamed tissue site. Swelling is caused by vascular permeability and accumulation of protein and fluid at the inflamed tissue site. Pain is due to the release of chemicals (e.g. bradykinin) at the inflamed tissue site that stimulate nerve endings. Loss of function may be due to several causes.

Inflammation is now recognized as a type of non-specific immune response to an injury or stimulus. The inflammatory response has a cellular component and an exudative component. In the cellular component, resident macrophages at the site of injury or stimulus initiate the inflammatory response by releasing inflammatory mediators such as TNFalpha, IFNalpha IL-1, IL-6, IL12, IL-18 and others. Leukocytes are then recruited to move into the inflamed tissue area and perform various functions such as release of additional cellular mediators, phagocytosis, release of enzymatic granules, and other functions. The exudative component involves the passage of plasma fluid containing proteins from blood vessels to the inflamed tissue site. Inflammatory mediators such as bradykinin, nitric oxide, and histamine cause blood vessels to become dilated, slow the blood flow in the vessels, and increase the blood vessel permeability, allowing the movement of fluid and protein into the tissue. Biochemical cascades are activated in order to propagate the inflammatory response (e.g., complement system in response to infection, fibrinolysis and coagulation systems in response to necrosis due to a burn or trauma, kinin system to sustain inflammation) (Robbins Pathologic Basis of Disease, Philadelphia, W.B Saunders Company).

Inflammation can be acute or chronic. Acute inflammation has a fairly rapid onset, quickly becomes severe, and quickly and distinctly clears after a few days to a few weeks. Chronic inflammation can begin rapidly or slowly and tends to persist for weeks, months, or years with a vague and indefinite termination. Chronic inflammation can result when an injury or stimulus, or products resulting from its presence, persists at the site of injury or stimulation and the body's immune response is not sufficient to overcome its effects.

Inflammatory responses, although generally helpful to the body to clear an injury or stimulus, can sometimes cause injury to the body. In some cases, a body's immune response inappropriately triggers an inflammatory response where there is no known injury or stimulus to the body. In these cases, categorized as autoimmune diseases, the body attacks its own tissues causing injury to its own tissues.

Hereditary Angioedema

Hereditary angioedema (HAE) is a rare inflammatory disease characterized by recurrent episodes of swelling around the head and extremities (Zuraw, B. L. N. Engl. J. Med. 359: 1027-36, 2008). Angioedema attacks occur with unpredictable frequency and are typically focused on the skin, and gastric, oropharyngeal, and laryngeal mucosas. Asphyxiation due to laryngeal swelling can result in mortality. HAE is caused by deficiency or malfunction of the serine protease inhibitor C1-INH (Kaplan, A. P. et al. J. Allergy Clin. Immunol. 109: 195-209, 2002). C1-INH is the primary inhibitor of coagulation factors 12 and 11 (Factor 11) of the intrinsic coagulation pathway as well as plasma kallikrein (Gigli, I. et al. J. Immunol. 104:574-581, 1970). C1-INH mediated inhibition of plasma kallikrein and Factor 12 results in inactivation of the kallikrein pathway and decreased levels of bradykinin (BK). C1-INH deficiency or dysfunction results in overproduction of BK, which is the mechanism by which HAE attacks are believed to occur. Type III HAE has been linked with mutations in the Factor 12 gene, which encodes coagulation protein Factor 12 (Cichon, S. et al. Am. J. Hum. Genet. 79: 1098-1104, 2006).

The kinin-kallikrein pathway consists of several proteins that play a role in inflammation, blood pressure control, coagulation, and pain. Plasma prekallikrein is the precursor of plasma kallikrein, which in turn liberates kinins from kininogens and also generates plasmin from plasminogen. Plasma prekallikrein is converted to plasma kallikrein by Factor 12a by the cleavage of an internal Arg-Ile peptide bond. Plasma prekallikrein, in turn, is the product of the KLKB1 gene (MacKenzie, J. A. et al. Appl. Physiol. Nutr. Metab. 35: 518-525, 2010. Plasma kallikrein works in association with Factors 11 and 12.

There is currently no animal model which directly replicates HAE. However, the increased vascular permeability associated with HAE has been replicated in rodent models with agents such as the angiotensin converting enzyme (ACE) inhibitor captopril, as well as the C1-INH knockout mouse (Han, E. D. et al. J. Clin. Invest. 109: 1057-1063, 2002).

SUMMARY

Provided herein are methods for modulating expression of kallikrein mRNA and protein. In certain embodiments, kallikrein specific inhibitors modulate expression of kallikrein mRNA and protein. In certain embodiments, kallikrein specific inhibitors are nucleic acids, proteins, or small molecules.

In certain embodiments, modulation can occur in a cell or tissue. In certain embodiments, the cell or tissue is in an animal. In certain embodiments, the animal is a human. In certain embodiments, kallikrein mRNA levels are reduced. In certain embodiments, kallikrein protein levels are reduced. In certain embodiments, kallikrein mRNA and protein levels are reduced. Such reduction can occur in a time-dependent manner or in a dose-dependent manner.

Also provided are methods useful for preventing, treating, and ameliorating diseases, disorders, and conditions. In certain embodiments, such diseases, disorders, and conditions are inflammatory conditions. In certain embodiments, the inflammatory condition may be an acute or chronic inflammatory condition. In certain embodiments, such inflammatory conditions may include hereditary angioedema (HAE), edema, angioedema, swelling, angioedema of the lids, ocular edema, macular edema, and cerebral edema.

Such diseases, disorders, and conditions can have one or more risk factors, causes, or outcomes in common. Certain risk factors and causes for development of an inflammatory condition include genetic predisposition to an inflammatory condition and environmental factors. In certain embodiments, a defect in an individual's genetic code for complement 1 esterase inhibitor (i.e., C1-INH, a protein that helps to regulate the immune system) is responsible for inflammatory conditions such as hereditary angioedema (HAE). In certain embodiments, genetic mutations lead to a deficiency in C1-INH (i.e., type I HAE) or an inability of existing C1-INH to function properly (i.e., type II HAE). In certain embodiments, genetic mutations in Factor 12 gene lead to hyperfunctionalization of Factor 12, which leads to hereditary angioedema (i.e., type III HAE). In certain embodiments, acquired angioedema may be the result of using angiotensin-converting enzyme inhibitors (i.e., ACE inhibitors) or angiotensin II receptor blockers (i.e., ARBs). In certain embodiments, an allergic reaction may lead to angioedema. Certain outcomes associated with development of an inflammatory condition include edema/swelling in various body parts including the extremities (i.e., hands, feet, arms, legs), the intestines (abdomen), the face, the genitals, the larynx (i.e., voice box); vascular permeability; vascular leakage; generalized inflammation; abdominal pain; bloating; vomiting; diarrhea; itchy skin; respiratory (asthmatic) reactions; rhinitis; anaphylaxis; bronchoconstriction; hypotension; coma; and death.

In certain embodiments, methods of treatment include administering a kallikrein specific inhibitor to an individual in need thereof. In certain embodiments, the kallikrein specific inhibitor is a nucleic acid. In certain embodiments, the nucleic acid is an antisense compound. In certain embodiments, the antisense compound is a modified oligonucleotide.

DETAILED DESCRIPTION

Figure 1:
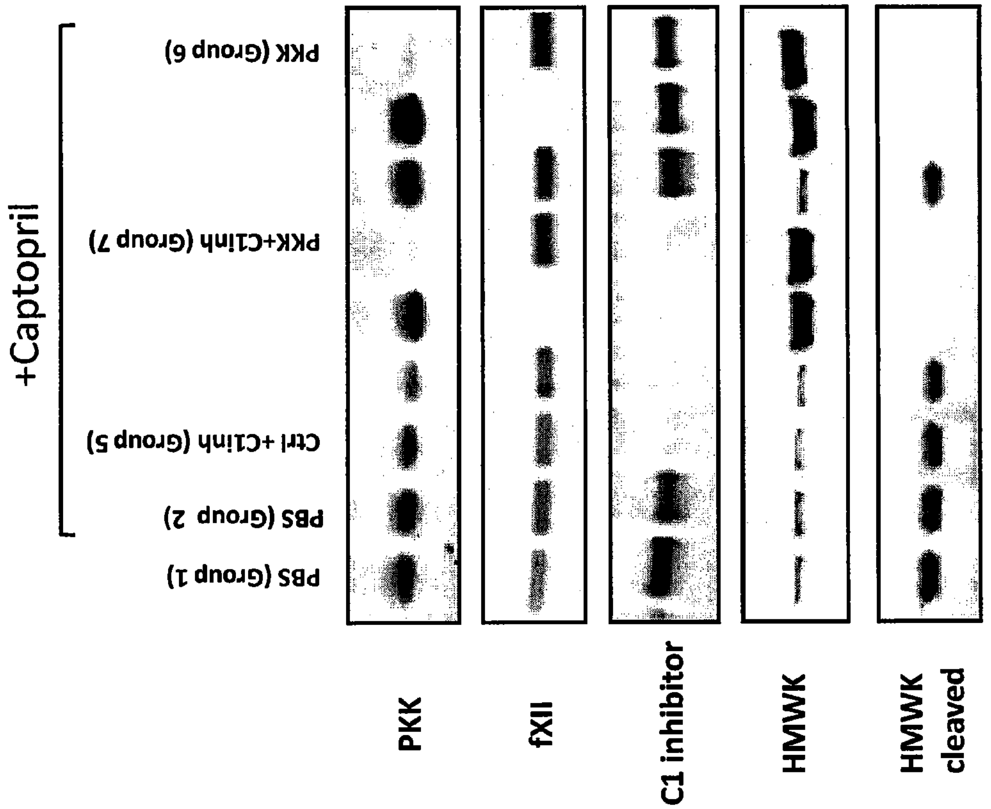
FIG. 1 provides Western blot quantification of HMWK from blood samples tested in Example 2.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and $2'-O(CH_2)_2-OCH_3$) refers to an O-methoxy-ethyl modification of the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"5-methylcytosine" means a cytosine modified with a methyl group attached to the 5' position. A 5-methylcytosine is a modified nucleobase.

"About" means within ±7% of a value. For example, if it is stated, "the compounds affected at least about 70% inhibition of kallikrein", it is implied that the kallikrein levels are inhibited within a range of 63% and 77%.

"Active pharmaceutical agent" means the substance or substances in a pharmaceutical composition that provide a therapeutic benefit when administered to an individual. For example, in certain embodiments an antisense oligonucleotide targeted to kallikrein is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" or "ameliorate" or "amerliorating" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, snoRNAs, miRNAs, and satellite repeats.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furanosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-$CH(CH_3)$—O-2'.

"Constrained ethyl nucleoside" (also cEt nucleoside) means a nucleoside comprising a bicyclic sugar moiety comprising a 4'-$CH(CH_3)$—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Coagulation factor" means any of factors I, II, III, IV, V, VII, VIII, IX, X, XI, XII, XIII, or TAFI in the blood coagulation cascade. "Coagulation factor nucleic acid" means any nucleic acid encoding a coagulation factor. For example, in certain embodiments, a coagulation factor nucleic acid includes, without limitation, a DNA sequence encoding a coagulation factor (including genomic DNA comprising introns and exons), an RNA sequence transcribed from DNA encoding a coagulation factor, and an mRNA sequence encoding a coagulation factor. "Coagulation factor mRNA" means an mRNA encoding a coagulation factor protein.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Identifying an animal at risk for developing an inflammatory condition" means identifying an animal having been diagnosed with an inflammatory condition or identifying an animal predisposed to develop an inflammatory condition. Individuals predisposed to develop an inflammatory condition include those having one or more risk factors for inflammatory conditions, including, having a personal or family history of one or more inflammatory conditions. Such identification may be accomplished by any method including evaluating an individual's medical history and standard clinical tests or assessments.

"Identifying an animal at risk for experiencing an attack of hereditary angioedema" means identifying an animal having been diagnosed with hereditary angioedema or identifying an animal predisposed to develop hereditary angioedema. Individuals predisposed to develop hereditary angioedema include those having one or more risk factors for hereditary angioedema, including, having a personal or family history of hereditary angioedema. Such identification may be accomplished by any method including evaluating an individual's medical history and standard clinical tests or assessments.

"Immediately adjacent" means there are no intervening elements between the immediately adjacent elements.

"Individual" means a human or non-human animal selected for treatment or therapy.

"Inflammatory condition" or"inflammatory disease" or "inflammatory disorder" or "inflammatory condition" means a disease, disorder or condition related to an inflammatory response to injury or stimulus characterized by clinical signs of increased redness (rubor), temperature (calor), swelling (tumor), pain (dolor) and/or loss of function (functio laesa) in a tissue. Examples of such diseases, disorders, and conditions include hereditary angioedema (HAE).

"Inhibiting kallikrein" means reducing expression of kallikrein mRNA and/or protein levels in the presence of a kallikrein specific inhibitor, including a kallikrein antisense oligonucleotide, as compared to expression of kallikrein mRNA and/or protein levels in the absence of a kallikrein specific inhibitor, such as a kallikrein antisense oligonucleotide.

"Internucleoside linkage" refers to the chemical bond between nucleosides.

"Kallikrein nucleic acid" (aka KLKB1, plasma kallikrein, Fletcher factor, kallikrein B) means any nucleic acid encoding kallikrein. For example, in certain embodiments, a kallikrein nucleic acid includes a DNA sequence encoding kallikrein, an RNA sequence transcribed from DNA encoding kallikrein (including genomic DNA comprising introns and exons), and an mRNA sequence encoding kallikrein. "Kallikrein mRNA" means an mRNA encoding a kallikrein protein. In certain embodiments, KLKB1 is the term generally associated with the gene. In certain embodiments, the expression product of KLKB1 translation is generally termed plasma prekallikrein. Plasma prekallikrein is cleaved by Factor 12a. In certain embodiments, the cleavage product is generally termed plasma kallikrein. Plasma kallikrein is the substrate that C1-INH acts upon. As used herein, "kallikrein" means KLKB1 and its expression products, including, for example, plasma prekallikrein and plasma kallikrein.

"Kallikrein specific inhibitor" refers to any agent capable of specifically inhibiting the expression of kallikrein mRNA and/or kallikrein protein at the molecular level. For example, kallikrein specific inhibitors include nucleic acids (including antisense compounds), peptides, antibodies, small molecules, and other agents capable of inhibiting the expression of kallikrein mRNA and/or kallikrein protein. In certain embodiments, by specifically modulating kallikrein mRNA expression and/or kallikrein protein expression, kallikrein specific inhibitors may affect other components of the coagulation cascade including downstream components. Similarly, in certain embodiments, kallikrein specific inhibitors may affect other molecular processes in an animal.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(═O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P═S) is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods for decreasing kallikrein mRNA and protein expression.

Certain embodiments provide methods for the treatment, prevention, or amelioration of diseases, disorders, and conditions associated with kallikrein in an individual in need thereof. Also contemplated are methods for the preparation of a medicament for the treatment, prevention, or amelioration of a disease, disorder, or condition associated with kallikrein. Kallikrein associated diseases, disorders, and conditions include inflammatory conditions. In certain embodiments, the inflammatory condition may be an acute or chronic inflammatory condition. In certain embodiments, such inflammatory conditions include hereditary angioedema (HAE), edema, angioedema, swelling, angioedema of the lids, ocular edema, macular edema, and cerebral edema Certain embodiments provide for the use of a kallikrein specific inhibitor for treating, preventing, or ameliorating a kallikrein associated disease. In certain embodiments, kallikrein specific inhibitors are nucleic acids (including antisense compounds), peptides, antibodies, small molecules, and other agents capable of inhibiting the expression of kallikrein mRNA and/or kallikrein protein.

In certain embodiments of the present invention, kallikrein specific inhibitors are peptides or proteins, such as, but not limited to, lympho-epithelial Kazal-type-related inhibitor (LEKTI) as described in *J Proteome Res* 2010; 9: 4389-4394; ecotin-Pkal as described in *Biol Chem* 2010; 391: 425-433; aprotinin as described in *J Hypertens* 1987; 5: 581-586; PK15 as described in *Nat Chem Biol* 2009; 5: 502-507; kallistatin as described in *Biol Chem* 2001; 382: 15-21 and *J Biol Chem* 1992; 267: 25873-25880; C1-inhibitor as described in *Thromb Haemost* 2004; 92: 1277-1283 and *Adv Biosci* 1978; 17: 93-101; CeKI as described in *Biol Chem* 2004; 385: 1083-1086; AdKi as described in *Toxicon* 2004; 43: 219-223; FE999024 as described in *Am J Pathol* 2001; 159: 1797-1805; Arginine-15-aprotinin as described in *Adv Exp Med Biol* 1989; 247B: 15-21; alpha-1-antitrypsin-Pittsburgh as described in *J Clin Invest* 1986; 77: 631-634; and kallikrein inhibitors as described in U.S. Pat. No. 7,235,530, USPPN 2006/0069020, USPPN 2008/0188409, USPPN 2008/0221031, USPPN 2009/0221480, USPPN 2009/0227494, USPPN 2009/0227495, USPPN 2009/0233852, USPPN 2009/0234009, USPPN 2009/0247453, USPPN 2009/0264350, USPPN 2009/0075887; USPPN 2009/0105142, USPPN 2010/0183625, and U.S. Pat. No. 4,973,668.

In certain embodiments of the present invention, kallikrein specific inhibitors are antibodies, such as, but not limited to, DX-2300 as described in *Biochem J* 2009; 422: 383-392.

In certain embodiments of the present invention, kallikrein specific inhibitors are small molecules, such as, but not limited to, Ecallantide (DX-88 by Dyax Corp) as described in *Ann Allergy Asthma Immunol* 2010; 105: 430-436 and *Drugs Today* 2010; 46: 547-555; Nafamostat mesilate as described in *J Anesth* 2010; 24: 549-552 and *Br J Aneaesth* 1998; 81: 963-964; CU-2010 as described in *Anesthesiology* 2009; 110: 123-130; VA999024 and VA999026 as described in *Immunopharmacology* 1996; 32: 115-118; PKSI-527 (trans-4-aminomethyl-cyclohexanecarbonylphenylalanine 4-carboxymethylanilide hydrochloride) as described in *Thromb Res* 2005; 116: 403-408; and kallikrein inhibitors as described in U.S. Pat. No. 4,153,687.

Certain embodiments provide for methods of treating, preventing, or ameliorating an inflammatory condition in an animal, comprising administering to the animal a therapeutically effective amount of a kallikrein specific inhibitor, wherein the inflammatory condition is ameliorated in the animal.

In certain embodiments, the animal is a human.

In certain embodiments, the inflammatory condition is hereditary angioedema (HAE).

In certain embodiments, the kallikrein specific inhibitor is an antisense compound. In certain embodiments, the antisense compound is a modified oligonucleotide.

In certain embodiments, the kallikrein specific inhibitor is a nucleic acid. In certain embodiments, the nucleic acid is a modified oligonucleotide.

In certain embodiments, the kallikrein specific inhibitor is a modified oligonucleotide.

In certain embodiments, the modified oligonucleotide consists of 12 to 30 linked nucleosides.

In certain embodiments, the modified oligonucleotide is a single-stranded oligonucleotide.

In certain embodiments, the modified oligonucleotide consists of 15, 16, 17, 18, 19, or 20 linked nucleosides.

In certain embodiments, the modified oligonucleotide has a nucleobase sequence that is 80%, 85%, 90%, 95%, or 100% complementary to a human kallikrein nucleic acid.

In certain embodiments, the modified oligonucleotide comprises at least one modified internucleoside linkage. In certain embodiments, each modified internucleoside linkage is a phosphorothioate internucleoside linkage.

In certain embodiments, at least one nucleoside of the modified oligonucleotide comprises a modified sugar. In certain embodiments, the modified sugar is a bicyclic sugar. In certain embodiments, the bicyclic sugar comprises a 4'-CH($CH_3$)—O-2' bridge.

In certain embodiments, the modified sugar comprises a 2'-O-methoxyethyl group.

In certain embodiments, at least one nucleoside of the modified oligonucleotide comprises a modified nucleobase. In certain embodiments, the modified nucleobase is a 5'-methylcytosine.

In certain embodiments, at least one nucleoside of the modified oligonucleotide comprises at least one tetrahydropyran modified nucleoside wherein a tetrahydropyran ring replaces the furanose ring. In certain embodiments, each of the at least one tetrahydropyran modified nucleoside has the structure:

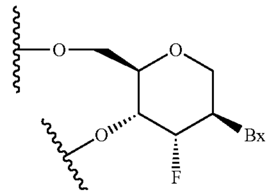

wherein Bx is an optionally protected heterocyclic base moiety.

In certain embodiments, the modified oligonucleotide of the compound comprises:

(i) a gap segment consisting of linked deoxynucleosides;

(ii) a 5' wing segment consisting of linked nucleosides;

(iii) a 3' wing segment consisting of linked nucleosides, wherein the gap segment is positioned immediately adjacent to and between the 5' wing segment and the 3' wing segment and wherein each nucleoside of each wing segment comprises a modified sugar. In some such embodiments, each cytosine in the modified oligonucleotide is a 5-methylcytosine.

In certain embodiments, the modified oligonucleotide of the compound comprises:

(i) a gap segment consisting of ten linked deoxynucleosides;

(ii) a 5' wing segment consisting of five linked nucleosides;

(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage. In some such embodiments, each cytosine in the modified oligonucleotide is a 5-methylcytosine.

Certain embodiments provide the use of kallikrein specific inhibitors as described herein in the manufacture of a medicament for treating, ameliorating, or preventing an inflammatory condition such as hereditary angioedema.

Certain embodiments provide the use of a kallikrein specific inhibitor as described herein in the manufacture of a medicament for treating, preventing, or ameliorating an inflammatory condition as described herein in a patient who is subsequently administered an additional agent or therapy as described herein.

Certain embodiments provide a kit for treating, preventing, or ameliorating an inflammatory condition as described herein wherein the kit comprises:

(i) a kallikrein specific inhibitor as described herein; and alternatively (ii) an additional agent or therapy as described herein.

A kit may further include instructions for using the kit to treat, prevent, or ameliorate an inflammatory condition as described herein by combination therapy as described herein.

In certain embodiments, provided is a compound comprising a modified oligonucleotide. In certain embodiments, the compound comprises a modified oligonucleotide consisting of 12 to 30 linked nucleosides.

In certain embodiments, the modified oligonucleotide targets a kallikrein nucleic acid. In certain embodiments, the kallikrein nucleic acid may be selected from, but is not limited to, one or more of GENBANK Accession No. NM_000892.3 (incorporated herein as SEQ ID NO: 1), GENBANK Accession No. DC412984.1 (incorporated herein as SEQ ID NO: 2), GENBANK Accession No. CN265612.1 (incorporated herein as SEQ ID NO: 3), GENBANK Accession No. AK297672.1 (incorporated herein as SEQ ID NO: 4), GEN- BANK Accession No. DC413312.1 (incorporated herein as SEQ ID NO: 5), GENBANK Accession No. AV688858.2 (incorporated herein as SEQ ID NO: 6), GENBANK Accession No. CD652077.1 (incorporated herein as SEQ ID NO: 7), GENBANK Accession No. BC143911.1 (incorporated herein as SEQ ID NO: 8), GENBANK Accession No. CB162532.1 (incorporated herein as SEQ ID NO: 9), the complement of GENBANK Accession No. NT_016354.19 truncated from nucleobases 111693001 to 111730000 (incorporated herein as SEQ ID NO: 10), GENBANK Accession No. NM_008455.2 (incorporated herein as SEQ ID NO: 11), GENBANK Accession No. BB598673.1 (incorporated herein as SEQ ID NO: 12), the complement of GENBANK Accession No. NT_039460.7 truncated from nucleobases 6114001 to 6144000 (incorporated herein as SEQ ID NO: 13), GENBANK Accession No. NM_012725.2 (incorporated herein as SEQ ID NO: 14), the complement of GENBANK Accession No. NW_047473.1 truncated from nucleobases 10952001 to 10982000 (incorporated herein as SEQ ID NO: 15), GENBANK Accession No. 3763_123_A (incorporated herein as SEQ ID NO: 16), GENBANK Accession No. XM_002804276.1 (incorporated herein as SEQ ID NO: 17), the complement of GENBANK Accession No. NW_001118167.1 truncated from nucleobases 2358000 to 2391000 (incorporated herein as SEQ ID NO: 18), and GENBANK Accession No. 3804_126_A (incorporated herein as SEQ ID NO: 19).

In certain embodiments, the compound may comprise a modified oligonucleotide comprising a nucleobase sequence at least 80%, at least 85%, at least 90%, at least 95%, at least 96%, at least 97%, at least 98%, or at least 99% complementary to an equal length portion of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, the complement of SEQ ID NO: 10, SEQ ID NO: 11, SEQ ID NO: 12, the complement of SEQ ID NO: 13, SEQ ID NO: 14, the complement of SEQ ID NO: 15, SEQ ID NO: 16, SEQ ID NO: 17, the complement of SEQ ID NO: 18, or SEQ ID NO: 19.

In certain embodiments, the compound may comprise a modified oligonucleotide comprising a nucleobase sequence at least 80%, at least 85%, at least 90%, at least 95%, at least 96%, at least 97%, at least 98%, or at least 99% complementary to an equal length portion of a human sequence. In certain embodiments, the compound may comprise a modified oligonucleotide comprising a nucleobase sequence at least 80%, at least 85%, at least 90%, at least 95%, at least 96%, at least 97%, at least 98%, or at least 99% complementary to an equal length portion of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or the complement of SEQ ID NO: 10.

In certain embodiments, the compound may comprise a modified oligonucleotide comprising a nucleobase sequence 100% complementary to an equal length portion of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or the complement of SEQ ID NO: 10.

In certain embodiments, the compound may comprise a modified oligonucleotide comprising a nucleobase sequence 100% complementary to an equal length portion of a human sequence. In certain embodiments, the compound may comprise a modified oligonucleotide comprising a nucleobase sequence 100% complementary to an equal length portion of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or the complement of SEQ ID NO: 10.

In certain embodiments, the nucleobase sequence of the modified oligonucleotide is 100% complementary to a nucleobase sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or the complement of SEQ ID NO: 10.

Certain embodiments provide a method comprising, (1) identifying an animal at risk for experiencing an attack of hereditary angioedema; and (2) prophylactically administering to the at risk animal a therapeutically effective amount of a modified oligonucleotide consisting of 12 to 30 linked nucleosides, wherein the modified oligonucleotide is at least 90% complementary to a Factor 12 nucleic acid.

Certain embodiments provide a method comprising, (1) identifying an animal at risk for developing an inflammatory condition; and (2) prophylactically administering to the at risk animal a therapeutically effective amount of a modified oligonucleotide consisting of 12 to 30 linked nucleosides, wherein the modified oligonucleotide is at least 90% complementary to a Factor 12 nucleic acid.

In certain embodiments, expression of kallikrein mRNA is reduced.

In certain embodiments, expression of kallikrein protein is reduced.

In certain embodiments, the inflammatory condition is an acute inflammatory condition.

In certain embodiments, the acute inflammatory condition is hereditary angioedema.

In certain embodiments, the prophylactic administering of a modified oligonucleotide prevents edema.

In certain embodiments, the prophylactic administering of a modified oligonucleotide prevents vascular permeability.

In certain embodiments, the prophylactic administering of a modified oligonucleotide prevents vascular leakage.

In certain embodiments, the prophylactic administering of a modified oligonucleotide prevents inflammation.

Certain embodiments provide a method comprising prophylactically treating an inflammatory condition in an animal by administering to the animal a therapeutically effective amount of a modified oligonucleotide consisting of 12 to 30 linked nucleosides, wherein the modified oligonucleotide is at least 90% complementary to a kallikrein nucleic acid.

In certain embodiments, the inflammatory condition is an acute inflammatory condition.

In certain embodiments, the acute inflammatory condition is hereditary angioedema.

Certain embodiments provide a method comprising inhibiting edema in an animal by administering to the animal a therapeutically effective amount of a modified oligonucleotide consisting of 12 to 30 linked nucleosides, wherein the modified oligonucleotide is at least 90% complementary to a kallikrein nucleic acid.

Certain embodiments provide a method comprising inhibiting vascular permeability in an animal by administering to the animal a therapeutically effective amount of a modified oligonucleotide consisting of 12 to 30 linked nucleosides, wherein the modified oligonucleotide is at least 90% complementary to a kallikrein nucleic acid.

Certain embodiments provide a method comprising inhibiting vascular leakage in an animal by administering to the animal a therapeutically effective amount of a modified oligonucleotide consisting of 12 to 30 linked nucleosides, wherein the modified oligonucleotide is at least 90% complementary to a kallikrein nucleic acid.

Certain embodiments provide a method comprising inhibiting inflammation in an animal by administering to the animal a therapeutically effective amount of a modified oligonucleotide consisting of 12 to 30 linked nucleosides, wherein the modified oligonucleotide is at least 90% complementary to a kallikrein nucleic acid.

In certain embodiments, the animal is a human.

In certain embodiments, the kallikrein nucleic acid is a human kallikrein nucleic acid.

In certain embodiments, the human kallikrein nucleic acid is SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or the complement of SEQ ID NO: 10.

In certain embodiments, the modified oligonucleotide is 100% complementary to a human kallikrein nucleic acid.

In certain embodiments, the modified oligonucleotide is a single-stranded oligonucleotide.

In certain embodiments, wherein the modified oligonucleotide comprises at least one modified internucleoside linkage.

In certain embodiments, the modified internucleoside linkage is a phosphorothioate internucleoside linkage.

In certain embodiments, the modified oligonucleotide comprises at least one nucleoside having a modified sugar.

In certain embodiments, the modified sugar is a bicyclic sugar.

In certain embodiments, the bicyclic sugar comprises a 4'-$CH(CH_3)$—O-2' bridge.

In certain embodiments, the modified oligonucleotide comprises at least one tetrahydropyran modified nucleoside wherein a tetrahydropyran ring replaces the furanose ring.

In certain embodiments, each of the at least one tetrahydropyran modified nucleoside has the structure:

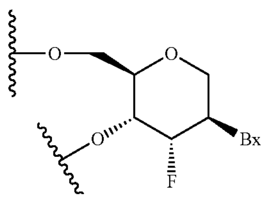

wherein Bx is an optionally protected heterocyclic base moiety.

In certain embodiments, the modified sugar comprises a 2'-O-methoxyethyl group.

In certain embodiments, at least one nucleoside comprises a modified nucleobase.

In certain embodiments, the modified nucleobase is a 5-methylcytosine.

In certain embodiments, the modified oligonucleotide is co-administered with any of the group selected from a serine protease inhibitor C1-INH recombinant protein, Factor 12 antisense oligonucleotide, CINRYZE, BERINERT, KALBITOR, Icatibant, Ecallantide, attenuated androgens, anabolic steroids, and antifibrinolytic agents (e.g., epsilon-aminocaproic acid and tranexamic acid).

Certain embodiments provide, a modified oligonucleotide consisting of 12 to 30 linked nucleosides fully complementary to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or the complement of SEQ ID NO: 10 for use in the treatment of an inflammatory condition.

In certain embodiments, the inflammatory condition is hereditary angioedema.

Certain embodiments provide use of a modified oligonucleotide as described herein in the manufacture of a medicament for treating an inflammatory condition.

In certain embodiments, the administering is parenteral administration. In certain embodiments, the parenteral administration is any of subcutaneous or intravenous administration.

Certain embodiments provide a method comprising, increasing or stabilizing HMWK in an animal in need thereof by administering to the animal a therapeutically effective amount of a modified oligonucleotide consisting of 12 to 30 linked nucleosides, wherein the modified oligonucleotide is at least 90% complementary to a kallikrein nucleic acid.

Certain embodiments provide a method of treating an inflammatory condition in an animal in need thereof by increasing or stabilizing HMWK in the animal by administering to the animal a therapeutically effective amount of a modified oligonucleotide consisting of 12 to 30 linked nucleosides, wherein the modified oligonucleotide is at least 90% complementary to a kallikrein nucleic acid.

In certain embodiments, the inflammatory condition is associated with low levels of HMWK.

In certain embodiments, the inflammatory condition is associated with high levels of bradykinin.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a kallikrein nucleic acid is 12 to 30 subunits in length. In other words, such antisense compounds are from 12 to 30 linked subunits. In other embodiments, the antisense compound is 8 to 80, 12 to 50, 15 to 30, 18 to 24, 19 to 22, or linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a kallikrein nucleic acid may be shortened or truncated. For example, a single subunit may be deleted from the 5' end (5' truncation), or alternatively from the 3' end (3' truncation). A shortened or truncated antisense compound targeted to a kallikrein nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a kallikrein nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-$(CH_2)$n-O-2' bridge, where n=1 or n=2). Preferably, each distinct region comprises uniform sugar moieties. The wing-gap-wing motif is frequently described as “X-Y-Z”, where “X” represents the length of the 5' wing region, “Y” represents the length of the gap region, and “Z” represents the length of the 3' wing region. As used herein, a gapmer described as “X-Y-Z” has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers of the present invention include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 5-8-5, or 6-8-6.

In certain embodiments, the antisense compound has a “wingmer” motif, having a wing-gap or gap-wing configuration, i.e. an X-Y or Y-Z configuration as described above for the gapmer configuration. Thus, wingmer configurations of the present invention include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to a kallikrein nucleic acid possess a 5-10-5 gapmer motif.

In certain embodiments, antisense compounds targeted to a kallikrein nucleic acid possess a 3-14-3 gapmer motif.

In certain embodiments, antisense compounds targeted to a kallikrein nucleic acid possess a 2-13-5 gapmer motif.

In certain embodiments, antisense compounds targeted to a kallikrein nucleic acid possess a 5-8-5 gapmer motif.

In certain embodiments, antisense compounds targeted to a kallikrein nucleic acid possess a 6-8-6 gapmer motif.

In certain embodiments, an antisense compound targeted to a kallikrein nucleic acid has a gap-widened motif.

In certain embodiments, a gap-widened antisense oligonucleotide targeted to a kallikrein nucleic acid has a gap segment of fourteen 2'-deoxyribonucleotides positioned immediately adjacent to and between wing segments of three chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a kallikrein nucleic acid has a gap segment of thirteen 2'-deoxyribonucleotides positioned immediately adjacent to and between a 5' wing segment of two chemically modified nucleosides and a 3' wing segment of five chemically modified nucleosides. In certain embodiments, the chemical modification comprises a 2'-sugar modification. In another embodiment, the chemical modification comprises a 2'-MOE sugar modification.

Target Nucleic Acids, Target Regions and Nucleotide Sequences

Nucleotide sequences that encode kallikrein include, without limitation, the following: GENBANK Accession No. NM_000892.3 (incorporated herein as SEQ ID NO: 1), GENBANK Accession No. DC412984.1 (incorporated herein as SEQ ID NO: 2), GENBANK Accession No. CN265612.1 (incorporated herein as SEQ ID NO: 3), GENBANK Accession No. AK297672.1 (incorporated herein as SEQ ID NO: 4), GENBANK Accession No. DC413312.1 (incorporated herein as SEQ ID NO: 5), GENBANK Accession No. AV688858.2 (incorporated herein as SEQ ID NO: 6), GENBANK Accession No. CD652077.1 (incorporated herein as SEQ ID NO: 7), GENBANK Accession No. BC143911.1 (incorporated herein as SEQ ID NO: 8), GENBANK Accession No. CB162532.1 (incorporated herein as SEQ ID NO: 9), the complement of GENBANK Accession No. NT_016354.19 truncated from nucleobases 111693001 to 111730000 (incorporated herein as SEQ ID NO: 10), GENBANK Accession No. NM_008455.2 (incorporated herein as SEQ ID NO: 11), GENBANK Accession No. BB598673.1 (incorporated herein as SEQ ID NO: 12), the complement of GENBANK Accession No. NT_039460.7 truncated from nucleobases 6114001 to 6144000 (incorporated herein as SEQ ID NO: 13), GENBANK Accession No. NM_012725.2 (incorporated herein as SEQ ID NO: 14), the complement of GENBANK Accession No. NW_047473.1 truncated from nucleobases 10952001 to 10982000 (incorporated herein as SEQ ID NO: 15), GENBANK Accession No. 3763_123_A (incorporated herein as SEQ ID NO: 16), GENBANK Accession No. XM_002804276.1 (incorporated herein as SEQ ID NO: 17), the complement of GENBANK Accession No. NW_001118167.1 truncated from nucleobases 2358000 to 2391000 (incorporated herein as SEQ ID NO: 18), and GENBANK Accession No. 3804_126_A (incorporated herein as SEQ ID NO: 19).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for kallikrein can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in kallikrein mRNA levels are indicative of inhibition of kallikrein expression. Reductions in levels of a kallikrein protein are also indicative of inhibition of target mRNA expression. Further, phenotypic changes are indicative of inhibition of kallikrein expression. For example, reduced or prevented inflammation can be indicative of inhibition of kallikrein expression. In another example, reduced or prevented edema/swelling can be indicative of inhibition of kallikrein expression. In another example, reduced or prevented vascular permeability can be indicative of inhibition of kallikrein expression. In another example, reduced or prevented vascular leakage can be indicative of inhibition of kallikrein expression. In certain embodiments, vascular permeability is measured by quantification of a dye, such as Evans Blue.

Hybridization

In some embodiments, hybridization occurs between an antisense compound disclosed herein and a kallikrein nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a kallikrein nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a kallikrein nucleic acid).

Non-complementary nucleobases between an antisense compound and a kallikrein nucleic acid may be tolerated provided that the antisense compound remains able to specifically hybridize to a target nucleic acid. Moreover, an antisense compound may hybridize over one or more segments of a kallikrein nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a kallikrein nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a kallikrein nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a kallikrein nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a kallikrein nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a kallikrein nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(═O)—$N(R_m)(R_n)$, and O—$CH_2$—C(═O)—$N(R_l)$—$(CH_2)_2$—$N(R_m)(R_n)$, where each $R_l$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-$(CH_2)$—O-2' (LNA); 4'-$(CH_2)$—S-2; 4'-$(CH_2)_2$—O-2' (ENA); 4'-$CH(CH_3)$—O-2' and 4'-$CH(CH_2OCH_3)$—O-2' (and analogs thereof see U.S. Pat. No. 7,399,845, issued on Jul. 15, 2008); 4'-$C(CH_3)(CH_3)$—O-2' (and analogs thereof see published International Application WO/2009/006478, published Jan. 8, 2009); 4'-$CH_2$—$N(OCH_3)$-2' (and analogs thereof see published International Application WO/2008/150729, published Dec. 11, 2008); 4'-$CH_2$—O—$N(CH_3)$-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—$C(H)(CH_3)$-2' (see Chattopadhyaya et al., *J. Org. Chem.,* 2009, 74, 118-134); and 4'-$CH_2$—C—(═$CH_2$)-2' (and analogs thereof see published International Application WO 2008/154401, published on Dec. 8, 2008).

Further reports related to bicyclic nucleosides can also be found in published literature (see for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 2007, 129(26) 8362-8379; Elayadi et al., *Curr. Opinion Invest. Drugs,* 2001, 2, 558-561; Braasch et al., *Chem. Biol.,* 2001, 8, 1-7; and Orum et al., *Curr. Opinion Mol. Ther.,* 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from $-[C(R_a)(R_b)]_n-$, $-C(R_a)=C(R_b)-$, $-C(R_a)=N-$, $-C(=O)-$, $-C(=NR_a)-$, $-C(=S)-$, $-O-$, $-Si(R_a)_2-$, $-S(=O)_x-$, and $-N(R_a)-$;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl ($C(=O)-H$), substituted acyl, CN, sulfonyl ($S(=O)_2$-$J_1$), or sulfoxyl ($S(=O)$-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl ($C(=O)-H$), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is $-[C(R_a)(R_b)]_n-$, $-[C(R_aR_b)]_n-O-$, $-C(R_aR_b)-N(R)-O-$ or $-C(R_aR_b)-O-N(R)-$. In certain embodiments, the bridge is 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—N(R)-2' and 4'-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-methyleneoxy (4'-$CH_2$—O-2') BNA, (B) β-D-methyleneoxy (4'-$CH_2$—O-2') BNA, (C) ethyleneoxy (4'-$(CH_2)_2$—O-2') BNA, (D) aminooxy (4'-$CH_2$—O—N(R)-2') BNA, (E) oxyamino (4'-$CH_2$—N(R)—O-2') BNA, and (F) methyl(methyleneoxy) (4'-$CH(CH_3)$—O-2') BNA, (G) methylene-thio (4'-$CH_2$—S-2') BNA, (H) methylene-amino (4'-$CH_2$—N(R)-2') BNA, (I) methyl carbocyclic (4'-$CH_2$—$CH(CH_3)$-2') BNA, and (J) propylene carbocyclic (4'-$(CH_2)_3$-2') BNA as depicted below.

(A)

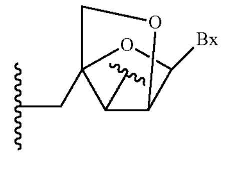

-continued (B)

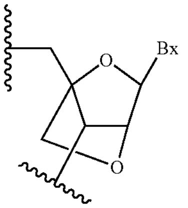

(C)

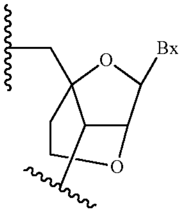

(D)

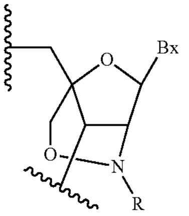

(E)

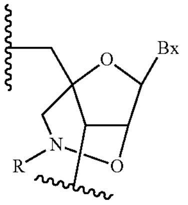

(F)

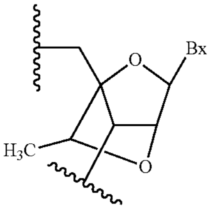

(G)

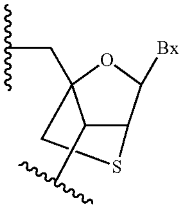

(H)

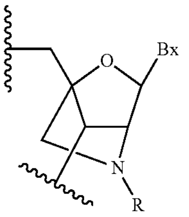

-continued (I)

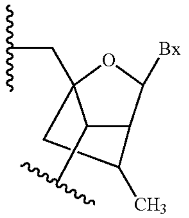

(J)

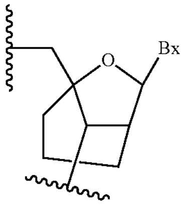

wherein Bx is the base moiety and R is independently H, a protecting group or $C_1$-$C_{12}$ alkyl.

In certain embodiments, bicyclic nucleosides are provided having Formula I:

I

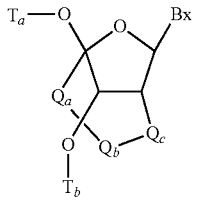

wherein:

Bx is a heterocyclic base moiety;

-Qa-Qb-Qc- is —$CH_2$—N($R_c$)—$CH_2$—, —C(═O)—N($R_c$)—$CH_2$—, —$CH_2$—O—N($R_c$)—, —$CH_2$—N($R_c$)—O— or —N($R_c$)—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

II

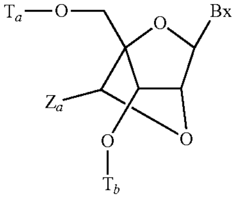

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_x$, $NJ_cJ_c$, $SJ_c$, $N_3$, OC(═X)$J_c$ and $NJ_e$C(═X)$NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

III

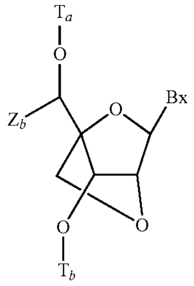

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(═O)—).

In certain embodiments, bicyclic nucleosides are provided having Formula IV:

IV

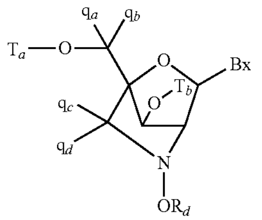

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

V

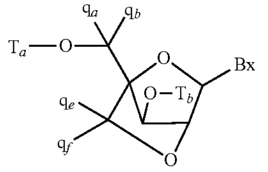

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron,* 1998, 54, 3607-3630). BNAs and preparation thereof are also described in WO 98/39352 and WO 99/14226.

Analogs of methyleneoxy (4'-$CH_2$—O-2') BNA and T-thio-BNAs, have also been prepared (Kumar et al., *Bioorg. Med. Chem. Lett.,* 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of T-amino-BNA, a novel comformationally restricted high-affinity oligonucleotide analog has been described in the art (Singh et al., *J. Org. Chem.,* 1998, 63, 10035-10039). In addition, T-amino- and 2'-methylamino-BNA's have been prepared and the thermal stability of their duplexes with complementary RNA and DNA strands has been previously reported.

In certain embodiments, bicyclic nucleosides are provided having Formula VI:

VI

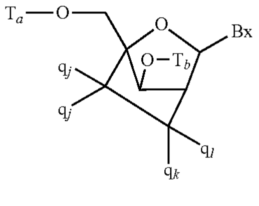

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$; and $q_i$ and $q_j$ or $q_l$ and $q_k$ together are $=C(q_g)(q_h)$, wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'-CH=CH—$CH_2$-2' have been described (Freier et al., *Nucleic Acids Research,* 1997, 25(22), 4429-4443 and Albaek et al., *J. Org. Chem.,* 2006, 71, 7731-7740). The synthesis and preparation of carbocyclic bicyclic nucleosides along with their oligomerization and biochemical studies have also been described (Srivastava et al., *J. Am. Chem. Soc.,* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocyclic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.,* 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.,* 2002, 10, 841-854), fluoro HNA (F-HNA) or those compounds having Formula VII:

VII

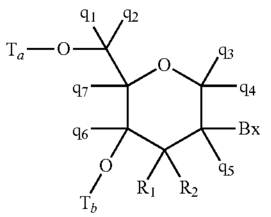

wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-$O(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.,* 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-$CH(CH_3)$—O-2') bridging group. In certain embodiments, the (4'-$CH(CH_3)$—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a kallikrein nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a kallikrein nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of kallikrein nucleic acids can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a kallikrein nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (invitrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a kallikrein nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of kallikrein nucleic acids can be assessed by measuring kallikrein protein levels. Protein levels of kallikrein can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human kallikrein are commercially available.

In Vivo Testing of Antisense Compounds

Antisense compounds, for example, antisense oligonucleotides, are tested in animals to assess their ability to inhibit expression of kallikrein and produce phenotypic changes, such as, reduced inflammation, edema/swelling, vascular permeability, and vascular leakage. In certain embodiments, inflammation is measured by measuring the increase or decrease of edema, temperature, pain, color of tissue, and abdominal function in the animal. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from liver tissue and changes in kallikrein nucleic acid expression are measured.

Certain Indications

In certain embodiments, the invention provides methods of treating an individual comprising administering one or more pharmaceutical compositions of the present invention. In certain embodiments, the individual has an inflammatory condition. In certain embodiments, the individual is at risk for developing an inflammatory condition, including, but not limited to, hereditary angioedema (HAE), edema, angioedema, swelling, angioedema of the lids, ocular edema, macular edema, and cerebral edema. This includes individuals with an acquired problem, disease, or disorder that leads to a risk of inflammation, for example, genetic predisposition to an inflammatory condition, environmental factors, and exposure to certain medications, including, for example, ACE inhibitors and ARBs. In certain embodiments, the individual has been identified as in need of anti-inflammation therapy. Examples of such individuals include, but are not limited to those having a mutation in the genetic code for complement 1 esterase inhibitor (i.e., C1-INH) or Factor 12. In certain embodiments, an abnormal code can lead to a deficiency in C1-INH (i.e., type I HAE), an inability of existing C1-INH to function properly (type II HAE), or hyperfunctional Factor 12 (i.e., type III HAE). In certain embodiments the invention provides methods for prophylactically reducing Factor 12 expression in an individual. Certain embodiments include treating an individual in need thereof by administering to an individual a therapeutically effective amount of an antisense compound targeted to a Factor 12 nucleic acid.

In one embodiment, administration of a therapeutically effective amount of an antisense compound targeted to a kallikrein nucleic acid is accompanied by monitoring of kallikrein levels in the serum of an individual, to determine an individual's response to administration of the antisense compound. An individual's response to administration of the antisense compound is used by a physician to determine the amount and duration of therapeutic intervention.

In certain embodiments, administration of an antisense compound targeted to a kallikrein nucleic acid results in reduction of kallikrein expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a kallikrein nucleic acid results in a change in a measure of inflammation, swelling, hypertension, and/or vascular permeability. In certain embodiments, administration of a kallikrein antisense compound increases the measure by at least 15, 20, 25, 30, 35, 40, 45, 50, 55, 60, 65, 70, 75, 80, 85, 90, 95 or 99%, or a range defined by any two of these values. In some embodiments, administration of a kallikrein antisense compound decreases the measure by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to kallikrein are used for the preparation of a medicament for treating a patient suffering or susceptible to an inflammatory condition including hereditary angioedema (HAE).

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease, disorder, or condition as the one or more pharmaceutical compositions of the present invention. In certain embodiments, such one or more other pharmaceutical agents are designed to treat a different disease, disorder, or condition as the one or more pharmaceutical compositions of the present invention. In certain embodiments, such one or more other pharmaceutical agents are designed to treat an undesired side effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention are co-administered with another pharmaceutical agent to produce a combinational effect. In certain embodiments, one or more pharmaceutical compositions of the present invention are co-administered with another pharmaceutical agent to produce a synergistic effect.

In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

In certain embodiments, pharmaceutical agents that may be co-administered with a pharmaceutical composition of the present invention include anticoagulant or antiplatelet agents. In certain embodiments, pharmaceutical agents that may be co-administered with a pharmaceutical composition of the present invention include serine protease inhibitor C1-INH recombinant protein, Factor 12 antisense oligonucleotide, CINRYZE, BERINERT, KALBITOR, Icatibant, Ecallantide, attenuated androgens, anabolic steroids, and antifibrinolytic agents (e.g., epsilon-aminocaproic acid and tranexamic acid).

In certain embodiments, pharmaceutical agents that may be co-administered with a kallikrein specific inhibitor of the present invention include, but are not limited to, an additional kallikrein inhibitor. In certain embodiments, the co-administered pharmaceutical agent is administered prior to administration of a pharmaceutical composition of the present invention. In certain embodiments, the co-administered pharmaceutical agent is administered following administration of a pharmaceutical composition of the present invention. In certain embodiments the co-administered pharmaceutical agent is administered at the same time as a pharmaceutical composition of the present invention. In certain embodiments the dose of a co-administered pharmaceutical agent is the same as the dose that would be administered if the co-administered pharmaceutical agent was administered alone. In certain embodiments the dose of a co-administered pharmaceutical agent is lower than the dose that would be administered if the co-administered pharmaceutical agent was administered alone. In certain embodiments the dose of a co-administered pharmaceutical agent is greater than the dose that would be administered if the co-administered pharmaceutical agent was administered alone.

In certain embodiments, the co-administration of a second compound enhances the anti-inflammatory effect of a first compound, such that co-administration of the compounds results in an anti-inflammatory effect that is greater than the effect of administering the first compound alone. In other embodiments, the co-administration results in anti-inflammatory effects that are additive of the effects of the compounds when administered alone. In certain embodiments, the co-administration results in anti-inflammatory effects that are supra-additive of the effects of the compounds when administered alone. In certain embodiments, the first compound is an antisense compound. In certain embodiments, the second compound is an antisense compound.

EXAMPLES

Non-limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Murine Kallikrein (KLKB1) mRNA

Antisense oligonucleotides targeting a murine kallikrein nucleic acid were tested for their effects on kallikrein mRNA in vitro. Cultured mouse primary hepatocytes at a density of 10,000 cells per well were transfected using Cytofectin reagent with 12.5 nM, 25 nM, 50 nM, 100 nM, or 200 nM of antisense oligonucleotide. After a treatment period of approximately 24 hours, RNA was isolated from the cells and mouse kallikrein mRNA levels were measured by quantitative real-time PCR using the murine primer probe set RTS3313 (forward sequence TGCCTGCTGTTCAGCTTTCTC, designated herein as SEQ ID NO: 21; reverse sequence TGGCAAAGTCCCTGTAATGCT, designated herein as SEQ ID NO: 22; probe sequence CGTGACTCCACCCAAAGAGACAAATAAACG, designated herein as SEQ ID NO: 23). Kallikrein mRNA levels were adjusted according to total RNA content, as measured by RIBOGREEN.

The chimeric antisense oligonucleotides were designed as 5-10-5 MOE gapmers. The gapmers are 20 nucleotides in length, wherein the central gap segment is comprised of ten 2'-deoxynucleosides and is flanked on both sides (in the 5' and 3' directions) by wings comprising five nucleosides each. Each nucleoside in the 5' wing segment and each nucleoside in the 3' wing segment has a 2'-MOE modification. The internucleoside linkages throughout each gapmer are phosphorothioate (P═S) linkages. All cytosine residues throughout each gapmer are 5-methylcytosines. Results demonstrate that kallikrein mRNA levels were significantly reduced in a dose dependent manner.

ISIS 482584 (GGCATATTGGTTTTTGGAAT; incorporated herein as SEQ ID NO: 40), which was one of the antisense oligonucleotides tested in the assay, is targeted to SEQ ID NO: 11 (GENBANK Accession No. NM_008455.2) with a target start site of 1586 and a target stop site of 1605. ISIS 482584 reduced kallikrein mRNA in a dose dependent manner yielding a half maximal inhibitory concentration ($IC_{50}$) of 84 nM.

TABLE 1

Dose-dependent antisense inhibition of murine kallikrein

| Dose | % inhibition |
|---|---|
| 12.5 nM | 0 |
| 25.0 nM | 36 |
| 50.0 nM | 17 |
| 100.0 nM | 60 |
| 200.0 nM | 83 |

C57BL/6J-Tyrc-2J mice were treated with 2.5 mg/kg, 5.0 mg.kg, 10.0 mg/kg, 20.0 mg/kg, 40.0 mg/kg, or 80.0 mg/kg (corresponding to 5.0 mg/kg, 10.0 mg/kg, 20.0 mg/kg, 40 mg/kg, 80 mg/kg, or 160 mg/kg per week) of ISIS 482584 administered subcutaneously twice a week for 3 weeks. Kallikrein mRNA and protein expression was reduced in a dose dependent manner. Kallikrein mRNA was reduced by greater than 90% inhibition at a dose of 160 mg/kg per week.

Example 2

In Vivo Effect of Antisense Inhibition of Murine Kallikrein (KLKB1) in an Angioedema Mouse Model Hereditary angioedema (HAE) is characterized by local swelling and increase in vascular permeability in subcutaneous tissues (Morgan, B. P. N. Engl. J. Med. 363: 581-83, 2010). It is caused by a deficiency of the C1 inhibitor, a protein of the complement system. Two mouse models were used in this study, including, an established mouse model of C1-INH deficiency and a captopril-induced edema model, both of which causes vascular permeability, a hallmark of HAE. Reversal of vascular permeability is accompanied by increased plasma levels of high molecular weight kininogen (HMWK).

In the first model, angioedema was induced by treatment with Captopril, a known antihypertensive agent, which increases vascular permeability in mice and replicates the pathology of hereditary angioedema.

In the second model, angioedema was induced by treatment with ISIS 461756, an antisense oligonucleotide which targets murine C1 inhibitor mRNA, which increases vascular permeability in mice and replicates the pathology of hereditary angioedema. ISIS 461756 (SEQ ID NO: 41; AAAGTGGTTGATACCCTGGG) is a 5-10-5 MOE gapmer targeting nucleosides 1730-1749 of NM_009776.3 (SEQ ID NO: 20).

The effect of HOE-140 and ISIS 482584, an antisense oligonucleotide inhibitor of kallikrein, were evaluated in the Captopril and ISIS 461756-induced mouse models of vascular permeability. Some of the murine groups were treated with HOE-140, a selective antagonist of the bradykinin B2 receptor, which blocks vasodilation and vascular permeability (Cruden and Newby, Expert Opin. Pharmacol. 9: 2383-90, 2008). Other mice were treated with ISIS 482584, which inhibits kallikrein mRNA expression. The effect of treatment with HOE-140 was compared with the effect of treatment with ISIS 482584.

Treatment

The various treatment groups for this assay are presented in Table 2.

Group 1 consisted of 4 C57BL/6J-Tyrc-2J mice treated with PBS administered subcutaneously twice a week for 4 weeks. No other treatment was administered to Group 1 which served as a control group to measure the basal level of vascular permeability.

Group 2 consisted of 8 C57BL/6J-Tyrc-2J mice treated with PBS administered subcutaneously twice a week for 4 weeks. At the end of the treatment, the mice were intraperitoneally administered 20 μg of captopril. Group 2 served as a PBS control group for captopril-induced vascular permeability.

Group 3 consisted of 8 C57BL/6J-Tyrc-2J mice treated with PBS administered subcutaneously twice a week for 4 weeks. On day 14, the mice were treated with 50 mg/kg of the antisense oligonucleotide targeting C1 inhibitor, ISIS 461756, administered subcutaneously twice a week for 2 weeks. At the end of the treatment period, the mice were intraperitoneally administered 20 tag of captopril. Group 3 served as a PBS control group for captopril and ISIS 461756-induced vascular permeability.

Group 4 consisted of 8 C57BL/6J-Tyrc-2J mice treated with PBS administered subcutaneously twice a week for 4 weeks. On day 14, the mice were treated with 50 mg/kg of the antisense oligonucleotide targeting C1 inhibitor, ISIS 461756, administered subcutaneously twice a week for 2 weeks. At the end of the treatment period, the mice were intraperitoneally administered 20 μg of captopril. The mice were then also intraperitoneally administered 30 μg of HOE-140. Group 4 served as a positive control for inhibition of vascular permeability with HOE-140.

Group 5 consisted of 8 C57BL/6J-Tyrc-2J mice treated with 40 mg/kg of control oligonucleotide ISIS 141923, a 5-10-5 MOE gapmer with no known murine target, (CCTTCCCTGAAGGTTCCTCC; SEQ ID NO: 42) administered subcutaneously twice a week for 4 weeks. On day 14, the mice were treated with 50 mg/kg of the antisense oligonucleotide targeting C1 inhibitor, ISIS 461756, administered subcutaneously twice a week for 2 weeks. At the end of the treatment period, the mice were intraperitoneally administered 20 μg of captopril. Group 5 served as a control group for captopril and ISIS 461756-induced vascular permeability.

Group 6 consisted of 8 C57BL/6J-Tyrc-2J mice and was treated with 40 mg/kg of ISIS 482584 administered subcutaneously twice a week for 4 weeks. At the end of the treatment period, the mice were intraperitoneally administered 20 μg of captopril. Group 6 served as the experimental treatment group for examining the effect of kallikrein ASO on captopril-induced vascular permeability.

Group 7 consisted of 8 C57BL/6J-Tyrc-2J mice treated with 40 mg/kg of ISIS 482584 administered subcutaneously twice a week for 4 weeks. On day 14, the mice were treated with 50 mg/kg of the antisense oligonucleotide targeting C1 inhibitor, ISIS 461756, administered subcutaneously twice a week for 2 weeks. At the end of the treatment period, the mice were intraperitoneally administered 20 μg of captopril. Group 7 served as the experimental treatment group for examining the effect of kallikrein ASO on captopril and ISIS 461756-induced vascular permeability.

All the groups were then injected with 30 mg/kg of Evans Blue solution into the tail vein. The mice were sacrificed 30 min after the Evans Blue solution administration and colons, feet, ears, and intestines were harvested. Blood samples were taken through cardiac puncture.

TABLE 2

Treatment groups

| Group No. | Treatment | Captopril | ISIS 461756 | HOE-140 |
|---|---|---|---|---|
| 1. (N = 4) | PBS | No | No | No |
| 2. (N = 8) | PBS | Yes | No | No |
| 3. (N = 8) | PBS | Yes | Yes | No |
| 4. (N = 8) | PBS | Yes | Yes | Yes |
| 5. (N = 8) | ISIS 141923 | Yes | Yes | No |
| 6. (N = 8) | ISIS 482584 | Yes | No | No |
| 7. (N = 8) | ISIS 482584 | Yes | Yes | No |

Quantification of Vascular Permeability

The harvested tissues from the feet, colon, ears, and intestines were placed separately in formamide solution overnight to leach out the Evans Blue dye. The formamide solution containing ear and feet tissue was heated to 55° C. and left overnight. The color intensity of the dye-infused formamide solution was then measured at $OD_{600nm}$, and is presented in Table 3. Mice displaying any manifestation of angioedema take up more dye and, therefore, demonstrate high OD values.

As presented in Table 3, treatment with ISIS 482584 prevents vascular permeability in mice treated with captopril (Group 6) and in mice treated with captopril and ISIS 461756 (Group 7) compared to the respective PBS control groups (Groups 2 and 3). Measures of vascular permeability in mice of Groups 6 and 7 were also reduced in most of the tissues in comparison to the mice treated with the control oligonucleotide, ISIS 141923 (Group 5), where vascular permeability was induced with captopril and ISIS 461756. Measures of vascular permeability in the colon and feet tissues of both the treatment groups (Groups 6 and 7) were comparable to basal levels, as observed in mice treated with only PBS (Group 1). Reduction in vascular permeability in mice treated with ISIS 482584 was comparable to that seen in mice treated with the bradykinin 2 receptor antagonist, HOE 140, which served as a positive control in this assay.

Therefore, antisense inhibition of kallikrein mRNA may be beneficial for the treatment and prevention of vascular permeability, which is symptomatic of HAE.

TABLE 3

| OD$_{600\ nm}$ of Evans Blue dye to measure vascular permeability | | | | | | | | |
|---|---|---|---|---|---|---|---|---|
| Group No. | Treatment | Captopril | ISIS 461756 | HOE-140 | Colons | Intestines | Feet | Ears |
| 1 | PBS | No | No | No | 0.26 | 0.16 | 0.11 | 0.02 |
| 2 | PBS | Yes | No | No | 0.49 | 0.29 | 0.12 | 0.07 |
| 3 | PBS | Yes | Yes | No | 0.49 | 0.34 | 0.11 | 0.12 |
| 4 | PBS | Yes | Yes | Yes | 0.14 | 0.18 | 0.07 | 0.09 |
| 5 | ISIS 141923 | Yes | Yes | No | 0.44 | 0.29 | 0.14 | 0.08 |
| 6 | ISIS 482584 | Yes | No | No | 0.27 | 0.30 | 0.07 | 0.14 |
| 7 | ISIS 482584 | Yes | Yes | No | 0.21 | 0.34 | 0.07 | 0.06 |

Quantification of High Molecular Weight Kininogen (HMWK)

Western blot quantification of HMWK from blood samples are presented in FIG. 1.

As shown in FIG. 1, samples from Groups 1 and 2 have low levels of HMWK as compared to Groups 6 and 7 indicating that vascular permeability is reversed in Groups 6 and 7. Also as shown in FIG. 1, samples from Groups 1 and 2 have increased HMWK cleavage product as compared to Groups 6 and 7. Thus, lack of HMWK is caused by kallikrein cleavage of HMWK into cleavage products (including bradykinin and HKa).

Example 3

In Vivo Effect of Antisense Inhibition of Murine Kallikrein (KLKB1) on Basal Permeability and Captopril-Induced Permeability in Mice Basal permeability is the level of vascular permeability occurring in the tissues of naïve, untreated mice. The effect of ISIS 482584 in the prevention of vascular permeability, either basal or captopril-induced, was evaluated.

Treatment

The various treatment groups for this assay are presented in Table 4.

Group 1 consisted of 8 mice and was treated with PBS administered subcutaneously twice a week for 4 weeks. No other treatment was administered to Group 1 which served as a control group to measure the basal levels of vascular permeability.

Group 2 consisted of 8 mice and was treated with PBS administered subcutaneously twice a week for 4 weeks. At the end of the treatment period, the mice were intraperitoneally administered 20 µg of captopril. Group 2 served as the negative control group for captopril-induced vascular permeability.

Group 3 consisted of 8 mice and was treated with PBS administered subcutaneously twice a week for 4 weeks. At the end of the treatment period, the mice were intraperitoneally administered 30 µg of HOE-140. Group 3 served as a positive control for inhibition of basal vascular permeability.

Group 4 consisted of 8 mice and was treated with PBS administered subcutaneously twice a week for 4 weeks. At the end of the treatment period, the mice were intraperitoneally administered 20 µg of captopril. The mice were also intraperitoneally administered 30 µg of HOE-140. Group 4 served as a positive control for inhibition of captopril-induced vascular permeability.

Group 5 consisted of 8 mice and was treated with 40 mg/kg of ISIS 482584 administered subcutaneously twice a week for 4 weeks. Group 5 served as an experimental treatment group for examining the effect of ISIS 482584 on basal vascular permeability.

Group 6 consisted of 8 mice and was treated with 40 mg/kg of ISIS 482584 administered subcutaneously twice a week for 4 weeks. At the end of the treatment period, the mice were intraperitoneally administered 20 µg of captopril. Group 6 served as an experimental treatment group for examining the effect of ISIS 482584 on captopril-induced vascular permeability.

All the groups were then injected with 30 mg/kg of Evans Blue solution. The mice were sacrificed 30 min after the Evans Blue solution administration and colons, feet, ears, and intestines were harvested.

TABLE 4

| Treatment groups | | | |
|---|---|---|---|
| Group No. | Treatment | Captopril | HOE-140 |
| 1. (N = 8) | PBS | No | No |
| 2. (N = 8) | PBS | Yes | No |
| 3. (N = 8) | PBS | No | Yes |
| 4. (N = 8) | PBS | Yes | Yes |
| 5. (N = 8) | ISIS 482584 | No | No |
| 6. (N = 8) | ISIS 482584 | Yes | No |

Quantification of Vascular Permeability

The harvested tissues from the feet, colon, intestine, and ears were placed separately in formamide solution overnight to leach out the Evans Blue dye. The formamide solution containing feet and ear tissue was heated to 55° C. and left overnight. The color intensity of the dye-infused formamide solution was then measured at OD$_{600nm}$, and is presented in Table 5. Mice displaying any manifestation of angioedema take up more dye and, therefore, demonstrate high OD values.

As presented in Table 5, mice treated with ISIS 482584 demonstrated reduced basal vascular permeability compared to the PBS control (Group 5 vs. Group 1). The reduction in basal vascular permeability by treatment with ISIS 482584 was comparable to that caused by treatment with HOE-140 (Group 3, which served as the positive control). Mice treated with ISIS 482584 also demonstrated reduced captopril-induced vascular permeability in most tissues compared to the PBS control (Group 6 vs. Group 2). The reduction in captopril-induced vascular permeability by treatment with ISIS 482584 was comparable to that caused by treatment with HOE-140 (Group 4, which served as the positive control).

TABLE 5

| OD$_{600\ nm}$ of Evans Blue dye to measure vascular permeability | | | | | | | |
|---|---|---|---|---|---|---|---|
| Group No. | Treatment | Captopril | HOE-140 | Colon | Feet | Intestine | Ears |
| 1 | PBS | No | No | 0.27 | 0.08 | 0.23 | 0.06 |
| 2 | PBS | Yes | No | 0.61 | 0.08 | 0.24 | 0.01 |

TABLE 5-continued

| OD$_{600\ nm}$ of Evans Blue dye to measure vascular permeability | | | | | | | |
|---|---|---|---|---|---|---|---|
| Group No. | Treatment | Captopril | HOE-140 | Colon | Feet | Intes-tine | Ears |
| 3 | PBS | No | Yes | 0.18 | 0.06 | 0.21 | 0.03 |
| 4 | PBS | Yes | Yes | 0.29 | 0.03 | 0.14 | 0.00 |
| 5 | ISIS 482584 | No | No | 0.19 | 0.07 | 0.22 | 0.04 |
| 6 | ISIS 482584 | Yes | No | 0.37 | 0.05 | 0.22 | 0.00 |

Example 4

Dose-Dependent Effect of Antisense Inhibition of Murine Kallikrein (KLKB1) on Captopril-Induced Vascular Permeability The effect of varying doses on ISIS 482584 on captopril-induced vascular permeability was evaluated.

Treatment

The various treatment groups for this assay are presented in Table 6.

Group 1 consisted of 4 mice and was treated with PBS administered subcutaneously twice a week for 3 weeks. No other treatment was administered to Group 1 which served as a control group to measure the basal levels of vascular permeability.

Group 2 consisted of 8 mice and was treated with PBS administered subcutaneously twice a week for 3 weeks. At the end of the treatment period, the mice were intraperitoneally administered 20 μg of captopril. Group 2 served as the control group for captopril-induced vascular permeability.

Group 3 consisted of 4 mice and was treated with PBS administered subcutaneously twice a week for 3 weeks. At the end of the treatment period, the mice were intraperitoneally administered 20 μg of captopril. The mice were also intraperitoneally administered 30 μg of Icatibant (HOE-140). Group 4 served as a positive control for inhibition of captopril-induced vascular permeability.

Groups 4, 5, 6, 7, 8, and 9 consisted of 8 mice each and were treated with 2.5 mg/kg, 5 mg/kg, 10 mg/kg, 20 mg/kg, 40 mg/kg, or 80 mg/kg (corresponding to 5 mg/kg, 10 mg/kg, 20 mg/kg, 40 mg/kg, 80 mg/kg, or 160 mg/kg per week), respectively of ISIS 482584 administered subcutaneously twice a week for 3 weeks. At the end of the treatment period, the mice of all the groups were intraperitoneally administered 20 μg of captopril. Groups 4-9 served as the experimental treatment groups for examining the effect of varying doses of ISIS 482584 on captopril-induced vascular permeability.

All the groups were then injected with 30 mg/kg of Evans Blue solution in the tail vein. The mice were sacrificed 30 min after the Evans Blue solution administration and colons, feet, ears, and intestines were harvested. Blood samples were taken through cardiac puncture.

TABLE 6

| Treatment groups | | | | |
|---|---|---|---|---|
| Group No. | Treatment | Dose (mg/kg/wk) | Captopril | HOE-140 |
| 1. (N = 4) | PBS | — | No | No |
| 2. (N = 8) | PBS | — | Yes | No |
| 3. (N = 4) | PBS | — | Yes | Yes |
| 4. (N = 8) | ISIS 482584 | 160 | Yes | No |
| 5. (N = 8) | ISIS 482584 | 80 | Yes | No |
| 6. (N = 8) | ISIS 482584 | 40 | Yes | No |
| 7. (N = 8) | ISIS 482584 | 20 | Yes | No |
| 8. (N = 8) | ISIS 482584 | 10 | Yes | No |
| 9. (N = 8) | ISIS 482584 | 5 | Yes | No |

Quantification of Vascular Permeability

The harvested tissues were placed in formamide solution overnight to leach out the Evans Blue dye. The formamide solution containing feet and ear tissue was heated to 55° C. and left overnight. The color intensity of the dye-infused formamide solution was then measured at OD$_{600nm}$, and is presented in Table 7. Mice displaying any manifestation of angioedema take up more dye and, therefore, demonstrate high OD values.

As presented in Table 7, mice treated with higher doses of ISIS 482584 (Groups 4, 5, and 6) had reduced levels of captopril-induced vascular permeability compared to the corresponding PBS control group (Group 2). The reduction in vascular permeability in mice of these treatment groups (Groups 4 and 5) was comparable to the levels of basal vascular permeability (as shown in Group 1) as well as in mice treated with HOE-140 (Group 3).

TABLE 7

| OD$_{600\ nm}$ of Evans Blue dye to measure vascular permeability | | | | | | | | |
|---|---|---|---|---|---|---|---|---|
| Group No. | Treatment | Dose (mg/kg) | Captopril | HOE-140 | Colon | Feet | Intestine | Ears |
| 1 | PBS | — | No | No | 0.16 | 0.07 | 0.13 | 0.01 |
| 2 | PBS | — | Yes | No | 0.39 | 0.12 | 0.18 | 0.07 |
| 3 | PBS | — | Yes | Yes | 0.15 | 0.03 | 0.10 | 0.04 |
| 4 | ISIS 482584 | 160 | Yes | No | 0.26 | 0.10 | 0.15 | 0.05 |
| 5 | ISIS 482584 | 80 | Yes | No | 0.21 | 0.04 | 0.17 | 0.03 |
| 6 | ISIS 482584 | 40 | Yes | No | 0.36 | 0.10 | 0.20 | 0.05 |
| 7 | ISIS 482584 | 20 | Yes | No | 0.40 | 0.11 | 0.20 | 0.07 |
| 8 | ISIS 482584 | 10 | Yes | No | 0.41 | 0.10 | 0.19 | 0.05 |
| 9 | ISIS 482584 | 5 | Yes | No | 0.41 | 0.10 | 0.17 | 0.05 |

Quantification of Vascular Leakage

The blood drawn through cardiac puncture was immediately mixed with 3 times the volume of ice-cold ethanol. The solution was centrifuged at 15,000 g for 20 minutes at 4° C. to remove cell debris and precipitated plasma proteins. The ethanol extracts were further purified by ultra-filtration through a 10 kDa MWCO filter. The color intensity of the ethanol extracted plasma solution was then measured at OD$_{620nm}$. The results are presented in Table 8 as percentage increase or decrease of the OD values of the Group 1 PBS control. It was expected that tissues from mice displaying manifestation of angioedema would leak more dye from the plasma and, therefore, demonstrate low OD values, whereas treatment groups may display higher OD values due to reduced vascular leakage. Mice treated with 160 mg/kg/week and 80 mg/kg/week of ISIS 482584 (Groups 4 and 5) demonstrated less vascular leakage compared to the PBS negative control treated with captopril (Group 2). The results from Groups 4 and 5 were comparable to the positive control treated with HOE-140 (Group 3).

TABLE 8

Percentage of $OD_{620\ nm}$ of Evans Blue dye compared to the PBS basal control to measure vascular leakage

| Group No. | Treatment | Dose (mg/kg) | Captopril | HOE-140 | Plasma |
|---|---|---|---|---|---|
| 2 | PBS | — | Yes | No | −43 |
| 3 | PBS | — | Yes | Yes | 5 |
| 4 | ISIS 482584 | 160 | Yes | No | 91 |
| 5 | ISIS 482584 | 80 | Yes | No | 40 |
| 6 | ISIS 482584 | 40 | Yes | No | −31 |
| 7 | ISIS 482584 | 20 | Yes | No | −26 |
| 8 | ISIS 482584 | 10 | Yes | No | −20 |
| 9 | ISIS 482584 | 5 | Yes | No | −23 |

Example 5

Dose-Dependent Effect of Antisense Inhibition of Murine Kallikrein (KLKB1) on Basal Permeability in Mice The effect of varying doses on ISIS 482584 on basal vascular permeability was evaluated.

Treatment

The various treatment groups for this assay are presented in Table 9.

Group 1 consisted of 8 mice and was treated with PBS administered subcutaneously twice a week for 3 weeks. No other treatment was administered to Group 1 which served as a control group to measure the basal levels of vascular permeability.

Group 2 consisted of 4 mice and was treated with PBS administered subcutaneously twice a week for 3 weeks. At the end of the treatment period, the mice were intraperitoneally administered 30 μg of HOE-140. Group 2 served as a positive control for inhibition of basal vascular permeability.

Groups 3, 4, 5, 6, 7, and 8 consisted of 8 mice each and were treated with 2.5 mg/kg, 5 mg/kg, 10 mg/kg, 20 mg/kg, 40 mg/kg, or 80 mg/kg (corresponding to 5 mg/kg, 10 mg/kg, 20 mg/kg, 40 mg/kg, 80 mg/kg, or 160 mg/kg per week), respectively of ISIS 482584 administered subcutaneously twice a week for 3 weeks. Groups 4-9 served as the experimental treatment groups for examining the effect of varying doses of ISIS 482584 on basal vascular permeability.

All the groups were then injected with 30 mg/kg of Evans Blue solution in the tail vein. The mice were sacrificed 30 min after the Evans Blue solution administration and colons, feet, and ears were harvested and examined for permeability defects. Blood samples were taken through cardiac puncture.

TABLE 9

Treatment groups

| Group No. | Treatment | Dose (mg/kg/week) | HOE-140 |
|---|---|---|---|
| 1. (N = 8) | PBS | — | No |
| 2. (N = 4) | PBS | — | Yes |
| 3. (N = 8) | ISIS 482584 | 160 | No |
| 4. (N = 8) | ISIS 482584 | 80 | No |
| 5. (N = 8) | ISIS 482584 | 40 | No |
| 6. (N = 8) | ISIS 482584 | 20 | No |
| 7. (N = 8) | ISIS 482584 | 10 | No |
| 8. (N = 8) | ISIS 482584 | 5 | No |

Quantification of Vascular Permeability

The harvested tissues from the feet, colon, and ears were placed in formamide solution overnight to leach out the Evans Blue dye. The formamide solution containing feet and ear tissue was heated to 55° C. and left overnight. The color intensity of the dye-infused formamide solution was then measured at $OD_{600nm}$, and is presented in Table 10. Higher OD values are associated with higher levels of permeability.

As presented in Table 10, most of the tissues of mice treated with ISIS 482584 at all doses (Groups 3-8) demonstrated reduced basal vascular permeability compared to the PBS control (Group 1). The reduction in basal vascular permeability of the ISIS oligonucleotide-treated groups was comparable to the same demonstrated in the positive control group treated with HOE-140 (Group 2).

TABLE 10

$OD_{600\ nm}$ of Evans Blue dye to measure vascular permeability

| Group No. | Treatment | Dose (mg/kg/week) | HOE-140 | Colon | Feet | Ears |
|---|---|---|---|---|---|---|
| 1 | PBS | — | No | 0.27 | 0.17 | 0.013 |
| 2 | PBS | — | Yes | 0.24 | 0.09 | 0.047 |
| 3 | ISIS 482584 | 160 | No | 0.25 | 0.11 | 0.019 |
| 4 | ISIS 482584 | 80 | No | 0.24 | 0.09 | 0.014 |
| 5 | ISIS 482584 | 40 | No | 0.27 | 0.11 | 0.011 |
| 6 | ISIS 482584 | 20 | No | 0.26 | 0.11 | 0.009 |
| 7 | ISIS 482584 | 10 | No | 0.31 | 0.10 | 0.015 |
| 8 | ISIS 482584 | 5 | No | 0.32 | 0.11 | 0.009 |

Quantification of Vascular Leakage

The blood drawn through cardiac puncture was immediately mixed with 3 times the volume of ice-cold ethanol. The solution was centrifuged at 15,000 g for 20 minutes at 4° C. to remove cell debris and precipitated plasma proteins. The ethanol extracts were further purified by ultra-filtration through a 10 kDa MWCO filter. The color intensity of the ethanol extracted plasma solution was then measured at $OD_{620nm}$. The results are presented in Table 11 as percentage increase or decrease of the OD values of the Group 1 PBS control. It was expected that treatment groups may display higher OD values due to reduced vascular leakage. All the mice in the ISIS oligonucleotide-treated groups demonstrated significantly reduced vascular leakage compared to the PBS negative control.

TABLE 11

Percentage of $OD_{620\ nm}$ of Evans Blue dye compared to the PBS basal control to measure vascular leakage

| Group No. | Treatment | Dose (mg/kg/week) | HOE-140 | Plasma |
|---|---|---|---|---|
| 2. (N = 8) | ISIS 482584 | 160 | No | 95 |
| 3. (N = 8) | ISIS 482584 | 80 | No | 93 |
| 4. (N = 8) | ISIS 482584 | 40 | No | 83 |

TABLE 11-continued

| Percentage of $OD_{620\ nm}$ of Evans Blue dye compared to the PBS basal control to measure vascular leakage | | | | |
|---|---|---|---|---|
| Group No. | Treatment | Dose (mg/kg/week) | HOE-140 | Plasma |
| 5. (N = 8) | ISIS 482584 | 20 | No | 56 |
| 6. (N = 8) | ISIS 482584 | 10 | No | 36 |

Quantification of High Molecular Weight Kininogen (HMWK)

Figure 2:
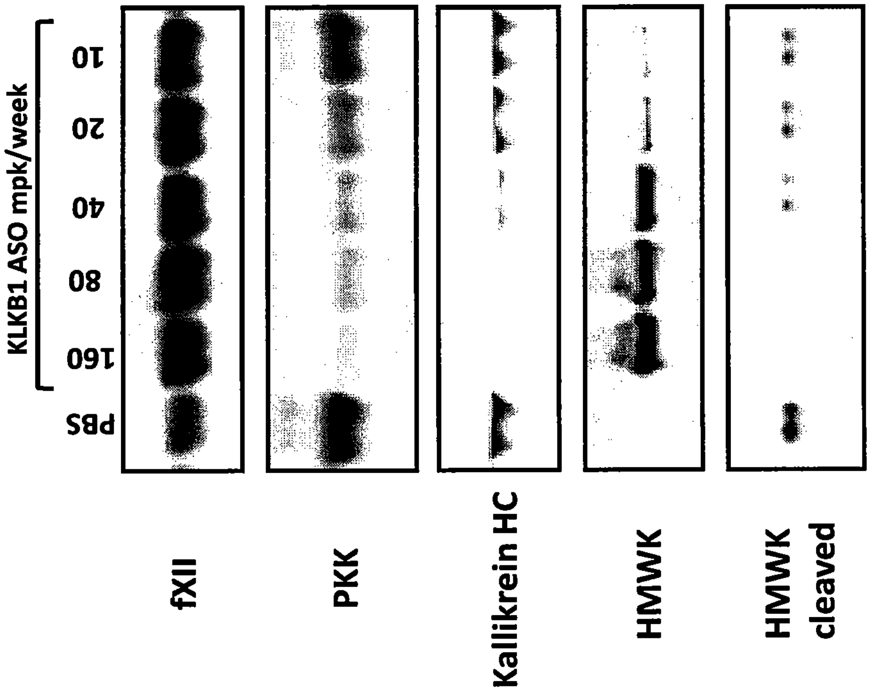
FIG. 2 provides Western blot quantification of HMWK from blood samples tested in Example 5.

Western blot quantification of HMWK from blood samples are presented in FIG. 2 and Tables 12 and 13.

As shown in Table 12, Groups treated with 482584 have higher levels of HMWK as compared to PBS control, increasing in a dose-dependent manner. Treatment with kallikrein antisense oligonucleotide results in stabilization of HMWK. Thus, vascular permeability is reduced in ISIS 482584-treated groups in a dose-dependent manner. As shown in Table 13, Groups treated with ISIS 482584 have lower HMWK cleavage product as compared to PBS control, decreasing in a dose-dependent manner. Thus, reduced HMWK is caused by kallikrein cleavage of HMWK into cleavage products (including bradykinin and HKa). Data are presented in Intensity Units as measured by densitometer.

TABLE 12

| Quantification of HMWK by densitometer | | | |
|---|---|---|---|
| Group No | Treatment | Dose (mg/kg/week) | Intensity Units |
| 1 | PBS | — | 89 |
| 3 | ISIS 482584 | 160 | 21358 |
| 4 | ISIS 482584 | 80 | 7279 |
| 5 | ISIS 482584 | 40 | 873 |
| 6 | ISIS 482584 | 20 | 608 |
| 7 | ISIS 482584 | 10 | 507 |

TABLE 13

| Quantification of HMWK cleavage product by densitometer | | | |
|---|---|---|---|
| Group No | Treatment | Dose (mg/kg/week) | Intensity Units |
| 1 | PBS | — | 401738 |
| 3 | ISIS 482584 | 160 | 19936 |
| 4 | ISIS 482584 | 80 | 204482 |
| 5 | ISIS 482584 | 40 | 388135 |
| 6 | ISIS 482584 | 20 | 403360 |
| 7 | ISIS 482584 | 10 | 414774 |

Example 6

Combination Therapy of Antisense Oligonucleotides Targeting Kallikrein (KLKB1) and Factor 12 on Captopril-Induced Vascular Permeability in Mice Mice were treated varying doses of ISIS 410944, a 5-10-5 MOE gapmer targeting Factor 12 (GCATGGGACA-GAGATGGTGC; SEQ ID NO: 43), and ISIS 482584 in a captopril-induced vascular permeability model.

Treatment

The various treatment groups for this assay are presented in Table 14.

Group 1 consisted of 4 mice and was treated with PBS administered subcutaneously twice a week for 3 weeks. No other treatment was administered to Group 1 which served as a control group to measure the basal levels of vascular permeability.

Group 2 consisted of 8 mice and was treated with PBS administered subcutaneously twice a week for 3 weeks. At the end of the treatment period, the mice were intraperitoneally administered 20 μg of captopril. Group 2 served as the control group for captopril-induced vascular permeability.

Group 3 consisted of 4 mice and was treated with PBS administered subcutaneously twice a week for 3 weeks. At the end of the treatment period, the mice were intraperitoneally administered 20 μg of captopril. The mice were also intraperitoneally administered 30 μg of HOE-140. Group 3 served as a positive control for inhibition of captopril-induced vascular permeability.

Groups 4, 5, 6, 7, and 8 consisted of 8 mice each and were treated with 2.5 mg/kg, 5 mg/kg, 10 mg/kg, 20 mg/kg, or 40 mg/kg (corresponding to 5 mg/kg, 10 mg/kg, 20 mg/kg, 40 mg/kg, or 80 mg/kg per week), respectively of ISIS 482584 and ISIS 410944 each administered subcutaneously twice a week for 3 weeks. At the end of the treatment period, the mice of all the groups were intraperitoneally administered 20 μg of captopril. Groups 4-8 served as the experimental treatment groups for examining the effect of ISIS 410944 and ISIS 482584 on captopril-induced vascular permeability.

All the groups were then injected with 30 mg/kg of Evans Blue solution in the tail vein. The mice were sacrificed 30 min after the Evans Blue solution administration and colons, feet, ears, and intestines were harvested.

TABLE 14

| Treatment groups | | | | |
|---|---|---|---|---|
| Group No. | Treatment | Dose (mg/kg/wk) of each ASO | Captopril | HOE-140 |
| 1. (N = 4) | PBS | — | No | No |
| 2. (N = 8) | PBS | — | Yes | No |
| 3. (N = 4) | PBS | — | Yes | Yes |
| 4. (N = 8) | ISIS 482584 + ISIS 410944 | 80 | Yes | No |
| 5. (N = 8) | ISIS 482584 + ISIS 410944 | 40 | Yes | No |
| 6. (N = 8) | ISIS 482584 + ISIS 410944 | 20 | Yes | No |
| 7. (N = 8) | ISIS 482584 + ISIS 410944 | 10 | Yes | No |
| 8. (N = 8) | ISIS 482584 + ISIS 410944 | 5 | Yes | No |

Quantification of Vascular Permeability

The harvested tissues from the feet, colon, and ears were placed in formamide solution overnight to leach out the Evans Blue dye. The formamide solution containing feet and ear tissue was heated to 55° C. and left overnight. The color intensity of the dye-infused formamide solution was then measured at $OD_{600nm}$, and is presented in Table 15. Higher OD values are associated with higher levels of permeability.

As presented in Table 15, most of the tissues of mice treated with a combination of ISIS 482584 and ISIS 410944 at all doses (Groups 3-8) demonstrated reduced vascular permeability compared to the PBS control (Group 1). The reduction in vascular permeability of the ISIS oligonucleotide-treated groups was comparable to the same demonstrated in the basal PBS control (Group 1), as well as the positive control group treated with HOE140 (Group 2). Combination of kallikrein and Factor 12 antisense oligonucleotides results in synergistic decrease in permeability. As expected, a corresponding synergistic decrease in vascular leakage was also observed.

TABLE 15

| OD$_{600\ nm}$ of Evans Blue dye to measure vascular permeability | | | | | | | | |
|---|---|---|---|---|---|---|---|---|
| Group No. | Treatment | Dose (mg/kg/wk) of each ASO | Captopril | HOE-140 | Colon | Feet | Intestines | Ears |
| 1 | PBS | — | No | No | 0.24 | 0.11 | 0.13 | 0.01 |
| 2 | PBS | — | Yes | No | 0.38 | 0.15 | 0.11 | 0.05 |
| 3 | PBS | — | Yes | Yes | 0.23 | 0.06 | 0.15 | 0.04 |
| 4 | ISIS 482584 + ISIS 410944 | 80 | Yes | No | 0.19 | 0.07 | 0.11 | 0.04 |
| 5 | ISIS 482584 + ISIS 410944 | 40 | Yes | No | 0.19 | 0.07 | 0.12 | 0.03 |
| 6 | ISIS 482584 + ISIS 410944 | 20 | Yes | No | 0.22 | 0.08 | 0.12 | 0.04 |
| 7 | ISIS 482584 + ISIS 410944 | 10 | Yes | No | 0.38 | 0.13 | 0.13 | 0.05 |
| 8 | ISIS 482584 + ISIS 410944 | 5 | Yes | No | 0.53 | 0.12 | 0.13 | 0.03 |

Example 7

Combination Therapy of Antisense Oligonucleotides Targeting Kallikrein (KLKB1) and Factor 12 on Basal Vascular Permeability in Mice Mice were treated with varying doses of ISIS 410944, an antisense oligonucleotide targeting Factor 12, and ISIS 482584 in a basal vascular permeability model.

Treatment

The various treatment groups for this assay are presented in Table 16.

Group 1 consisted of 8 mice and was treated with PBS administered subcutaneously twice a week for 3 weeks. No other treatment was administered to Group 1 which served as a control group to measure the basal levels of vascular permeability.

Group 2 consisted of 4 mice and was treated with PBS administered subcutaneously twice a week for 3 weeks. At the end of the treatment period, the mice were intraperitoneally administered 30 μg of HOE-140. Group 2 served as a positive control for inhibition of basal vascular permeability.

Groups 3, 4, 5, 6, and 7 consisted of 8 mice each and were treated with 2.5 mg/kg, 5 mg/kg, 10 mg/kg, 20 mg/kg, or 40 mg/kg (corresponding to 5 mg/kg, 10 mg/kg, 20 mg/kg, 40 mg/kg, or 80 mg/kg per week), respectively of ISIS 482584 and ISIS 410944 each administered subcutaneously twice a week for 3 weeks. Groups 3-7 served as the experimental treatment groups for examining the effect of ISIS 410944 and ISIS 482584 on basal vascular permeability.

All the groups were then injected with 30 mg/kg of Evans Blue solution in the tail vein. The mice were sacrificed 30 min after the Evans Blue solution administration and colons, feet, ears, and intestines were harvested.

TABLE 16

| Treatment groups | | | |
|---|---|---|---|
| Group No. | Treatment | Dose (mg/kg/wk) | HOE-140 |
| 1. (N = 8) | PBS | — | No |
| 2. (N = 4) | PBS | — | Yes |
| 3. (N = 8) | ISIS 482584 + ISIS 410944 | 80 | No |
| 4. (N = 8) | ISIS 482584 + ISIS 410944 | 40 | No |
| 5. (N = 8) | ISIS 482584 + ISIS 410944 | 20 | No |
| 6. (N = 8) | ISIS 482584 + ISIS 410944 | 10 | No |
| 7. (N = 8) | ISIS 482584 + ISIS 410944 | 5 | No |

Quantification of Vascular Permeability

The harvested tissues from the feet, colon, intestines, and ears were placed in formamide solution overnight to leach out the Evans Blue dye. The formamide solution containing feet and ear tissue was heated to 55° C. and left overnight. The color intensity of the dye-infused formamide solution was then measured at OD$_{600nm}$, and is presented in Table 17. Higher OD values are associated with higher levels of permeability.

As presented in Table 17, most of the tissues of mice treated with a combination of ISIS 482584 and ISIS 410944 at all doses (Groups 2-7) demonstrated reduced vascular permeability compared to the PBS control (Group 1). The reduction in vascular permeability of the ISIS oligonucleotide-treated groups was comparable to the same demonstrated in positive control group treated with HOE140 (Group 2). Combination of kallikrein and Factor 12 antisense oligonucleotides results in synergistic decrease in permeability. As expected, a corresponding synergistic decrease in vascular leakage was also observed.

TABLE 17

OD$_{600\ nm}$ of Evans Blue dye to measure vascular permeability

| Group No. | Treatment | Dose (mg/kg/wk) | HOE-140 | Colon | Feet | Intestines | Ears |
|---|---|---|---|---|---|---|---|
| 1 | PBS | — | No | 0.19 | 0.08 | 0.10 | 0.004 |
| 2 | PBS | — | Yes | 0.14 | 0.04 | 0.08 | 0.008 |
| 3 | ISIS 482584 + ISIS 410944 | 80 | No | 0.14 | 0.04 | 0.09 | 0.01 |
| 4 | ISIS 482584 + ISIS 410944 | 40 | No | 0.15 | 0.05 | 0.10 | 0.006 |
| 5 | ISIS 482584 + ISIS 410944 | 20 | No | 0.15 | 0.04 | 0.10 | 0.007 |
| 6 | ISIS 482584 + ISIS 410944 | 10 | No | 0.15 | 0.06 | 0.10 | 0.004 |
| 7 | ISIS 482584 + ISIS 410944 | 5 | No | 0.14 | 0.05 | 0.13 | 0.002 |

Example 8

Inhibition of Factor 12 Protein Activation by ISIS 482584

The effect of antisense inhibition of kallikrein mRNA on Factor 12 protein activation was evaluated.

Treatment

The various treatment groups for this assay are presented in Table 18.

Group 1 consisted of 8 mice and was treated with PBS administered subcutaneously twice a week for 3 weeks. No other treatment was administered to Group 1 which served as a control group to measure Factor 12 activation.

Groups 2, 3, 4, 5, and 6 consisted of 8 mice each and were treated with 2.5 mg/kg, 5 mg/kg, 10 mg/kg, 20 mg/kg, or 40 mg/kg (corresponding to 5 mg/kg, 10 mg/kg, 20 mg/kg, 40 mg/kg, or 80 mg/kg per week), respectively of ISIS 482584 administered subcutaneously twice a week for 3 weeks. Groups 2-6 served as the treatment groups for measuring the effect of ISIS 482584 on Factor 12 activation.

At the end of the treatment period, plasma was harvested from the mice for the Spectrozyme® Factor 12a based amidolytic assay for Factor 12 in plasma.

TABLE 18

Treatment groups

| Group No. | Treatment | Dose (mg/kg/wk) |
|---|---|---|
| 1. (N = 8) | PBS | — |
| 2. (N = 8) | ISIS 482584 | 80 |
| 3. (N = 8) | ISIS 482584 | 40 |
| 4. (N = 8) | ISIS 482584 | 20 |
| 5. (N = 8) | ISIS 482584 | 10 |
| 6. (N = 8) | ISIS 482584 | 5 |

Assay for Factor 12 Activation in Plasma

Plasma (5 μL) was added to 85 μL of PBS with 1 ug/ml dextran sulfate (500 kDa) in a 96 well polypropelene microplate and the solution was incubated for 5 minutes at room temperature. Spectrozyme® FXIIa (10 μL of a 2 mM solution) and 0.2 mM KALLISTOP™ solution was added and the absorbance kinetic was measured at 405 nm. Factor 12 activation was measured in the linear phase of absorbance accumulation. The results are presented in Table 19 as a percentage of Factor 12 activation measured in the PBS control sample. As observed in Table 19, inhibition of kallikrein by ISIS 482584 results in decreased activation of Factor 12 by its substrate, implying the that PKK is required for proper factor 12 activation.

TABLE 19

Percentage Factor 12 activation compared to the PBS control

| Dose (mg/kg/wk) | % F12 activation |
|---|---|
| 80 | 14 |
| 40 | 24 |
| 20 | 47 |
| 10 | 63 |
| 5 | 82 |

Example 9

In Vivo Effect of Antisense Inhibition of Murine Kallikrein (KLKB1) on C1-INH Antisense Oligonucleotide-Induced Vascular Permeability Vascular permeability induced by ISIS 461756, an antisense oligonucleotide which targets murine C1 inhibitor mRNA, increases vascular permeability in mice and replicates the pathology of hereditary angioedema. The effect of ISIS 482584 on this model was evaluated.

Treatment

One group of 8 mice was treated with 40 mg/kg ISIS 482584 administered subcutaneously twice a week for 3 weeks (weekly dose of 80 mg/kg). A second group of 8 mice was treated with 40 mg/kg of the control oligonucleotide, ISIS 141923, administered subcutaneously twice a week for 3 weeks (weekly dose of 80 mg/kg). A third group of 8 mice was treated with PBS administered subcutaneously twice a week for 3 weeks. On day 14, all the groups were treated with 12.5 mg/kg ISIS 461756 administered subcutaneously twice a week for 3 weeks (weekly dose of 25 mg/kg). A control group of mice was treated with PBS administered subcutaneously twice a week for 3 weeks but was not administered ISIS 461756.

At the end of the treatment period, all the groups were injected with 30 mg/kg of Evans Blue solution into the tail vein. The mice were sacrificed 30 min after the Evans Blue solution administration and colons, feet, ears, and intestines were harvested. The liver was also harvested for RNA analysis.

RNA Analysis

RNA was isolated from the liver for RT-PCR analysis of C1-INH and kallikrein mRNAs. The primer probe set for C1-INH is RTS3218 (forward sequence GAGTCCCCCAGAGCCTACAGT, designated herein as SEQ ID NO: 24; reverse sequence TGTCATTTGTTATTGTGATGGCTACA, designated herein as SEQ ID NO: 25; probe sequence CTGCCCTCTACCTGGCCAACAACCA, designated herein as SEQ ID NO: 26). The primer probe set for kallikrein is RTS3287 (forward sequence ACAAGTGCATTTTACAGACCAGAGTAC, designated herein as SEQ ID NO: 27; reverse sequence GGTTGTCCGCTGACTTTATGCT, designated herein as SEQ ID NO: 28; probe sequence AAGCACAGTGCAAGCGGAACACCC, designated herein as SEQ ID NO: 29). The results are presented in Table 20 as percent inhibition compared to the PBS control not treated with ISIS 461756. The data indicates that ISIS 461756 significantly reduced C1-INH mRNA expression and that treatment with ISIS 482584 significantly reduced kallikrein expression.

TABLE 20

Percent inhibition of mRNA expression in mice treated with ISIS 461756 compared to the untreated PBS control

| Treatment | C1-INH mRNA | kallikrein mRNA |
|---|---|---|
| PBS | 76 | 0 |
| ISIS 141923 | 79 | 0 |
| ISIS 482584 | 77 | 78 |

Quantification of Vascular Permeability

The harvested tissues from the feet, colon, and intestines were placed in formamide solution overnight to leach out the Evans Blue dye. The formamide solution containing feet tissue was heated to 55° C. and left overnight. The color intensity of the dye-infused formamide solution was then measured at $OD_{600nm}$. The data is presented in Table 21 as percent increase or reduction compared to the PBS control not treated with ISIS 461756. The data indicates that treatment with ISIS 482584 prevented vascular permeability induced by ISIS 461756.

TABLE 21

Percent change in vascular permeability in mice treated with ISIS 461756 compared to the untreated PBS control

| Treatment | Colon | Feet | Intestines |
|---|---|---|---|
| PBS | 13 | 70 | 27 |
| ISIS 141923 | 2 | 80 | 14 |
| ISIS 482584 | −23 | 2 | −25 |

What is claimed is:

1. A method comprising, prophylactically treating hereditary angioedema (HAE) in an animal identified as having HAE by administering to the animal a therapeutically effective amount of a compound comprising a modified oligonucleotide consisting of 12 to 30 linked nucleosides, wherein the modified oligonucleotide is at least 90% complementary to a KLKB1 nucleic acid.

2. The method of claim 1, wherein the prophylactic administering of the compound comprising a modified oligonucleotide prevents or ameliorates edema.

3. The method of claim 1, wherein the prophylactic administering of the compound comprising a modified oligonucleotide prevents or ameliorates vascular permeability.

4. The method of claim 1, wherein the prophylactic administering of the compound comprising a modified oligonucleotide prevents or ameliorates vascular leakage.

5. The method of claim 1, wherein the prophylactic administering of the compound comprising a modified oligonucleotide prevents or ameliorates inflammation.

6. The method of claim 1, wherein the animal is a human.

7. The method of claim 1, wherein the KLKB1 nucleic acid is a human KLKB1 nucleic acid.

8. The method of claim 7, wherein the human KLKB1 nucleic acid is SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or the complement of SEQ ID NO: 10.

9. The method of claim 8, wherein the modified oligonucleotide is 100% complementary to a human KLKB1 nucleic acid.

10. The method of claim 9, wherein the modified oligonucleotide is a single-stranded oligonucleotide.

11. The method of claim 10, wherein the modified oligonucleotide comprises at least one modified internucleoside linkage.

12. The method of claim 11, wherein the modified internucleoside linkage is a phosphorothioate internucleoside linkage.

13. The method of claim 8, comprising at least one nucleoside having a modified sugar.

14. The method of claim 13, wherein the modified sugar is a bicyclic sugar.

15. The method of claim 14, wherein the bicyclic sugar comprises a 4'-CH($CH_3$)—O-2' bridge.

16. The method of claim 13, wherein the modified sugar comprises a 2'-O-methoxyethyl group.

17. The method of claim 8, wherein at least one nucleoside comprises a modified nucleobase.

18. The method of claim 17, wherein the modified nucleobase is a 5-methylcytosine.

19. The method of claim 8, comprising co-administering the compound comprising a modified oligonucleotide and any of the group selected from a serine protease inhibitor Cl-INH recombinant protein, CINRYZE, BERINERT, KALBITOR, Icatibant, Ecallantide, attenuated androgens, anabolic steroids, antifibrinolytic agents, epsilon-aminocaproic acid, tranexamic acid.

20. The method of claim 8, wherein the administering is parenteral administration.

21. The method of claim 20, wherein the parenteral administration is any of subcutaneous or intravenous administration.

22. The method of claim 8, wherein the compound comprises a conjugate.

* * * * *

SEQUENCE LISTING

```
<160> NUMBER OF SEQ ID NOS: 43

<210> SEQ ID NO 1
<211> LENGTH: 2252
<212> TYPE: DNA
<213> ORGANISM: Homo sapiens
<220> FEATURE:
<221> NAME/KEY: CDS
<222> LOCATION: (78)..(1988)

<400> SEQUENCE: 1

agaacagctt gaagaccgtt catttttaag tgacaagaga ctcacctcca agaagcaatt      60

gtgttttcag aatgatt tta ttc aag caa gca act tat ttc att tcc ttg       110
                   Leu Phe Lys Gln Ala Thr Tyr Phe Ile Ser Leu
                   1               5                   10

ttt gct aca gtt tcc tgt gga tgt ctg act caa ctc tat gaa aac gcc      158
Phe Ala Thr Val Ser Cys Gly Cys Leu Thr Gln Leu Tyr Glu Asn Ala
            15                  20                  25

ttc ttc aga ggt ggg gat gta gct tcc atg tac acc cca aat gcc caa      206
Phe Phe Arg Gly Gly Asp Val Ala Ser Met Tyr Thr Pro Asn Ala Gln
        30                  35                  40

tac tgc cag atg agg tgc aca ttc cac cca agg tgt ttg cta ttc agt      254
Tyr Cys Gln Met Arg Cys Thr Phe His Pro Arg Cys Leu Leu Phe Ser
    45                  50                  55

ttt ctt cca gca agt tca atc aat gac atg gag aaa agg ttt ggt tgc      302
Phe Leu Pro Ala Ser Ser Ile Asn Asp Met Glu Lys Arg Phe Gly Cys
60                  65                  70                  75

ttc ttg aaa gat agt gtt aca gga acc ctg cca aaa gta cat cga aca      350
Phe Leu Lys Asp Ser Val Thr Gly Thr Leu Pro Lys Val His Arg Thr
                80                  85                  90

ggt gca gtt tct gga cat tcc ttg aag caa tgt ggt cat caa ata agt      398
Gly Ala Val Ser Gly His Ser Leu Lys Gln Cys Gly His Gln Ile Ser
            95                  100                 105

gct tgc cat cga gac att tat aaa gga gtt gat atg aga gga gtc aat      446
Ala Cys His Arg Asp Ile Tyr Lys Gly Val Asp Met Arg Gly Val Asn
        110                 115                 120

ttt aat gtg tct aag gtt agc agt gtt gaa gaa tgc caa aaa agg tgc      494
Phe Asn Val Ser Lys Val Ser Ser Val Glu Glu Cys Gln Lys Arg Cys
    125                 130                 135

acc agt aac att cgc tgc cag ttt ttt tca tat gcc acg caa aca ttt      542
Thr Ser Asn Ile Arg Cys Gln Phe Phe Ser Tyr Ala Thr Gln Thr Phe
140                 145                 150                 155
```

-continued

```
cac aag gca gag tac cgg aac aat tgc cta tta aag tac agt ccc gga      590
His Lys Ala Glu Tyr Arg Asn Asn Cys Leu Leu Lys Tyr Ser Pro Gly
                160                 165                 170

gga aca cct acc gct ata aag gtg ctg agt aac gtg gaa tct gga ttc      638
Gly Thr Pro Thr Ala Ile Lys Val Leu Ser Asn Val Glu Ser Gly Phe
            175                 180                 185

tca ctg aag ccc tgt gcc ctt tca gaa att ggt tgc cac atg aac atc      686
Ser Leu Lys Pro Cys Ala Leu Ser Glu Ile Gly Cys His Met Asn Ile
        190                 195                 200

ttc cag cat ctt gcg ttc tca gat gtg gat gtt gcc agg gtt ctc act      734
Phe Gln His Leu Ala Phe Ser Asp Val Asp Val Ala Arg Val Leu Thr
    205                 210                 215

cca gat gct ttt gtg tgt cgg acc atc tgc acc tat cac ccc aac tgc      782
Pro Asp Ala Phe Val Cys Arg Thr Ile Cys Thr Tyr His Pro Asn Cys
220                 225                 230                 235

ctc ttc ttt aca ttc tat aca aat gta tgg aaa atc gag tca caa aga      830
Leu Phe Phe Thr Phe Tyr Thr Asn Val Trp Lys Ile Glu Ser Gln Arg
                240                 245                 250

aat gtt tgt ctt ctt aaa aca tct gaa agt ggc aca cca agt tcc tct      878
Asn Val Cys Leu Leu Lys Thr Ser Glu Ser Gly Thr Pro Ser Ser Ser
            255                 260                 265

act cct caa gaa aac acc ata tct gga tat agc ctt tta acc tgc aaa      926
Thr Pro Gln Glu Asn Thr Ile Ser Gly Tyr Ser Leu Leu Thr Cys Lys
        270                 275                 280

aga act tta cct gaa ccc tgc cat tct aaa att tac ccg gga gtt gac      974
Arg Thr Leu Pro Glu Pro Cys His Ser Lys Ile Tyr Pro Gly Val Asp
    285                 290                 295

ttt gga gga gaa gaa ttg aat gtg act ttt gtt aaa gga gtg aat gtt     1022
Phe Gly Gly Glu Glu Leu Asn Val Thr Phe Val Lys Gly Val Asn Val
300                 305                 310                 315

tgc caa gag act tgc aca aag atg att cgc tgt cag ttt ttc act tat     1070
Cys Gln Glu Thr Cys Thr Lys Met Ile Arg Cys Gln Phe Phe Thr Tyr
                320                 325                 330

tct tta ctc cca gaa gac tgt aag gaa gag aag tgt aag tgt ttc tta     1118
Ser Leu Leu Pro Glu Asp Cys Lys Glu Glu Lys Cys Lys Cys Phe Leu
            335                 340                 345

aga tta tct atg gat ggt tct cca act agg att gcg tat ggg aca caa     1166
Arg Leu Ser Met Asp Gly Ser Pro Thr Arg Ile Ala Tyr Gly Thr Gln
        350                 355                 360

ggg agc tct ggt tac tct ttg aga ttg tgt aac act ggg gac aac tct     1214
Gly Ser Ser Gly Tyr Ser Leu Arg Leu Cys Asn Thr Gly Asp Asn Ser
    365                 370                 375

gtc tgc aca aca aaa aca agc aca cgc att gtt gga gga aca aac tct     1262
Val Cys Thr Thr Lys Thr Ser Thr Arg Ile Val Gly Gly Thr Asn Ser
380                 385                 390                 395

tct tgg gga gag tgg ccc tgg cag gtg agc ctg cag gtg aag ctg aca     1310
Ser Trp Gly Glu Trp Pro Trp Gln Val Ser Leu Gln Val Lys Leu Thr
                400                 405                 410

gct cag agg cac ctg tgt gga ggg tca ctc ata gga cac cag tgg gtc     1358
Ala Gln Arg His Leu Cys Gly Gly Ser Leu Ile Gly His Gln Trp Val
            415                 420                 425

ctc act gct gcc cac tgc ttt gat ggg ctt ccc ctg cag gat gtt tgg     1406
Leu Thr Ala Ala His Cys Phe Asp Gly Leu Pro Leu Gln Asp Val Trp
        430                 435                 440

cgc atc tat agt ggc att tta aat ctg tca gac att aca aaa gat aca     1454
Arg Ile Tyr Ser Gly Ile Leu Asn Leu Ser Asp Ile Thr Lys Asp Thr
    445                 450                 455

cct ttc tca caa ata aaa gag att att att cac caa aac tat aaa gtc     1502
Pro Phe Ser Gln Ile Lys Glu Ile Ile Ile His Gln Asn Tyr Lys Val
```

-continued

```
460                 465                 470                 475

tca gaa ggg aat cat gat atc gcc ttg ata aaa ctc cag gct cct ttg      1550
Ser Glu Gly Asn His Asp Ile Ala Leu Ile Lys Leu Gln Ala Pro Leu
                480                 485                 490

aat tac act gaa ttc caa aaa cca ata tgc cta cct tcc aaa ggt gac      1598
Asn Tyr Thr Glu Phe Gln Lys Pro Ile Cys Leu Pro Ser Lys Gly Asp
            495                 500                 505

aca agc aca att tat acc aac tgt tgg gta acc gga tgg ggc ttc tcg      1646
Thr Ser Thr Ile Tyr Thr Asn Cys Trp Val Thr Gly Trp Gly Phe Ser
        510                 515                 520

aag gag aaa ggt gaa atc caa aat att cta caa aag gta aat att cct      1694
Lys Glu Lys Gly Glu Ile Gln Asn Ile Leu Gln Lys Val Asn Ile Pro
    525                 530                 535

ttg gta aca aat gaa gaa tgc cag aaa aga tat caa gat tat aaa ata      1742
Leu Val Thr Asn Glu Glu Cys Gln Lys Arg Tyr Gln Asp Tyr Lys Ile
540                 545                 550                 555

acc caa cgg atg gtc tgt gct ggc tat aaa gaa ggg gga aaa gat gct      1790
Thr Gln Arg Met Val Cys Ala Gly Tyr Lys Glu Gly Gly Lys Asp Ala
                560                 565                 570

tgt aag gga gat tca ggt ggt ccc tta gtt tgc aaa cac aat gga atg      1838
Cys Lys Gly Asp Ser Gly Gly Pro Leu Val Cys Lys His Asn Gly Met
            575                 580                 585

tgg cgt ttg gtg ggc atc acc agc tgg ggt gaa ggc tgt gcc cgc agg      1886
Trp Arg Leu Val Gly Ile Thr Ser Trp Gly Glu Gly Cys Ala Arg Arg
        590                 595                 600

gag caa cct ggt gtc tac acc aaa gtc gct gag tac atg gac tgg att      1934
Glu Gln Pro Gly Val Tyr Thr Lys Val Ala Glu Tyr Met Asp Trp Ile
    605                 610                 615

tta gag aaa aca cag agc agt gat gga aaa gct cag atg cag tca cca      1982
Leu Glu Lys Thr Gln Ser Ser Asp Gly Lys Ala Gln Met Gln Ser Pro
620                 625                 630                 635

gca tga gaagcagtcc agagtctagg caatttttac aacctgagtt caagtcaaat      2038
Ala

tctgagcctg gggggtcctc atctgcaaag catggagagt ggcatcttct ttgcatccta   2098

aggacgaaaa acacagtgca ctcagagctg ctgaggacaa tgtctggctg aagcccgctt   2158

tcagcacgcc gtaaccaggg gctgacaatg cgaggtcgca actgagatct ccatgactgt   2218

gtgttgtgaa ataaaatggt gaaagatcaa aaaa                               2252


<210> SEQ ID NO 2
<211> LENGTH: 578
<212> TYPE: DNA
<213> ORGANISM: Homo sapines

<400> SEQUENCE: 2

atgctctctc tctctcctgc tgccttgtga agaaggtacc tgcttcccct tcaccttcca     60

ccataattct gaacacggat aggatgttca tggaatatgt tgacaggaca aaaagttgaa    120

actgttggca gaaacccaaa gtcaatattg aagccaagca aaatattgcc tgcagtgcca    180

cattagaaca gcttgaagac cgttcatttt taagtgacaa gagactcacc tccaagaagc    240

aattgtgttt tcagaatgat tttattcaag caagcaactt atttcatttc cttgtttgct    300

acagtttcct gtggatgtct gactcaactc tatgaaaacg ccttcttcag aggtggggat    360

gtagcttcca tgtacacccc aaatgcccaa tactgccaga tgaggtgcac attccaccca    420

aggtgtttgc tattcagttt tcttccagca agttcaatca atgacatgga gaaaaggttt    480

ggttgcttct tgaaagatag tgttacagga accctgccaa aagtacatcg aacaggtgca    540
```

```
gtttctggac attccttgaa gcaatgtggt catcaaat                          578


<210> SEQ ID NO 3
<211> LENGTH: 681
<212> TYPE: DNA
<213> ORGANISM: Homo sapiens

<400> SEQUENCE: 3

ggaagccatt cactagtcag attgaccaga gattgttggt gggctgtctg ttggggtcta     60

tgcacaggat ttctgctgga gttctaagga caaaaagttg aaactgttgg cagaaaccca    120

aagtcaatat tgaagccaag caaaatattg cctgcagtgc cacattagaa cagcttgaag    180

accgttcatt tttaagtgac aagagactca cctccaagaa gcaattgtgt tttcagaatg    240

attttattca agcaagcaac ttatttcatt tccttgtttg ctacagtttc ctgtggatgt    300

ctgactcaac tctatgaaaa cgccttcttc agaggtgggg atgtagcttc catgtacacc    360

ccaaatgccc aatactgcca gatgaggtgc acattccacc caaggtgttt gctattcagt    420

tttcttccag caagttcaat caatgacatg gagaaaaggt ttggttgctt cttgaaagat    480

agtgttacag gaaccctgcc aaaagtacat cgaacaggtg cagtttctgg acattccttg    540

aagcaatgtg gtcatcaaat aagtgcttgc catcgagaca tttataaagg agttgatatg    600

agaggagtca attttaatgt gtctaaggtt agcagtgttg aagaatgcca aaaaaggtgc    660

accagtaaca ttcgctgcca g                                              681


<210> SEQ ID NO 4
<211> LENGTH: 2175
<212> TYPE: DNA
<213> ORGANISM: Homo sapiens
<220> FEATURE:
<221> NAME/KEY: CDS
<222> LOCATION: (255)..(1799)

<400> SEQUENCE: 4

agaacagctt gaagaccgtt catttttaag tgacaagaga ctcacctcca agaagcaatt     60

gtgttttcag tttcctgtga gggagttttc tctgtgtccc cacaaggcat gattctgggt    120

ctatggtgac ttaagagggc cacacaacaa tgagtattta attttcctca gatgtatggc    180

tacaataaac atctatagga tgtctgactc aactctatga aaacgccttc ttcagaggtg    240

gggatgtagc ttcc atg tac acc cca aat gcc caa tac tgc cag atg agg      290
                Met Tyr Thr Pro Asn Ala Gln Tyr Cys Gln Met Arg
                1               5                   10

tgc aca ttc cac cca agg tgt ttg cta ttc agt ttt ctt cca gca agt      338
Cys Thr Phe His Pro Arg Cys Leu Leu Phe Ser Phe Leu Pro Ala Ser
        15                  20                  25

tca atc aat gac atg gag aaa agg ttt ggt tgc ttc ttg aaa gat agt      386
Ser Ile Asn Asp Met Glu Lys Arg Phe Gly Cys Phe Leu Lys Asp Ser
    30                  35                  40

gtt aca gga acc ctg cca aaa gta cat cga aca ggt gca gtt tct gga      434
Val Thr Gly Thr Leu Pro Lys Val His Arg Thr Gly Ala Val Ser Gly
45                  50                  55                  60

cat tcc ttg aag caa tgt ggt cat caa ata agt gct tgc cat cga gac      482
His Ser Leu Lys Gln Cys Gly His Gln Ile Ser Ala Cys His Arg Asp
                65                  70                  75

att tat aaa gga gtt gat atg aga gga gtc aat ttt aat gta tct aag      530
Ile Tyr Lys Gly Val Asp Met Arg Gly Val Asn Phe Asn Val Ser Lys
            80                  85                  90

gtt agc agt gtt gaa gaa tgc caa aaa agg tgc acc aat gac att cgc      578
Val Ser Ser Val Glu Glu Cys Gln Lys Arg Cys Thr Asn Asp Ile Arg
```

```
        95                  100                 105

tgc cag ttt ttt tca tat gcc acg caa aca ttt cac aag gca gag tac      626
Cys Gln Phe Phe Ser Tyr Ala Thr Gln Thr Phe His Lys Ala Glu Tyr
    110                 115                 120

cgg aac aat tgc cta tta aag tac agt ccc gga gga aca cct acc gct      674
Arg Asn Asn Cys Leu Leu Lys Tyr Ser Pro Gly Gly Thr Pro Thr Ala
125                 130                 135                 140

ata aag gtg ctg agt aac gtg gaa tct gga ttc tca ctg aag ccc tgt      722
Ile Lys Val Leu Ser Asn Val Glu Ser Gly Phe Ser Leu Lys Pro Cys
                145                 150                 155

gcc ctt tca gaa att ggt tgc caa atg aac atc ttc cag cat ctt gcg      770
Ala Leu Ser Glu Ile Gly Cys Gln Met Asn Ile Phe Gln His Leu Ala
            160                 165                 170

ttc tca gat gtg gat gtt gcc agg gtt ctc act cca gat gct ttt gtg      818
Phe Ser Asp Val Asp Val Ala Arg Val Leu Thr Pro Asp Ala Phe Val
        175                 180                 185

tgt cgg acc atc tgc acc tat cac ccc aac tgc ctc ttc ttt aca ttc      866
Cys Arg Thr Ile Cys Thr Tyr His Pro Asn Cys Leu Phe Phe Thr Phe
    190                 195                 200

tat aca aat gta tgg aaa atc gag tca caa aga aat gtt tgt ctt ctt      914
Tyr Thr Asn Val Trp Lys Ile Glu Ser Gln Arg Asn Val Cys Leu Leu
205                 210                 215                 220

aaa aca tct gaa agt ggc aca cca agt tcc tgt act cct caa gaa aac      962
Lys Thr Ser Glu Ser Gly Thr Pro Ser Ser Cys Thr Pro Gln Glu Asn
                225                 230                 235

acc ata tct gga tat agc ctt tta acc tgc aaa aga act tta cct gaa     1010
Thr Ile Ser Gly Tyr Ser Leu Leu Thr Cys Lys Arg Thr Leu Pro Glu
            240                 245                 250

ccc tgc cat tct aaa att tac ccg gga gtt gac ttt gga gga gaa gaa     1058
Pro Cys His Ser Lys Ile Tyr Pro Gly Val Asp Phe Gly Gly Glu Glu
        255                 260                 265

ttg aat gtg act ttt gtt aaa gga gtg aat gtt tgc caa gag act tgc     1106
Leu Asn Val Thr Phe Val Lys Gly Val Asn Val Cys Gln Glu Thr Cys
    270                 275                 280

aca aag atg att cgc tgt cag ttt ttc act tat tct tta ctc cca gaa     1154
Thr Lys Met Ile Arg Cys Gln Phe Phe Thr Tyr Ser Leu Leu Pro Glu
285                 290                 295                 300

gac tgt aag gaa gag aag tgt aag tgt ttc tta aga tta tct atg gat     1202
Asp Cys Lys Glu Glu Lys Cys Lys Cys Phe Leu Arg Leu Ser Met Asp
                305                 310                 315

ggt tct cca act agg att gcg tat ggg aca caa ggg agc tct ggt tac     1250
Gly Ser Pro Thr Arg Ile Ala Tyr Gly Thr Gln Gly Ser Ser Gly Tyr
            320                 325                 330

tct ttg aga ttg tgt aac act ggg gac aac tct gtc tgc aca aca aaa     1298
Ser Leu Arg Leu Cys Asn Thr Gly Asp Asn Ser Val Cys Thr Thr Lys
        335                 340                 345

aca agc aca cgc att gtt gga gga aca aac tct tct tgg gga gag tgg     1346
Thr Ser Thr Arg Ile Val Gly Gly Thr Asn Ser Ser Trp Gly Glu Trp
    350                 355                 360

ccc tgg cag gtg agc ctg cag gtg aag ctg aca gct cag agg cac ctg     1394
Pro Trp Gln Val Ser Leu Gln Val Lys Leu Thr Ala Gln Arg His Leu
365                 370                 375                 380

tgt gga ggg tca ctc ata gga cac cag tgg gtc ctc act gct gcc cac     1442
Cys Gly Gly Ser Leu Ile Gly His Gln Trp Val Leu Thr Ala Ala His
                385                 390                 395

tgc ttt gat ggg ctt ccc ctg cag gat gtt tgg cgc atc tat agt ggc     1490
Cys Phe Asp Gly Leu Pro Leu Gln Asp Val Trp Arg Ile Tyr Ser Gly
            400                 405                 410

att tta aat ctg tca gac att aca aaa gat aca cct ttc tca caa ata     1538
```

-continued

```
Ile Leu Asn Leu Ser Asp Ile Thr Lys Asp Thr Pro Phe Ser Gln Ile
        415                 420                 425

aaa gag att att att cac caa aac tat aaa gtc tca gaa ggg aat cat     1586
Lys Glu Ile Ile Ile His Gln Asn Tyr Lys Val Ser Glu Gly Asn His
    430                 435                 440

gat atc gcc ttg ata aaa ctc cag gct cct ttg aat tac act gaa ttc     1634
Asp Ile Ala Leu Ile Lys Leu Gln Ala Pro Leu Asn Tyr Thr Glu Phe
445                 450                 455                 460

caa aaa cca ata tgc cta cct tcc aaa ggt gac aca agc aca att tat     1682
Gln Lys Pro Ile Cys Leu Pro Ser Lys Gly Asp Thr Ser Thr Ile Tyr
                465                 470                 475

acc aac tgt tgg gta acc gga tgg ggc ttc tcg aag gag aaa ggg aga     1730
Thr Asn Cys Trp Val Thr Gly Trp Gly Phe Ser Lys Glu Lys Gly Arg
            480                 485                 490

ttc agg tgg tcc ctt agt ttg caa aca caa cgg aat gtg gcg ttt ggt     1778
Phe Arg Trp Ser Leu Ser Leu Gln Thr Gln Arg Asn Val Ala Phe Gly
        495                 500                 505

ggg cat cac cag ctg ggg tga aggctgtgcc cgcagggagc aacctggtgt        1829
Gly His His Gln Leu Gly
    510

ctacaccaaa gtcgctgagt acatggactg gattttagag aaaacacaga gcagtgatgg   1889

aaaagctcag atgcagtcac cagcatgaga agcagtccag agtctaggca atttttacaa   1949

cctgagttca agtcaaattc tgagcctggg ggtcctcat ctgcaaagca tggagagtgg    2009

catcttcttt gcatcctaag gacgaaagac acagtgcact cagagctgct gaggacaatg   2069

tctggctgaa gcccgctttc agcacgccgt aaccaggggc tgacaatgcg aggtcgcaac   2129

tgagatctcc atgactgtgt gttgtgaaat aaaatggtga aagatc                  2175


<210> SEQ ID NO 5
<211> LENGTH: 569
<212> TYPE: DNA
<213> ORGANISM: Homo sapiens

<400> SEQUENCE: 5

agtgccacat tagaacagct tgaagaccgt tcatttttaa gtgacaagag actcacctcc     60

aagaagcaat tgtgttttca gtttcctgtg gatgtctgac tcaactctat gaaaacgcct    120

tcttcagagg tggggatgta gcttccatgt acaccccaaa tgcccaatac tgccagatga    180

ggtgcacatt ccacccaagg tgtttgctat tcagttttct tccagcaagt tcaatcaatg    240

acatggagaa aaggtttggt tgcttcttga aagatagtgt tacaggaacc ctgccaaaag    300

tacatcgaac aggtgcagtt tctggacatt ccttgaagca atgtggtcat caaataagtg    360

cttgccatcg agacatttat aaaggagttg atatgagagg agtcaatttt aatgtgtcta    420

aggttagcag tgttgaagaa tgccaaaaaa ggtgcaccaa taacattcgc tgccagtttt    480

tttcatatgc cacgcaaaca tttcacaagg cagagtaccg gaacaattgc ctattaaagt    540

acagtcccgg aggaacacct accgctata                                      569


<210> SEQ ID NO 6
<211> LENGTH: 392
<212> TYPE: DNA
<213> ORGANISM: Homo sapiens
<220> FEATURE:
<221> NAME/KEY: misc_feature
<222> LOCATION: (379)..(379)
<223> OTHER INFORMATION: n is a, c, g, or t

<400> SEQUENCE: 6
```

```
ttgaagaccg ttcattttta agtgacaaga gactcacctc caagaagcaa ttgtgttttc      60

agaatgattt tattcaagca agcaacttat ttcatttcct tgtttgctac agtttcctgt     120

ggatgtctga ctcaactcta tgaaaacgcc ttcttcagag gtggggatgt agcttccatg     180

tacaccccaa atgcccaata ctgccagatg aggtgcacat tccacccaag gtgtttgcta     240

ttcagttttc ttccagcaag ttcaatcaat gacatggagg gtttggttgc ttcttgaaag     300

atagtgttac aggaaccctg cctcaaataa gtgcttgcca tcgagacatt tatggagttg     360

atatgagagg agtcaattnt atgtgtctgg tt                                   392


<210> SEQ ID NO 7
<211> LENGTH: 802
<212> TYPE: DNA
<213> ORGANISM: Homo sapiens
<220> FEATURE:
<221> NAME/KEY: misc_feature
<222> LOCATION: (760)..(760)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t
<220> FEATURE:
<221> NAME/KEY: misc_feature
<222> LOCATION: (796)..(796)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t

<400> SEQUENCE: 7

gggtaatcct cttcagttac ttcaggtcat ctagatgtat acgtgcaggc ctgggcccag      60

aggcgacatt cctgtcttct tatattaata agaaaaagaa aacgaaatag tggttgccac     120

atgaacatct tccagcatct tgcgttctca gatgtggatg ttgccagggc tctcactcca     180

gatgcttttg tgtgtcggac catctgcacc tatcacccca actgcctctt ctttacattc     240

tatacaaatg tatggaaaat cgagtcacaa aggcgagtat gcatggaaaa tcgcatcaca     300

aaggcgagta tgcatgggga gcacttgctg ctgtactttc atcactttta tagtctgagt     360

tcttaaaagt ttcgttcatt tccctcaaaa cacttgaacc tgcagtttca gtaggtactg     420

ttctgccagg tgcagattag ttaagagatt agcagacttc tctgcctatc ttctcttact     480

ttaaaacaaa tgttaccatt gaatcaagga agcaatagcc atgagaaaaa agaaggatct     540

gacgcctttg aatgaagatt caaaacatga tcttcatgtt ttgtattagc ttggagtaaa     600

atccacttgc tggcaatata gcccttaagc ttgttgcctc ttctctttgt ttcagaaact     660

agagccctgt ttattctgat caaggctctg gcccactgtc tttatctcag ataacccacc     720

ctcttctgca cacagcatgg agctaagaga aggtgtctan gtatgtatat catcngcagc     780

ataaatccca gaattngtcn tn                                              802


<210> SEQ ID NO 8
<211> LENGTH: 2058
<212> TYPE: DNA
<213> ORGANISM: Homo sapiens

<400> SEQUENCE: 8

tcacctccaa gaagcaattg tgttttcaga atgattttat tcaagcaagc aacttatttc      60
```

-continued

```
atttccttgt ttgctacagt ttcctgtgga tgtctgactc aactctatga aaacgccttc    120
ttcagaggtg gggatgtagc ttccatgtac accccaaatg cccaatactg ccagatgagg    180
tgcacattcc acccaaggtg tttgctattc agttttcttc cagcaagttc aatcaatgac    240
atggagaaaa ggtttggttg cttcttgaaa gatagtgtta caggaaccct gccaaaagta    300
catcgaacag gtgcagtttc tggacattcc ttgaagcaat gtggtcatca aataagtgct    360
tgccatcgag acatttataa aggagttgat atgagaggag tcaattttaa tgtgtctaag    420
gttagcagtg ttgaagaatg ccaaaaaagg tgcaccaata acattcgctg ccagtttttt    480
tcatatgcca cgcaaacatt tcacaaggca gagtaccgga acaattgcct attaaagtac    540
agtcccggag gaacacctac cgctataaag gtgctgagta acgtggaatc tggattctca    600
ctgaagccct gtgccctttc agaaattggt tgccacatga acatcttcca gcatcttgcg    660
ttctcagatg tggatgttgc cagggttctc actccagatg cttttgtgtg tcggaccatc    720
tgcacctatc accccaactg cctcttcttt acattctata caaatgtatg gaaaatcgag    780
tcacaaaggc gagtatgcat ggaaaatcgc atcacaaaga aatgtttgtc ttcttaaaac    840
atctgaaagt ggcacaccaa gttcctctac tcctcaagaa aacaccatat ctggatatag    900
ccttttaacc tgcaaaagaa ctttacctga accctgccat tctaaaattt acccgggagt    960
tgactttgga ggagaagaat tgaatgtgac ttttgttaaa ggagtgaatg tttgccaaga   1020
gacttgcaca aagatgattc gctgtcagtt tttcacttat tctttactcc cagaagactg   1080
taaggaagag aagtgtaagt gtttcttaag attatctatg gatggttctc caactaggat   1140
tgcgtatggg acacaaggga gctctggtta ctctttgaga ttgtgtaaca ctggggacaa   1200
ctctgtctgc acaacaaaaa caagcacacg cattgttgga ggaacaaact cttcttgggg   1260
agagtggccc tggcaggtga gcctgcaggt gaagctgaca gctcagaggc acctgtgtgg   1320
agggtcactc ataggacacc agtgggtcct cactgctgcc cactgctttg atgggcttcc   1380
cctgcaggat gtttggcgca tctatagtgg cattttaaat ctgtcagaca ttacaaaaga   1440
tacacctttc tcacaaataa aagagattat tattcaccaa aactataaag tctcagaagg   1500
gaatcatgat atcgccttga taaaactcca ggctcctttg aattacactg aattccaaaa   1560
accaatatgc ctaccttcca aaggtgacac aagcacaatt tataccaact gttgggtaac   1620
cggatggggc ttctcgaagg agaaaggtga aatccaaaat attctacaaa aggtaaatat   1680
tcctttggta acaaatgaag aatgccagaa aagatatcaa gattataaaa taacccaacg   1740
gatggtctgt gctggctata aagaaggggg aaaagatgct tgtaagggag attcaggtgg   1800
tcccttagtt tgcaaacaca atggaatgtg gcgtttggtg ggcatcacca gctggggtga   1860
aggctgtgcc cgcagggagc aacctggtgt ctacaccaaa gtcgctgagt acatggactg   1920
gattttagag aaaacacaga gcagtgatgg aaaagctcag atgcagtcac cagcatgaga   1980
agcagtccag agtctaggca atttttacaa cctgagttca agtcaaattc tgagcctggg   2040
gggtcctcat ctgcaaag                                                 2058
```

<210> SEQ ID NO 9
<211> LENGTH: 577
<212> TYPE: DNA
<213> ORGANISM: Homo sapiens

<400> SEQUENCE: 9

```
gttaccattc taaaatttac ccgggagttg actttggagg agaagaattg aatgtgactt     60
```

-continued

```
ttgttaaagg agtgaatgtt tgccaagaga cttgcacaaa gatgattcgc tgtcagtttt    120

tcacttattc tttactccca gaagactgta aggaagagaa gtaaaggaaa ttttattttt    180

caaagacagt tgacatgacc atttcatatt ctctttcccc ctgtgaaggc ttactctttc    240

tactgttcat ttcatctagg tgtaagtgtt tcttaagatt atctatggat ggttctccaa    300

ctaggattgc gtatgggaca caagggagct ctggttactc tttgagattg tgtaacactg    360

gggacaactc tggtgagtaa cctcactttt tcgtggacct gtcagggatg tctgtcatgt    420

tgatagtttg cttagtctta aggaattatg tgtcttgttc tccttggtta gaagggactt    480

tgattcactt ctaattccaa ccattagcgt caacgctctc ttttcagtct gcacaacaaa    540

aacaagcaca cgcattgttg gaggaacaaa ctcttct                             577
```

<210> SEQ ID NO 10
<211> LENGTH: 37000
<212> TYPE: DNA
<213> ORGANISM: Homo sapiens

<400> SEQUENCE: 10

```
agagcctctg cctagatttc acaggatgtg tggaaacacc tggctgtcca ggcagaagcc     60

tgctgcaggg acccagccct catggagaac ctctattagg gcagtgcaga ggtgaactgt    120

ggggttggag cccacacaca gagaccccac tggagcactg cccagtggag ctgtgaaaag    180

agttccccca tcttccagat gccagaatgg tagatccact gactggaaag ttgcaggcac    240

tcagtgccgg cccatgaagg cagccgtagg ggctgtaccc tgcaaagcca cagggacaga    300

gctgcccaag gccttaacag cccacacctt gcatcagcat gccctgggtg tgagacaggg    360

gctccaagga gattattttg gagctttaaa atttaatgac ttccctgcta ggttttgcat    420

atgcttggga cctgtggccc ctttattttg gccaatttct cccatttgga atgggaacat    480

ttacccaatt cctgtaccca cattgtgttt tggaagtaac taacttgttt tttattttaa    540

aggctcattg agggaaggga cttgccttgt ctcaaatgag actttggact cggacttttg    600

ggttactgtg gaatgagtta agactttggg ggactgttgg aaagacatca ttggttttga    660

aatctgaaaa ggacatgaga tttgggaaag gccaggggaa gaatgatatg gtttggctct    720

gtgtcctcat ccaaatctcg tcttgaattg taatccccac atgggattac atgggagggg    780

cctggtgaga ggtgattgga tcatggaggt ggtttcccct gtgctgtgat ctcatgatag    840

tgagggattt aaaagtgaca gtttcccctg cacatacaca ctctctctct cgtatcacct    900

tgtgaagaag gtgtctgctt cccctctgcc ttccatcgtg attataagtt tcctgaggcc    960

tccccagcca tgggtaactg tgagtcagtt aaacctcttt tgtttataaa ttacccagtc   1020

tcaggtagta tctttacagc agtgtgaaac tggactaata catctgggaa attctttttg   1080

tctccttcct ttctgaagga cagctttgcc tgatattata ttcttggttg ccaggttttg   1140

tactttcaat actttgaata tatcatccca ctctctcttg gcctacatga tttctgctga   1200

gaaatccacc aataatctta tgaagcttcc cttgtatgtg aagaattgct tttctcttgc   1260

ttctttgaaa attctctctt tgtcatggtg aggatttctt tttttttttt ttttttttag   1320

atggagtcta gctctgttgt ccaggctgga gtgcagtgtg cagtggcgca atctcggctc   1380

actgcaagct ccgtctcctg ggttcacacc attttcctgt ctcagcctct ggagtagctg   1440

agactacagg tgcccaccac cacgcctggc taaatttttt ttgtattttt agtagagatg   1500

gggtttcact gtgttagcca ggatggtctc gatctcctga cctcatgatc cacccatctt   1560

ggcctcccaa agtgctggga ttacaggcat gagccactgc acctggccga ggatctcttt   1620
```

-continued

```
atatttaatc tatttggagt tcttttgggc ttcataaatc tggatgttta tttcatttat   1680
gtctccaaat tttgagagtt ttctattctt attttttaa ataagtttct gcaactttct   1740
ctttctctac ttcttctgga actcttctaa tgcatattaa ttttcttaac agtgtcctat   1800
aagtcttgtc agctttctgc aatttttatc attcctttta ttactctgac tgggtaattt   1860
caaatgacct gtatctgagc atgctgattc tttctcctgc ttgatctagt ctgctgctga   1920
agctgtttgt gaatttttttc aattcagtca ttttgttctt tagctccaga atttctgttt   1980
cattcttttt tatggttcct atctatcttt ttgttgaact tctaattttg ctcatgtatt   2040
gttttcctga ttttgtttac tgtctatcta tattgttttg tagcttattg agctttctta   2100
aggcaattat ttttagctct tgtcatgcag taaagatctc catttcttta gggtcacctc   2160
ctgctgcttt atttccttcc tttggtggtt tcttgtttcc ccgattattt gtgatcagtg   2220
tggccttgca ctgaagtagg cacctatttc agtctttaca tactagcttc agcagagaaa   2280
gccattcact agtcagattg accagagatt gttggtgggc tgtctgttgg ggtctatgca   2340
caggatttct gctggagttc taaggtggga agggctggat tctgggttca ttcactgtgg   2400
ttgtctgtat tctgtgcaca aggactggct tgaagcatgg atccttgggg gctgacttgg   2460
cactgaaatg agccttaagc ctgcgtctgc aggggccagc ctaacatggg gatcacctgg   2520
cacctgagtt catggggata ggcctgttcc tgagtttatt caggctgtcc tgggaacaag   2580
gtccactggg gtgagcccag catctgggtc cacatggccc agcatggagc caagatctct   2640
ggaggctgac ctggtgctgg atctgcaggg gatggcctgg attctaggcc catgggtgcc   2700
aacttggagc ctggggttgc tggggctaac gtggaggcta gatagagtct tgggggccag   2760
gctagagctg gagcaggcct gaagtctagg ttttgtgtgg ccatcttgga gcctgaagcc   2820
ccaggggctg acctggtctg gggtgagcat ggggctgagg ccacagaggc tggtctggcc   2880
tgtggcaggc ctgaatcctg gtgctggggt ttactggagt gggcttggtg cttgggatct   2940
gtggtgaagt taggttctat cttaactgtc cctcctccat gcaagagggc atctctctcc   3000
atactgtgct gcccaggctt gaaggtgaga tgacaccggt aatgtgaaat tgtccttcct   3060
atacacttct atgtgtcttt tcttatttct gtgctgcaac caggtggcat aacctctcac   3120
ctgattcctt agctctagtg aagttatttt cgtgcatgga tacttgttcg aattgatgtt   3180
tctgcaaggg atgagcgcta gaaactcctg ttctgacaaa ctcctattcc tattcttgct   3240
gacatcactc cctgaaatag ttaatatact taacagctga acacggatag gatgttcatg   3300
gaatatgttg acaggacaaa aagttgaaac tgttggcaga aacccaaagt caatattgaa   3360
gccaagcaaa atattgcctg cagtgccaca ttagaacagc ttgaagaccg ttcattttta   3420
agtgacaaga gactcacctc caagaagcaa ttgtgttttc aggtagcaaa tttttattat   3480
tctgattgtt tccaaataaa ctataatttt taagtataat tttttacttt atgagaaaat   3540
taatcattta tattctaatt tcctgagtat gtagagagta tagataatgt tcctttatgt   3600
agaaatattt aaatgtaaga tgattttaaa tcagaaagaa tatttgattg atttaaaatt   3660
tttaaatggg ctttaatatt ttcagaggtt ttctttactt agggattttt ggactgacat   3720
tattgccatt atttattaat tttgtttttg cccaaatcaa gaggtttcat aattgtttac   3780
tctctctcta ccaattccct ttccaacatt actagccaca gagttggcca atgaacaata   3840
aacacaacag tagtctggag gtctcaattt gtatcttggg aagcattata aattttccaa   3900
ctccctagac acaaatgtac caaaaaaaaa cccttgtttt ctataccagt aattgtgtgc   3960
```

-continued

```
tttgtcttgc aattcagaca tttacaagaa aatctaaatc accttaaatt aagatttatg   4020
ttaaatgtgg tctaaaacca gcagagttat gtattgtttt cttttttaga atgattttat   4080
tcaagcaagc aacttatttc atttccttgt ttgctacagt ttcctgtggt aagtgaatta   4140
tctataaaac atggaattca ggctaagaca ggagtagcca agcaagtggc accacccctg   4200
gagaaagcta ttgaacatac agcttcgggg gtggagattg tccctgatga ttcaggacac   4260
gtgtctattt aatgttccac aacaaggacc acttgtcagg tatattgctg tagacatatg   4320
ttgcagacca gaggaaggag ctcagaagta ggaatgtctt gggacttgtg ttaacaaaaa   4380
cttctgttcg cagatgacac tctgcaaagc aaaacttgaa acaaaaaaaa attagtcctc   4440
tatttttatt atcaacagta aaaaattaaa ctttatctga aaattcaaaa gagtgctagg   4500
cattttatag tgtctgggtc caatccaagt atctgttagg aacaccatac atagttttac   4560
tctggaccgc tagggaacca tttcaaaaat gaaagtaact ggtttaaatt taacttagca   4620
aaccatgcat ttggatagtt ctaggtgaat agctttcaac accagattta gatctcattt   4680
ctctattaat ttcattaatt tttggagaat aaaaatgatt ctggacattt cattaatcat   4740
tacagaggga gttttctctg tgtccccaca aggcatgatt ctgggtctat ggtgacttaa   4800
gagggccaca caacaatgag tatttaattt tcctcagatg tatggctaca ataaacatct   4860
ataggtaagg tttacattca taaagagacc tttttttttc caggaaaaaa gacttttatt   4920
ccccctaaat cacaactccc ctgtgtctgt ccctcaaccc tgatttctct tctaaaccgt   4980
aatttacaaa cccatgtgca aacccactga aaggtgagaa ggagcataag ccagagacac   5040
tgggaaccac agccaactac agggggtttt tcattttttt gttttgtttt gtttttttggc  5100
aaaataaatc atgattatgg ctaggaaaat cagggatgta agtaagcaaa aatttagaaa   5160
ctacatattg catgtagtcc ccaaattcag aaacagtcat cgttaaacat cttttattta   5220
gtctttcaga tatttttcta catataccta tttgcacatt tcacaaaaaa gagttattaa   5280
ctgtggacac tctttgactt gcattttcca cttatagcta tcttttggtg caaataagta   5340
atatattttg gagcttgcta ttcttctctt tttatggtat ttttgtgtgc acattcttat   5400
gctcttattc agttatttct gtagaataca atttttgaaa taaaaatact agattcaaag   5460
gtgtgaatat ttttgaaggt tttgtggtgt ggtatcatga aattaggttt cagaaagttt   5520
actccatagt tgactttttc taccagctaa taagagtgct catttacccc acttaggcca   5580
actctaacag gcttctgttg ctttgcatcc tgacatattt atctttctgg aaacagtgtc   5640
ctaatttatt tctgcagagc tactgcctct cagttttggt ccatgtggtt ctggtgaccc   5700
tgattcttct gctgaaccag aaagtgcaca catcctcctg gctgtggtga cccaatcaga   5760
gccaacgtct tgcaatgaag cttttcttta gacatctaga aataagactc ttatgttttt   5820
tttttccaat ttgacttgaa acttaagaca atacacaggc ctgagttgtt ggtactattt   5880
tgctactacg tggagcttga gagtaatggt aacaccaaga ctggagcaag tggaaggaga   5940
catattgtcc actgatgcta tcagttgagc acaatgtgca gttacttttt aagccagatt   6000
caccatgggc tttttggctc ctgaaccaat agatttcatt tgttttcaag ccactttgta   6060
ctaggttttc catcatttgc aatcaaaacc agtatacaaa cactggttat ttaatttttc   6120
atttttgcta atctcaggga taaaatggct tctagttgtt ttaacttggc tatatttgtg   6180
attcttccca ttttcatata cttactaatc acttctattt cttttgtaaa ttatcttttc   6240
atatttgtta tctaattctt taaaatttga gtactttaat tctcattatt gtttgtggaa   6300
ttgttaaaca agactgaata atctgcccaa agtccatgga catgggggcc catgtaaaag   6360
```

-continued

```
ctttgaaagc caccatcatt atgagataaa ttatataata gtactttaca taggctccaa   6420
aatacagcac agacacagct atcattgtca tggtcatcat tatcatcatg atcaccaact   6480
tatgaggata agcaagaaca cctactagaa gtttctttcc attcagcaac aaaattggtg   6540
tctttctagt cactcccttc cctgactgtc acatagcagt tcacagaggc tcagttgcag   6600
aatgagaagc tctgggccag gacctgccat tgtatgcatc cttgcatggg aactgggggc   6660
tggaagagga gtgactgctt gataattatg agtcagtcaa aaccaccaac tgtctgaaaa   6720
aaataggcct ttttgtaact agtattgtca ctaaaccaac tcctccatgt tttgtgcata   6780
catgaaatct aggcaataca cttgtattcc caaaagcttc cacttgaaga gatctgtgct   6840
ctttccaaat ataaacctta cccgagaggt ggtcatcttg gccacacctc agagagggag   6900
agaggcagtc ttgttgggtt gggtggtcat aatggggctc agggccaaat ccccaggggg   6960
taggatagtg cagagaagat ggcactctcc agtgcttaat aaaatgcacg tggtctaagc   7020
tgcccactcc ctcaaaggca ataaaaaata ggtactattt aaattgaaga gtaactactg   7080
ccccagggaa tggacaggtt gtcattggaa tagccatggt taatggtccc agttgacaac   7140
tgaaatgaat gtgctacctg aacaggaaag cttattaacc agatttcaaa gacagtcttt   7200
cccggtaaat ccaaatttac aaattaaagc cagtaaagac accgaattct ctaataatat   7260
gtggggtgca gtatatttta gagctgggaa taattccaaa cagcaaatag ttcaaaattt   7320
attttcaatt tagcatatgc atgcatttgc ttaaactgtc ttaaaaatga gtaaaaaata   7380
ctgtcagttt gtttcaatca tactgagatg aggaacaatg tttagcattg catgctagaa   7440
aaggacacag gattgggagt cagggctggg tgaccgtcac aggactttca ctaactgtgt   7500
ggatcttggg caagtctgtg tgccctgaga ctcagttatt taactttctt ttaaaaaaca   7560
tagtccagat gcagataaca aagcctgcct ctaatttccc ttacagaatt gtgagaagct   7620
ggtggagatg tttgttacaa aagtgttttg aaaatagagc aaatattatt ctttttaagg   7680
catgatgttt tcatagcatg tcaggcaaca ggaaaaaact aagttaggat tttattttat   7740
tgtggggaat ttatgtgcaa attattgtgc aatttaatga aaataagcca atgttttata   7800
cagaagtacc cagaaaatta aataacacta tacattgttc aaatagttgc cttaatatat   7860
tttattttct cagcataatt agagttgtat tatacaggtc tttgagtagt cagtcagtgg   7920
gagaagttaa gacaacagat atctttttat taaaattatt atatgaatta tcgcaaatta   7980
atttttatgg ttctgtcaca ggatgtctga ctcaactcta tgaaaacgcc ttcttcagag   8040
gtggggatgt agcttccatg tacaccccaa atgcccaata ctgccagatg aggtgcacat   8100
tccacccaag gtgtttgcta ttcagttttc ttccagcaag ttcaatcaat gacatggaga   8160
aaaggtaaaa gttggtattt cattattgga gaagctgttt ttcaaaactg aatcagtttt   8220
gtgcagaaag gtgtagtata actgagagtt cttcctcaca cggggttcaa ggaccagctt   8280
cagcaaaatc ccgtcaagtg gttcttacaa atgcagattc ctaggccaca acccagatct   8340
gctgaaccaa agtttcttgt gaccaggaat ctgcatttta aacaatcact gtgtttcttt   8400
aaagtagtag aagctagtca ttttctattc aaagcctcaa aatgcttgaa tatcattggg   8460
ctaagggatt gtctcaagaa agagtctaac aggtgcacat ttcatctgaa taaagaaaca   8520
gatttaactg tgtgacccat gatcacatta gcggatagca cagtccaaag aaaataacat   8580
aagacaagca ttttgctgag aatgtaattg agaaagatct agaacttgtg attttgggac   8640
agggcagttc taaatggggc ctatagtgag ccagtttggg cacctgtggc atgatgctat   8700
```

-continued

```
gtatggtgtg tgtgtgtatg tgtgcttgtg cttgtgtgaa tatgtattat taactggaaa   8760
tttgtaaaag tattggaaaa atagtactta cgattttgtg tgtgtgtgtg atggagtctc   8820
gctttgtagc ccaggctgga gtgcagtggc gtgatctcgg ctcactgcaa cttccacctc   8880
ccaggttcaa gcgattctcc tgcctcagcc tcccaagtag ctgggattac aggcacgcac   8940
caccacgtcc agctaatttt tgtagtttta gtagagacgg ggtttcacca cattggccag   9000
gctggccttg aactcctgac ctcgtgatcc acctgcctct acctcctaat gtgctgggat   9060
tacaggcatg agccaccgca cccagcggta attacaattt ttattaggtc agagagatgc   9120
ttattaatca cgagccacag tttcatctta atgatttttc cttttgatta atatccagag   9180
taagcttttc tttgttgttc ccatttccat gttcataact ctttactcat cttcactcta   9240
tgtgagttta ccaactagaa attggatagt cattctctga tcccacatgt taaacttgta   9300
gagaaaactc agattgtatg tgaggatcat catattaaaa gtggaggaag gttctagaat   9360
tcttataaat aatgaaatta acatgaaggt ggacatctaa gacagaggga agtcttccat   9420
taagtgcaga ctacaaggag ttaataagca agatgaacac gatatacaaa tccagctctt   9480
atcactaagt taacttttta agtaaatgaa agtatttgca aaaataatta ccaattgaga   9540
acatagttgc ctgaaagttt aagaacacag gaaaaatcat taactcttta atatggttga   9600
tttcctgtac ttaaaaaatg tgagtgtaaa gaaaacgcag tgatggagtt agatattatg   9660
gggtgttata aaattagctc taagagtgtt ctttccagca agtattgggg aagctatatt   9720
attttcctta ttcctggttt tatttgttag tgtgtagaaa atgctagaca tttcctcaat   9780
gtatgtttat tattctactt cctaagtaaa gctactttta aaataggttt ggttgcttct   9840
tgaaagatag tgttacagga accctgccaa aagtacatcg aacaggtgca gtttctggac   9900
attccttgaa gcaatgtggt catcaaataa gtggtaagtt gtgaatttct tagctacatt   9960
tgagttaata ttggatctcg cttagaacag cttttgctca aagtttgtac tgctacagct  10020
ttttggaagg catcactcat aaagatagga gatggggcag tattctggac acaaaagagg  10080
gacccatatt catctggaca cttctattgt ctttataaat caacacatac ttaatgagcc  10140
tctattattt atgaggttag cgctcaagtg taagatttgc agaaaatgaa tccaaataat  10200
tgtgtctcgt ttccagataa gaatttttaa gaaaacacaa gggaacatct ctctcaagtt  10260
cacttgaggg taatttttac atcagtgatt ctcaaccagc agtgattttg tctcttccac  10320
tggggacatt tgacaatgtc tggagacatt tttggtggct acaactaggg aggatgctat  10380
tagcatttac taagtagagg ccagaatgtt tgaatgctga ccaacattct acaaggcaca  10440
gggcagtcgt ccacagcaaa taattttctg gcccaaaacg tcaacagtgc tgacatcaag  10500
aaactctgtg atataccact aggcccaaat tgaagaactg agttctgcaa atcttgctaa  10560
gaataatact tcctaaagga aacttgagga ctaggatgct agagaacttt gattctgaca  10620
tctgaagcta ctgatgtctt gggaaacagt ttccaatgct atcctaataa atttaagaca  10680
aatgaactat ttctcaaaca tgactgggac tgataagaaa gtgaaaagtg ctgaaaagat  10740
tcaactgatg ggttgtcaga atcttaaaat aactgctgtt attctatgta tgactatata  10800
tcattactat tttattttca ttatgcacaa ttaattttgt aggttcaaat ttcagatgtt  10860
tttaaatttg tcatcctttc ctccctcatt gatatcacct cttcaatacg tacacacttt  10920
gagcctgctg tttgcatttt aaccagttat caaaggatgg caatgccttc attataaatg  10980
tgggcctgac ttagccagta taataggtgt agtctacgtg aggtggagta catttcctat  11040
tttaaaagat caatttttat gttaatccaa tttggtataa attattcgag taagtgctat  11100
```

-continued ttctgattgt tgtatcttgt agcaaaattt aaagaaaaag taatttgtgc ctttctcaat 11160
attcctgtta ttgttcatgt attctaaaac tcactgttac tcacttagct tgcttttaat 11220
gtttttaaa gtgaaaaatt gttcccaagt acataaaatc tctacactca agaacaattc 11280
tagtcaaaag catttagagc ttccgtatga acacttaaag agtttttatt tgtaagagtc 11340
gcatcccaac tcttagcctg ttcttttctc acatgcagaa aaataggaaa gagacttcgt 11400
ttccacagtc tgcaaattcc tgtgtttaag aaccacagtg aataatccac ctccctgccc 11460
aactcatcgt actgtcatat agttttcctg acagtttgtg tattttctgt ctttcccacc 11520
cttaaattta gttttatgac ttcaaccata cttcttagga gtggaaaggt atctgtagta 11580
gattatggtt tattccacat aatcttgggg aataaaactt taaaaaagta tacagtttat 11640
acttctggtt acattacttc cttaaccaaa agtctaacca agaaatttga atctttaaaa 11700
aaaaaagagg ccgggcgcgg tggctcacgc ctgtaatccc agcactttgg gaggccgaga 11760
cgggcggatc acgaggtcag gagatcgaga ccatcctggc tgacacggtg aaaccccgtc 11820
tctactaaaa atacaaaaat tagccgggcg tggtggcgcg cgcctgtagt cccagctact 11880
cgggaggctg aggcaggaga atggcgtgaa cccgggaggc ggagcttgca gtgagtcgag 11940
atcgcgccac tgcgctccag cctgggcgac agagcgagac tccgtctcaa aaaaaaaaaa 12000
aaaaaaaaga gcctaatttt gcttcactgt ctgtgaaaag aattatctgt atcttttgca 12060
tgtaagacaa atctcaatga aaagggtgct taaatagaag ttaacactat tttaaagcaa 12120
gaatggaagt ggtttcatca tgcgtaaaca acaactctcc acattttgta atgattgatc 12180
tggatgcaat ttgtcatcag acaggagaag tcgaaagcaa agaaataaca ctgggagata 12240
gagaagctct ttcattcaat gcgaaaggtc aaaggcacat cagtttcttt aataatgcaa 12300
acctcagcac acattatcag tgtcctcatt attattgcct tgtttatttc ccactgctca 12360
ttgataattt caacgtgaaa tttacctgta ttgctgcatg catcttgcag tttaagaagt 12420
gaagtaaccc aatttcaaag ctagtgcttt agggaaaata ttggattgta tttacttcaa 12480
gcagagttcg ataatttatg tacataataa aaattttaaa tcccttagtt aatatagcag 12540
ttgccaaaac tgggctatta tcattctaaa ctaccaaccc aaatggtagt gggtatctaa 12600
tctacctcta gaaagaaaat ggactgtatt tgctctatgt atttttcttg tacagcttgc 12660
catcgagaca tttataaagg agttgatatg agaggagtca attttaatgt gtctaaggtt 12720
agcagtgttg aagaatgcca aaaaaggtgc accagtaaca ttcgctgcca gtttttttca 12780
tatgccacgc aaacatttca caaggcagag taccggtgag tacaattcaa ggtgtgtgtt 12840
ctttgtattg gtgcctccag gatttcactg tattcttctt aacctctttt gttcccaaac 12900
taaaaaccaa acagggcttt tattctaacc actttcctca tttacttact ctattttatt 12960
tttttatctt ttatttattt atttatttat tgagatggag tcgcgctctg tcgcccaggc 13020
tagagtgcag tggcgtaatc tcgactcact acaacctccg cttcccgggt tcaagcgatt 13080
ctcctgcctc agcctcccga gtagctggga ttacaggcgt ccgccaccat gcctggctaa 13140
tttttgtatt tttagtagag tcggggtttt actatgttgg tcaggctggt ctcgaactcc 13200
tgatcttgtg atccacccac ctcagcctcc caaagcgctg ggattacagg catgagccac 13260
tgcgcctcgc ccttcatttt ttaattaaat aattcattta atttcatttg tttctctact 13320
cttttcccct ggcatgtaat tgtaccgcat cttcaaagcc tgacatcctc ttcccctact 13380
tctccaaagc tgattcttgc aggtctttcc tcaaataccg tcccctccaa aagcccattt 13440

-continued ctgagcattc tcttttaagt cacactcagc tctgtttatt tcattcatag agctaatcac 13500
aatttgatat taacttgtga tttttttcct tatttttaaa tcttattttt atttgcatag 13560
atgtatgggg tacaagtgta attttgttac tttgatgtat tttacagtgg taaagtctgg 13620
gcttttggta tatccatcac tggagtcatg tacattgtac ccactaagct atttttcaac 13680
gcccgccccc ttcccacctc tctgtcacct tcccagtctc tactgtctat cgctccatgc 13740
tctactcaat tttggtgtca ttttttcctg aagcaaaatt ttggtgtcat tttttctgaa 13800
gtcattttct gaagtctgtg tcatttttcg ctttcctgaa gcgaattttg gtgtcatttt 13860
tcctgaagtt ccgtttgccc cacacatagg ccttgcttat agaatgaggg tttagtgtca 13920
cggagtctcc tgcctcattc tcaccctaac ttttccttta ccccttttgcg aggggaagga 13980 tgtccattag gttaataatg cagacccccta acccactcat tatcagggtc attgtttttc 14040
cactgtgcat tttaatacta actgttacct gcactgctcc ctgcccctca aagtgcagaa 14100
agcaaagtaa cctcttttct tcccattcag gaacaattgc ctattaaagt acagtcccgg 14160
aggaacacct accgctataa aggtgctgag taacgtggaa tctggattct cactgaagcc 14220
ctgtgccctt tcagaaattg gtaattgtag gactacttca ctttgtgatt gtggtaggtg 14280
gaataggagc ccccagagac gtccctgtgc tgagccctgg gacctgtgcg tgtgttccca 14340
tagctggcaa aagcgtttct gtcaatggca tgcagttacg ggcttcgaga tggggagttt 14400
actctggatt ttctgaatgg gcccaatgta ctcacagggt tgagtgctca caaggctcat 14460
aagaaaaaga gagaggcgga aggctcagag ccagagagag aggtttgaag gtattacact 14520
gctggctttg aagatgaagg tccgtgagcc aaggaatgca ggcggcctct agaagttgaa 14580
aagggcgagg aaagagtttc cctgtggagc gtcctggagg aagaagccct gctgatgtct 14640
tgattttagc ccagtaagac ccaatctcta gaacagtaag ataattaatt tgtgttgttt 14700
ttaaccacta agtttgtggt tatgccccta gagcagcagt tataggaaac tagtacagtg 14760
atactgttag agttatagga cagtgatata ggacagtgat actgttatag ttataggaaa 14820
ctagtacagt gatactgtta gagttatagg acagtgatat aggacagtga tattgttata 14880
gttataggaa actagtacag tgatactgtt agagttatag gtacagtgat attgttatag 14940
ttataggaaa ctagtacagt gatactgtta caggtacagt gatataggac agtgatactg 15000
ttataggaaa ctagtacagt gatactgtta gagttatagg tacagtgaca taggacagtg 15060
atactgttat agttatagga aactagtaca gtgatactgt tagagttata ggtagagtga 15120
tataggacag tgatactgtt atagttatag aaaactagta cagtgatact gttatagtta 15180
taggacagtg atataggaca gtgatattgt tatagttata ggaaactagt acagtgatac 15240
tgttagagtt ataggtacag tgatatagga cagtgatatt gttatagtta taggaaacta 15300
gtacagtgat actgttagag ttataggtac agtgatattg ttatagttat aggaaactag 15360
tacagtgata ctgttatagg tacagtgata taggacagtg atactgttat aggaaactag 15420
tacagtgata ctgttagagt tataggtaca gtgacatagg acagtgatac tgttatagtt 15480
ataggaaact agtacagtga tactgttaga gttataggta cagtgatata ggacagtgat 15540
actgttatag ttataggaaa ctagtacagt gatactgtta tagttatagg acagtgatat 15600
tgttatagtt ataggaaact agtacagtga tactgttaga gttataggta cagtgatata 15660
ggacagtgat attgttatag ttataggaaa ctagtacagt gatactgtta tagttatagg 15720
acagtgatat aggacagtga tattgttata gttataggaa actagtacgg tgatactgtt 15780
atagttatag gtacagtgat attgttatag ttataggaaa ctagtacagt gatactgtta 15840
gagttatagg tacagtgata taggacagtg atattgttat agttatagga aactagtaca 15900
gtgatactgt tatagttgta ggacagtgat attgttatag ttataggaaa ctagtacagt 15960
gatactgtta gagttatagg tacagtgata taggacagtg atactgttat agttatagga 16020
cagtgatatt cttatagtta ccgtggtata gttatagtta aaggtacagt gatattgtta 16080
tagttatagg acagtgatat tgttatagtt ataggacagt gatgtagtta cagtgatata 16140
ggtacagtga tattgttata gttataggac agtgatatag ttataggaca gtgatattgt 16200
tacagttata ggtacagtga cgttgtaata gttataggac agtgatattg ttatagttat 16260
aggtacagtg atgttgtagc aaaactgtaa ggtcattcct tggttgtgtc cctatctagt 16320
gaaatgactc taccaggggt agggaaataa aactctgtcg tttcacacat aaaggtaatt 16380
tcaatggaat tatccagaaa attgccatga cattccacct catttagcat gtcaggatgt 16440
taatgacaag atgttactaa aagcaaatcc cttacggcca gttttccgca gtactgggtg 16500
ctggctctgt gcctggccct gtattgggtg ctgggctagg atttccctgt ggaagattgg 16560
gaaggttggt tacaaggtgg ctattttcct gtctcctctt tgcgacagca caccttctcc 16620
atggtgtgtg ccaggttcac gtgtactggt gatttaattt taacgttcat attatttttt 16680
tctgggagag tttttgaagg ctgccaggag gcaggactcg atgcaaacat gctccattct 16740
gtacccagcc ctgttgctgg aaggatttgc tgcacttacc cagggaacag gcaagctcgt 16800
gctgtggctc tgggctgtca cagctgctgt ccacacctgg gagagcaccc tggatggctc 16860
atctgtgtac ttgctttctt gttaaattgc agtgagttca catgtgattt aatcggatca 16920
aatggccttt acagactgat aaaaatatgg ctgtttcagg tggtgttttg agctgctaag 16980
ggcgtggctt ttcactgagt acgtggtccc cgttcctcag ggaacaccca gtagccacat 17040
gcctcctaaa cctagagtag ggctgtctcc tggcctaact gcccaaatga gattcataag 17100
ttagggatga tctgtagtta tcactacaga tttgtccttg gtttcaccaa ggattttcct 17160
aattttacaa acaaaacccc taaggctcct ggaaggaggg tagaagtgaa ggtgctccgg 17220
gggcaacaca gctgatgagc tgaaccagaa ctcgaccctt gggtcacaca catttcacag 17280
tgctcactcc accttttgtt tttttaatgg atttaatggt gttttaaagc ctcctgcctc 17340
tcaacacata tgaattcatt atatttacag atttccttct cttgtggtcc atcttcctgc 17400
atagatcttg agagatgtca ggctaaccac gtttcctcag ttaatttaac aaaaccattt 17460
gcaactctga catggaaaat tcctaccatg tgacttatta atttatcaat tgagatggta 17520
cacatatttt caagccaaaa ggaggaaaac ataaattgga aaaaaaaggt tttttattt 17580
ttatcacctc tggggaagaa agtctgataa acgaagctgg ttgataaaat tgcaattagg 17640
ggaagcaaca tcatggtttc tgttcggagg ctaaccagat ggcatacttg aaatagagaa 17700
tgtcctagaa atcaactggt tgcttggcca aaatatctat aaatagtgcc caacatatta 17760
gataggaaaa gcaaagtaaa aacaatttta acaggttagg acattgggct gaagtattgc 17820
atatatttaa tgtcatgtgc gtccgtgtga agagaccact aaacaggctt tgtgtgagca 17880
agaaagcttt ttaatcacct gggtgcaggc aggctgagtc cgaaaagaga gtcagtgaag 17940
ggagatgggg tggggacgtt ttataggatt tgggtaggta gtggaaaatt acagtcaaag 18000
ggggttgttc tctggcgggc agcggtgggg ggtcacaagg tgctcagtgg gggagcttct 18060
gagccaggag aaggaatttc acaaggtaac gtcatcagtt aaggcaggaa ccggccattt 18120
tcacttcttt tgtctttctt cagttacttc aggtcatcta gatgtatacg tgcaggcctg 18180

-continued

```
ggcccagagg cctgacattc ctgtcttctt atattaataa gaaaaagaaa acgaaatagt  18240
ggtaaagtgt tggggtggcg aaagtttttg ggggtggtat ggagagataa tgggcgatgt  18300
ttctcagggc tgcttcgagc gggattaggg gcggcgtggg aacctacagt gggagagatg  18360
aagctgaagg aatattttat ggtaaggggt gatattgtgg ggttgttaga agcagcattt  18420
gtcatataga atgattggtg atggcctgga tatggttttg tgtgaaatga gaaactaaat  18480
ggaagacaca aggtctgaat aagagaagga gaaaaacagg tgttaaagga ctaagaattg  18540
ggaggaccca ggacatctaa ttagagagtg cctaaggggg ttcagtgtaa ttacttgctt  18600
ggttggtgag tttttgggct ctatccttga cagagtcctc ctttttaagt tggaggctga  18660
gcttggtgag gtgtgttttt aaaagaccat tagtctgttc tacctttcct gaagattgag  18720
gatggtgagg ggtatgaagg ttttactgaa taccaagagc ctgagaaact gcttgggtga  18780
tttgactaat aaaggccggt ctgttatcgg attgtataga gatggaaagg ccaaactgag  18840
gaattatgtc tgacagaagg gaagaaatga ccacggtggc cttctcagac cctgtgggaa  18900
aggcctctac ccatccagtg aaagtgtcta cccagaccaa gaggtatttt agtttcctga  18960
ctccgggtat gtgagtaaag tcaatctgcc agtcctgggc gggggcaaat ccccgagctt  19020
gatgtgtagg gaagggaggg ggcctgagca atccctgagg aggagtggag tagcagatgg  19080
aacactgagc agttattttt tgaggataga tttttacgac ggaaaggaaa agtgaggttt  19140
taagaggtgg gttagtggct tgtaacttac atggaagagt ttatgaaatg atgacagaat  19200
agaatgggcc tgtgaggctg gaggagatat tttccttggt ccaagaatta tttgccttgt  19260
gtgggaagag attgataggt ggaagtttca atgggggagt agatgggagt gacagatgag  19320
gaagaaaaaa actggctgtg agggatagaa gttggaatgc tcgctgcttt tttagctacc  19380
ttatcagcat aggcattgtc ctgagcagtg ggatctgatg ccttttggtg gcccttgcag  19440
tgaatggctt cagcttcctt tggaagtaaa gtggccttga gaggagtttt tattaaagag  19500
gcattaagat ggagaaccct tgtgtagtga ggaaacctcc ttcagcccat ataaccgcat  19560
ggtggtgcag aatatggaag gcatatttag agtcagtata aatattgaca cgtagtccct  19620
ttgcaagagt gagggcctga gttaaggcaa tgagttcagc ttgctgagag gtagtggagc  19680
ggggcagagc agtagcctca gtgatagatg tggaagatac tacagcatag cctgcctttg  19740
ctggtgagtg gtgattaggc ctggtggaac tgccatcaat aaaccaagtg tgatcagggt  19800
aaggaacagg aaagaaggaa atatggggaa atggagtgga tgtcaggtgg atcagagaga  19860
tacagtcatg gggtggggg ccagcctaaa acagtaaggt caagttgttt gaacagaaag  19920
gctacagggc gtggtcctgg ctcttgtgta agaattttga ctgcgcagcc ctgcacttcg  19980
gctgtgtgta atgaaaaggg ttgggatgag ttagggagag ctagtgtggg agcagtttct  20040
agggctgttt ttaaggaatg gcaagaggag tggctaaagg atttaggatc tttggggtca  20100
gctagctttg cttttgtgag tttatataat ggtttagtca ggatggtaaa acttagtatc  20160
caaaggcgga agtacttaac catacctagg aagaaaagga gttgttttgt agaaggggtt  20220
ggggtttggg agatgagcca gacacaatca gcagggagag cacatgtgtt ttcatgaaga  20280
attatgccga gataggtaat ggatgaggaa gaaatttggg cttgactgaa gtaatggggg  20340
ctgtcctcga agccttgtgg cagtacagcc caagtaagtt gctgaggctg acgggtgtca  20400
gggtcagtcc aagtgaaagc gaagagaggc tgggatgaag ggtgcaaagg aatagtaaag  20460
aaagcatgtt tgagatccag aacagaataa tgggttgtgg agggaggtat tgaggatagg  20520
agagtatatg gctttggtac catggggtga ataggcaaga caatttggtt aatgaggcac  20580
```

agatcctgaa ctaacctgta aggcttgtcc ggtttttgga caggtaaaat gggggaattg 20640
taaggagagt ttataggctt caaaaggcca cgctgtaaca ggtgagtgat aacaggcttt 20700
aatcctttta aagcatgctg tgggatggga tattggcatt gagcggggta agtgtgatta 20760
ggttttaatg ggatggtaag gggtgcacga taggttgcca aggagggagc agaggtgtcc 20820
tatacttgtg gattaaggtg gggacacaca aggggaggat gtgaaggagg ctttgaactg 20880
gggaaagggt ggcattgagg tgtggctgtg gcctaagaac agtcagggaa gcggataatt 20940
gagttaaaat gcctcgacct agtaagggag ctgggcaggt ggtgataact aaaaaggagt 21000
gcataaaaga atgttgtcca agttggcacc agagttgggg agttttaaga ggtttagaag 21060
cctggcggtc aatacctaca acagttatgg aggcaaggga aacaggccct tgaaaagaac 21120
gtaatgtgga gtgggtagcc tctgtattaa ttaagaaggg gatggattta ccctccactg 21180
taagagttac ctaaagcatc tgtgatggtc caggaggctt ctaaggtgat cgggcagcgt 21240
cagtcttcag ccgctaagcc aagaagatct gggaagcagt cagtcagaga gccttgggcc 21300
agagttccag gggctctggg agtggcagcc aggccagtta gacagtccga tttctagtgg 21360
ggtcccacac agatgagaca cagcttagga ggaatcccag gctgcgggca ttccttggcc 21420
cattggccag atttctggca cttgaaacaa gatcctgatg gaggaggtcc tgtaggaatg 21480
cttgaccact gcagtttagg cattttgaag tttttgtgtg tgctggagat gtggctgggt 21540
tttgtctcac agcagaggca aggaatcgca actcagaaat acattgctac ttggctgcct 21600
ctattattgt acatcttgaa ggcgaggtta attaagtcct cttgtggggt ttgagggctg 21660
gaatctaatt tttggagttt ttttttgttt gtttttttggt tttttttttt taatgtcagg 21720
agctgactgg gtgataaaat gcatattgag aataagaggc cttctgaccc ttctgggtct 21780
agggctgtaa agcgtctcag ggttgctgcc aaacgggcca tgaactgggc tgggtttttc 21840
atatttgatg aaaaagagcc taaacgctaa ctgatttggg agaggtcgga taaataaaaa 21900
ggaacattaa tcttgactat gcctttagct ccaaccacct ctttaagagg aaattgttgg 21960
gcaggtgggg gagggctagt cgtggaatga aactgtaagc tggaccgggt gtgaggaggg 22020
gaggtgatag aaggattata gggtggagga gcagaggctg aggaagaatt gggatctggc 22080
ttggcctggc aaggagcagc ctggggagga ggggagaggt cagatgggtc catagaaaag 22140
gaggattgga aagactcagc aacacttggg gttgggattg agaggacaga tgggttggga 22200
ttgaggggac agatgggagg gaaagaagga agatttggga caagttgcat tgggaacaga 22260
gactagggag ggaccaatgt gtaaaagaat gcctggacgt caggcacctc agaccgtttg 22320
cccattttat gacaagaatt atctagatct tgtaggatgg aaaaatcgaa agtgccgttt 22380
tctggctatt tggaaccatt gtcgagtttg tattggggtt aagcagcatt gcagaagaaa 22440
ataaggcatt taggttttag gtcaggtgtg agttgaagag gttttaagtt cttgagaaca 22500
taggctaagg gagaagaagg aggaatggag ggtggaaagt tgcctatagt gaaggaggca 22560
agcccagaga aaagagaggg tagagacatg gagagaaggg gtgggggggt gcttgccccc 22620
aggaaagtgg ttcttgccac taagggtgaa ggatcaaggc aggcattcgc gcggtgatca 22680
gatacctctg aaacgtgggt gaataatcaa gcaggtgtcc ctgcagtgat taaacagcaa 22740
ggaaagacta tcttcccaag tccatgacca gtgccagagt tttgggttca tggataaaac 22800
gcgtctcctc tgtctctacc agaaaatgaa aggaattgaa attaagagaa gggagagatt 22860
gaaggatggc gccaagattg aaaggaaaaa gaggttgagg gatagggaga gaggttggat 22920

-continued

```
aagagagtaa aaagaggctg cttacccaat ttaaaatcgg tgagatgttc cttgggcttg  22980
ttggtctgag gaccagaggt catgggtgga tctttctcat ggagcaaaga gcagggggac  23040
aggggattga tttcccaagg gaggtcccct gatctgagtc acagcaccaa atatcacgtg  23100
tgtccatgcg aagagaccac caaacaggct ttgtgtgagc aagaaagctt tttaatcacc  23160
tgggtgcagg cgggctgagt ccaaaaagag agtcagtgaa gggagatagg ggtggggacg  23220
ttttatagga tttgggtagg tagtggaaaa ttacagtcaa agggggttgt tctctggcgg  23280
gcaggggtgg ggggtcacaa ggtgctcagt gggggagctt ctgagccagg agaaggaatt  23340
tcacaaggta acgtcatcag ttaaggcagg aaccggccat tttcacttct tttgtcattc  23400
ttcagttact tcaggccatc tggatgtatg catgtaggct tgggcccaga ggcctgacat  23460
ttaacatgga taaatgtaaa gttcttagaa tcatacatac actttggaaa agatggggct  23520
taatcgcact ttataagact tgaaggatgt ttgagaatca ctatgaaact gctgaaaata  23580
ccaagaaaat ttaattctta tgtatataaa taatgtgtct gttttacatg aatcccttct  23640
acaagcttgg tatttaatat ggcatatatt gtttttttcat agtagattta aaatttttga  23700
tatctaattt agataacata aaattaaccc tttgaaagtg tacaactccg tggtttttag  23760
tatatccacc tgattgcaca acgatcacca ctgtctagtt ccagaacatt tttatcacca  23820
caaaagaaag gctgtatcca ggccgggcac ggtggctcac gcctgtaatc ccagcacttt  23880
gggaggccga ggcgggcgga tcacggggtc aggagattga aaccatcctg ggtaacacgg  23940
tgaagcccta tctgtactaa agatacaaaa aaattagctg ggcatgatgg cagatgcctg  24000
tagtcccagc tactcaggag gctgaggcag gagaatggcc tgaacccagg aagcggagct  24060
tgcagtgagc caagattgcg ccactgcact ccagcctggg cgacagagca agactccatc  24120
tcacaaaaaa ataataaaaa taaaataaaa aaaaaaaaga aaggctgtct ttctcctttc  24180
ccattggccg tctttctcca ttccctactc ctccaatccc ctggcaacca ctaaatctac  24240
tttccatgtc tgtggacttg actcttcggg acattttaca taaatggaat catgcaatgc  24300
agcacatttt gcatctggct tttttcacct ggcgtgtttt caaggctcat tcgtattcta  24360
gcatatatca atactttgtt cctatttagg actaaataag attctattgt atgaataaaa  24420
catattttgt ttatatactt agtttgatga acatttgagt tgtttctgga tttttttttt  24480
tttttttttg cctcttatga ataatgctgc tatggacaac agtttttggg taggcatgca  24540
ttttaaattc tcttatgtat atacttagga ttaaaattgc tggatcacag agtaactcca  24600
tgtttaactt tttgatgaat tgccaaactg tttttgagag cagctacaca atgttacatt  24660
cttaccagca acaattgagg gcttcagtct ctctacaacc ttaacaacac ttgttattgt  24720
ctttgtaatt attgcctttc taggcagtgt gaagtggtgt ctcactgtgg ttttgatatg  24780
catttcccta atgactaaca atgttgtgta tcttttcgtg tgctcatttt caatttgaat  24840
acattctttg ggaaaatctc tgtttaaatc ttttggccat taaaaataat tgggttattt  24900
tcattgttga gttgtatgaa ctctttatat actctggata ctacactctt atgacatata  24960
ttattttcaa aaattttctg tgcatctgca ggtcatcttt tcactttact gatggtgttc  25020
tttgaagcac caaagttttt aaacttgatg aaatccagtc tggctttatt cttgcacgtg  25080
ctttacctaa aacgccaaaa cctaattcat ggttttgaag atttttgctt atgatttgtt  25140
cttagaggtt tatagtttta gctcttacat ttaggcattt gatgcatttt aaattaaatt  25200
ttgtatatgg tgtaaagtag caatccaact taattcttgc atgtgggtat tcagttattc  25260
cattgtcttg aaaccctttt caaaatcaat tgtctataaa tgtaagagtt tatttttgga  25320
```

-continued

```
ccatcagttc tatcctgttg acctatatat gcctatccta atgccagtta cacacagtct  25380
tgattaccat aactttgcag taagttttga actcagacag tctgagtgct tttattttgt  25440
cctttttcaa gattaatttg gttattccgg atcttttgca tttccatatg aattttagga  25500
tggttgtcaa tttctgcaat agaaaagcag caggattttg atagagagtg cattgaatct  25560
gtagaccaat gagtatcaat ggaattatgt gttatcaaat ttagtaaact acataaacga  25620
tatgtacaca actaaaacaa aactaagata taagatcata ttaatgtaat gataataaaa  25680
gtggattgtc tcctgttcta attttaatag gcacaaggca tttttgttaa tcacttctta  25740
ttaaagaatt ttttataata ttcaggaaaa tacaacaaaa aaacccttac attcctaagg  25800
cctcagagtc agagtaatat aaaggaaatg taaacacatg ctgagtaatg caagcatttg  25860
gcaatggtgg tgactggagc tgggagcaca gcttttattt ctctgaaata ggaatttgcc  25920
ccttagagtt agaccaattt tgccttcctc taaatggcaa acagtttgga gatactttaa  25980
aggacatttt ttcacttagg atgtttagta ctatgaataa taaatagtca caatttcctt  26040
aactatggtg acaaaataca agcaaattta gcctcatgtc atttcctaag gaacatcttc  26100
tctctgtgag ttcacaggtt gccacatgaa catcttccag catcttgcgt tctcagatgt  26160
ggatgttgcc agggttctca ctccagatgc ttttgtgtgt cggaccatct gcacctatca  26220
ccccaactgc ctcttcttta cattctatac aaatgtatgg aaaatcgagt cacaaaggcg  26280
agtatgcatg gaaaatcgca tcacaaaggc gagtatgcat ggggagcact tgctgctgta  26340
ctttcatcac ttttatagtc tgagttctta aaagtttcgt tcatttccct caaaacactt  26400
gaacctgcag tttcagtagg tactgttctg ccaggtgcag attagttaag agattagcag  26460
acttctctgc ctatcttctc ttactttaaa acaaatgtta ccattgaatc aaggaagcaa  26520
tagccatgag aaaaaagaag gatctgacgc ctttgaatga agattcaaaa catgatcttc  26580
atgttttgta ttagcttgga gtaaaatcca cttgctggca atatagccct taagcttgtt  26640
gcctcttctc tttgtttcag aaactagagc cctgtttatt ctgatcaagg ctctggccca  26700
ctgtctttat ctcagataac ccaccctctt ctgcacacag catggagcta agagaagggt  26760
gtctagttat gtaatatcat cggcagcata aattcccaga atttgttctt tgattttttt  26820
gtttgttttt ccagttagaa ggtggaactt catcattgtc ctcttttcag gttgtctgtg  26880
cctattagtt ttctccagag ggagaggtgg cttgatttac atttaatctc tgcaatttat  26940
tagagtcctg tagttggatt tactttgaag agagtttccc agaagaataa aatttgctgc  27000
gttgcttttt gggtgtgagc tgcttttgta tttgcctaat gcctttaatg caaatttctt  27060
tctttctctc ttgctttttt ttaaaaaaaa tagaaatgtt tgtcttctta aaacatctga  27120
aagtggcaca ccaagttcct ctactcctca agaaaacacc atatctggat atagcctttt  27180
aacctgcaaa agaactttac ctggtaatgt gatttgataa taatattaca taaaatgtaa  27240
cctatttcat gacttttaac agcaacagtg atgaaacaat cctcaaggta acagaaactt  27300
gtgtaaatgt cgttcattgc ttttcccatc tgatatcttt ttgtgtttat aattgacaca  27360
gaaccctgcc attctaaaat ttacccggga gttgactttg gaggagaaga attgaatgtg  27420
acttttgtta aaggagtgaa tgtttgccaa gagacttgca caaagatgat tcgctgtcag  27480
tttttcactt attctttact cccagaagac tgtaaggaag agaagtaaag gaaattttat  27540
ttttcaaaga cagttgacat gaccatttca tattctcttt ccccctgtga aggcttactc  27600
tttctactgt tcatttcatc taggtgtaag tgtttcttaa gattatctat ggatggttct  27660
```

-continued

```
ccaactagga ttgcgtatgg gacacaaggg agctctggtt actctttgag attgtgtaac  27720
actggggaca actctggtga gtaacctcac tttttcgtgg acctgtcagg gatgtctgtc  27780
atgttgatag tttgcttagt cttaaggaat tatgtgtctt gttctccttg gttagaaggg  27840
actttgattc acttctaatt ccaaccatta gcgtcaacgc tctcttttca gtctgcacaa  27900
caaaaacaag cacacgcatt gttggaggaa caaactcttc ttggggagag tggccctggc  27960
aggtgagcct gcaggtgaag ctgacagctc agaggcacct gtgtggaggg tcactcatag  28020
gacaccagtg ggtcctcact gctgcccact gctttgatgg gtaagtgttg gatgcatctc  28080
atccagagtc ttatcttggc ttttcatttt gaaggatcta tgatcagctg cttcaccgcc  28140
atgtgacttt atgaatagag acgtgttaaa gcggggatgg tattcacaac atttaactta  28200
tagggtccaa gcactgacca acctgaccat tagaacagag tgtggtctct gtacagggca  28260
gatggcgctg agtgggtatt ctccacagaa agagaaacga agacagtacc ccactcctcc  28320
aacccaccac ccaccaccaa tcccaccacc aattccacca ccaatcctgc cacccaccac  28380
caatctcacc accaatccca ccaccaatcc taccacccac catcaatctc agcaccaatc  28440
ccaccaccaa tcccaccacc aatcccacca cctaccccac caccaatccc gccacccacg  28500
accaatccca ccaccgatcc cgccaccaat cccaccacca atcccaccac ctaccccacc  28560
accaatcccg ccacccacga ccaatcccac caccgatccc gccaccaacc accaatccca  28620
ccaccaatcc caccaccaat ccctgatgtg ttcttcaaag acttatttgt caggcccata  28680
gaaatgttac ttcttgctct ttgattcata aatatactaa gtcataataa tttttaaaag  28740
tgagagtttc gtactctgta tatttcaatg tatataattt gatctatttc aatttattgg  28800
tcaaatagta gacatgttag gtaagtctta aaatactgag gctttggagt tagacagaac  28860
atggcttaag tgacagcttt gctgcttatt agaggtgtgg ccctagaaga tttgtaaatc  28920
cctctgagct ttatttgatc taaaatatga atagtaatag tcccgaattt gtaacgttgt  28980
tgggaagatt aagtgacaca tttaaaatgc ttagtactgt gtgtagaaca taaacacttc  29040
aaaaaatgta aactgtgatt tctatattca ataagaaatg tagaaatgga caaagcatat  29100
aaaaagcaaa agaaatacta gaagacactt gatttttctc aaaaataaac acaccaagta  29160
tttttgtttt agtgaaattc atgcttacat gctgtatact aggattgaac atactgccac  29220
caaaatatag cagtcggtgg tacatgtggg tggagcaaga cccctccacc ttgtcatcgt  29280
gtgaaggggc tctgccatac atgaccttgc atgtgacttt aaggtggttg gcctggaaga  29340
aaagtcccaa gatgggaaat agtaggtgtc ttttttacta aatgcactcc aatttgggac  29400
caaaaatttt cattcttgaa ggctcagtat tgtgagttta taagagataa tagacataaa  29460
agtgtaatga tttcattgca aataaaaaaa ggcccctttg cacctgatat ctccatcatt  29520
tttctagaat tttgtgcaca catgccttgc actacttggt gatgataaag atttccagat  29580
ctttgcacag aataaggctt tgctttagat cagaattttg gatgtactta gtatacattc  29640
atcttttaaa taatctattt acattttcat actttccaaa atacagatat attttatttt  29700
atttatatat ttatttaatt tattttttga gatggagtct ctctctgttg cccagagtag  29760
agtgcagtgg cacaatcttg gttcactgca gcctctgcct cccgggttca agcgattctc  29820
ctgcctcagc ctcctgagta gctgggatta caggcgcgcg ccacacctgg ctaatttttg  29880
tatttttagt agagacgagg tttcatcatg ttggtcaggc tggtctcgaa ctcctggcct  29940
caagggatcc acccacctcg gcctcccgaa gtgctgggat tacaggtgtg ggccactgtg  30000
cccagctgta tagagatatt ttaaacaaca ctaaagtcct cctactttga ctaattagaa  30060
```

gagcattaga agatcagcct gacttcttga cagttctgaa tttagtggag caatgaggtt 30120
cagctttggt gaatgagctt aatttttcca tgataaactg ctagtttctt cccactacag 30180
tgtctctcaa aaatgggaca gcaacattct ttttgttttc acttgcagta agcatgatgc 30240
aattacataa atgtacactt ttcaatttgt taaatagaat cttcagagat tcactactgc 30300
cgctattggt gatgaaaaat taccagaagg aggaattagg taggagaaaa tgtgtcctat 30360
gtatttcctt cccagttctt tgaaagagag tgataggaaa aaggaacact attgaaggaa 30420
ggactgccca gtttcaaaca ggtatttatt tttctctcct aggcttcccc tgcaggatgt 30480
ttggcgcatc tatagtggca ttttaaatct gtcagacatt acaaaagata cacctttctc 30540
acaaataaaa gagattatta ttcaccaaaa ctataaagtc tcagaaggga atcatgatat 30600
cgccttgata aaactccagg ctcctttgaa ttacactggt atgtagcata tgtaagaagg 30660
tggagagcag aattgcgctg gttgatattt tcatatcagt ttgaacaaga gggcagacct 30720
agagagactg tcgtcgtttt ctgactggtg gagttgaggg aaacgtgagg gttgctggga 30780
agtgaagacc ccgcgacttg ccgtgaaatc tcttctactt aaagagcaag acatgtgaat 30840
taattctttc agggagggat acaactgcat gcaggtgatg gaaataatgg gcgtgggaaa 30900
tgtctgtgcc gtctgagagg cactgggctt gctttgacaa gagtagcaga actgtcattg 30960
ctttgggctt agggatattc gaatgtgtga gggcaagtgg gatcagatat ctacttccag 31020
gtataatttg ggtaggaaag agactcatgc agaaagaagc cctggaaggc cagagcatcg 31080
tggtcagagg tgttgccttt ggagggtcat tgctgccagg agccgaatac ccactgtatc 31140
caataacatt catggtcagg aatggtggct cacacctgta atcccaacac tttgggatgc 31200
ccaggtggga ggattgcttg aggccaggag tttgagacca gcctgggcaa cacagtgaga 31260
ccccgtctct acataaaatt agaaaaaaac aattaactgg gtgtggtggt gtgcacctgt 31320
agtcccagct agtcaagagg ctgagacaag aggatctctt gagcccagga gctcaaggct 31380
gtagtgagcc aagatcgtgc cactgcacac aaacaattat gtgacctcgg gcaagttgct 31440
ttacctcttt acacctctta atttccttat ctgtaaaatg aggatgataa tttcttcctg 31500
ggtctgttgt aataattaat acatcaaagc acttcatgtc tggaacagtg aagataccct 31560
gctatgacta ttaaggatag tatacatgga ataagacaca ggaacttcta aatgcttttg 31620
accatagatt taggttctga gttttaagaa tttaactcag gaaattgtaa caccaaaaat 31680
gtcatgtgaa aaatggtggt gacaaatttt cttgaatcat tagccttaga ggttgggcag 31740
aaagcaaaaa attattcttg atgctactct atagaaagag aagacagaaa aagagaaaga 31800
tgtattttta aagtctatat ccataacttt atttgaccaa actctaattt aaaaattatg 31860
tttcagaatt ccaaaaacca atatgcctac cttccaaagg tgacacaagc acaatttata 31920
ccaactgttg ggtaaccgga tggggcttct cgaaggagaa aggtaagcat gacgctttaa 31980
atattgcttc tagagtaagt ctcacatgtt gaaatacatg gagtgggtcg ttttaatcgg 32040
tttctgtctg aaattatatc taaactcttt atctttccta tctatttatt cccaaatatt 32100
tattcagtta ttcttaaaaa atgtattttt gctttggctt gaaaaaaaat tttagggaga 32160
cttttaagca tcttacttca ttataaagat cagttgcttg actttgcatg aagcagattg 32220
ggcccttcta gggctgacaa gcccgtgcaa gaccacccgc tcctcagtgt tagtagcgtt 32280
cccgtctccc aaaaccatgt tctcccttga tgctaatggc cgggagcaca ggcaggtgtg 32340
tcgtctcact atggagaata atatttgtgt cattctttac agaagaaggt agcttgccaa 32400

-continued actgtctcca tctttcccga ttcagtcttt tgttcaagta attcacattt ttagattttt 32460
tattggtaat ctgagacaag aagaaattta aagtaatctt cactaagcca tgaaagctcc 32520
caacattgtt ctccatgaga gatgctggcc tgcatttatt caaaaacaaa agacccctct 32580
gttgccaaag ctcggagggc ttttcagaaa cgatatagtt gtaaattata attttgaata 32640
tataaagcaa aaaaatgaaa agtgagaact tccaggcttt ggattgttgt aggtgataaa 32700
tataaaatgg gatttctggg gggctgctac tgagatgagg ggatggcaga aaacatggaa 32760
gcaaggtctc tggtcagccc agggtgctgg gcttgtccca acaccacgta ggcaataaga 32820
ggacagtaca gggtgccgtc tctctccctc ttcctctctc tgtctctctc tctctgtgtg 32880
tgtgtgtgtg tgtgtgtgta acactacctt cccaattttt actgtctatt tgtattcaaa 32940
gataaggtcc ttatgaaaaa tacactgctc tgattcactt taaaacttat ttccatattt 33000
attatttatt gtgggaataa taatattccc aatattatta tttattattt aagttattat 33060
tattaacttc cctctgaggt tatatattgg ttactcacag gtgaaatcca aaatattcta 33120
caaaaggtaa atattccttt ggtaacaaat gaagaatgcc agaaaagata tcaagattat 33180
aaaataaccc aacggatggt ctgtgctggc tataaagaag ggggaaaaga tgcttgtaag 33240
gtaactcatg agattatgaa aaacacaata ggctgcttga gaaaattcat ttcaaaatat 33300
attttccaat agcataattc aatcatagtt tttaaaaaaa ttcagagaca aatgatctga 33360
taaattgata agcaactttt aacaaattga atatacataa tatatattta tattatttat 33420
gatatatgtc acaatctatg catgtgctat ttaagagggg caaatataca tgcaataatt 33480
gtgctagaat ataaaaacat tagacttcat cattgggatg atgatatcaa gatttctttg 33540
ttagatttat ttcagataga aaaggggata cgaaaaatgc aggcacatga gatacttgga 33600
gaactttaag aaagagtgag tgtgtgtgtg tgtgtgtgtg tgtgtgtgtg tgtgtctggc 33660
aagcaaggtc ttgcacacac acagcacttt gggaggccaa tgcaggtgga tcacttgagc 33720
ctaggaattt gagaccagtc tgggcaatgt gatgaaaccc atctctacaa aaaaatatga 33780
aagtatctgt gtgtgtgtgt tgctgtgtag tggactacag aactttagag gcagtcactt 33840
atttgaatcc cattgtcgta actttctact attttatttt tccactgtga ctcagggaga 33900
ttcaggtggt cccttagttt gcaaacacaa tggaatgtgg cgtttggtgg gcatcaccag 33960
ctggggtgaa ggctgtgccc gcagggagca acctggtgtc tacaccaaag tcgctgagta 34020
catggactgg attttagaga aaacacagag cagtgatgga aaagctcaga tgcagtcacc 34080
agcatgagaa gcagtccaga gtctaggcaa tttttacaac ctgagttcaa gtcaaattct 34140
gagcctgggg ggtcctcatc tgcaaagcat ggagagtggc atcttctttg catcctaagg 34200
acgaaaaaca cagtgcactc agagctgctg aggacaatgt ctggctgaag cccgctttca 34260
gcacgccgta accaggggct gacaatgcga ggtcgcaact gagatctcca tgactgtgtg 34320
ttgtgaaata aaatggtgaa agatcacgat tagcaagtgt tttcttctgg ttgtgaaaca 34380
gaactgaaag taagtggttg aggttccagc acagttcctg ggatccctct aattgcactg 34440
cttcctctgg aactcagtat atctcaaaga tgtaatttcc tctccgtgct gcacctggtc 34500
ggccactgaa acccactatt gcctgcttca cgtgtggcaa agagctagcg ggcttgggtt 34560
ttgttctgcc gagaggaagg gagaacaccc actttttataa gaaagagatg ggttacctga 34620
acccatgggc acctttgcct cttggcctcc taactttgct accagggcat ggctaggagg 34680
gtccaggctg cgcgtgctga ggagctcgag gggctgcagc attgcacagc cttcatggca 34740
ggcaaggaat ctgctttgca aggggcatta gccctggagg ctcagtggat atgggctatt 34800

```
gcaatagtaa ttcaaggagc atttttaggc ctggcgtggt ggctcacgcc tgtaattcca  34860
acagtttagg agatcaaggc aggtggatca cttgagcata ggagttcgag actagcctgg  34920
ccaatgtgac gaaaccccat ctccacaaaa attagctggg catggtggtg cgcacctgta  34980
atcccagctc ccccagaagc tgaggcagga ggaccgcttg agcccgggga tgtcgtggct  35040
gcagtgagct gagatggcac cactgcatca ctgcattcca gcctgggcaa cagagtgaga  35100
ctgtctcaaa aaaaggaagc attgttaggt ataaattatt attattatta ttattagtag  35160
tagtagtagt agtagtagta ctgagacgga gtcttgctct gttgcccagg ctggagtgca  35220
gtggtgcaat cttggctcac tgcaatctct gcctcccggg ttcacgccat tctcctgcct  35280
cagcctccgg agtagctggg actacaggca cccgccactg tgcttggcta atttttttgta  35340
tttttagtag agacgggttt caccatgtta gccagaatgg tctcgatctg ctgaccttgt  35400
gatccacccg cctcggcctc ccaaagtgct gggattacag gcttgagcca ccacacccag  35460
ccctgttagg tataaattat ttcataaaat tcagacttgt aaatttatgg tagcctttgg  35520
aatgggtgat agatgtccta tgccacacaa attcctcaca tgccgaggct caccgtaact  35580
gataccagct cgcttgattc agttcagtta aactgaacaa catttacaca gaattggcga  35640
tttacaaaat cttatgtaag ttaagtagaa aaacagaaaa aagttttctg aaagagtttg  35700
ggtttttcct tcaatgctca agacagaggt ccccaacctt tttggcacca gggaccagtt  35760
ttgtggaaga cagtttttcc atggaccagc atggtggtgg gggatgattc tggaatgatt  35820
caagtgcatg acatttatta tgcactttat ttctattatt actacattgt aatatataat  35880
gaaataatta tgcaactcac cataatgtag aatcagtggg agctctgagc ttgttttcct  35940
gcaactagac agtcccatct gagggtgatg ggagacagtg acagatcatc aggcattaga  36000
ttctcataag gagcctagat ccctcacatg tgcagttcat aacagggttt gagctcctat  36060
gagagtctca tgctgctgcg gatctggcag gaggcagagc tcaggcggtt atgcttgctg  36120
gcctgccact cacctcctgc tgtgcggcct ggctgctaac aggccatgga ccaggtactg  36180
ttctgggccc cgggggttgg gaacccctgc tcagagacac accgggtggt aggaggagct  36240
aaaggtggag agggtgaagg aaaatatgag gtctgggcta tccacaaacc agatagcagg  36300
aaactgaaga gttaaacatt tacttcagaa ttgaatggct tttgtaaaat ctggctagat  36360
tccatgaaac gattttaaaa atgcactatt taaattttgc ctttgcatgc gatgaagaca  36420
ttagtctttg ttcatgtgga tgttttttta tgtttaaaag ggaaaaaatg gtttgcaatg  36480
aaacttttat ctcagtcttt gagtattgat catggggtgt tggaacagga ctttggaatg  36540
cttgcagggt aaacctttgg cctctgttag tcagggaatg acctagtttg gcaaaacaga  36600
ggagagtttt gaaatatgga actttcccga ggcatacatt gtcattttaa agtggtcaat  36660
caaagcccag taggactggg ctggtgtctt ggtgactcac tgtgtgctca tatacagggg  36720
taactgagga gcccttcaca caggtctagc ctcgtgggac taaaaagtgt gacatgggct  36780
aggaaaatgc gaggctggga tgccttcact cccatgagga agcgtgacgg gaggaggcgt  36840
gggccactgg cagttctact tcacaaaggc tgctggcagt gtcaatcctg caagctggcc  36900
ttgccctcct gtggcggcag tgtacacgtg gcatgcaagc acatgcacaa gccacctggc  36960
tccaaggtca gccaagggct ccaacatctg tctcagtccc                        37000
```

<210> SEQ ID NO 11
<211> LENGTH: 2472
<212> TYPE: DNA

```
<213> ORGANISM: Mus musculus
<220> FEATURE:
<221> NAME/KEY: CDS
<222> LOCATION: (96)..(2012)

<400> SEQUENCE: 11

agaccgccct cggtgccata ttcagagggc ttgaagacca tcttcatgtg aagactccct      60

ctcctccaga accacaacgt gaccatcctt ccagg atg att tta ttc aac cga        113
                                       Met Ile Leu Phe Asn Arg
                                       1               5

gtg ggt tat ttt gtt tcc ttg ttt gct acc gtc tcc tgt ggg tgt atg       161
Val Gly Tyr Phe Val Ser Leu Phe Ala Thr Val Ser Cys Gly Cys Met
            10                  15                  20

act caa ctg tat aaa aat acc ttc ttc aga ggt ggg gat cta gct gcc       209
Thr Gln Leu Tyr Lys Asn Thr Phe Phe Arg Gly Gly Asp Leu Ala Ala
        25                  30                  35

atc tac acc cca gat gcc cag tac tgt cag aag atg tgc act ttt cac       257
Ile Tyr Thr Pro Asp Ala Gln Tyr Cys Gln Lys Met Cys Thr Phe His
    40                  45                  50

ccc agg tgc ctg ctg ttc agc ttt ctc gcc gtg act cca ccc aaa gag       305
Pro Arg Cys Leu Leu Phe Ser Phe Leu Ala Val Thr Pro Pro Lys Glu
55                  60                  65                  70

aca aat aaa cgg ttt ggt tgc ttc atg aaa gag agc att aca ggg act       353
Thr Asn Lys Arg Phe Gly Cys Phe Met Lys Glu Ser Ile Thr Gly Thr
                75                  80                  85

ttg cca aga ata cac cgg aca ggg gcc att tct ggt cat tct tta aag       401
Leu Pro Arg Ile His Arg Thr Gly Ala Ile Ser Gly His Ser Leu Lys
            90                  95                  100

cag tgt ggc cat caa ata agt gct tgc cac cga gac ata tac aaa gga       449
Gln Cys Gly His Gln Ile Ser Ala Cys His Arg Asp Ile Tyr Lys Gly
        105                 110                 115

ctt gat atg aga ggg tcc aac ttt aat atc tct aag acc gac aat att       497
Leu Asp Met Arg Gly Ser Asn Phe Asn Ile Ser Lys Thr Asp Asn Ile
    120                 125                 130

gaa gaa tgc cag aaa ctg tgc aca aat aat ttt cac tgc caa ttt ttc       545
Glu Glu Cys Gln Lys Leu Cys Thr Asn Asn Phe His Cys Gln Phe Phe
135                 140                 145                 150

aca tat gct aca agt gca ttt tac aga cca gag tac cgg aag aag tgc       593
Thr Tyr Ala Thr Ser Ala Phe Tyr Arg Pro Glu Tyr Arg Lys Lys Cys
                155                 160                 165

ctg ctg aag cac agt gca agc gga aca ccc acc agc ata aag tca gcg       641
Leu Leu Lys His Ser Ala Ser Gly Thr Pro Thr Ser Ile Lys Ser Ala
            170                 175                 180

gac aac ctg gtg tct gga ttc tca ctg aag tcc tgt gcg ctt tcg gag       689
Asp Asn Leu Val Ser Gly Phe Ser Leu Lys Ser Cys Ala Leu Ser Glu
        185                 190                 195

ata ggt tgc ccc atg gat att ttc cag cac tct gcc ttt gca gac ctg       737
Ile Gly Cys Pro Met Asp Ile Phe Gln His Ser Ala Phe Ala Asp Leu
    200                 205                 210

aat gta agc cag gtc atc acc ccc gat gcc ttt gtg tgt cgc acc atc       785
Asn Val Ser Gln Val Ile Thr Pro Asp Ala Phe Val Cys Arg Thr Ile
215                 220                 225                 230

tgc acc ttc cat ccc aac tgc ctt ttc ttc acg ttc tac acg aat gaa       833
Cys Thr Phe His Pro Asn Cys Leu Phe Phe Thr Phe Tyr Thr Asn Glu
                235                 240                 245

tgg gag aca gaa tca cag aga aat gtt tgt ttt ctt aag acg tct aaa       881
Trp Glu Thr Glu Ser Gln Arg Asn Val Cys Phe Leu Lys Thr Ser Lys
            250                 255                 260

agt gga aga cca agt ccc cct att cct caa gaa aac gct ata tct gga       929
Ser Gly Arg Pro Ser Pro Pro Ile Pro Gln Glu Asn Ala Ile Ser Gly
```

-continued

```
        265                 270                 275

tat agt ctc ctc acc tgc aga aaa act cgc cct gaa ccc tgc cat tcc      977
Tyr Ser Leu Leu Thr Cys Arg Lys Thr Arg Pro Glu Pro Cys His Ser
    280                 285                 290

aaa att tac tct gga gtt gac ttt gaa ggg gaa gaa ctg aat gtg acc     1025
Lys Ile Tyr Ser Gly Val Asp Phe Glu Gly Glu Glu Leu Asn Val Thr
295                 300                 305                 310

ttc gtg caa gga gca gat gtc tgc caa gag act tgt aca aag aca atc     1073
Phe Val Gln Gly Ala Asp Val Cys Gln Glu Thr Cys Thr Lys Thr Ile
                315                 320                 325

cgc tgc cag ttt ttt att tac tcc tta ctc ccc caa gac tgc aag gag     1121
Arg Cys Gln Phe Phe Ile Tyr Ser Leu Leu Pro Gln Asp Cys Lys Glu
            330                 335                 340

gag ggg tgt aaa tgt tcc tta agg tta tcc aca gat ggc tcc cca act     1169
Glu Gly Cys Lys Cys Ser Leu Arg Leu Ser Thr Asp Gly Ser Pro Thr
        345                 350                 355

agg atc acc tat ggc atg cag ggg agc tcc ggt tat tct ctg aga ttg     1217
Arg Ile Thr Tyr Gly Met Gln Gly Ser Ser Gly Tyr Ser Leu Arg Leu
    360                 365                 370

tgt aaa ctt gtg gac agc cct gac tgt aca aca aaa ata aat gca cgt     1265
Cys Lys Leu Val Asp Ser Pro Asp Cys Thr Thr Lys Ile Asn Ala Arg
375                 380                 385                 390

att gtg gga gga aca aac gct tct tta ggg gag tgg cca tgg cag gtc     1313
Ile Val Gly Gly Thr Asn Ala Ser Leu Gly Glu Trp Pro Trp Gln Val
                395                 400                 405

agc ctg caa gtg aag ctg gta tct cag acc cat ttg tgt gga ggg tcc     1361
Ser Leu Gln Val Lys Leu Val Ser Gln Thr His Leu Cys Gly Gly Ser
            410                 415                 420

atc att ggt cgc caa tgg gta ctg aca gct gcc cat tgc ttt gat gga     1409
Ile Ile Gly Arg Gln Trp Val Leu Thr Ala Ala His Cys Phe Asp Gly
        425                 430                 435

att ccc tat cca gat gtg tgg cgt ata tat ggc gga att ctt agt ctg     1457
Ile Pro Tyr Pro Asp Val Trp Arg Ile Tyr Gly Gly Ile Leu Ser Leu
    440                 445                 450

tcc gag att acg aaa gaa acg cct tcc tcg aga ata aag gag ctt att     1505
Ser Glu Ile Thr Lys Glu Thr Pro Ser Ser Arg Ile Lys Glu Leu Ile
455                 460                 465                 470

att cat cag gaa tac aaa gtc tca gaa ggc aat tat gat att gcc tta     1553
Ile His Gln Glu Tyr Lys Val Ser Glu Gly Asn Tyr Asp Ile Ala Leu
                475                 480                 485

ata aag ctt cag acg ccc ctg aat tat act gaa ttc caa aaa cca ata     1601
Ile Lys Leu Gln Thr Pro Leu Asn Tyr Thr Glu Phe Gln Lys Pro Ile
            490                 495                 500

tgc ctg cct tcc aaa gct gac aca aat aca att tat acc aac tgt tgg     1649
Cys Leu Pro Ser Lys Ala Asp Thr Asn Thr Ile Tyr Thr Asn Cys Trp
        505                 510                 515

gtg act gga tgg ggc tac acg aag gaa caa ggt gaa acg caa aat att     1697
Val Thr Gly Trp Gly Tyr Thr Lys Glu Gln Gly Glu Thr Gln Asn Ile
    520                 525                 530

cta caa aag gct act att cct ttg gta cca aat gaa gaa tgc cag aaa     1745
Leu Gln Lys Ala Thr Ile Pro Leu Val Pro Asn Glu Glu Cys Gln Lys
535                 540                 545                 550

aaa tac aga gat tat gtt ata aac aag cag atg atc tgt gct ggc tac     1793
Lys Tyr Arg Asp Tyr Val Ile Asn Lys Gln Met Ile Cys Ala Gly Tyr
                555                 560                 565

aaa gaa ggc gga aca gac gct tgt aag gga gat tcc ggt ggc ccc tta     1841
Lys Glu Gly Gly Thr Asp Ala Cys Lys Gly Asp Ser Gly Gly Pro Leu
            570                 575                 580

gtc tgt aaa cac agt gga cgg tgg cag ttg gtg ggt atc acc agc tgg     1889
```

```
Val Cys Lys His Ser Gly Arg Trp Gln Leu Val Gly Ile Thr Ser Trp
        585                 590                 595

ggt gaa ggc tgc gcc cgc aag gac caa cca gga gtc tac acc aaa gtt     1937
Gly Glu Gly Cys Ala Arg Lys Asp Gln Pro Gly Val Tyr Thr Lys Val
    600                 605                 610

tct gag tac atg gac tgg ata ttg gag aag aca cag agc agt gat gta     1985
Ser Glu Tyr Met Asp Trp Ile Leu Glu Lys Thr Gln Ser Ser Asp Val
615                 620                 625                 630

aga gct ctg gag aca tct tca gcc tga ggaggctggg taccaaggag           2032
Arg Ala Leu Glu Thr Ser Ser Ala
                635

gaagaaccca gctggcttta ccacctgccc tcaaggcaaa ctagagctcc aggattctcg   2092

gctgtaaaat gttgataatg gtgtctacct cacatccgta tcattggatt gaaaattcaa   2152

gtgtagatat agttgctgaa gacagcgttt tgctcaagtg tgtttcctgc cttgagtcac   2212

aggagctcca atgggagcat tacaaagatc accaagcttg ttaggaaaga gaatgatcaa   2272

agggttttat taggtaatga aatgtctaga tgtgatgcaa ttgaaaaaaa gaccccagat   2332

tctagcacag tccttgggac cattctcatg taactgttga ctctggacct cagcagatct   2392

cagagttacc tgtccacttc tgacatttgt ttattagagc ctgatgctat tctttcaagt   2452

ggagcaaaaa aaaaaaaaaa                                               2472


<210> SEQ ID NO 12
<211> LENGTH: 260
<212> TYPE: DNA
<213> ORGANISM: Mus musculus

<400> SEQUENCE: 12

gagtgtaaac actggagcca agcaaagacc gccctcggtg ccatattcag aggggttgaa     60

gaacatcttc atgtgaagaa tccctctcct ccagaagcac aacgtgacca tccttccagg    120

atgaatttat tcgaccgagt gggttatttt gtttccttgt ttggtactgt ctcctgtggg    180

tgtatgagtg gactgttaaa taatacctct gcagaggtgg ggatctagtt ggcatctaga    240

cccctgagga cgagtagtga                                                260


<210> SEQ ID NO 13
<211> LENGTH: 30000
<212> TYPE: DNA
<213> ORGANISM: Mus musculus

<400> SEQUENCE: 13

atgagaagtt attttaaatt taattttta aagtttattt attcacccct tgccacgctc      60

tccagtcgag tcagtttgac aagcagaagc ttggaagctg gccgtgagga aaagagtttc    120

atggaagctc cctcctggag tctggcactc tctttaatct ctttaaccca tacattaatt    180

ttccactccc atgttagtct agtgtatgga tccacgtgcc ctctattaag cattacccta    240

ttataagtgc catttaagat tgaattctga catagctaaa gcctctccca gtgttccaag    300

atcccagttt acagcaaggt agtttaacct attcagtaac taattaagca ttacaataga    360

cagagccatt aactcagttg tctgcagaaa gagcctggga atctcactga gatagaaatc    420

tttactacag gctacattcc atgccaagag caagttgata tactatactg atatatgggg    480

aattcttcag acaagataag attttacaag acctaggaat ttaggggtcc atgacactac    540

attattcttg aggcctgtca agagttaaaa ccccctggtg ctattaacac taaagtgtga    600

aactcttgcc tggcattagc ctgatcctag gcagggctgg taatttctat tgtaaacatt    660
```

-continued

```
tatctagttc ctgcaaattc ctttcttgct tgtatctggt aaatttcagt gtaccttgtc    720
ttattgtgat ttgtagctcc tgataattcg ttgtaatata aaatagtcta atgttcgacc    780
agagattaca ttcagattca acacctctct tgtgtgcatc tgtttgtcaa tttaatccta    840
agctttgccc acctactcta gagacccgtt ctacacagac acagggaccc agagggtctg    900
cagcaacctc ttgcatggtt atgtgtgcac acacagaaga agtataggtg tggtggtcaa    960
aggacacttt tagggggttg ccttactccc tccactgtgc aggttctggg gatagaactc   1020
cagtcattag gcttgacagt aaatgccttt gaccccctga gatatcctgc aagctccacc   1080
atgattttag gctttaaaaa catgcaaacc tattagtcat ttatctcttc aatagattct   1140
gggttagcca actgtgcagt tagagttgaa tgtgcaaggc tgtttgaatc tcgggtccat   1200
agaaaatagc ctggcatcag ggtccattgc aattacattg atgattgagt ccctgggctc   1260
atgcttggat acccagttca atggggccag tatcttatga tcgaggactg gcttaaagtg   1320
cagatgttga aatgagccta gaaactgagc ctccagaggc aatgtccaaa ctcaagccca   1380
cgggcatgag tttgttccca aatctacaat tacagtcctg gaaaagattc tacgggggta   1440
gtagacccgg tgactgggcc tgaggttaac atcctggagc ctgggtctgc agggtctggc   1500
cggatactgg aatttcctgg gatgggcttg ttttcagacc cgtgaaaagt aatgtttaca   1560
tcactcttct tcatgcattt ggaacacatc tccttgctgc gctgcttagg attggtagga   1620
gggtttcacg gttaatgtga aaagtctaac attcctcaat gcatattcac taggtccaca   1680
ttttcaaccg gggttggggg gtgcaaccta tcatctggat tccttaacaa ctcggaaggc   1740
attttttttt gtgcacagag aattgttccc atggattctt ctgcaaaggg acccattttg   1800
gagcctccag ctctgtcatc gtgtttatat gacttcttga aattggtaac atattaagta   1860
gctgaacctg gactgggatg tccgtggact atattgacag gttaaacagt tgaaactgat   1920
gccagaaacc cagtgtaaac actggagcca agcaaagacc gccctcggtg ccatattcag   1980
agggcttgaa gaccatcttc atgtgaagac tccctctcct ccagaaccac aacgtgacca   2040
tccttccagg tagctgcttt ctaccggtct tgttatttcc tgtgtcttgg gttttttttt   2100
ttcaatataa ctatttctgc atgaacaaaa gctcactggt ataatgcact aatttcctga   2160
gtttttagaa aatctacaag gagttgtttt tctttctata caaatatatt aatgtaaaat   2220
atttaaaaac caagaataag tttttgattc ttttcaaaga tgtcctttct gtgaaggttg   2280
tgggtgatat tattgtcctt attcataata attttgcatt aatctggaaa tttaataagt   2340
gtttttaatt atttgtatta actctttaca aaattattag aaataaatct tcaaaattaa   2400
caataaatac actaatacac actgatagta atctagaggt ctcaatttgg atcttgggaa   2460
gcatgataaa tattttaatt ttctatatac aaaatatccc acagccaaat cttccttctc   2520
ctggtgatta tgtgctgtga tttgcaactt agacatttat caaaaaggtg aagtctacat   2580
gaagttaaat tgtctattaa atacatggta aacatgatct caacctagta gttatatgta   2640
tattttttc tttcaaagga tgattttatt caaccgagtg ggttattttg tttccttgtt   2700
tgctaccgtc tcctgtggta agtattagtt taaggagttc aaattaatag tgtgtgagag   2760
aggaatggtc ttgcaatcta taccactcct ggaggaagcc tttaactgta cagctttggg   2820
ggacaaggca gctgttgata ctccaaggca agaacttaga tacattaccc caaacacaga   2880
tgaacagggg gaggaactta gagacatcac tgcacctgtt agcagaaata tctgttttga   2940
gtttactctt taacagagcc tctcccaccc ccgcagagtt gtttgtcttt ataatatcag   3000
ccttctaaat aaaaactcta cctgaaaatt ggaaataata tcagatattg cataatgatt   3060
```

```
tgagtctaat ccaggtatct gattagtata tagtattttt aatataagac atacagagcc   3120
atttctaaac tgaaagtacc tgctttgggt ttcacaagta tagtatccct ttggcagtct   3180
ggagggacag ctttcaacac tcgatgtcag tgctctttcc ctgtttattc ctttgctttt   3240
caggatatga gcatggatgg ccctgaacag cccctctcaa cagtcattat agagggagat   3300
ttccctgggt ataacatgtc aggtgtattc tgagtcaaag ctgacttaga tatagccaca   3360
cgcaaggatt gttttcttct tctttttttt tttttttttt tttttttggt tttttggttt   3420
tttggttttt caagacaggg tttctctgtg tagccctggc tgtcctggaa ctcactctgt   3480
agaccaggct ggcctcgaac tcagaaatcc acctgcctct acctcctgag tgctgggatt   3540
aaaggcgtgt gccaccacgc ctggcaagga ttgttttctt gactttcaag tatatggcaa   3600
agataggctt gtccttgtaa gtagaagtca tttctctagg taagctcttt tttcccatcc   3660
ctctctgctc cctacatctg gcccatcatc tgtaactgct ctcctgtacc ataactactg   3720
ccatgttcaa accaactaaa cacgaatagt gataaccaga gatgctatgg gccatggcta   3780
taaaattcat aatcatgaca ggaaaatgag acatgggaat acatataata cttgaaaaca   3840
aatactttat ataatcctaa agtacaaaat aatgatcgcc aatttttttct ttagtctttc   3900
atatttttcc gcatgaatct atctgttgta taaagtgtta ttcatgaata ataattttaa   3960
ttaaaaatta tgaacactaa tgaaaaataa ttttaactta cctttggtat ttatagctaa   4020
tgttaatgca aatgaacatt tatgttattt gttcttcttc atggatattt tgtaagtatg   4080
gacattctct gcacatatcc aattatttct atagattaaa tttttggaaa taaagatttt   4140
agatagagga gtatgaatac ctttgaaggc tttatagcat gcattatggt attagcttct   4200
agacaggcat tctctgtttg gttttcccca caagcatgtg gaagtgaatt aacaatacaa   4260
tctcttagaa atgagatgtc aatattaaat acgttttatg ttaaaaaata aaatttacag   4320
gttcacaaca ctggtttaaa cagctaggtt aacaaagatt aaatttgaaa caatcaatat   4380
ttgtgcgctg gctttgatca caaatgaaag aaaatcaagc agtacagctt taatataaat   4440
gagtttaaga gttcagaaat ccatgtgccc agtgaatggc ttctggagta cttagacact   4500
gcccaatgat ggcacccgca catagtgtgt ctgcattgct ttactgcatt gtacgctgct   4560
gccttcatct caggatgcac aatagcaagg caggaccagc agcccaagtc gccttggaaa   4620
caaaagtaaa tcggagcctt ttcctaagtc tgagaacaag cctgttacag actagctctg   4680
gtcaggtcat tgtaccagct ctgtgtgcag ttctggctct ggtctgattg gctggagcat   4740
caacagcaga agcatcacct ccagcaacat atggaccacc acttgtagat ggttcctcag   4800
gaggaaatct ggatgccaat tcagcaaggt ggctctatgc caggctacaa agtaacagat   4860
gcctattgga gctcactgtt ctaagtgggc aggcatggtg caggaggagc tgagagttct   4920
acatcttcat caaaaggctg ctagcagaat actgagttcc aggcagatag gatgagggtc   4980
ttataggcca cacccacagt gacacaccta ctcctacaag cacacctact cccacagggc   5040
cacaccttct aatagtgtca ctccctgaga tgaacacata caaaccatca cagtgcccat   5100
ttgctgcaaa gagaggcttc gttgatgtgg gacagtcact acagttatct agggaaggtg   5160
gtcatctcac tgttagcagc tttcatatac ttacagttat ttacactcct ttggtaaatt   5220
atcttttcat atctgacatt gaatgtttaa aacattttag catttatcta tttttgtatc   5280
tatgtctgca cacgcatgtg cacatataca catgtgctgt ggagcacgtg tggagatgaa   5340
ggggcatctt gtggaggtca agaggtcaat ttgaaaactg aagggcctca ttacaggttg   5400
```

-continued

```
tttaggttaa ataaactctg tacaaataat gctgttgtta taatcattac caccaccttc   5460
gttatcattg ctgccgttat cattgcaact gaggaggata agcagtccca cagttagaat   5520
gtgtctagtc actctttttc attgcctgag tcacatgtta gtttaccaac attcaattgc   5580
aggatagaaa cttccaggct atcagcggat cacagtttgt gtttgtgttt gtgtacgtct   5640
ctgtgcaatg ggatggcaag ggagcctctg cttgataatt atgagatgct aaccacataa   5700
aaaaacaagt ctctttatag ctatcctcac cactgggcct actattcagt gcattgtgca   5760
aatgggacac cttagggtat acacttggga acatatattc ctaggagaat ttacccagga   5820
atatctgttc tttccaaata taaacctgac ttaagaggta ggcatggtga cacctctctg   5880
ataagaagaa aaacaatatt gctaggttgg ttcatccaaa cttgtctcag tggcaggatc   5940
cccatataga tagaacatag aaactcttac ctctttagtg cttattaaaa gacatgttgt   6000
ctagacaacc attccttgaa aagtaaggac aatgtgggca atgttgccac tggagtattc   6060
cataattaat gaaaacctga ctggtgaaaa cagacaggct gcctaaggtg gaaagctaag   6120
tacaaagatt tgaacggaat cttttcaggg agatcccagt tcttcaatgg atttaaagag   6180
ctgctctcta atgatatgtg gggtgcagga tacccacatg atggagtcag cagaagcgat   6240
gtatctcagt ttattttcaa gttagcttac tttaattttt tttttaattt gaaaggtatt   6300
agcctttttt tctgatttat tgaaaatatt cttttctcat gccatatatc ctgattatat   6360
attttccttc cctctactcc tccaagttcc tccccagctc ccatcttctc cccatccact   6420
ccctttctgc ctctcattag ataagaacaa ggtttctaag agacaacacc tatacagaac   6480
aacataaaat ataataagat gaagcaaaaa ccaccacagc aaagttggac aaggcaagtc   6540
aacagaagga gaagagcccc caagagaagg gacaagagtc agagacccat tcaggagtgc   6600
catgaaaatt ctcaggggaa ggctacaaaa tatacgtaga ggaccctgtg cagatctgtg   6660
taggccctgg tgcttcagtc tctgtttgct cacaggagcc ttacttagtt ggttcagagg   6720
accttgtttt cttggtgtcc tctggcccct ctagctctga gactccttct gtctcctctt   6780
tcacagggat ggatctctca gctctgagag gaaggatttg atgaagacat accactcaga   6840
gctgtgtgtc ctaaggactc tgactctccc ctctccgttc tcctctctct actcttctcc   6900
ctctctctcc cctcttctct ttcttctctc ctctctcatc tctcctccct cccctcccca   6960
ctctgtaaaa tgtctgagtg tgggtttctg caaatacatt ttctttatca agaaatgagc   7020
aacagaaaaa cagtacccaa tacttattat tttgcttaaa taaggctggc taaacatcaa   7080
catgcaacat tgcatgttag aaaaagggga cagacaggat tgagagtcag aaagagtaag   7140
tttatgtccc aggatatcta ttcactgtgt gatattagcc acatttgaac tctgagactc   7200
agttattgac ttctttcatg aaaaaagggg gaaaagagag gtgcaactaa tggtcctgac   7260
ctcaagttgc cctccaagtg ttgtcctaaa aagcattttg aaaaaaatgc tgtattttca   7320
tttctaaggt gagatgtttt cacagcatgt tagacagcag gcagaaaaaa attatactgt   7380
attttagtag ataatttatg taaaaattat tatataggta ataaaagagt caacttctat   7440
gcataaatgt tcataagatg actttaaata gcatgctgta ttgtttgaca gttgtcagac   7500
ccgtgaagtt gtaatgacta ttaggataaa taaaacagga atgtcaaaac agatgcattt   7560
ctattaaaat ggttacactt tcccccaaaa tcaactttta aatcacaggg tgtatgactc   7620
aactgtataa aaataccttc ttcagaggtg gggatctagc tgccatctac accccagatg   7680
cccagtactg tcagaagatg tgcacttttc accccaggtg cctgctgttc agctttctcg   7740
ccgtgactcc acccaaagag acaaataaac ggtaagatgt gatggtttgt cattgccagg   7800
```

-continued

```
ttagatgtta cttaaactgc ttccagttat atgccaaaat agtgccatgt ttctcagagt   7860
gttcaaagac tctttgcatc agaagctcct aggctgggtc ttttcaatgc agacccaaag   7920
tactgaaccc agagacagac tctaaacagc cacaacactt gttcacagtg ataggaggta   7980
gtgatgctac agccaaggcc tgaagacaga gcatgtgaca agaaagggtc cttcctcaca   8040
ctgcaatact tagccttttt tcactttcaa catgttattc tgtccccaca tgtacatctg   8100
ttatgtatat aaatgttatt agctgggtta tgcatatgag ggagaacctg agggtttttt   8160
ttctttctga gattatatgg cttcccttaa tattaaaaat actaagtcca tccattttcc   8220
tacaattttt gtgatttcat ttctcttcag cgcataatag cattgcatta catattttct   8280
gttttattca tttgtgtatt aattaattta ttataaatgc tgcaaataaa acaatcacag   8340
aaccaaatta accagactca gagactgtgc aactcagtga acttctatcc agttacagta   8400
attgtttgaa aaggaagcca gggaatgtca caatgcactt gatactttca ctatcaaatt   8460
tatattttaa tcatatatat tgctttctaa taaatggtga caatttcacc tgcatagaga   8520
aatatattta attgctttac tagctaccat atttataggg agcaaagttg agaaagtata   8580
agccaggaat tttgttgata ataaatttga gacccagtag gcaagtctca atagtgcctg   8640
cagtggacca gtttacactt ttagaatatg cattttctct ctctctctct ctctccctct   8700
ctctctctcc ctctctctct ctccctctct ctctctctct ctctctctct ctctctctgt   8760
gtgtgtgtgt gtgtgtgtgt gtgtgtgtat gtgtgtgtgt tttattaggt ggtaattttg   8820
gcaagaacaa ttattaaaaa tatatttgga aattttacct taattttctt tcatttgatc   8880
aagagccaaa tgtaaatttt tgcttctttt tccatacaca taactttcat cttcaactat   8940
gtgaatttaa gaattagaat tttaaaactc attctctgat ccctacatgc taatctgtac   9000
caaaaaaaac ccaaacaaac aaacaaacaa acaaaaaaac ccagaccata tgtgagattt   9060
acatttttaa aaaaattgaa ccaggttcta agattcttat aaatagcaac gttaacatag   9120
cgttgatatt gaagacagaa aaagcctccc attacatgga cactaccggg aatcaataca   9180
ccagatgaac atcacatgca gacctaactc atagctgagt cagttttttt aaaagtaaat   9240
taaaatcttt ataacaataa tcaccatttt agaaaatgtg gatgtttcag acaggagaat   9300
cgtaagttta aagtcagctt gtgtaagtta acaagatcct ttgtcaaagc aaactaagta   9360
aaagcttggg gtggcatggg gggaggaaaa ggctggtgat aattattagg atttgattag   9420
catatttgaa gcccaggctc tcctcctcag taccacataa actaagaaca aaaccaatga   9480
tcttttggaa agaggagcca gcgacgttca gaatgagaaa agaatcatca acccttcagt   9540
gtggttggct ctccgcactt gcagcgtaaa cagtaagaaa aacaacgcta tagagagcat   9600
ggacttgtcg caagaacgtt ctcttcagca agtgacaagg ccatgttatt agtttcctga   9660
ccctgggctt tatttattaa catgtacaaa atactgcatc atttcttaat gtgtgtttgt   9720
tcaattccgc ttttaaaatg tgttttttta aaaaacaggt ttggttgctt catgaaagag   9780
agcattacag ggactttgcc aagaatacac cggacagggg ccatttctgg tcattcttta   9840
aagcagtgtg gccatcaaat aagtggtaag atgtggattt tttttcccaa ctaaatttga   9900
gttaataaca ctcaaactca gagtagcttt tgctgcaagt ttatactatg atggactttt   9960
agacgagacc accaagaaag ataatagagc tgaggcagca tcatggctgt aagaaggggg  10020
tactttcacc ttgataatgt tcacatcttt atcagttata gtgctcagcc ttaacgggcc  10080
tctattacct atggtattca cacacaatgt aagatttgtg ggaaatgaat atgcacccag  10140
```

-continued

```
ataataggcc ttccctgttt ccgcaacaga ctttttaggt aagactcggg gacatctcat  10200
cccaaagtgg attttggggt aattggtggt cacccccaga actgactttg ccctctccat  10260
gtcaaagaac agctgaaaat gtctggagac agtttagatt gttaaaattg gggaaaatgg  10320
tactttacgg taatgctcag agttggtgca gtcagactca gcagaaaaca ttctggccac  10380
cacggggcca ttgataaggg attaagactg tggttctcag ccttcctaat gctgcagctc  10440
tttaatacag attctcttgt ggtggaggtt accagctata cacttttcat cgccacctca  10500
taactgtaat tttgctactc taataaatca tagttgtaaa catttgtgtt ttccaatggt  10560
cttaggcgac ccctgtgaaa gggtcttgca acccctccaa aatgggttgt gacccacggg  10620
ttgagcaatg ccggtttaag aaatcttatt tttgccactc ggtccagact gaaagactga  10680
gttctgtcca tcttgctaag cgtaatattt cttacaagga atgtgaacgc taggatgtta  10740
gagcgctttc tctgtgactg ctgttgcaac tgatgtctta gaacacacca tcttaattct  10800
cagaccatct taaaggctta ggataaagaa ggcattttta taagatgaca gggactgtta  10860
gaaagtgaaa gtgctaaaaa agaatgaggc ggtgagttcg attatattgc tttgttttta  10920
cgtccttcat tccgtaggtt caaatttcaa atgttctcat tttgctccag taataataac  10980
agccctctca ccacataaac attcagtgtc tgcagtttaa attttaggca atgaatgaag  11040
aatgacaatg gcttagctat aaatccatat atttatatgt acatatattt aacctgaagt  11100
gaactacatc aagatcaatc cataaactaa cttgctgtat attgcttgat gaagtgtcta  11160
attactgtga ccaacgacaa cattttaaaa aatagaacta ttgtgacttc cccaaagctg  11220
cttagttgtc tttttctccc cctaactttg taactttttt ccaaatactt tcaagaaaga  11280
tcttcaagtt aaaaagggat ctcaaggagc cagttttagt aaaaactatt gagaggtggg  11340
cttaaagtgt acagataatc attaagaaaa tattttattt gtttctacct tatcccaacc  11400
ctcagctcat ttcttttctt atctgaagca aatttaaaag aaccttattt ttacaattta  11460
cagtttccta ccctgtaaac tgctgggagt ttaggacccc tacaccctaa cataatgctt  11520
tcctttttt ttattggata gtttctttat ttacatttca aatgttataa cctttcctgg  11580
ttccctcccc caccccaagt cccctatccc atccccctct ctctgcttct attaggctac  11640
tcccccaccc acccacccac tcccgcctcc ccacccaggc attctcctac actggggcat  11700
caagccttca caggaccaaa ggcctttcct cccattgatg cctgacaagg ccatcctctg  11760
ctatatattc ggctagagcc atgggtccct ccatgtgtac tctttggttg gtgatttagt  11820
ccctgggagc tctgggggt ctggttggtt gatattgttg ttcttcctat ggggttgcaa  11880
acccctcag ctcctttcta ttagtttgta tatgcatagt gtctcctgtg tttaattaat  11940
ttcacaattt ttagaaactt atagttatgt acaatagaat attgtttgtg ctaacacaca  12000
cacacacaca cacacacaca cacacactgc ttgcttaact aagtatctaa ttaaaacaaa  12060
acgtaagagc ttaatttggc ttaatttctg ttaaaagaat caactatttt caatatataa  12120
gataaattcc agtaaaagga tgcttaaata gaattgaaga aacctttaaa aactggtgtg  12180
ctagcacatg gctatcatct cagtaccagg gaagcagagg caaagaacat tttaagttca  12240
aagccagtct ggtctgaaat tcgagattgc cacattcagc atggcttggg ggctggaaaa  12300
ctgagtaaga acattaaggg aagaaaggac agacacacag acccatgtgc agggaagctg  12360
gaatagtgtg agttatgaga ctgaacccct aacccccaga atgcttgtta catacacagg  12420
ggaagggtta aatagtctca gagggcggtc aggcaatctc tcctcttggt ctataatcat  12480
cttggagtag aaggtgaagt tgctggtcat tgtgcacact ggtcaattgc tcctaaacac  12540
```

tactgctgag acccagggat atctctgccc ttttcccatg ggtctgagcc actgatcctt 12600
cacatgtggt cctcagacta cagaccacag acttcacctg ctcctttcac atttactggg 12660
gtttcccatg gttaccacag gagttccaaa ccagccaggc tagaaaggac aaggaaggat 12720
gcagtggctg cggtggtggc cagtggtggt ggtggtggtg gtcatagaac ttaagagagg 12780
tttaaagcaa gaagggaaat gatttcactg tgcgtataaa taaattgaga cagtctgtta 12840
aaagatttga cacaggcatc agtgttgtga ctaatagtca caaatagcaa tcagacctga 12900
ataggcgaag gaagagaaac tgatgcagat catgattttg ttttgttttg tttttttggt 12960
tgtttgcatt gttggtggtg gttgttggtt tgggtttttt tttttgcgta tttgtttttt 13020
gttttgtttt tgacccagaa gtcaaaggtt cgccgtttgt caaatacttt gtgtctctgg 13080
cacacactat caggacccct gttgctgttg ccttccttgc ttatcagtgc ctctgctagc 13140
ttccatgtgg aagtgcattg ttttgtattg ttgcatactc gttgcagttt aagaggcaaa 13200
ataacctgtt tttaatgctg gggccaggta aacacacccg aggtgagcta atgtccagca 13260
gtgtttgata atttagacat gcaaaaaaca ttttaattcc tgtacttacc agggaagtca 13320
ccaaaatggg ataccaacct tcaaaaatga ctctgaggga agagcagttt atttgtgtct 13380
aaaaagaagt ttggtcgaac gtctctgtgt ttcctttcag cttgccaccg agacatatac 13440
aaaggacttg atatgagagg gtccaacttt aatatctcta agaccgacaa tattgaagaa 13500
tgccagaaac tgtgcacaaa taattttcac tgccaatttt tcacatatgc tacaagtgca 13560
ttttacagac cagagtaccg gtgagtgagg cacagatccg agaggacact ccagggatgt 13620
gttagcatga aaaaaaaaat cttccctcca gtcaaggtgc aaggggcatg caatccccag 13680
ccctgcccct attttattcc ttatttacat agttaatttc aatgtaattt cctcctaaag 13740
gtagcaaact ccctgtagtc aactgatagg ctgtgtatgg gcatagtgtc agacaatggt 13800
gtctgccact ccattcgcag aagggaaaag catctgttga ttgatgttgc ccaactgtgc 13860
ccctctgtgg ttatcaattc gataacgaat attatccgca cgtctttgtg cgccccaaca 13920
aaggaagcat aacaacatct tttgtgacat ccaggaagaa gtgcctgctg aagcacagtg 13980
caagcggaac acccaccagc ataaagtcag cggacaacct ggtgtctgga ttctcactga 14040
agtcctgtgc gctttcggag ataggtaact agatgacgat tattccactg tgattgcgat 14100
gccctaaaca agagtgccaa gaaataccca cgtgccattc ccagggacct ggggaatatg 14160
atgccttttt atagatgtga ttgcatggaa atacttggca atcggaatga tgttgggtta 14220
ccagaatatg cccctgccca ggctcaaggg ttcttatatg ataaagagag aaacagaggg 14280
gtcagtgtca gagtagaaag acttgaatgg tctatattgc tgcctttaaa gatggaagaa 14340
gagtccaaaa gcaaagggta gcagaaatta aaaagggcac agaacaggtc tccctgttaa 14400
ttatataaat atattatatt tatcttccaa aggactataa aggcagaaac cacaacatga 14460
taattttggg aagccaaatt cactcatatc ctatttgggt gtgggcaagg cttgattttg 14520
caatatacat ccagcaggtg cctcagtcgt ccaagcaagc aagcgtttca cacaaaatcg 14580
gaacttagca actagcctgt taaatctttg ccccgttacc ttgcaagaat agctgaggcc 14640
gtggcatatt ttgtaacact caggcaattt tattttttgc ccagctgtac caggaagtgg 14700
tccatcaatg gacagggtac attcaatgta agaacaactt cttcatggct tatatgagct 14760
taaaggaaca ttttgttttt acaagccgag cagagtaaac gtatcctcta attatattgt 14820
tcccaatcat cggaccttat gctgtgctgt agcgtggtag aaaatcacag gtcaatgtgc 14880

-continued atgtgtggaa gatacagaga acaaacagag gccttggttt agagcaacct gcccttgtgg 14940
ggtaactgac ctagtccagt gagagcagga acaggtatta cccaattcac gtggaatgca 15000
acttcacgac tttgcactag gccatactgc caccttggga agcaagcgtc accaggattt 15060
ttgctgcggg caaagcacac tccagccaga acagcacact gctgcaaggg tgttttaaac 15120
acaggtttaa agacaaggtt tttttttgtt ttgtttttgt ttttttttt gtttttgttt 15180
tttttctgcc tcaagtgctg tccacagtct caacaagtga ggtctgctag cattctgtct 15240
aaactccacc cccacagtta cctggcaaca gccaggtagg ctccttcctc tcttaccctc 15300
ttgggctctc ccctactctc ccccctccc tactcccttc cctcctctct ccacatgctc 15360
atggctagac tctacttctc tactctcttc ttctctctgc ctttctctgc ctctactact 15420
ctcttaactc tcccccccc ccatgccctg aataaactct attctattct ataccttcta 15480
taccttcgtg tagctggtcc ccagggggaa aggctgcctt ggcatggacc tgcagagata 15540
tcccttccc ccacacttca ccatacccc atagaacata tcttaatatc tctatatctt 15600
ttttataatc acaacattgg ttaaaggctt gttttcagag tttaggcatg gactttgaaa 15660
gctttggaga taatcatagt tgccctgtta atggatcaat actatttaca attctaatta 15720
aaaggactcc tcttttcctg ttgtaggttt ggcatttgcc ctgatctgta ttttcatctt 15780
aggaggcaga tgtcatgtcc cataatcacc aggatccatt gcttctcccc accttcccct 15840
ctctcttttt cccctcctat ccctcctcct ttgtaccccg tctccttctc cctctccttc 15900
ccctccctct ctccccctcc tcctctcttc ctcccccttt cccccttccc ctctctcttc 15960
ctcccccttt ccctctctcc gtcccctcct cctccccctc cgtctctctt ttgtctttct 16020
ccctcctttc ttccttcttc ctctttctgt agacacatgc tctcaaggaa agggctggaa 16080
acactaggca aaacaggagt caggtctgat aaacttaagc cctgtgagca gaattttcca 16140
gggagcttct tgacaaaccg agtgatgatt gttgtctggg aacgagggac agtggctttg 16200
gaggtgctcc aaccattctg acatgttgat tttcagcaca tccatggggc tgttttccag 16260
gtctctatgg atctgagaaa ggggcacaaa tataaggcag ttcaacccca cacagctctt 16320
gctgaaggtc agccatttgt ttctatctca ggattagtct caattgtgtg tccctttggt 16380
taatttctag ggattaaaaa aaaagtgact tgactcattt tactagtatt taacatagtt 16440
ataaaagaag acgaatgcag gctggtggta acatttgcct ttaatcccag tgttcaggag 16500
gtaaaggctg agttcaaggc tagcccggtc tacagagtga gttccagaac aaccagggct 16560
acacagagaa agcctatatt gaaaacaaac aaacaaacaa acaaacaaga tggattctgg 16620
gcacttgtat tctctcagcc tcgctaacat tctgtaacac ttttaattaa cagagtgacc 16680
cacttagggt tattgttgtt gtgatgaaac accataacca aagcaactca gggaggaaag 16740
gtttagttca gtttatactt ctggataaca gtgaagaaag tccaggaggg tgggacctca 16800
aacagggcaa gaacacggag gcaggagctg atgcagaggg ggtggaagaa tgctgcttac 16860
tgccttgctc atcatggctt gctcagcctg ctttcttata gaacccagga ccaccagcct 16920
atggatggca ctacctacca tggactgggc ccaactctga tcactaatta agaaaatgcc 16980
ctataggctt gccttcagct ggatcctatg gaggcattga tgctccctct tctctgatga 17040
ctctagcttc tgtcaagttg acataaaacc agccaggtca tatagctaac aacctaacgt 17100
tggagtggaa aatgtctttg gaaagccaga tgctcatctt gcctgggtca ggttctgcat 17160
tttgtgtgga acaataggaa gctggagtat agccaactag ggcaaccatc ttgacggaat 17220
tcttagaagt aatggaaaat ttagaaacca gtaaaggaag atgttaagta tattcaactt 17280

```
gaacagaaga ctgccttggc gtttggcgaa gtctcctctg ttctgaaagg ctgtcattag  17340
ggactgggtc agtacacaat cccgtagggt tgttttagaa aggtaggact ttgtagaaag  17400
taattttttg aagtccctaa catcttcagc ggtccagaaa agaagttgac tttgtcacat  17460
ggtggtgaac tccttttcaa ctacaaatgt cccaggaaag ttgtaaagtg acatgccagg  17520
gatgtcttgg agatacagtt gtaggttggc atggttacct gaacattctc ttccagtagc  17580
aaggctcttc atgatttttt tttttaattc aagtggtaga atcagcttcc aagactacac  17640
aagtgggatg tgagctctct tgatccaact gtcttgagtt tgactggcct atcgttattc  17700
ttaagtgtcc attttattag tatggaatca aattgattct tacatgctat cgaattgagc  17760
aactcatgta aatagcataa ataaaaatag atgaaaaata aaatgatata aggggggatg  17820
aaaatgaagc ttttctgttc tcatcgaagg gcatgcttgt tagccctttg gaatttatgt  17880
taatgtcttt tcattaaaat gcttctcaca atactcagaa acaaagcatg aaacagcatg  17940
ttcccaaggc ttagtcataa tacaagggaa actcgagtca tctaatgtcc tattagaaat  18000
gacagtgctg cttattctac agcacccagt tgctgtcttt cccagtagaa caacttttac  18060
ttttttagca aagaacaaac tacaaattct gagataagtt aacaggcttt cctcctctta  18120
ttgaaatgga ttctctctct ctctctctct ctctctctct ctctctctct ctctctctct  18180
ctctcacaca cacacacaca cacacacaca cacacacaca caatatatcc tgatcccggt  18240
ttccactccc attactcctc ccacaacacc tcccctccat ttctatcatt agaaaagaaa  18300
caggcttcta agtaataaaa caaggcaaaa atgaaacaag aaaacaaaac cgaacacatt  18360
gaacttgaac aaattgaaga aacaaacgag agaaggcaca agattcagag agctacacac  18420
acgtccgcac actcaggaat ccccattaaa aatagtcaag tggaagctat acccagggga  18480
cctcttgcag accagtgcag ccccagtgca tgctgcctca gtctctcaac gggcagtttt  18540
taacacaggg tgctgattcc cgccaatatc aattgtcata atcaccttag ttactatgtt  18600
gaaacaaaca caagcaaact cgggcattgt gtcactgagg aatgttcacc gctgagttca  18660
caggttgccc catggatatt ttccagcact ctgcctttgc agacctgaat gtaagccagg  18720
tcatcacccc cgatgccttt gtgtgtcgca ccatctgcac cttccatccc aactgccttt  18780
tcttcacgtt ctacacgaat gaatgggaga cagaatcaca gaggtgagtg tgagcggcgt  18840
gcgccccctt ctagcccttt ccgttccttg cgagggtctt gctcgttgcc ctaacagcgc  18900
tggagcctgt ggtttaaccg gatgcttttc agccaggtgc aggttacttc acagattaac  18960
aaattcttcc cttccataaa acaagcctac tatttagtca aaccacagcg gcagaggcag  19020
aagggagcag gaagcattct cactggcatt aaggtttggg attggcttgg gttacagctg  19080
ctcatgcaaa ctgtccttta atcttgtgag aaaccagagc cctgcttatc cagatctagg  19140
gtctagtctg acctcttcat ctttacacag catttccttt atgtacgccg tggggcctgc  19200
agaaggatgt gtgtggacat aataccatgg gtagcataaa tccaaaccaa cagtcttttg  19260
atgccttctc tttttccttt ttctaattag aaggtggact ttaatcctct gtcctctttt  19320
ctggatgtct gtacctacca ggtatttttt gccagaggga gaggtgactc tacttacatt  19380
taagccctgt gatatttttg gagtcttgca gtctgactga ctgaaaataa tttctcagaa  19440
gaataccatt tatggagttg cttagagagg aaggaaggaa ggaaggaagg aaggaaggaa  19500
ggaaggaagg aaggaaggaa ggaaggaagg aaagaaggaa ggagagagag agagagagag  19560
agagagaaag agaaagagaa agaaagaaag aaagaaagaa agaaagaaag aaagaaagaa  19620
```

agaaagaaag aaaggaagga aggaaggtag gtctgtctag tgcttctaat gctgtcttct 19680
tcttctttct catttatttt taatagaaat gtttgttttc ttaagacgtc taaaagtgga 19740
agaccaagtc cccctattcc tcaagaaaac gctatatctg gatatagtct cctcacctgc 19800
agaaaaactc gccctggtaa tgactcaatc ttagtggcac atggcatgtg tccgggtttg 19860
gttcttggtt gcttgataaa tactatgacc aaaagcaagt tgggagagaa aggagtttgt 19920
tttgttcaca tgtcccagtc atagctgatt cctgagggaa gtcaggctag aaactcaagc 19980
agaagcagag gcagggactg ggcagagacc atggagaaat gttgcttctt agcttgcttc 20040
tgtgaatata tatatatata tatatatatt catgctacct gcccagaatt gacactgacc 20100
tggttagacg gaccctcttc catccatcat taatccaaag aacatcccac agacatgcct 20160
ataagttagt ctgaggaaga cgattctcag actgatggtc catcttttca ggtgactcta 20220
ttttgtatca agttgacaaa cactaacagc cacatggtgc agcacatctt ggggtcctct 20280
aagagttaat gaaatggttc tcacgactct agaaactttg ccaatgtgac tcgtttcctg 20340
acttgtgata tatcctttga tatttgtgta tggtgcagaa ccctgccatt ccaaaattta 20400
ctctggagtt gactttgaag gggaagaact gaatgtgacc ttcgtgcaag gagcagatgt 20460
ctgccaagag acttgtacaa agacaatccg ctgccagttt tttatttact ccttactccc 20520
ccaagactgc aaggaggagg ggtaaggaaa cctttctttg atgatcagca aggtaattgt 20580
tttctagttt tctccctgtg tgggggttta attttagact gttcatttat ttccaggtgt 20640
aaatgttcct taaggttatc cacagatggc tccccaacta ggatcaccta tggcatgcag 20700
gggagctccg gttattctct gagattgtgt aaacttgtgg acagccctgg tgagtgaggt 20760
tcgtttgtta cggaactgca tggctggctt ggctgttgtg attaatgtct tggtcttatg 20820
tgatgggatt gtttatatgg tttctgttat ggtttgtata tgggagtggc actatcagaa 20880
ggtgtgaccc tgttggagta ggtgtgtcac tgtgggtgtg ggctttaaga ccctcatcct 20940
agctgtctgg aagtcagtat tctgctagca gccttcagat taaggtgtag aattctcagc 21000
tcctcctgaa ccaagtctgc ctgcatgctg ccatgttccc accttgatga tagtggactg 21060
aacctctgaa acctgtaagc cagccccaat taaaacttgt ccttggtcat ggtgtctgtt 21120
cacagccgtg aaaccctaac taagacagtt tccttggata aagggaaaga atgcttatct 21180
gtgtctaatc ctgccacatc tcaacacttt tcagactgta caacaaaaat aaatgcacgt 21240
attgtgggag gaacaaacgc ttctttaggg gagtggccat ggcaggtcag cctgcaagtg 21300
aagctggtat ctcagaccca tttgtgtgga gggtccatca ttggtcgcca atgggtactg 21360
acagctgccc attgctttga tgggtaagtt tcagggtcat cttattatac caatgtgtgt 21420
gtgtgtgtgt gtgtgtgtgt gtgtgtgtgt gtgtgtgtgt gtgtgcatgt agaggttaat 21480
ctcgggtatc tacttgtact gcttgttcat cttatttgtt gagatagggt aattcactga 21540
acctagtgct aacctttttg actagacaga taggtatctg cctgtctctg tctcctggta 21600
catccttagc cctagttctg ggttggggat ctgaacttga atcctcaggt ttgagaacca 21660
agccctttgc ccactctgcc atctccttgg ccctgagata tttgttttta ggacaagaaa 21720
agtttcaaag tccttgccta gaaaatatta taattttaaa ttcagcctgt atatccttta 21780
cgtggttaat ttaaaattca aaggaaaggt aggtagattt ttaagcaaca aaataccttt 21840
aattcctgct ggggcttatt ttaatcagta cagctacatg aaggctcgga taatgagagc 21900
aactgttttt ggggttggta gactgaacct gattctccca aaggttcttc aaaaggcaca 21960
gaagcactcc tgtgctctta cttgaaataa acagaaagta atttttaagt acgtcttgag 22020
tgtttccagc cacagcgttt atactgtgaa ctgtaatcct ttaggaacac agtgcaacag 22080
aatatgagcg tcttccaaga ttttagcaac agtaaagggt ccctgaaggg acactgataa 22140
aaatgaatcc acaataaaaa gtatgacaaa cccgaggcat tctgagagcc ctctcctgtg 22200
ctgtgtctga ggattcctct gcagcctttg ttcctgacac acaacatcat gcttactgtg 22260
cactgtgcat atcgccaggc tgcgtagtac cagcagatgg taccctaaac ccaatcaatc 22320
agactgagga ttctttaatg gtgtgaaact ggtgtgtgtg gtatgtgtgc cttaggattt 22380
ctgctcttac aggaacataa cagtataatt ttaaacaatt taaaaaaaaa cattaagatg 22440
tctcttgtca cagtgtgtct ttggattgta cagtgttaaa ctctgatttt cagtgttgct 22500
ccagctggtt agttgagttt cataaaaact cattgaatga acttgggctt ggatattaga 22560
gtttccaaaa ctttctaaac cgtccttaat ctaagactat catttggttc tccacattta 22620
tgtgaagtgg tgcttctcag ctttatcagt tataaaagta aaaaattaag gaactcctaa 22680
aaacattgag gttgttcttc gtcttttagt atgaaatact tagacatgtt ttaattattt 22740
atgtggaaat aaacaagccc attattctat taatatgagc gtttgctaat aagtggtaaa 22800
aattctccat acatcaaaaa ttgtcttgca gtaaatttct ttataatata ttaccagtaa 22860
atgtttaata tgtgtacctg cttcatatag tcacacacag agacataaaa ataaaatctt 22920
ttcaggcaaa agggagtctt aaatggaaga aagttttatt acaaactaaa tcttcaaagt 22980
ccaatacgac tgctgtaagc aatgacaggt tgccttgcca ggaaaaggtg actaggtcat 23040
atggaatgtt gtctttcttt tctctccacc ccttcaagaa aatgtgctaa gaaaaaggag 23100
cggaggaagg atgccaacgt tactttgttt ccctcctaga attccctatc cagatgtgtg 23160
gcgtatatat ggcggaattc ttagtctgtc cgagattacg aaagaaacgc cttcctcgag 23220
aataaaggag cttattattc atcaggaata caaagtctca gaaggcaatt atgatattgc 23280
cttaataaag cttcagacgc ccctgaatta tactggtatg cagcatattt aagaggaacc 23340
tgcacaactc aatggtattg gtgtcaattt ccacttcagt ttgcatgaga agagagatct 23400
gcagcaattg tctttgtgtc ctggttggtg aggctgaggg agagatgagg ccacctgggc 23460
agtagaaatc ccgtgtcttc ccatacattc actgctatct gaggggcaaa aaagcttcat 23520
tactttctca gagtggcatg caactgagtg tatggtattg gtctaggaaa gattttgaca 23580
tctggggaca ttgggcatct tctgacaaga ttggcagaat gactatggct taggaatata 23640
caaccatatg aaagtgaacg ggactagatg ttagtgccca agaataccct ggttgacaat 23700
ggggggacac ggagcatgga gctgctttgg aggcacatca ctccacagga atggaatgtc 23760
tgccaacacc attacctgca agtgtctgtg aacagtcatg agaccttaga cagcttggct 23820
ttcctccttc cacctctaat atctgctgca cgcgtgctga tctccgtgtt gcttccttgc 23880
aatcattaag caacgtattc aaataaagcc ctgggagagt atggctattt ttgctctgtt 23940
tctgaattct gctacagtgt atattaaaca agacataaga aagtagacat atgtttgcca 24000
ataaattttg gttgaagagt ccctcttccc catagaaatt tcgttccaaa atgccataca 24060
gaatgtgaga attgtcttga attgtgggct ttagaaattg ctcagaaagc tggagggtcg 24120
ttctttttag ttttagtaat gggtttcatt atatttcata catatgcata gtatgatgta 24180
attgtattca catccttcac tctctcttgt cattttcact cctgcagttc tccctgctcc 24240
tcccaagtag tcccagactg gtcattcttg ctttgttgct ttgtagaaaa agaataagag 24300
aaaaagatag atactaattt ttgaagttcc catctatggt ttcaattagt ccaaatctat 24360

-continued

```
tcatgaaatt ttctttcaga attccaaaaa ccaatatgcc tgccttccaa agctgacaca  24420
aatacaattt ataccaactg ttgggtgact ggatggggct acacgaagga acaaggtaca  24480
gtatggcatg tgaaatgttc ctgtcttaca tgctaaagta catagagtag atccactcaa  24540
caagccttac tcatgacctt tctgttcatt ccaaactatt ggtcctctga ttcccaagaa  24600
tgtgaatttt tttacattaa acatcaatga gctaatcctt taagaatatt actcataata  24660
gagattattt ttatgagtct gcattaagaa ctgtggccct atgatactat caagtccact  24720
gaatcccatg tggtcctcag tacttactgt gtccctgttt gctaagttct cccttggtat  24780
caatagctaa ggtgccagca tctctcttga agaacagttc ttaatattta tttaaatgcc  24840
ttcttgtaaa aaatctgaca tttcctctaa ttatgccatt aaatccttat gtaaaataca  24900
tagattcata aagagagaaa agtagattgc agtacagtta ccaacatttg ttaatagaat  24960
tttacatagt gatgatcata tttgattatt agtgtactca gttgcaaatt gttttaaaat  25020
ctaccataat gttgaagtag ttatgggcat aaacaacatt ttcctttctg tcgtaactac  25080
aattcaaagt atctgtgacc cttacactac agtgctgcca acaatatcac attcctgcat  25140
tagttatctg aacttaaaac tgaagggcgt ctgcagcttt atttgaaagg ttgagaatat  25200
agaggcgagt ttttcgcttt cccttccgct gagtgtatgg atgcctcgat tgtgtggctc  25260
tgaactcaag acccctgtgt gctgagactt gagctatttc tctagaaata agaatgcttt  25320
ctttctagac tgagtgccag ataaccagca ttagacatat ttgagtgatt ttttttaaag  25380
gagatgattg gctgtgtctt ctttatattt cctgaaccag tcagtactgt attcaattag  25440
ttcccatttt ccactacatt tacttggcta cctatatgtg gacacacaca tatatacatg  25500
catatacata catacataca tacaaacata catacaaaca tctgagaaat atagacatgg  25560
gtagacatta agttatctgt aaatgtatca tttattgcag aacaaaatac tactctgctg  25620
tcagatgttt gggatgtatt ctcataaatt gtacatttta ttataatttg aatttctaaa  25680
acaatgaaag gcaagaacat cctttaaagg tacaaatgtg tgagacaaca tttttttgagg  25740
ggggcatcgg ttgatatagg aggatgcctg agatcataga aacaagtctg cagaggcttg  25800
ggtgctagcg agtctgaaat atgtcactag aaggaaggca gcacggatca ctgctccttc  25860
atctccttct cccccttctc cttctccctc tcccggtctc tcttctccct ccacctcttg  25920
cttcccttct ccctcccttt ccctctgccc tatttattga acttcctctc cttaaaggca  25980
cttcttgatt gcttcatagg tgaaacgcaa aatattctac aaaaggctac tattcctttg  26040
gtaccaaatg aagaatgcca gaaaaaatac agagattatg ttataaacaa gcagatgatc  26100
tgtgctggct acaaagaagg cggaacagac gcttgtaagg taatggggaa aaaatacaca  26160
atagttccat gaagacagtt cattcaaaaa cgaatctcca aagttatatt tcattagttt  26220
tggttctgaa gttccagagt taaacgattt gaaggctatt tgaaacgata gcctttaaca  26280
aattaaacac acatagtgca tattatatgt tacttataat agttatgcta gaatatgtat  26340
tgctgtgaca ggtatgtcac agtgaggaca ggggcatgcc aaatttaagg acaattttta  26400
catgccatgg tcatgctaaa atacaagaaa agtagattta tttgaacttg gagtaaagat  26460
gctaagtctg ttgggtttat ctgagaatgg gagagggaat aaattggcct tgtaaccatt  26520
cacttatttt tttttcatg gctaatggga tgcacagaaa ttgagaggct ccgtggtggt  26580
gtgtaaagtg tgactgccaa atattaaaga catctgtcta tgagcaaggg gctccttatt  26640
tgcatcatca ccattacccc tctctacctt tgtatttctc taccctctgt gacccaggga  26700
gattccggtg gccccttagt ctgtaaacac agtggacggt ggcagttggt gggtatcacc  26760
```

-continued agctggggtg aaggctgcgc ccgcaaggac caaccaggag tctacaccaa agtttctgag 26820
tacatggact ggatattgga gaagacacag agcagtgatg taagagctct ggagacatct 26880
tcagcctgag gaggctgggt accaaggagg aagaacccag ctggctttac cacctgccct 26940
caaggcaaac tagagctcca ggattctcgg ctgtaaaatg ttgataatgg tgtctacctc 27000
acatccgtat cattggattg aaaattcaag tgtagatata gttgctgaag acagcgtttt 27060
gctcaagtgt gtttcctgcc ttgagtcaca ggagctccaa tgggagcatt acaaagatca 27120
ccaagcttgt taggaaagag aatgatcaaa gggttttatt aggtaatgaa atgtctagat 27180
gtgatgcaat tgaaaaaaag accccagatt ctagcacagt ccttgggacc attctcatgt 27240
aactgttgac tctggacctc agcagatctc agagttacct gtccacttct gacatttgtt 27300
tattagagcc tgatgctatt ctttcaagtg gagcaaaaaa aaaaaaaaaa aaaaaaaaaa 27360
aaaaaaaaaa aaaaaaaaaa aaaactgaga aagaggtaga aatctttgta acatttcatt 27420
tagaataaaa agagtctcta cttgaacctg atgggacatc taaaccacct ttctggccat 27480
tgctgcagag ttctgcatgg tcatgactgc atgaggtttc ctacccctgg agcagagcca 27540
tctgggcatg agggttgctt gtataaactt catgttcctc cctcaggaaa taacctctct 27600
gcctaggtta ttgaggaata tcctctctgc caggacagcc cttaagactg tgggaaagaa 27660
ctcttaaaac ataagttcaa gaatatataa tttctcagct atgtaaaata taaggataca 27720
atatgaattg tataaggaga ttcgattcgt ggacctaaaa gaacaaaggc agctgcacta 27780
tgagccagct tgtcagaaag atactactga aggagataaa gagataaaga gatttaggga 27840
gtggtgataa cagggcaaga tcccagccag ctaagtttat tatttgtgct tacataggca 27900
ggcagagtcc tgagttcaag atcagcctgg gacagagcta gtttagaccc agggttggtg 27960
ggaatcccac ccagctagct tgttgtctat gctaagaaag acaggcagat ctctgaattc 28020
atttggcatg tttttttttt ttaaaaaaag tacctgatgt cttttcttaa gaatcaagag 28080
gctagagtca tggaatgctg actcatgggt taaacaaaag ggaatctaga gtaagtgact 28140
gagttgatat gtaaataaaa gactgggctt tagtctgcaa gagctgagct acctggatga 28200
gctgtctgga gatctctgta gagcagaata ctagtctcta atttttttag attttttttt 28260
tttctagtag ctactcagag agaactgctt agagaatgaa atgaacattg ctattttagt 28320
tgtgttgttt tgtttttttt tttttctaga aaatccaaaa atattttata gaagcttctc 28380
tgactctagt cagaaaaccc atgagctagc cagagagctt ttggattttt ttttcctagc 28440
aagagaaagc tgtctcaaga agagacagct gtctcaagca aaagagctgc cttgagcaga 28500
aagctatctc tatcagactg catagccaag agctatctgc agaaagctgt ccagctgtct 28560
agactacaag gctgtcagct tgcaacccat catatgactt tgagttgttt ctttcaccgc 28620
tcccagacac cccttctcgc aggaacctcc ctccaagcca aggctggtcc tgggcacctt 28680
gccacatggt cttggctaca gatgtgtgca agacctgtaa ggctatattt ttcttcttgt 28740
gtgcagctcc tgcaataggc ctatcacaca gtactcacac agggcaaggg atctgatgag 28800
aacctcctgg ggaaccctcg gggttcagct gatgctgtat tctgcaatag taattcatgt 28860
aatgtcattg ggtgtaaagt gttgtataaa attcaagctt ccaattgagt tgaaagtgaa 28920
aagcaatctt ggaatggatg acattaatcc tcatgcaaga caaatttcca gcttcccatt 28980
gattcataaa gtgggtcatc tgtgcttaac tccatttagt taacctggtt aatatttaga 29040
cagaattagc catttacgaa ctactgtgca agttaaacag acaaatagaa aagtgaaatt 29100

```
tcctaaagaa gattaaactt ttccttgcat atataaaggc ttgttgagta gtgcagaggg  29160

ttaaatatgg aagatcctgt gggttatcta cagagttcac catgggaagt gtaagaggtg  29220

gaagcaaatg gctttggaaa aatcttccaa gcacacaact tcaactttta attttgtaca  29280

ccatttcatc ttaatctgtg tggcagttgt tttatattta aaaagaaaga agtggttctc  29340

aatgaaaatc ttgtatctca aggtttcata ttaataaccc taacaggtat ttacacaagg  29400

tgtcacagta cttactgggt aaactttggg ctttggtttc tcaaggaatg gcctcatttg  29460

agcaaaacag agttttgaaa tgagggattt ccctatggcg taaagtacca tgatcacgtt  29520

gccagctgga gtccagctgg gctggaatgc tctgcttttc attgtgtgtt cctgcacaaa  29580

gtagcccgtc ttccactcga agccttaaga ggctgagaaa atgagagggc cggataacat  29640

cacttttaca agacaaagtg gaggcaggag gccctagatc tttggcaggt ccatccaaga  29700

aagggagtgt cacctctgga atggaacaat gccggcactg ttcttcctgg gccgcacgtg  29760

gagagcacac agcacaccac taacacttct agagctcaac gggaagctca aagggctgtc  29820

tgatctctat ctattttttt tcttgtagtt cttgcttatg gctaccagcc ctacaaactg  29880

tcaacaactc tgaaggatgc tcttgcatct ctgcctctct ctttcatcag tacttcatgt  29940

gaataggaat gtggcaaata ggagagattt gggtttgctg ttattatttt tgttgctgtg  30000
```

<210> SEQ ID NO 14
<211> LENGTH: 2513
<212> TYPE: DNA
<213> ORGANISM: Rattus norvegicus
<220> FEATURE:
<221> NAME/KEY: CDS
<222> LOCATION: (65)..(1981)

<400> SEQUENCE: 14

```
tgaagactag cttcatgtga agactccttc tcctccagca gcacaaagca accatccttc     60

cagg atg att tta ttc aaa caa gtg ggt tat ttt gtt tcc ttg ttc gct     109
     Met Ile Leu Phe Lys Gln Val Gly Tyr Phe Val Ser Leu Phe Ala
     1               5                   10                  15

aca gtt tcc tgt ggg tgt ctg tca caa ctg tat gca aat acc ttc ttc     157
Thr Val Ser Cys Gly Cys Leu Ser Gln Leu Tyr Ala Asn Thr Phe Phe
                20                  25                  30

aga ggt ggg gat ctg gct gcc atc tac acc ccg gat gcc cag cac tgt     205
Arg Gly Gly Asp Leu Ala Ala Ile Tyr Thr Pro Asp Ala Gln His Cys
            35                  40                  45

cag aag atg tgc acg ttt cac ccc agg tgc ctg ctc ttc agc ttc ctt     253
Gln Lys Met Cys Thr Phe His Pro Arg Cys Leu Leu Phe Ser Phe Leu
        50                  55                  60

gcc gtg agt cca acc aag gag aca gat aaa agg ttt ggg tgc ttc atg     301
Ala Val Ser Pro Thr Lys Glu Thr Asp Lys Arg Phe Gly Cys Phe Met
    65                  70                  75

aaa gag agc att aca ggg act ttg cca aga ata cac cgg aca ggg gcc     349
Lys Glu Ser Ile Thr Gly Thr Leu Pro Arg Ile His Arg Thr Gly Ala
80                  85                  90                  95

att tct ggt cat tct tta aaa cag tgt ggc cat caa tta agt gct tgc     397
Ile Ser Gly His Ser Leu Lys Gln Cys Gly His Gln Leu Ser Ala Cys
                100                 105                 110

cac caa gac ata tac gaa gga ctg gat atg aga ggg tcc aac ttt aat     445
His Gln Asp Ile Tyr Glu Gly Leu Asp Met Arg Gly Ser Asn Phe Asn
            115                 120                 125

ata tct aag acc gac agt att gaa gaa tgc cag aaa ctg tgc aca aat     493
Ile Ser Lys Thr Asp Ser Ile Glu Glu Cys Gln Lys Leu Cys Thr Asn
        130                 135                 140
```

-continued

```
aat att cac tgc caa ttt ttc aca tat gct aca aaa gca ttt cac aga      541
Asn Ile His Cys Gln Phe Phe Thr Tyr Ala Thr Lys Ala Phe His Arg
    145                 150                 155

cca gag tac agg aag agt tgc ctg ctg aag cgc agt tca agt gga acg      589
Pro Glu Tyr Arg Lys Ser Cys Leu Leu Lys Arg Ser Ser Ser Gly Thr
160                 165                 170                 175

ccc acc agt ata aag cca gtg gac aac ctg gtg tct gga ttc tca ctg      637
Pro Thr Ser Ile Lys Pro Val Asp Asn Leu Val Ser Gly Phe Ser Leu
                180                 185                 190

aag tcc tgt gct ctc tca gag atc ggt tgc ccc atg gat att ttc cag      685
Lys Ser Cys Ala Leu Ser Glu Ile Gly Cys Pro Met Asp Ile Phe Gln
            195                 200                 205

cac ttt gcc ttt gca gac ctg aat gta agc cat gtc gtc acc ccc gat      733
His Phe Ala Phe Ala Asp Leu Asn Val Ser His Val Val Thr Pro Asp
        210                 215                 220

gcc ttc gtg tgt cgc acc gtt tgc acc ttc cat ccc aac tgc ctc ttc      781
Ala Phe Val Cys Arg Thr Val Cys Thr Phe His Pro Asn Cys Leu Phe
    225                 230                 235

ttc aca ttc tac acg aat gag tgg gag acg gaa tca cag agg aat gtt      829
Phe Thr Phe Tyr Thr Asn Glu Trp Glu Thr Glu Ser Gln Arg Asn Val
240                 245                 250                 255

tgt ttt ctt aag aca tct aaa agt gga aga cca agt ccc cct att att      877
Cys Phe Leu Lys Thr Ser Lys Ser Gly Arg Pro Ser Pro Pro Ile Ile
                260                 265                 270

caa gaa aat gct gta tct gga tac agt ctc ttc acc tgc aga aaa gct      925
Gln Glu Asn Ala Val Ser Gly Tyr Ser Leu Phe Thr Cys Arg Lys Ala
            275                 280                 285

cgc cct gaa ccc tgc cat ttc aag att tac tct gga gtt gcc ttc gaa      973
Arg Pro Glu Pro Cys His Phe Lys Ile Tyr Ser Gly Val Ala Phe Glu
        290                 295                 300

ggg gaa gaa ctg aac gcg acc ttc gtg cag gga gca gat gcg tgc caa     1021
Gly Glu Glu Leu Asn Ala Thr Phe Val Gln Gly Ala Asp Ala Cys Gln
    305                 310                 315

gag act tgt aca aag acc atc cgc tgt cag ttt ttt act tac tca ttg     1069
Glu Thr Cys Thr Lys Thr Ile Arg Cys Gln Phe Phe Thr Tyr Ser Leu
320                 325                 330                 335

ctt ccc caa gac tgc aag gca gag ggg tgt aaa tgt tcc tta agg tta     1117
Leu Pro Gln Asp Cys Lys Ala Glu Gly Cys Lys Cys Ser Leu Arg Leu
                340                 345                 350

tcc acg gat ggc tct cca act agg atc acc tat gag gca cag ggg agc     1165
Ser Thr Asp Gly Ser Pro Thr Arg Ile Thr Tyr Glu Ala Gln Gly Ser
            355                 360                 365

tct ggt tat tct ctg aga ctg tgt aaa gtt gtg gag agc tct gac tgt     1213
Ser Gly Tyr Ser Leu Arg Leu Cys Lys Val Val Glu Ser Ser Asp Cys
        370                 375                 380

acg aca aaa ata aat gca cgt att gtg gga gga aca aac tct tct tta     1261
Thr Thr Lys Ile Asn Ala Arg Ile Val Gly Gly Thr Asn Ser Ser Leu
    385                 390                 395

gga gag tgg cca tgg cag gtc agc ctg caa gta aag ttg gtt tct cag     1309
Gly Glu Trp Pro Trp Gln Val Ser Leu Gln Val Lys Leu Val Ser Gln
400                 405                 410                 415

aat cat atg tgt gga ggg tcc atc att gga cgc caa tgg ata ctg acg     1357
Asn His Met Cys Gly Gly Ser Ile Ile Gly Arg Gln Trp Ile Leu Thr
                420                 425                 430

gct gcc cat tgc ttt gat ggg att ccc tat cca gac gtg tgg cgt ata     1405
Ala Ala His Cys Phe Asp Gly Ile Pro Tyr Pro Asp Val Trp Arg Ile
            435                 440                 445

tat ggc ggg att ctt aat ctg tca gag att aca aac aaa acg cct ttc     1453
Tyr Gly Gly Ile Leu Asn Leu Ser Glu Ile Thr Asn Lys Thr Pro Phe
        450                 455                 460
```

-continued

```
tca agt ata aag gag ctt att att cat cag aaa tac aaa atg tca gaa     1501
Ser Ser Ile Lys Glu Leu Ile Ile His Gln Lys Tyr Lys Met Ser Glu
    465                 470                 475

ggc agt tac gat att gcc tta ata aag ctt cag aca ccg ttg aat tat     1549
Gly Ser Tyr Asp Ile Ala Leu Ile Lys Leu Gln Thr Pro Leu Asn Tyr
480                 485                 490                 495

act gaa ttc caa aaa cca ata tgc ctg cct tcc aaa gct gac aca aat     1597
Thr Glu Phe Gln Lys Pro Ile Cys Leu Pro Ser Lys Ala Asp Thr Asn
                500                 505                 510

aca att tat acc aac tgc tgg gtg act gga tgg ggc tac aca aag gaa     1645
Thr Ile Tyr Thr Asn Cys Trp Val Thr Gly Trp Gly Tyr Thr Lys Glu
            515                 520                 525

cga ggt gag acc caa aat att cta caa aag gca act att ccc ttg gta     1693
Arg Gly Glu Thr Gln Asn Ile Leu Gln Lys Ala Thr Ile Pro Leu Val
        530                 535                 540

cca aat gaa gaa tgc cag aaa aaa tat aga gat tat gtt ata acc aag     1741
Pro Asn Glu Glu Cys Gln Lys Lys Tyr Arg Asp Tyr Val Ile Thr Lys
    545                 550                 555

cag atg atc tgt gct ggc tac aaa gaa ggt gga ata gat gct tgt aag     1789
Gln Met Ile Cys Ala Gly Tyr Lys Glu Gly Gly Ile Asp Ala Cys Lys
560                 565                 570                 575

gga gat tcc ggt ggc ccc tta gtt tgc aaa cat agt gga agg tgg cag     1837
Gly Asp Ser Gly Gly Pro Leu Val Cys Lys His Ser Gly Arg Trp Gln
                580                 585                 590

ttg gtg ggt atc acc agc tgg ggc gaa ggc tgt gcc cgc aag gag caa     1885
Leu Val Gly Ile Thr Ser Trp Gly Glu Gly Cys Ala Arg Lys Glu Gln
            595                 600                 605

cca gga gtc tac acc aaa gtt gct gag tac att gac tgg ata ttg gag     1933
Pro Gly Val Tyr Thr Lys Val Ala Glu Tyr Ile Asp Trp Ile Leu Glu
        610                 615                 620

aag ata cag agc agc aag gaa aga gct ctg gag aca tct cca gca tga     1981
Lys Ile Gln Ser Ser Lys Glu Arg Ala Leu Glu Thr Ser Pro Ala
    625                 630                 635

ggaggctggg tactgatggg gaagagccca gctggcacca gctttaccac ctgccctcaa   2041

gtcctactag agctccagag ttctcttctg caaaatgtcg atagtggtgt ctacctcgca   2101

tccttaccat aggattaaaa gtccaaatgt agacacagtt gctaaagaca gcgccatgct   2161

caagcgtgct tcctgccttg agcaacagga acgccaatga gaactatcca aagattacca   2221

agcctgtttg gaaataaaat ggtcaaagga tttttattag gtagtgaaat taggtagttg   2281

tccttggaac cattctcatg taactgttga ctctggacct cagcagatca cagttacctt   2341

ctgtccactt ctgacatttg tgtactggaa cctgatgctg ttcttccact tggagcaaag   2401

aactgagaaa cctggttcta tccattggga aaaagagatc tttgtaacat ttcctttaca   2461

ataaaaagat gttctacttg gacttgaaaa aaaaaaaaaa aaaaaaaaaa aa           2513


<210> SEQ ID NO 15
<211> LENGTH: 30000
<212> TYPE: DNA
<213> ORGANISM: Rattus norvegicus

<400> SEQUENCE: 15

attcctccag cccctgtatc acgtcaaact cgaaactcca gctccaggac tagctgcagg     60

cattgatgct tctgcgctgt ttccattctg tgatcatgtc ttctccatac ctacctctaa    120

gttttccatg aggtctcaaa gtaaaagctt taagaagaaa aaaaaagtgt tgtccagcag    180

gtttcagtaa gctttgctgg agaggaccag ataataaaat cttagtttgc ttgtttgttt    240
```

-continued

```
tgttgttgtt actgaagacc gttctataat cataggaagt aggcaggcat acatcgtgca    300
gcagtgaatg gacatggttg tgttccatta aaacttcagc tagaaggaca aatcccaagc    360
aagatttgtt ctgtaaacag tggattatta actcagtact gggtggatct gaacatgaac    420
ttccagtgta ataaaaaggt agaaaagcag aagtgtgaag aatcccgaga gctcagggga    480
gaccactgct tctgctcaca ttcctggccc aagaggactc cccctggaga cctctggaca    540
caagaaccga ggagcagtct ggttcctgcc tgtacccaga actgacactg taacacatct    600
acacagtgga gtattactca gctattaaaa acaatgactt catgaaattt ataggcaaat    660
ggatggaagt agaaaatatc gtgagtgagg tcacccaatc acaaaagacc cacacggtat    720
gccctcactg ataagtggat attagcccaa aagctcggat tacccaagat acaatccaca    780
gaccacagga agctcaagaa gaaggaccac caaagatgca gatgcttcag tccttcttag    840
aagggggaca aaaatattca taggagaaga taaggagaca aagtttggag cagagactca    900
atgaatggtc attcagagct gccccacctg gtgatccagc ccacatgcat acagccacca    960
aacccagaca gtatttctca tgccaagaaa tgcatgctga caggagcctg atatagttgt   1020
ctccagagag actttgccag ctcatgacaa aaacagaaga gaatgtttgc agccaatcat   1080
tgaactgaaa ccagggtccc tgttggagga gttagtgaaa agattgatgc aaccccgtaa   1140
gaacaacaat accaaccaac cagagctccc agggactaaa ctaacttcca aagagtactc   1200
atgaacaggc caatgtctcc agctgtatgt atgtagcaca ggatggcctt tctgggcacc   1260
agaggaagaa gcccctggtc ctgccaaggc tggaccctcc cccagtgtag ggaatgtca    1320
agatggagag gtgggaagag gtaggttttt gggttgggaa aaggtgataa catttgaaat   1380
gtaaatttta aaaatccaat ttaaaaaagg tagaaaacca ataccttgct ttgattctcc   1440
tataggagct gtctacccca cccccacatt gaggtgtgcc tccaggaaat ttcaatagaa   1500
gtatacacac acacacacac acacacacac acacacacac acacacacac acttgtaaag   1560
gcaaataggt aagaatcaag ctgttagtcc ccaaataaag agatatgacc attttcaaaa   1620
tgggagacct atgcctgaat tgtgtgtccc tagtataaag cacttctctt tcttcagcat   1680
aagcacttaa acgcatttcc catgtataat ttatttaaaa tgggttcttg atatgcttgt   1740
aatataatga tatcttggta tacatgaaca ctgtaacatt atttccactc taaagttact   1800
taacacagtc accatctcag acaattatta tgtatgttac gaatacctgc ataccagggt   1860
acagtgtgta cacctataat ccagcactct gaagatctag attcagtggt tctcaacctg   1920
gggagagggg tcacatatca gatatttaca attcataaaa gcagcaaaat tacaattatg   1980
acgtagcaac aaaatacctt tatggttggg gatcactata catgaggaac tatattaagt   2040
cgcagcttag aaaggttgag aactactgct ctataggatg caaagacagc tcaggggtgc   2100
tcttgaagag aacccaagct cagttcccag caaccacatc aggtggctca caaggacctg   2160
tgtctccagc tccaggggac ctgattccct ctgtcggtct gcaacgtgca tgcatttgca   2220
gtgaaagaga cacatcatta gaaataaaat aaatggttaa aatttaacta atgttgctat   2280
tgctgggcat gggatcttgc agtctattag ttctaaaagc tgaaattttg tatcctttca   2340
caaacaccac ccatgacacc aagtttcaga tcctgacact caccatccca cttgtttcta   2400
gggcttgcct ttttcaaatg ccacatgtaa gtatagctct tcaaatggcc atatgttttt   2460
atatctccac cagttttgca tcactgcaat ccaatacctt gagcccctat gtcgaattta   2520
taatctgccc atcagttgac tttaatttat ttagggttgc ttataagttc ctaatttttt   2580
tcttttggtg attttgtttt tcttttctga ttatttgtga tcttctggct ttgtgttggt   2640
```

-continued

```
gtttgcactt ttagataaga ggctatttta aatttaattt ttaaaaattt atttattcac   2700
ccattgcaag gctatgtgtg tgtgttctgt gcaggttctg gggattggac tcaggtcatc   2760
aggcttgatg gcaaatgctt ttgacctact gagatgtctt gtaagctcca cgatgatttt   2820
agacttttaa agcttgcttc actgggcaaa cctagtagtc atgtatctca tcaatggatt   2880
ctgggttagc caactgtgta gttagagttg gatatgcaag gctaggtttg aatcttgggt   2940
ccacagaaaa gagcattgca tcagggtcca ccgtgattac attgatgact gaattcctag   3000
agcccatgct tgaatcctca gatcagtggg gccacgatct tatgattgag gactgcctta   3060
acatgttgat attgaaatga acctgaaaac tgagcctcca gtggccatgt taacgaactc   3120
aagcccgtgg gcatgggttt gttcctgaat ctacaatcgc tgtcctggaa atgagccctg   3180
gaaatgggac aatctggtgg ctggcctgag gtatcatcct ggagcctggg tctgcagggt   3240
cagcctgata actgggattt cctggaatgg acttgtttac atctgtcttt attcataggg   3300
aacacatcgc cattctgtgc tgcccaggct tagtagcagg gttttatggt taaagtgaag   3360
gatcgaacac tcttcaatgc ctattcacta tgtccacagt ttcaccgggg gctgtaacct   3420
atcatctggc tttcttaaca cttggaaagg catggggaat tgttcccatg gattcttctg   3480
caaagggatg cgtggtggag attccaattt tgtcatggtg tttacatgac tttctggaat   3540
cggtaacata ttaagtactt gaacctggac tggaaggtcc atggactgta ttgacaggtc   3600
aaacagaaga cactgatgcc agaagcccag tgtcaacact ggagccaagc agagaccaac   3660
ctcagtgcca tattcggaga gcttgaagac tagcttcatg tgaagactcc ttctcctcca   3720
gcagcacaaa gcaaccatcc ttccaggtag ctactctcca ccattctcat tgtagcctat   3780
gtcttaggaa tttatttttt taaaaaagta taactatatc tgcatgaaaa agtctattgg   3840
tgtaatgcac taatttcctg agggtttaga aaatctacaa ggaattgttt ttctttgtac   3900
agctatatta atgtaaaata ttttaaagcc aaggataagc ttttgattct tttcaaagat   3960
gctctttatg tgggggttgt gggtgatatt attgtactca ttcataataa ttttgcataa   4020
atctagaaat ttaataagtg tttaattatt tgtatcaact ctctttacaa aattaataga   4080
aataattctt caaaattaac aataaataca ctaatacaca ctaattgtag tctagaggtc   4140
tcaatttgta tcttggggag catgataaat attttaattt tctatatcca aaatgtcccc   4200
tcctccaaat cctctttctc ctggtgatta tgtgttgtga tttgcaattt agacatttac   4260
caaaaaggtg aagtgtacat taaattaaat tgtctattaa atacatggta aacatgatct   4320
caacctagta gtagctaaat ttattttttt ctttcaaagg atgattttat tcaaacaagt   4380
gggttatttt gtttccttgt tcgctacagt ttcctgtggt aagtattagc ctgggagttc   4440
aaattaagtt agtgtgtgaa actataccac tcctggagaa agcctttaaa agctttgggg   4500
aagaaggcag ctgctgatag tccaaggcaa gaacctctcc ttagatacat tactcctgac   4560
acagaacggg gtgggggggg aacttagaag cttcaatgct tctgctagca gaaatttctg   4620
tatcaagatt tctctctagc agagtcctcc caccccaaag atttgcttgt gtttattacc   4680
agccctctaa ataaaaactc tacctgaaaa tcggaaagaa tatcagatat tgcataatga   4740
ttgagtccaa tccaagcttc tgattagtat atggtatttt taatataagg catagagagc   4800
catttctgaa ctgaaaacac ctgctttgga tttaatgagt gtagtaaccc tttggtagtg   4860
tggatggaca gctttaacac tagatgtcag tgttctttct ctgtgaattc cattacggtt   4920
cagaatgtga gcatggccct ggacaccccc ttctcaatag tcattataga gtgagatttc   4980
```

-continued cctgggcata tcatagtatt ccgatcaaag ctgactttgt ctagccacac ctcaagggct 5040
gatcttgact ctcaagtatt tggcaaagat gagcttatcc ttgtcaatag aagccatttc 5100
tctgggtaaa ctcattgttt tccctctctg ctccctccat ctggcccatc aactgtaact 5160
gcttttctgt gccacaacta ctgccatgat caaaccaatt aaacacgagc agtggtagtc 5220
agagatgcta tgggccatgg ctataaaatt tacgatcatg acaggaacgt gagacatgga 5280
aatacattta atacttgaga acaagtactt tacatagtcc taaagtacaa aataatgatt 5340
gcttgctttt ctttagtctt tcttattttt ctgcatgaat ctgttgtata aaagtgttat 5400
tcgtgaataa taattttaat gagaaattat gactattaat gacaaatcat ttttgactta 5460
cctttgctat ttatagctaa tgttaacaca aacaagcact tttgtcattc gttcttcttc 5520
acgctattct gtatgcatgt gacattctat gcacacattc aattatttct actgattcaa 5580
attttagaaa taaaaatttt tagatacaaa catgtgaata cctttgaagg ttttatggca 5640
tgcattatgg tattagcttc cagaaaggca tcctctgttt ggttttccct acgagcatgt 5700
gggagtgttc aaccatccca gttagagtga gccctaacag gcatctgtta ctttgtagtc 5760
tggcgtagga tcaccgttct aaaatagcat ccagatttct tcctgaggaa ccatctccaa 5820
cggatggccc acatggtact ggagatgatt ctcctgctgc agtcagacca gaactgcaga 5880
cagtgctggt gtgatgacct gaccagagct agtcttgtaa caggcttttt ctcagactta 5940
gaaaaaggct cagatttatt tttatttcca actcaacttg agctgctggt cctgccttac 6000
tagtgtgcat cttgagatga aggcagcatc acacaataga gtaaatcaac gctgacacac 6060
tgtgcatgga tgccattcct gagcagtgtc tagtgctcca taagccattg gctgtggaca 6120
catgggtttc tgaactgtta aactcattta tattcaaact gctctgattg attttctttt 6180
atttgtgaac aaagccagca cacaaatatt gtttcaagtt taatctttgt taacctggct 6240
gtttaaccca gtgttctgag tctgagactc ttacattttg ttttttaac ataaaatgta 6300 tttaatattg acatatcatt tctaagagat tatattgtta attcagaaaa agaatgtgtt 6360
atctacattc ttaaaatatc ataaagattt agacaatgat ttcttttta gaaagttatc 6420 taaattatca ctaatatgaa atatcaggtg gaatatcgtg tatttgtttt tctagtttag 6480
aaagaattaa tctgtagctt gtatgtattg actttgtgaa tgatgatagt ttttaaatgt 6540
ttttaattga cactaggatt ataccacccc tttcctccct ctagtttctc ctaggaacac 6600
ttccttgagc ttctcccatg ttcccctcac tctgaagctg attgcctctc ttttcattta 6660
gtattaatgc tacatatgta catatgtaca cagagatgta tgaatgcaac ttgttgagtc 6720
catttttgtt tgtgggtata tggtttgtgt gtgcttgtgc atattgaaca actagtaagt 6780
gggctcagct ctggaaaagg ttaattctct ttctccaaaa ggtcattagc tgcctatagt 6840
tctttgtcta aggtggggcc ccatgaaatt ccccctcca tgttactaca tccattgata 6900
ttgccatcgt tctggtccct tctgggaggg actgtttcac agcaaacttc ctgatattct 6960
ggctatcatt acctttctgt gttctctttc atgatatccc tcgagccata ggtttgggat 7020
atgagatgta gatatatcga ctggggctgg gagccccaca gtatgttgac ctccgcattg 7080
tgtccagttg tggatttttg tgatggtgtc tgtcttagtt agggttttac tgctgtgaac 7140
agacaccatg accaagataa gtcttataaa ggacagcatt taattggggc tggcttacac 7200
attcagaggt tcagcccatt atcatcaagg caggaacatg gtagtgtcca aggcaggcgt 7260
tgttcaggca gagctgagag ttctgtcttc atctgaaagc tactagcaga atgctgagtt 7320
ccaggcagtt aggatgaggg tcttaaagcc cacacccaca gtggcacatc tactccaaca 7380

-continued

```
gggccacacc ttcgaatcat gctaatccct gagttgagca aatacaaacc atcagtgtcc   7440
atttgctacc aagagaggct tctttgatga gagagagtag ctacctttat ctaggaaggg   7500
tggctcctgc actgttagca gcttttatac acatatagtt acttttatta attcggtaaa   7560
ttatcttttc atatctgatg ctgaatttta aaagttttag catttattta tttttactct   7620
atatctgcac atgcgtatac atatatacac atgtgctgtg gagcacatgt ggagatgaga   7680
ggacaacatg tggaggctca gttttctctc tgccactcac ctagagtttt gagttaagat   7740
gcttcattta tctatggaat tttccctttt ctttcttttt gattatgtac atttttaata   7800
tgactaaata actcagtcat ggtccatgga cctgcagttt attgaaagac atcattatag   7860
atcaattagg tcatacagac tctgtgcaaa caaggctgtc attgttctaa tcattactgc   7920
tcaccatcgt tatcattgct gccatcatca actgaggagg ataatccatt ctccagttag   7980
aatgtttcga ctcattcatt ctcattgact gagtcacgtg ttagtttacc aacactcaac   8040
tgcaggatag aaacttctag gctgccactc gatgatggtt tgtgattttg tatgtgtctg   8100
tgcaatggga tagtgaggga gtctctgctc aataattatg agatgctaac acattaaaaa   8160
aaaaagcaag tctctttata gctactgtca gcactgggcc tgctactcag tgtgttgtgc   8220
aaatgggaca gcctgggttg tacacttggg aacatatatt cctaggagca attacccagg   8280
aaaatctcct ctttccaaat ataaatctga cttaagaagg taggcatggc aacacccctc   8340
tgataagaag aaaaacagta ttgcaaggtt gcctcatcca aattggactc agtggcagga   8400
tctccatata agtagaacat agaaactctt aactttccgg ttcttattga aaaacgtatt   8460
gtctagatag ctattcctta acaaacaatg gcaacatgga caacactgcc actggagtat   8520
tgcataatta atgaaaactt gactgctgaa aatggacagg ctgcctgttg gaaagctaag   8580
taaaatgatt tgaactgaat cttttcaggg aaatccgaat tcttcaatgg atttaaagac   8640
agttctctaa tgatatatgg ggtgcaggat acccacataa tggagttgtg agtcagcaca   8700
agcagtgtat cttattttca agttagctta ctttcatttt tgtaataatt tgaaaattat   8760
ttagcctttc cccattatat tgaaaataga gtcttttctc atgcaatata ttctgattat   8820
gacttcccct cttcttcccc ttccagttcc acccccacct cccatcttct cctggtctaa   8880
tccctttctg cctctcatta gataagaaca aaacttctaa gagatagcaa tcagacacaa   8940
caaaataaaa tataataaaa cagaaaccat cacatgaaag ttgtacaagg caacccaaca   9000
gaaggaaaag agcctaagag aaggcacaag aatcggagac ccattcagga gtcccataaa   9060
aatactcagc tgaaagctat aaaatatatg tagaggaccc tgtgcagacc tgtctaggcc   9120
ctggttcttc agtctctgct catatgagcc tgacttagtg gaatcacagg actttgtttt   9180
cttggtgtcc tccatcccct ctaggtctta gagtctttct ccctcctctt tcacaggaat   9240
ccctcagctc tgaggggagg gatttgatgg agacacacca tcagagctat gtgtcctaag   9300
gactctgact cttccttctc ttcccctccc cccatctctc tctctctctc tctctctctc   9360
tctctctctc tctgtgtgtg tgtgtgtgtg tgtgtgtgtg tgtgtgtaat gtctgaatgt   9420
gggtctctac aaatacaatt ttattaagaa atgagctagt aggaaatcag tactcaatat   9480
ttattatttt atttaagtaa ggctgggtaa acagcatcat gggacagcac ctgctgtgct   9540
ggaaaaaagg acagaaaagg attgtgagtc aggaaggatg agtttatgtc cgaggatatt   9600
tattcactgt gtggtactaa tgacatctga actctgagac tcagttattg acttccttca   9660
tggaaaaaaa aaaggaaaaa acaaaaaaaa agaaatgcaa ataatagtcc tgacctcaag   9720
```

-continued

```
tcgcccttaa agcgctgagg aatctaggga gattgttgtc ctaaaagcgt tttgaaaaaa   9780
tgctgtattt ccatttttaa ggtgagatgt ttccccagcc tgttagacag caggcagaaa   9840
aaatatattt taacagatac tttatgtaaa attatatagg caataaaaat tttattgcat   9900
aaatttattc aattttatgc ataaatgtcc ataggatgac tttatttatt ttttttttt   9960
acgccccgcg ggggcccata ggatgacttt aaatagcgtg ctgtattgtt taaacagttg  10020
tcatatgttt cattctacct gtgtggttgt atatatcttt gggtagtcat tgggataaat  10080
aaaaaggaaa aacaacatag atgtatttct actaaaatgg ttacactttc tccggaatca  10140
acttttatat cacagggtgt ctgtcacaac tgtatgcaaa taccttcttc agaggtgggg  10200
atctggctgc catctacacc ccggatgccc agcactgtca gaagatgtgc acgtttcacc  10260
ccaggtgcct gctcttcagc ttccttgccg tgagtccaac caaggagaca gataaaaggt  10320
aagatgtccg tgagtccaac caaggagaca gataaaaggt aagatgtccg tgagtccaat  10380
caaggagaca gataaaaggt aagatgtgct gttttatcac tgccgggtga gacgtttctc  10440
aaatagcttc ctgtcgtatg caaaattggt gtcatagttc tcagagtgtt cacagactga  10500
ttgcatcaga agctcctagg ctgggttttc tccaatgcaa actactagag tgctgaaccc  10560
agagacggag attctaaacg accacggcat ttgttcacac agcataggag ggagtgatgc  10620
ttcagccaag gcctgaagac agagcgtgta acaagaacgg gtccttcctc acgctgtaat  10680
acttagcttt cttcttcact ttcaacacgc tatactgtcc ccacgtgtac acttgttatg  10740
tgtataaata tgttattagt caggttctgc atctgaggga gaacatgagt tttttccttt  10800
ctgagattat gtggcttcac ttaatatcac acattctaag tccatccatt ttcatacagt  10860
ttttgtgatt tgatttttct tcagcactaa atagcattcc tttatatatt ttctgtttta  10920
ttcatgattt attatgcatt aattataatt tactacaaat gctacaaatg aaacaatcac  10980
acacccaaat taaccagatc cagagactgt acaattcagg gaccttctat ccagttacag  11040
tagtcatttg aaaaggaagc atggaacttc gcaaggattc tatactttat caaatatata  11100
tatatatata tatattttaa tcatatatat atattgcttg ctgatagaag gtgaaaattt  11160
cacctgcata aagaaatata tttgttttac ttgttaccgt atttatgggg agcaaagttg  11220
aagatgtaca aaccaggaat tttgttgata atagatttga aatccagcag gcaagcctca  11280
atggtatatg tagtgagcct ctctctctct ctctctctct ctctctctct ctctctctct  11340
ctctctgtgt atgtgcatgc atgtgcatgt atgcatgtgc gtgtatcatt aagtggtaat  11400
tttggcaagg acaaatatta gaaatatagt tcggaatttt accttaattt tctttcattt  11460
gatcaatagt caaatgtaaa tttttgcctt ccattttcat acacattact tttatcttcg  11520
gtctatctga atttaagaat tagaaatttg aaactcattc tctgatctct acatgcttac  11580
ctgtacaaaa caaaataaaa caacaaaaac aaaaccaaaa cccagactgt atgtgtgatt  11640
cacttttttt aaaacttgaa ctaggtccta ggattcttat aaagagtaaa gttaacaccg  11700
agctgatatt gaagattgaa aaaacctccc cttatatgga aactaccaga tcaataaacc  11760
agatgaatat cacatacaga cccaacttag ctgattcaaa ttttttaaag taaattacaa  11820
tatttataaa aataatcacc attttagaaa acgtagaagt ttcagacagg agaatcattg  11880
gttttaaaat cagcttgtgt aagttaacaa gatcttttct caaaatagac taaataaaag  11940
ctggcagtgg aatgggaaga acgaggctgt tgagtgatta gcacttgatg aacatatctg  12000
aagcccaggc tttcctcctc agtcccacat aaaccaaaac caaaaccgat tatcttctgg  12060
aaagaggagc tatgaaataa tcctcaactc tgggatgtgg gtggccttct gcactcgaag  12120
```

catgaacact aagaaaacca acgattgtag atagtatgaa cttgtcttaa gaatgtcctt 12180
tccagcacat gtcgagaaat gtaattagtt tcctgacctt attttattta ttaacatatc 12240
caaaatgctg tataatttct taatgtgtat ttgtcgtttt attccccttt taaaatgtga 12300
ttttttttta aaccaggttt gggtgcttca tgaaagagag cattacaggg actttgccaa 12360
gaatacaccg gacaggggcc atttctggtc attctttaaa acagtgtggc catcaattaa 12420
gtggtaagat gtggattttt tttccaacta aatttatgtt actagcactc aaactcagag 12480
tagtttttgc tgaaagtcta tactatgatg gacttttaga agagaacacc gagaaagata 12540
acagacggag cagcatcatg gacctaagga ggggtctttc ttcctgataa tgttcatgtc 12600
tttatcagtt gtaatgcacg gccttaaagg gcttccatta tctatagtac tcacacacaa 12660
tgtaagattt gtgggaaatg aatgtgtagt ccagataata ggtcttctgt tccatagcag 12720
acatttcaga taagattcag gacacatctc accccaaagt gaaccctgga gagtaagtca 12780
ttgtcaccac cagaactgat tgtgcccttt ccacatcaaa caacagttgg tattctctgg 12840
ggacaattta ggtggttaca actgggagag atggtactct atggtaatgg ccaaggttgg 12900
tgcagtcaga cacaacaaca acaaaaaaag ttctgaaaag ttctggcccc cactagggtc 12960
attgagaagg gtttaagata gtggctctca actgtcctta cgctgcagct ctttctcttg 13020
ttgtggtggc tcccaaccat aaactattta catcaccatt tcataactat aattttgcta 13080
ctcttatgaa tcataattat aaatatttgt gttttccagt ggtcttaggc aactcctgtg 13140
aaagggtctt tcaatccccc caaaaggggt catgacccac aggttcagaa atgctggctt 13200
aagagatctt gtttgtcact cagtccagac tgcaggactg agttctgtca atcttgctaa 13260
gcatactatt tcttgcaagg ggtgtaaatg caaggatgtt agagagcttt ctctcaggcc 13320
accattgtaa ctgatgtcct aggaaacaac atcctaattt ccacaccatc ttaaaggctt 13380
aatacaaaga gggcgtttta ataaaacgat gggggctgtt agaaagtgaa agtgctaaca 13440
aagaatgagt tgggttgtat cgtttagctt tgtttttaac gtcattcatt ccgtaggctc 13500
aaatttcaaa tgttctcatt ttgccccaat aacaacaacc ctctcaccac atatacagtc 13560
agagtctgaa acttaagctt tagggagtta atgaagggtg acaatggctt agttataaat 13620
actgcttcac tggtgtaata tcttctctat cttataagat caaacccata taccaatata 13680
acttgctgca tattatttga tgaaatgttg tgtctaatta ttgtgaccaa caacaaaata 13740
taaaaaaata gaaacattat gccttttcca aagctgctta gttgtcacat gccccctccc 13800
ccctagctta accttcttca ctgagtttgg ctctaaagtt tatttgcaac tttctcccaa 13860
ataccttttga gaaagatctt caagttaaaa aatgtttgca ggaaccaatt ttagtaaaaa 13920
ctattgagag gcaggcttaa tatttacaga taatcattaa aaatatgttt tatttgtaac 13980
tacttcatcc caatcctcag ttcatttcct ttcttatctg aagcaaattt aaaagaaccc 14040
catttttatg atttacaatt ttctgccctg taaactgctg ggagcttagc acccctacac 14100
cctaacataa tgctttttca attagtttat atatacagtc tgtctcctgt gtttaaatta 14160
atttcacaat tcttagaaac ttatagttat gtacaataga atattgtttg tgctaacaca 14220
cacacacaca cacacacaca cacacactgc ttgcttaact aagaatctaa ttatgttgtc 14280
ttaaaaacaa aacctaagag cttaatttgg cttgatttct gttaaaagaa tcaactattt 14340
ttaacatgta agataaactt caatgaaggg atattttaaa taaactgaag aaacgtttta 14400
aaactggcgt gctagtgcat ggctataatc ccagcactag ggaagcaggg gcaaagaaca 14460
ttttaagttc aaagccagcc tgatctgaag tgggagatta ccacatccag catggcttgg 14520
gtcctggaaa actgagagga acatcaagag aataagaaag gacagacaca gagacccctg 14580
tccagagaag ctagaacagt gtgagctttg agcactgaac ctccaatccc cagagtgctt 14640
attagacaca gcacagtgga ggggttaact agtcacagag ggtgtctcc ctcttggtct 14700
ctcctcttgg tctgtaatca tcttggagta gaaggtgacg tcacggtaca cactggtcaa 14760
tagttcctaa acactgttgc tgagacccag ggaaggcttt gccgaagtcc catggggctg 14820
agccattggt ccttcacatg gctacggact tcaaactaca gatttcacct gctcctttca 14880
cagttactca gggcttccca tggttaccac aggagttcca agccagccag ttttgaaagg 14940
acaagaaagg gttcggtggc tgcggtggtg gtggtagtgg tgatggtggt taatagaatt 15000
taagaaagtt ttaaagcaag aaggaaaatg atttcattgt gcatataaat aaattgagat 15060
aatctgttaa agattcgaca cagatatcag tgttgtgact aacagtcaca aatcacaatc 15120
agacctgaat agatgaagga agagaaatag atgcagatcg tgattttgtt gatttgtctg 15180
tttttttgtt tcgttgttgt tgggttttgg tttggggttt ttgtttgttt gtttttgact 15240
cagaagtcaa aggctcgata tttgtcaatt actttgcgtc tctgtcacac actatcagga 15300
cggttgcttt cttggtttat caatacctct gatagccttc ttctgaaact gtattgttct 15360
gaattgttgc atatcccttg cagtttaaga agcagaataa cctgtgttta atgcaaaggt 15420
caggttaagc acacctgcgg tgagctaatg tctagcagca cttgataatt tagacacgtg 15480
ataaacattt taattcctgt acttaccagg gtggtcacaa aaatgggata ctagccttca 15540
aaatgactcc gagggctgag cagtttatct gtgtccaata tacatatatt ataatacata 15600
tatatacata tatgtatgta tatatatatg gtcgaatgtc tctctgtgtt tcatttcagc 15660
ttgccaccaa gacatatacg aaggactgga tatgagaggg tccaacttta atatatctaa 15720
gaccgacagt attgaagaat gccagaaact gtgcacaaat aatattcact gccaattttt 15780
cacatatgct acaaaagcat ttcacagacc agagtacagg tgagtgagtc atggttccct 15840
gagaggacat tccaggatgc atcagcatcc gcagtgaaaa agacaagtct gcttccctcc 15900
agtcaaagac aaggggtggg cagtcctgag ccccttcctt ccttaaattt cttagttaca 15960
tacttaattt cagtggaatt tcctcccaga gatagtgaac ttcgtttagt gactggtaag 16020
ctatgtatgg gcataatgtc agacaatgat gtccgccact ccatttgcag ccgcctgtcc 16080
cctttgcaga agggaaaagt gtctattgat cactaatggc ccaactgtgc ccctttgtgg 16140
taacaaatat tatctgcaca cctttgcaca cctcaaggaa ggaagcataa catcttttgt 16200
tgacactcag gaagagttgc ctgctgaagc gcagttcaag tggaacgccc accagtataa 16260
agccagtgga caacctggtg tctggattct cactgaagtc ctgtgctctc tcagagatcg 16320
gtaattagat gacgattatt cctctgtgtc tgtgatgtcc taaggaaggg ttcccagaaa 16380
catccacatg ctgttccccg ggacccagga atatgatgcc tttttataga tgtgattacg 16440
tggaaatagt ttgcaatcag agttatttgg gattaccaga atatgtgcct atccactctc 16500
aggggttctt agatgataaa gcgggtaaca gagaggtcag tgtcagaggt agatagactt 16560
gaaaggtgga acaagagtcc gaaagccaaa ggggtaccag tggtctgtag acattgaaaa 16620
ggacatagaa cagaggaaca gaagcaagcc aacctttgac tggcacccag gaagacttgc 16680
tttggccttc cagcctctag gaaaggtgat aaatttctgt tgctgtaacc tctagtttta 16740
ctataatatg cctacaacaa catcattaga agaggaagct ccaccataaa gaaaaccaca 16800
agatcattct gtggtatccg tatccagaga aatatgcaca ttgtcgtgaa tcaaccaagc 16860

-continued

```
cctgtaactt cacacacaga ggtagcgcta aatgaattac ccggacagtt gccttcaaat  16920
ttaggacacc aaggtgtcag tggtgagatt tactgagacc agtccactta tagtaaatag  16980
taccaatact gaatgctggc cctacaccag gccctgtgtt aggtttccga attctgtggt  17040
atgacctctg tctgaaagac tgagaagtca gaagcaacat agctctttcc ctatttgtgt  17100
tttcttttct ctatgtgtcc ccaccaggct gtgccattca gatggcttaa atatattaac  17160
tatttaattt taatattccc cttttctagt ttttggaaac ttgtctatag gagatagggc  17220
tctttattca acagtgttcc cttttgtata ctgcgcttat cttagactgc accctgcagc  17280
tatagccaga tgccagagga ctgggaaaca ggcaatttaa aactcaggat gctgactgct  17340
gcaaatacca attgtcataa tcaccttagt ttctatgttg aaaagcaagc aaactccaca  17400
tcgtgtcact gagaaatgtt caccactgag ttcacaggtt gccccatgga tattttccag  17460
cactttgcct ttgcagacct gaatgtaagc catgtcgtca cccccgatgc cttcgtgtgt  17520
cgcaccgttt gcaccttcca tcccaactgc ctcttcttca cattctacac gaatgagtgg  17580
gagacggaat cacagaggtg agtgtcagca gcatatgctc ccttcttagc cttttccggt  17640
cctagcagag gcttgcaagg gtcttgctgg tttccctaac agcgctggag cctgtggttt  17700
aacaggatgc ttttcagacg ggtgcaggtt acttcgcaga ttagcagatt catcctcaca  17760
ctttccttct tccataaaac aaacgcgcta ttcactcaga ccacagtggc aggggcaaag  17820
ggagcaggca gcgttctcac tggcattaag gttgaggatt ggcttgggta acagctgctc  17880
atgcaatcca tcctttaatc ttgtgagaaa tccgagccct gcttaccctg atctagggtc  17940
tagtctgacc tcttcatctt tacacaacac ttcctttatg tataccctgg ggccggcaaa  18000
aggatgcgtg tggacgtaat accgcaggca gcataaatcc aaaccaacag tcctttgatg  18060
ccttctcttt ttctttttct aattagaagg tggactttaa tcctctgtcc tcttctctgg  18120
ctgtctgtac ttactaggtt tttttttttt tttttttttt ttttgccgga gggagaggtg  18180
gctccattta catttaagcc ctgtgatatt ttggagtctt gttgtctgac tgactgaaga  18240
gaatttctca gaatacaatt tacagagttg ctttaaaaag aaaggaagaa agaaagaagg  18300
taagtaggta ggtaggaagg aaggaaggaa agaaggaagg aaggaaggaa agaaggaagg  18360
aagggtgggt cttagtcagg gtttctattc ctgcacaaaa catcatgacc aggaagcaag  18420
ttgaggagga aaggaattat tcagcttaca catccacatc gctgttcatc accaaaggaa  18480
gtcaggactg gaactcacac agggcaggag gcaggagctg atgcagaggc catggaggga  18540
tgttacttac tggcttgctt cccctggctt gttcagcttg ctctcttata gaacccaaga  18600
ccaccagccc agggacggca ccacccacaa tgggctgggt ccttccccct tgatcactgg  18660
ttgagaaaat gccttacagc tgggtctcat ggaggcattt cctcaaggga gtctcctttc  18720
tctgtgataa ctccagcttg tgtcaagctg acacacaaaa ccaatctgta caggaaggaa  18780
ggaaggaaag aaagaatatg tctagtgctt ctaatgctgt cttctttctc tttcttgttt  18840
atttttaata ggaatgtttg ttttcttaag acatctaaaa gtggaagacc aagtccccct  18900
attattcaag aaaatgctgt atctggatac agtctcttca cctgcagaaa agctcgccct  18960
ggtaatgtca ctcaacctcg atggcgtgtg acttgtgtcc tggtttggtt cttggttgct  19020
gtaataaata ccatgaccaa aagcaagttg gggaggagag aggtgttttg ttcacatgtc  19080
cctgttatag ccgattcctg agggaagtca ggctaggaac tcaagcagag gcaaagacag  19140
gaactgagca tagacctcag agaaatgctg cctttttgac ttgctcctgt gattgatcat  19200
```

-continued

```
atatgtgtat gtgtatgtat gtgtatgtgt gtgtttgtgt gtgtatgtgt atatgatgtg  19260
tagatgacgt atgtatatgt gtatgagttt gtgtgtgtgt ttgtgtatat gatgtgtaga  19320
tgacgtatgt atatgtgtat atgtgtacgt gtttgtgtgt gtatgtgtat atgatgtgta  19380
gatgtatgta tatgtgtatg tgtttgtatg tgtgtttgtg tgtgtatgtg tatatgtata  19440
ggttgtagat gtataagtat acgatgtata tgatgtatgc atcatgtgca tatgatgtgt  19500
gtgtgtgtgt gtgtgtgtgt gtatcagtag cccatgacca cctgcccaga gtggatactg  19560
ccccccagtt ggctgaccct cttctttcca tcattaatcc aaagaacatc ccatagacat  19620
tcctttaagt tagcctgagg gaggcaattc ttcaagggat gttccatctt ttcaggtgac  19680
tcttttatgt caagttgaca aacactaggt gtaccacatc ttgggagcct ctaagagtta  19740
atgaaatggg tctcaagtcc ctagaaacgt tgccaatatg ccttatgtcc tgacttgtca  19800
tatctccttt ggtgtttgta tgtggtgcag aaccctgcca tttcaagatt tactctggag  19860
ttgccttcga aggggaagaa ctgaacgcga ccttcgtgca gggagcagat gcgtgccaag  19920
agacttgtac aaagaccatc cgctgtcagt tttttactta ctcattgctt ccccaagact  19980
gcaaggcaga ggggtaaggg aacctttctt taacgataat cagcaaggta atttttttct  20040
agttttctct ctctgtgggt ttaattttgt actgttcatt tttttccagg tgtaaatgtt  20100
ccttaaggtt atccacggat ggctctccaa ctaggatcac ctatgaggca caggggagct  20160
ctggttattc tctgagactg tgtaaagttg tggagagctc tggtgagtga agctcacttg  20220
ttatggaact gcatggctgg cttgactgct gtgatgaatg tcttggtctt atataatggg  20280
attgtttata tggtttctgt tatggtttgt atgtgcttgg cccagggtgt ggccctgttg  20340
gagtaacttg ttggagtggg tgtgtcactg tgggtatggg ctataagacc ctcatgctag  20400
ctgcctggaa gtcagtattc tgctagcagc cttcagatga aggcaccatg catgcctgga  20460
tgccgccatg ttcccatctt ggcgataatg gactgaacct ttaaacctct aaaccagctc  20520
caattaaatg ttgtctttat aagagttgcc ttggtcatgg tgtctgttcg cacagtaaaa  20580
accctaacta agacagtttc cttggataaa gggagggaat gctgatctgt gtctaattct  20640
gccacacatc tcaacacttt tcagactgta cgacaaaaat aaatgcacgt attgtgggag  20700
gaacaaactc ttctttagga gagtggccat ggcaggtcag cctgcaagta aagttggttt  20760
ctcagaatca tatgtgtgga gggtccatca ttggacgcca atggatactg acggctgccc  20820
attgctttga tgggtaagtt ttcgatccat cttattttac caatgtgtgt gtgtgtgtgt  20880
gtgtgtgtgt gtgtgtgtgt gtgtgtgtgt gtgtgagcat gcacgtgtat ggacccttac  20940
ctgcacatgt gtatataaag aggttagcct caggtatctt cgtgtactgc ttgcttttct  21000
tatttgttga gacagggttg ttcactgagt ctagtgctaa cccttttgac tagactggct  21060
gcacagccag tcccagagat ctgtctgcct ctgtctcccg gcacattctt agccctagtt  21120
cagtgttggg gctctgaact tgaatgttca tgtttgagaa gcaagccctt tgcccactta  21180
gccatctcct tggccctgag gcatttgttt tgatgataat aaaagtttcc aagcctttgt  21240
ctagaaaata ttatgatttt aaatttagct tatatatctt ttacatggtc aatttaaaat  21300
tcaaaagata tgtaggtaca ttttaagcaa caaaataacc ttaattccta ctggggctta  21360
ttttaatcgt tacagctgct tgatggctct gatgtaatga aagcaattgc ttttaggtct  21420
ggtaaactga acttaattct cctaaagctt cttcaaaagg cacagaagca ttcccgtatt  21480
tttacttgta ataaatataa agcaattgtt aagtttgttt tgagtatttt caaccacagc  21540
ttttatactg tgctctgtaa tcctatatgg acacagttca gctgaatatg agcccctcaa  21600
```

agattttaga aacagtaaag ggatcctgaa ggaacactga ccaaaattca atcaaaataa 21660
aatgttatga caaacctgag gcattctgag aatcctctcc tgtgcatatt tcaggactcc 21720
actgggtttg taaacataca acatgcttac tgtgcactgt gcatgccacc atgctgtgta 21780
gtaccaacag atggtaccct aaagacaatc agactgaaga ttatgtaatg ttgtgaacca 21840
tggtgtctgt agtacgtgtg ccttaggttt tctgctctta caaaacataa gagtttaatt 21900
tcaaagaaca aaagcattaa aatgtgtctt gtcacagtcg cctttgggtt gtacagtgtt 21960
aaactttgat tttcaacatt gtttcataaa aactcattga atgaacttgg gtttgggtat 22020
tagagtttcc aaagctttct aaatggtcct taatctaaga ctatcatttg gtcctccata 22080
tgtatgtgaa gtggtgttct tagcattatc agttataaaa gtaaaatatt aagaaactct 22140
taaaagcatt gaggatgttc tttgtcttat agtatcaaat attcagacat attttaatta 22200
tgtatgtcga cataaataaa cacgttattc tattaagatg tgcatttgct gataagtggt 22260
aaaattatct gtgcaccaaa aattgtcttg tagtaagttt ctttataata tatcatcagt 22320
aaatgtttaa tatgtgtgcc tgcttcatgt aatcacacac aaaaacaaaa aattatcttt 22380
tcaggcaaaa gggagtctca catggacaaa gttttattat aaactaaatc ttcgaagtcc 22440
aatactgctg ctgtaaacaa caataggtgg ccttgccaga aaaagtaact aggtcatatg 22500
gaatgttttc gttcttctcc ctcctcccct tcaaagaaat gtgctaagaa aaaggagcaa 22560
ggaaggatgc caacgttact ttgttctcct gcttctctcc taggattccc tatccagacg 22620
tgtggcgtat atatggcggg attcttaatc tgtcagagat tacaaacaaa acgcctttct 22680
caagtataaa ggagcttatt attcatcaga aatacaaaat gtcagaaggc agttacgata 22740
ttgccttaat aaagcttcag acaccgttga attatactgg tatgcagcgt atttaagggg 22800
aaactgtaca attcacttgt attggcgtta gcttccagtt caatttgagc gagaagacag 22860
atctgcagca attgtctttg tgtcctggtt ggtggggctg agggagagat gaggctgcct 22920
gggaagtaaa aaccccacga cctaccatgc atttgctgct acttaagggg gcaaaagagc 22980
ttcattactt tctcagagtg caacggagtg tatggtattg aaacagttgg tatagggaag 23040
attttgacat ctggggacat tgggtatctt ttgacaagat tggcaggatg actcttgctt 23100
gggcttagga atatacaact atatgaacat gaatgggact agaggttagt gcctaagaag 23160
acactgggct gacagtggag gaacatgaag aatggaactg ccattggtgg cacatcactc 23220
cacagaaaca gaatgcctgc caataccatt agctgcaagt gtctgctaac agtcatgtgt 23280
ccttagacag ctcgcctttc ttccttccac ctctaatatc cactgtatgt gtgctgacta 23340
cttcattgct ttcttgcaat aattaagcaa gatattcaag taaaatacca ggacagcatg 23400
gctatgtttg ctctgcttct gaattctgtt acagtgtagg tttaccaaag cataaggatg 23460
tttaccaata cattttggtt gaagagtccc tcttccccat ggaaatttca ttctgaaatg 23520
ccattcaaac tgtgagaatt tccttgaatc atgggcttta gaaatggctg gagggccatt 23580
ctttatactc tttagtttca gcaatggttt cattatatct catacatggg catggtatgt 23640
tttgattgca tgcacccccct tcaccctctc ttgcccttcc cactcctgtt gttcgcccta 23700
ctcctcccgt gtagtcccac atggctcatt cttgctctgt tgctttgtag aaaaagaata 23760
aggcaaaaga tagatattaa tttttcagat ccctatctat ggttttaatt agcctaaatc 23820
tattcatgaa attttctttc agaattccaa aaaccaatat gcctgccttc caaagctgac 23880
acaaatacaa tttataccaa ctgctgggtg actggatggg gctacacaaa ggaacgaggt 23940

-continued

```
aagcctggca tgtggaatgt tcctctctta tgtgctaagg tacatggagt agagccactc  24000
aacaacccgt agtcatgatc cttctgtaga tccattcaac agcccttact catggccttt  24060
ctgttcattc caaaatgatc ccaagaatat gactttttg cattaaaaac tgatgagcta  24120
atccattaaa catattactc ataatagaga tcattttcat gactctgcat caagaactgt  24180
aaccctatgg tgctcttaag tccactgaag ctcatctgat ccccagttct cacagcatcc  24240
ctgtttacta tgctctccct tgctatgaat agccaaagtg ccagcatctc tttaaggaca  24300
gtgccatata tatatatata ttatagtata gtagtgccaa atatatatat ttgtagtata  24360
ataaatctaa ctttccctct aattatgctg ttaacttctt gtgtaaaata catagattca  24420
taaagacaag tagattgcag cacaattgcc attattttta gcagaatttc acacagggat  24480
aaacatacat ctgtattaat gtaatcctta gcaagttgtt tgaatatcta ccataatgtt  24540
taaataacta tgcacaagaa caatatcttc ctttctgttg taactacaat tcaaagaatc  24600
cgtgactctt acacagcagt gctggtgaca atatcacact tccgtatttg ttatctgcat  24660
ttgaaacaga gggtggggtt cagccttact tggaagggag agactgtaga ggccagtttt  24720
tctccttccc ttcctcggag tttatggata gatcagttgt atgcgtggct ctcaaatcaa  24780
gggatctgtg tgttaagact tgagacattt ctctagaaat aagcatgttt tccttttaga  24840
ctgagtgcca gatagcatgt ttgagtgatt tttttaaaaa aagagatgat tggctgtgtc  24900
ttctttatat tttctgaacc agttagtact gtattcaatt aatcctcatt ttcactatgt  24960
tgacttggct acaaatacgt ggacacacac atatacatgt gtgcacatgc acacacatac  25020
acacacatac atatacacac atacatacat acaaccaaga aatatagaaa tgggtgtaga  25080
acaaaatact tctctgctgt taaatgtttg ggatttattt tcataaattg tatatttgtg  25140
ttataatttg aatttataaa acaatgaaag gcaagagcat ccacgtatta aaggtacaaa  25200
tgtttaaaac aacatatttt tctgaggaga gccttggttg atacaggagg atggctgaga  25260
tcatagaaac caagtctgtg gtagcttggg tgatagggga gcttcagtca acacagatca  25320
ttgcttcttc atctccatct ccctccctg ctctccctcc acttcttgct tcctttctcc  25380
ctccctcttt ctcccctact tattgtattt cctctcttta atgctacttc ctgattgctt  25440
cataggtgag acccaaaata ttctacaaaa ggcaactatt cccttggtac caaatgaaga  25500
atgccagaaa aaatatagag attatgttat aaccaagcag atgatctgtg ctggctacaa  25560
agaaggtgga atagatgctt gtaaggtaac tctgggaaaa atacgtaata gttcactgga  25620
gactgctcat ccaaaagcaa atttcccaag ttacatttca ttagtttcag ttttgaagtt  25680
gcagagttaa gtgacatgga gacttttttt tttttaaaga tttattttta tttatgtgag  25740
tgtacactgt cactgttttc accagaagag ggcatcggat tccattacag atggttgtga  25800
gccaccatgt ggttgctggg aattgaactc agaacctctg gaagagcagt cagtgctctt  25860
agctgctgag ccatctctct agccccagac ctggagactt tttaaacagc ctttaacaaa  25920
ctaaacacac acaatgcaca tcatgtgttc cttataatag ttacgttaga atttgtattg  25980
actgtgacgg gtgtgtcaca gtcagtacag ggacatgcca tatttaagga caattttaca  26040
tacatggtca tgctaaaata caaggaaaca gatttatttg aactttgggt aaagatgcta  26100
aaattgttgg gtttatctga gaacgggaga gggaataaat tggccttgta accatccact  26160
tactttcttc atggctaatg gggtgcagag aaattgagaa gttgcatgtg tgatatgtaa  26220
aatatgatag caaaatgtta aagacatcta tctttgaaca aggggctcct aatttgaatc  26280
atcactgtta tagctctcta tcattttttt tctactcact gtgatccagg gagattccgg  26340
```

-continued

```
tggcccctta gtttgcaaac atagtggaag gtggcagttg gtgggtatca ccagctgggg  26400
cgaaggctgt gcccgcaagg agcaaccagg agtctacacc aaagttgctg agtacattga  26460
ctggatattg gagaagatac agagcagcaa ggaaagagct ctggagacat ctccagcatg  26520
aggaggctgg gtactgatgg ggaagagccc agctggcacc agctttacca cctgccctca  26580
agtcctacta gagctccaga gttctcttct gcaaaatgtc gatagtggtg tctacctcgc  26640
atccttacca taggattaaa agtccaaatg tagacacagt tgctaaagac agcgccatgc  26700
tcaagcgtgc ttcctgcctt gagcaacagg aacgccaatg agaactatcc aaagattacc  26760
aagcctgttt ggaaataaaa tggtcaaagg atttttatta ggtagtgaaa ttaggtagtt  26820
gtccttggaa ccattctcat gtaactgttg actctggacc tcagcagatc acagttacct  26880
tctgtccact tctgacattt gtgtactgga acctgatgct gttcttccac ttggagcaaa  26940
gaactgagaa acctggttct atccattggg aaaaagagat ctttgtaaca tttcctttac  27000
aataaaaaga tgttctactt ggacttgatg ggacagagca ccttttcata taaaccacct  27060
ttctggccat tgctgctgag tcctgcatgg tcatgagtaa ggagctcgtg acagggtttc  27120
ccacccctgg agcaaaacca gctagatgtt aggcttgttt gtataaattt caagttcctc  27180
ctttgggaag tattctctct gcctagatta ttgggggaat atcctctctg tcagggcagc  27240
ccttaagatt gtgggaaaca tgagaatata taatttctct acaatgcaaa atataaggat  27300
acagtctgaa ttatataagg agatccatgg acctaagaga acagaggcag ctacactatg  27360
agccagcttg tcagaaagat actactgaag gagttaaaga gataaagaga tttggggaat  27420
agctatcaca gggcaagatc ccacccagct aagtttatta tttgtgttta caaagacagc  27480
cagattcctg agttcaaggt catcctggga cagagctggt ttaggcccag ggtaatgggg  27540
gtcccactca gctagcttat tgtctatgct tttaaatgca ggcagatttc tgaattcatt  27600
tgccatgtta aaaaaaatgt acctgatgtc ttttcctaag atatacgggt ctagagtcat  27660
ggaatgctga ttcatgggtt aatcaaaagg gaacctagag taaacgcctg tactgataga  27720
tacataaaag tctgggcttt ggtctacaaa tgttgagcta tgtggatgag ctgtgtagag  27780
ctaaagattg aacagtggtc tctaattatt tttttagatt atttttttct agcagctacc  27840
cagagagaac ggcttagaga gtaaatattg ctattttaga ttttttttttc tagaaaatcc  27900
aagaattttt atagcagctt ttctgacact ggtcagaaaa cccatgagct atccagaaag  27960
cttttagatt tttttttttc aagagagaac tgtctcaagt agagacagct ctctcaatca  28020
gagagagctg cctggagcag aaagctatct cgatcagact acagagccaa gagctattta  28080
caaagagctg tctagggagc cattttaagc aggctataag gctgtcagct tgcaccccat  28140
catttgactt tgagttgttt ctttcaccac tctcaaacac cccttctctc aggaactcct  28200
ctccaagcca agactggttc ttggcacatt gccacatggt cttggctacg tatgcatgta  28260
agacctgtag ggctatattt ttcttcttgt gtgcagctcc aacaataggc ttatcacaca  28320
gtactcatac agggcacgga atctgatgag aatctccccc agggaaccct ttggagttcg  28380
gttgatactg tattctgcaa tagtaattca tggaatgtca ttggatgtaa agtgttgtat  28440
aaaattcagg cttgtagttg agttgaaagt aaaaagcaat cttggaaggg atgacagtaa  28500
tcctcatgta agacaaattt ccagcttccc agtgattcat aaagtggacc atatgggctt  28560
aactccattt agttaagctg attaatattt agaattagcc atttacaaac tattgtgcaa  28620
gttaaataga caaacagaaa agtgaaattt cctaaagaag attaaacctt tcactgcaaa  28680
```

-continued

```
ggtttgttga gtagtgcaga ggattaaata tggaaaagcc agtgggttat ccacagaatt  28740
tgccacggga agtggaggag gtggttatta tctgaggagc aaataaatgg cttttgtaaa  28800
atctgtctgg attcccatga aatcactccc ctttaaagca caccacttca acttttaatt  28860
ttgtatacaa tttcatctta atctgttctg tgtggaagtt attttatatt taaaatgaaa  28920
gaagtggttc tcaatgaaaa tcacgtatct caggatttca tactgataac cctaacaggt  28980
gttcacacaa ggtgtcagag tgctggctgg gtagaccttg ggctttggtt tctcaaggaa  29040
tggcctcatt tgatctaaac agttttgaaa tgtttaattt ccctggggca taaagtaaca  29100
ttataacatt gccagtggga gtccagttag attggaaggc tctgtttatt ttttgttgtg  29160
tgttccagca caaagtagcc tgtcttccac ttggggcctt atggggctag tgagaaagtg  29220
agaggcttga ataacatcac tgtcacaagg cagagaggag gcaggaggcc ctagatcttt  29280
ggcaggtcca tccaaaaaag ggagtgttat ctctgggaaa gaacacggtt cttcctgggt  29340
cacacatgca gaacacactg catactgttc acatgtgtgg agttcaaccc aaagctcaga  29400
gggctgtctc tcatcgttga cttttcttct tgtaattctt gcttatgcct gccagcccta  29460
tagattgtca gtaactagga aggaggttct ccctgactct gtctctctct ttcatcaata  29520
ctacatgtga atgagcatgt ggcacatgtc tccctttaga tttaccttta ttatctttgt  29580
tgatgtgttg tttaattgta tgtcacgtgg ttgctagtgc ctgacaccaa ctgatcaaag  29640
cgtaacttct gagcaactgc cttctaccag agtaaaatag agtagtcctt catgtcaaga  29700
tctcttcaaa gtcatacaca ggcacacaca catggacaca catgcaggaa agcatggaca  29760
cacatacaca tacacatgca tacacacgtg ttgtagttac cattattttg agtgtttact  29820
atacccccttt tttgccttta actatttatt aggtatttct accctacttt agataattta  29880
gttcccaaat aaaagacaca ggaatctttg gatttagaat aaactttaga gcactgggca  29940
gatatcaacc ctctatgcta tcttgtctgt ttccctatca aattgctgga gatactactt  30000
```

<210> SEQ ID NO 16
<211> LENGTH: 2252
<212> TYPE: DNA
<213> ORGANISM: Macaca mulatta
<220> FEATURE:
<221> NAME/KEY: misc_feature
<222> LOCATION: (830)..(939)
<223> OTHER INFORMATION: n is a, c, g, or t

<400> SEQUENCE: 16

```
agaacagctt gaagaccgtt catttttaag tgacaagaga ctcacctcca agaagcaatt    60
gtgtttgcag aatgatttta ttcaagcaag caacttattt catttccttg tttgctacag   120
tttcctgtgg atgtctgact caactatatg aaaacgcctt cttcagaggt ggggatgtag   180
cttccatgta caccccgaac gcccagcact gccagatgat gtgcacattc cacccaaggt   240
gtttgctatt cagttttctt ccagcaagtt ccatcaatga catggagaaa aggtttggct   300
gcttcttgaa agatagtgtt acaggaacct tgccaaaagt acgtcgagca ggtgcaattt   360
ctggacattc cttaaagcag tgtggtcatc aaataagtgc ttgccaccga gacatttata   420
aaggaattga tatgagagga gtcaatttta atgtatctaa ggttagcagt gttgaagaat   480
gccaaaaaag gtgcaccaat aacattcgct gccaattttt ttcatatgcc acacaaacat   540
ttcacaatgc agagtaccgg aacacttgcc tcttaaagca cagtcccgga ggaacgccta   600
ccactataaa ggtgctgaat aacgtggaat ctggattctc actgaagccc tgtgcccttt   660
cagaaattgg ttgtcacatg aacatcttcc agcatcttgc cttctcggat gtggatgttg   720
```

```
ccagagttct cgccccagat gcttttgtgt gtcgaaccat ctgcacctat catcccagct    780

gcctcttctt tacgttctat acgaatgcat ggaagatcga gtcacaaagn nnnnnnnnnn    840

nnnnnnnnnn nnnnnnnnnn nnnnnnnnnn nnnnnnnnnn nnnnnnnnnn nnnnnnnnnn    900

nnnnnnnnnn nnnnnnnnnn nnnnnnnnnn nnnnnnnnna accctgccat tctaaaattt    960

acccgggagt tgactttgga ggagaagaat tgaatgtgac tttcgttaaa ggagtgaatg   1020

tttgccaaga gacttgtaca aagatgattc gctgtcagtt tttcacttac tctttactcc   1080

cagaagactg taaggaggag aagtgtaagt gtttcttaag attatcttcg gatggttctc   1140

caactaggat tacatatggg acacaaggga gctctggtta ctctttgaga ttgtgtaaca   1200

ctggggacag ctctgtctgc acaacaaaaa caagctcacg cattgttgga ggaacaaact   1260

cttcttgggg agagtggccc tggcaagtga gcctgcaggt gaagctgatg gctcagaggc   1320

acctgtgtgg agggtcactc ataggacacc agtgggtcct cactgctgcc cactgctttg   1380

atgggcttcc cttaccggat gtttggcgca tttatagtgg cattttaaat ctgtcagaca   1440

ttacaaaaga aacacctttc tcacaaataa aagagatcat tattcaccaa aactatagaa   1500

tctcagaagg gaatcatgat atcgccttaa taaaactcca ggctcctttg aattacactg   1560

aattccaaaa accaatatgc ctaccttcca aaggtgacac aaacacaatt tataccaact   1620

gttgggtaac tggatggggc ttctcgaagg aaaaaggtga aatccaagat attctacaaa   1680

aggtaaatat tcctttggta acaaatgaag aatgccagaa aagatatcaa gattataaaa   1740

taacccaacg gatggtctgt gctggctata aagaaggggg aaaagatgct tgtaagggag   1800

attcaggggg tcccttagct tgcaaacaca atggaatgtg gcgtttggtg ggcatcacca   1860

gctggggcga aggctgtgcc cgcagggagc aacctggtgt ctacaccaaa gtcgctgagt   1920

acatggactg gattttagag aaaacacaga gcagtgatgg aaacgctcgg atgcaggcgc   1980

cagcatgagg agcagcccag agtcttggcg agttttacaa cctgggttca agtcaaattc   2040

tgagcctggg ggtcctcatc tgcaaagcat ggagagtggc atctactttg catcctgtca   2100

taaggacaaa agacagtgca ctcagagctg ctgaggacaa tgttttgctg aagccagctt   2160

tcagcattca gtaactggga gctgataatg tgaagtcgca accgagatct ccatgattgt   2220

gtgtcgtaaa ataaaatggt aaaagatcac aa                                 2252


<210> SEQ ID NO 17
<211> LENGTH: 2353
<212> TYPE: DNA
<213> ORGANISM: Macaca mulatta
<220> FEATURE:
<221> NAME/KEY: CDS
<222> LOCATION: (238)..(2109)

<400> SEQUENCE: 17

ggaagccgtt cactagtcag attgaccaga gattatgggt gggctgtctg ttggggtcta     60

tgcacaggat ttctgttgga gttctaagga caaaaagttg aaactgttgg cagaaaccca    120

aagtcaatat cgaagccaag gaaaacattg cctgcggtgc cacattagaa cagcttgaag    180

accgttcatt tttaagtgac aagagactca cctccaagaa gcaattgtgt ttgcaga      237

atg att tta ttc aag caa gca act tat ttc att tcc ttg ttt gct aca      285
Met Ile Leu Phe Lys Gln Ala Thr Tyr Phe Ile Ser Leu Phe Ala Thr
1               5                   10                  15

gtt tcc tgt gga tgt ctg act caa cta tat gaa aac gcc ttc ttc aga      333
Val Ser Cys Gly Cys Leu Thr Gln Leu Tyr Glu Asn Ala Phe Phe Arg
            20                  25                  30
```

```
ggt ggg gat gta gct tcc atg tac acc ccg aac gcc cag cac tgc cag      381
Gly Gly Asp Val Ala Ser Met Tyr Thr Pro Asn Ala Gln His Cys Gln
        35                  40                  45

atg atg tgc aca ttc cac cca agg tgt ttg cta ttc agt ttt ctt cca      429
Met Met Cys Thr Phe His Pro Arg Cys Leu Leu Phe Ser Phe Leu Pro
    50                  55                  60

gca agt tcc atc aat gac atg gag aaa agg ttt ggc tgc ttc ttg aaa      477
Ala Ser Ser Ile Asn Asp Met Glu Lys Arg Phe Gly Cys Phe Leu Lys
65                  70                  75                  80

gat agt gtt aca gga acc ttg cca aaa gta cgt cga gca ggt gca att      525
Asp Ser Val Thr Gly Thr Leu Pro Lys Val Arg Arg Ala Gly Ala Ile
                85                  90                  95

tct gga cat tcc tta aag cag tgt ggt cat caa ata agt gct tgc cac      573
Ser Gly His Ser Leu Lys Gln Cys Gly His Gln Ile Ser Ala Cys His
            100                 105                 110

cga gac att tat aaa gga att gat atg aga gga gtc aat ttt aat gta      621
Arg Asp Ile Tyr Lys Gly Ile Asp Met Arg Gly Val Asn Phe Asn Val
        115                 120                 125

tct aag gtt agc agt gtt gaa gaa tgc caa aaa agg tgc acc aat aac      669
Ser Lys Val Ser Ser Val Glu Glu Cys Gln Lys Arg Cys Thr Asn Asn
    130                 135                 140

att cgc tgc caa ttt ttt tca tat gcc aca caa aca ttt cac aat gca      717
Ile Arg Cys Gln Phe Phe Ser Tyr Ala Thr Gln Thr Phe His Asn Ala
145                 150                 155                 160

gag tac cgg aac act tgc ctc tta aag cac agt ccc gga gga acg cct      765
Glu Tyr Arg Asn Thr Cys Leu Leu Lys His Ser Pro Gly Gly Thr Pro
                165                 170                 175

acc act ata aag gtg ctg aat aac gtg gaa tct gga ttc tca ctg aag      813
Thr Thr Ile Lys Val Leu Asn Asn Val Glu Ser Gly Phe Ser Leu Lys
            180                 185                 190

ccc tgt gcc ctt tca gaa att ggt tgt cac atg aac atc ttc cag cat      861
Pro Cys Ala Leu Ser Glu Ile Gly Cys His Met Asn Ile Phe Gln His
        195                 200                 205

ctt gcc ttc tcg gat gtg gat gtt gcc aga gtt ctc gcc cca gat gct      909
Leu Ala Phe Ser Asp Val Asp Val Ala Arg Val Leu Ala Pro Asp Ala
    210                 215                 220

ttt gtg tgt cga acc atc tgc acc tat cat ccc agc tgc ctc ttc ttt      957
Phe Val Cys Arg Thr Ile Cys Thr Tyr His Pro Ser Cys Leu Phe Phe
225                 230                 235                 240

acg ttc tat acg aat gca tgg aag atc gag tca caa agg cga gta tgc     1005
Thr Phe Tyr Thr Asn Ala Trp Lys Ile Glu Ser Gln Arg Arg Val Cys
                245                 250                 255

atg gct agc act tgc tgc tgt act ttc atc aat ttt att tta gaa act     1053
Met Ala Ser Thr Cys Cys Cys Thr Phe Ile Asn Phe Ile Leu Glu Thr
            260                 265                 270

tta cct gaa ccc tgc cat tct aaa att tac ccg gga gtt gac ttt gga     1101
Leu Pro Glu Pro Cys His Ser Lys Ile Tyr Pro Gly Val Asp Phe Gly
        275                 280                 285

gga gaa gaa ttg aat gtg act ttc gtt aaa gga gtg aat gtt tgc caa     1149
Gly Glu Glu Leu Asn Val Thr Phe Val Lys Gly Val Asn Val Cys Gln
    290                 295                 300

gag act tgt aca aag atg att cgc tgt cag ttt ttc act tac tct tta     1197
Glu Thr Cys Thr Lys Met Ile Arg Cys Gln Phe Phe Thr Tyr Ser Leu
305                 310                 315                 320

ctc cca gaa gac tgt aag gag gag aag tgt aag tgt ttc tta aga tta     1245
Leu Pro Glu Asp Cys Lys Glu Glu Lys Cys Lys Cys Phe Leu Arg Leu
                325                 330                 335

tct tcg gat ggt tct cca act agg att aca tat ggg aca caa ggg agc     1293
Ser Ser Asp Gly Ser Pro Thr Arg Ile Thr Tyr Gly Thr Gln Gly Ser
```

-continued

```
            340                 345                 350

tct ggt tac tct ttg aga ttg tgt aac act ggg gac agc tct gtc tgc      1341
Ser Gly Tyr Ser Leu Arg Leu Cys Asn Thr Gly Asp Ser Ser Val Cys
        355                 360                 365

aca aca aaa aca agc tca cgc att gtt gga gga aca aac tct tct tgg      1389
Thr Thr Lys Thr Ser Ser Arg Ile Val Gly Gly Thr Asn Ser Ser Trp
    370                 375                 380

gga gag tgg ccc tgg caa gtg agc ctg cag gtg aag ctg atg gct cag      1437
Gly Glu Trp Pro Trp Gln Val Ser Leu Gln Val Lys Leu Met Ala Gln
385                 390                 395                 400

agg cac ctg tgt gga ggg tca ctc ata gga cac cag tgg gtc ctc act      1485
Arg His Leu Cys Gly Gly Ser Leu Ile Gly His Gln Trp Val Leu Thr
                405                 410                 415

gct gcc cac tgc ttt gat ggg ctt ccc tta ccg gat gtt tgg cgc att      1533
Ala Ala His Cys Phe Asp Gly Leu Pro Leu Pro Asp Val Trp Arg Ile
            420                 425                 430

tat agt ggc att tta aat ctg tca gac att aca aaa gaa aca cct ttc      1581
Tyr Ser Gly Ile Leu Asn Leu Ser Asp Ile Thr Lys Glu Thr Pro Phe
        435                 440                 445

tca caa ata aaa gag atc att att cac caa aac tat aga atc tca gaa      1629
Ser Gln Ile Lys Glu Ile Ile Ile His Gln Asn Tyr Arg Ile Ser Glu
    450                 455                 460

ggg aat cat gat atc gcc tta ata aaa ctc cag gct cct ttg aat tac      1677
Gly Asn His Asp Ile Ala Leu Ile Lys Leu Gln Ala Pro Leu Asn Tyr
465                 470                 475                 480

act gaa ttc caa aaa cca ata tgc cta cct tcc aaa ggt gac aca aac      1725
Thr Glu Phe Gln Lys Pro Ile Cys Leu Pro Ser Lys Gly Asp Thr Asn
                485                 490                 495

aca att tat acc aac tgt tgg gta act gga tgg ggc ttc tcg aag gaa      1773
Thr Ile Tyr Thr Asn Cys Trp Val Thr Gly Trp Gly Phe Ser Lys Glu
            500                 505                 510

aaa ggt gaa atc caa gat att cta caa aag gta aat att cct ttg gta      1821
Lys Gly Glu Ile Gln Asp Ile Leu Gln Lys Val Asn Ile Pro Leu Val
        515                 520                 525

aca aat gaa gaa tgc cag aaa aga tat caa gat tat aaa ata acc caa      1869
Thr Asn Glu Glu Cys Gln Lys Arg Tyr Gln Asp Tyr Lys Ile Thr Gln
    530                 535                 540

cgg atg gtc tgt gct ggc tat aaa gaa ggg gga aaa gat gct tgt aag      1917
Arg Met Val Cys Ala Gly Tyr Lys Glu Gly Gly Lys Asp Ala Cys Lys
545                 550                 555                 560

gga gat tca ggg ggt ccc tta gct tgc aaa cac aat gga atg tgg cgt      1965
Gly Asp Ser Gly Gly Pro Leu Ala Cys Lys His Asn Gly Met Trp Arg
                565                 570                 575

ttg gtg ggc atc acc agc tgg ggc gaa ggc tgt gcc cgc agg gag caa      2013
Leu Val Gly Ile Thr Ser Trp Gly Glu Gly Cys Ala Arg Arg Glu Gln
            580                 585                 590

cct ggt gtc tac acc aaa gtc gct gag tac atg gac tgg att tta gag      2061
Pro Gly Val Tyr Thr Lys Val Ala Glu Tyr Met Asp Trp Ile Leu Glu
        595                 600                 605

aaa aca cag agc agt gat gga aac gct cgg atg cag gcg cca gca tga      2109
Lys Thr Gln Ser Ser Asp Gly Asn Ala Arg Met Gln Ala Pro Ala
    610                 615                 620

ggagcagccc agagtcttgg cgagttttac aacctgggtt caagtcaaat tctgagcctg    2169

ggggtcctca tctgcaaagc atggagagtg gcatctactt tgcatcctgt cataaggaca    2229

aaagacagtg cactcagagc tgctgaggac aatgttttgc tgaagccagc tttcagcatt    2289

cagtaactgg gagctgataa tgtgaagtcg caaccgagat ctccatgatt gtgtgtcgta    2349

aaat                                                                  2353
```

<210> SEQ ID NO 18
<211> LENGTH: 33001
<212> TYPE: DNA
<213> ORGANISM: Macaca mulatta
<220> FEATURE:
<221> NAME/KEY: misc_feature
<222> LOCATION: (17364)..(18312)
<223> OTHER INFORMATION: n is a, c, g, or t
<220> FEATURE:
<221> NAME/KEY: misc_feature
<222> LOCATION: (23228)..(23609)
<223> OTHER INFORMATION: n is a, c, g, or t

<400> SEQUENCE: 18
actgttggaa agacatcatt ggttttgaaa tctgaaaagg acgtgagatt tgggaaaggc 60
caggggaaga atgatatagt ttggctccat gtccccaccc aaacctcatc ttgaattgta 120
atccctgcat gttgaaggag gggcctggtg ggaggtgata ggatcattgg ggtggtttcc 180
cctgtgctgt gttctcatga tagtgaggga tttaaaagta gctgtttccc ctgcacatgc 240
acactctgtc tctcctatca ccttgtgaag aaggtgtctg cttcccctct gccttccatc 300
atgattataa gtttcctgag gcctccccag ccatgggtaa ccgtgggtca gttcaacctc 360
ttttgtttat aaattgccca gtctcaggta gtatctttac agcaatgtga aactgaacta 420
atacatctgg gaaattcttt ttctctcctt cctttctgaa ggacagcttt gcctgatatt 480
atattcctgg ttgccaggtt ttgtactttc agtactttga atatatcatc ccattctctc 540
agcctacatg atttctgctg agaaatccac tgataatctt atgaagcttc ccttgtatgt 600
gaagaattgc ttttctcttg cttctttgaa aattctctct ttgtcatggt gaggatctct 660
ttatatttaa tctattggag ttcttttggg cttcataaat ctggatgttt atttcattta 720
tgtctccaaa ttttgagagt tttctgttct tatttttaaa aataagtttc tgcaactttc 780
tctttctctg cttcttctgg aactcttgtc atgcatatta gtttttcttaa cagtgtcctg 840 taatttttgt cagctttctg caatctttat cattcctttt attactctga ctgggtaatt 900
tcaaatgacc tgtatctgag tgtgctgatc ctttctcctg cttgatcaag tctgctgctg 960
aagatgtttg tgaatttttt caattcagtc attgtgttct tcagttcgag aatttctgtt 1020
tggttctttt tatggttcct atctatcttt ttgttgaact tctaattttg ctcatgtatt 1080
attttcctga ttttgtttac tgtctatcta tattgttttg tagctcactg agctttctta 1140
agataattat ttttaactct ttgtcatgca gtatagatct ccatttcttt agagtcgcct 1200
cctgctgctt tattttcttc ctttggtggt ttcttgtttc cctgattatt tgtgatcagt 1260
gtggccttgc attgaagtag gtacctattt cagtctttac atactagctt cagtagagga 1320
agccgttcac tagtcagatt gaccagagat tatgggtggg ctgtctgttg gggtctatgc 1380
acaggatttc tgttggagtt ctaaggtagg cagggctgga ttctgggttc attcattgtg 1440
gttgtctgta ttctgtgcac aaggactggc ttgaagcatg gatccttgag ggctgacttg 1500
gcactgaaat gagccttaag cctgagtctg caggggccag cctaacatgg ggatcaccta 1560
gcacctgagt tcatggggac agacctgttc ctgagtttat tcaggctgtc ctgggaccag 1620
ggtccactgg ggtgagccca gcatctgggt ccacatggcc aagatctctg gaggctgacc 1680
tggtgctgga tctgcagggg atggcctgaa ttctaggccc atgggtacca acttggagcc 1740
ttgggctgct ggggctaatg tggaggctag agtcttgggg gccaggctag agctggggca 1800
ggtctgaagt ctaggtcttc tgtggccacc ttggagtcta gacccccagg ggctgacctg 1860

-continued

```
gtctggggtg agcatggggc tgaggccaca gaggccagtc tggcctgtgg caggcctgaa   1920
tcctggtgcc ggggtttact ggagtgggct tggtgcttgg ggtctgtggt gaaggtgggt   1980
gctatcttaa ctgtctctct tccacgcaag agggtatctc tctccatgct gtgctgccca   2040
ggcttgaagg tggggtgaca ctggtaatgt gaaattgtcc ttcctatgca cttcaatgtg   2100
tcttttctta cttctgtgct gcaactgggt ggtacaacct ctcacctgat tcctgagctc   2160
tagtgaagtt attttcgtgc atggatactt attcaaattg atgtttctgc aagggatgag   2220
cactagaaac tcctgttctg acaaactcct attccggttc ttgctgacat cactccctga   2280
aatagttaat atacttaaca gctgaacacg gataggatgt tcacggaata tgttgacagg   2340
acaaaaagtt gaaactgttg gcagaaaccc aaagtcaata tcgaagccaa ggaaaacatt   2400
gcctgcggtg ccacattaga acagcttgaa gaccgttcat ttttaagtga caagagactc   2460
acctccaaga agcaattgtg tttgcaggta gcaaatttct attattctga ttgtttccaa   2520
agaaactata atttttaaag tatagttttt tactttatga gaaaattagt catttatatt   2580
ctaatttcct gagtatatag atagtagaga aggaactaat attcctttat gtagaaatat   2640
ttaaatgtaa gatgacttta aatcaaaaag aatacttgat tgatttaaaa tttttaattg   2700
ggctttaata ttttcagagg ttttctttac ttagggattt ttggactgac attattgcca   2760
ttatttatta attttctttt tgctcaaatc aagaggtttc ataactgttt aatctctctc   2820
tctaccaatt ccctttccaa cattactagc cacagagttt gccaatcaac aataaacaca   2880
acagtagtct ggaggtctca atttgtatct tgggaagcat tataaacttt ccaactccct   2940
agacacaaat gtagagaaaa aaccccttgt tttctatacc agaaactgtg tgctttgtct   3000
tgtaattcag acatttacaa gaaaatctgt atcaccttaa attaagattt atgttaaatg   3060
cagtctaaaa ccaacagagt tatgtattgt tttctttttt agaatgattt tattcaagca   3120
agcaacttat ttcatttcct tgtttgctac agtttcctgt ggtaagtgaa ttatctataa   3180
agcatgaaat tcaggctaag acaggagtag ccaagcaagt cgcaccacct ctggagaaag   3240
ctattgaaca tacagcttcg gggatggaga tagtccctga tgattcagga cacgtgtcta   3300
tttaatgttc cagaacaagt acgacttgtg agatatattg ctgtatacat acattgcaga   3360
ccagaggaag gagctcagaa gcgggaatgt cttgggactt gtgttaataa aaacttctgt   3420
tcacagatga cactctgcaa aacaaaactc aaaacaaaaa aattactcct ctatttttat   3480
caacattaaa aaattaaaca ttatctgaaa tttcaaaaga gtgctgggca ttatatagtg   3540
tctgggtcca atccaagtat ctgttaggta catgatacat agttttactc tggacagcca   3600
gggaaccatt tcaaaaatga aagtacctgg tttaaattta acttagcaaa ccaggcattt   3660
ggatagttct aggtgaataa ctttcaacac tagatttcga tctcatttct ctattaatat   3720
cattaatttt tggagaataa aaatgattct ggacatttca ttaatcgcta tagagggagt   3780
tttctctgtg tccccacaag gcatgattct gagtctatgg tgacttaaga gggccacata   3840
acaatgagta tttaactttc ctctcgtatg gctacaataa acgtctacag ggaaggttta   3900
cattcataaa gagactactt ttccaggaaa aaaggctttg attcccccta aatcacaact   3960
cccctgtgtc tgtccctcaa ccctgattgc ttttctaaac cgtaatttac caacccatgt   4020
gcaaacccac tgaaaactga aaaggagcat gagccaggga tactgtgaac cacggccacc   4080
tccaggtggt ttctcatttt ctgttttttt cttctggcaa aataaatcat gattatggct   4140
aggaaaatta aggatgtaaa taagcaaaaa actataaact acatattgca tgtagtcccc   4200
aaattcagaa gcagtcgttg ttaaacatct tttgtttagt ctttcagata tttttctaca   4260
```

-continued

```
tatgcctatt tgcacatttt acaaaaaaga gttattaact atggatactc tttgacttgc   4320
attttccact tacagctacc ttttggtgca aataaatgac atttttttgga gcttgctatt   4380
ctctttttat ggtatgtttg tgtgcacatt cttatgcact tagttatttc tgtagaatac   4440
attttttgaa ataaaaatac tagattcaaa ggtatgaata ttttagaagg ttttatggtg   4500
tggcatcatg aaattatctt tcagaaaagt tactccctag ttgacttctt ctaccagcta   4560
ataagagtcc ttatttaccc cacttaggcc aacactaaca ggcttctgtt gctttgcatc   4620
ccgacatgtt tatctttctg gaaacagtat cctaatttat ttctgcagag ctactgcctc   4680
tcagttttgg tccatgtggt tctggtgacc ctgactcttc tgctgaacca ggaagtgcac   4740
acatcctgct gactgcagtg acccaatcag agccaacatc ttgcaatgaa gcgtttgttt   4800
agacgtctag aaataggact cttacttttt tttttccaat ttaacttgaa acataagaga   4860
atacagaggc ctgagctgct ggtcctattt tgctactatg tggagcttga gagtaatggt   4920
aacaccatga ctggagcaag cggaaggaga ctattgtcca ctgatgctat ccgttgagca   4980
caatgtgggg ttactcctta agccagagtc accatgggct ttttggctcc tgaaccaata   5040
gatttcattt gtattcaagc cactttgtac taggttttcc atcatttgca atcaaaacca   5100
gtatacaaat actggttatt taatttttca tttttactaa tctcatggaa aactggcttc   5160
tagttgtttt aacttgcctg tatttgtgat tcttcccatt ttcgtgtact tactaatcac   5220
ttctatttct tttgtaaatt atcttttcat atttgtccac taattcttta aaattagagt   5280
acttttcttc tccttattgt ttatgtaatt gttaaacaag actgaataac ctgcccaaaa   5340
tccgtggaca tgggagccca tgtgaaagct ttgaaagcca ccatcattat gagataaact   5400
atataacagt actttacata tgctccaaaa tacagtacag acacggctat cattgtcatg   5460
atcatgatca tcattatcag catgatcacc aacttaggag gataagcaag aacacctact   5520
agaagtttct ttccattcag caacaaagtt ggcgtttttc tagtcactcc cttccctgac   5580
tgagtcacat ggcaggtcac agaggctcaa tggcagaatg ggaagctctg ggccagcacc   5640
agccattgtg tgcatccttg cgtgtgaacc taggtgctgg aagaggagtg actgcttgat   5700
aattatgagt cagtcaaaac caccaactgt ctgacaaaac agacctcttt gtaacctgta   5760
ttgtcactaa accaatgcct ccatgctttg tgcatacatg aaatctaggc aatacacttg   5820
tattccccaa agcttccatt tgaagagatc tgtgctcttc ccaaatgtaa accttacccg   5880
agaggtggtc atctggccgc acctctgaga gggatagaag tcttgctgtg ttgggtggtc   5940
agactggggc tcagggccag aattcccagg gggtaggatt gtgcagagaa gatggcactc   6000
tccagtgctt aataaaatgc acgtggtcta agttgcccat tccctcaaag gcaataaaaa   6060
aataggtact atttaaattg aagagtaact actgccccag cgaatggaca ggttgtcatc   6120
ggaatagcca tggttaatgc cccagcgaat ggacaggttg tcatcggaat agccatggtt   6180
aatgccccag cgaatggaca ggttatcatc ggagtagcca tggttaatgg tcagttgact   6240
gactgaaatg aatatgctgg ctgaccagga aagctcatta agcagacttg gaagagagtc   6300
tttccaggta aatccacatt tacaaattaa agcagtaatg acacctaatt ctctaataat   6360
aggtggggtg cagtgtattt tagagctggg aataattcca aacagcaaat agttcaaaat   6420
ttattttcca tttagcatat gcatgcattt gcttaaacta tcttaaaaat gagtaaaaaa   6480
tattgtcagt ttgcttgaat catactgaga tgcggaacaa tatttagcac tgcatgctag   6540
aaaaggacac aggattggga gtcagggctg ggtgactgtc gcaggatttt cattaagtgt   6600
```

-continued

```
gtggatcttg ggcaagtctg tatgccctga gattcagtta tttaactttc tttcaaaaaa   6660
cctaatccag atgcagataa caaaacctgc ttctaacttc ccttacagaa ttgtgagaag   6720
ctggtggaga tgtttgtaac caaagtgttt tgaaaataga gcaaatatta ttctttttaa   6780
ggcatgatat tttcatagca tgtcaggcaa cagggaaaaa ctaagttagg attttatttt   6840
attgtgggta atttatgtgc aaattttggt gcaatttaat gaaaataagc caaagtttta   6900
atgcagaagt gcccagaaaa ttaaataaca atctacattg ttcaaatggt tgccttaata   6960
tattttattt tctcagcata attagaatta tattatacag gtcttggagt agtcagtcag   7020
tgggagaagt taagacaaca gatatctttt tgttaaaatt attatttgaa ttatctcaaa   7080
ttaactttta tggttctatc acaggatgtc tgactcaact atatgaaaac gccttcttca   7140
gaggtgggga tgtagcttcc atgtacaccc cgaacgccca gcactgccag atgatgtgca   7200
cattccaccc aaggtgtttg ctattcagtt ttcttccagc aagttccatc aatgacatgg   7260
agaaaaggta aaagttgata tttcattatt ggagaagcca tttttctaaa ctgaatcggt   7320
tttgtgcaaa gaggtgtagt ataactgaga gttctgtctc agacggggct caaggaccag   7380
cttcagcaaa atcccttcaa gtggttctta ccaatgcaga ttcctcggca acaacccaga   7440
tttgctgaac caaagtttct tgggactaga aattgcattt taaacaatca ctgtgtttat   7500
ttaaagtagt agaagttagt cattttctat tcaaagcctc aaaatgcttg aacatcgttg   7560
ggctaagaga ttgtctccag aaagcatcta acaggcgaac atttcatctg aataaagaaa   7620
cagacttaac tgtgtgaccc gtgatcacat tagtggctag cacagtccga aggaaataac   7680
gtaagacaag cattttgcgg agaatataat tgagaaacat ctagaacttg tgattttggg   7740
acagggcaga tctgaatgac gcctaaagtg agccagtttg ggcacctatg gcatgatgct   7800
atgtatggta tgtgtgtgtt catgtgtgct tgtgcttgtg tgaatatgta ttattaactg   7860
gagatttgta aaagtattgg aaaaatacta cttatgattt tttttttttt tgagatggag   7920
tcttgctttg taacccaggc tggagtgcag tggcacgatc ttggctcact gcaacttccg   7980
cctcccaggt tcaagcgatt ctcctgcctt agcctcccaa gtagctggga ttacaggcac   8040
gcaccactac atctggctaa tttttgtatt tttagtagag acggggtttc accatattgg   8100
ccaggctggc cttgaactcc tgaccttgtg atccacctgc ctctgcctcc taaagtgctg   8160
ggattacagg cgtgagccac cgcacccggc tgtaattaca atttttatta catcagagag   8220
atgcttatta atcacaagct acagtttcat cttaatgatt ttcattttga ataagaataa   8280
gcttttcttt gttcttccca tttccatatt cataactctt ttctcatctt ctccacgtga   8340
gtttgtgaac tagaaattgg atagtcattc tctgatccta catgttaaac ttgtagagaa   8400
aacccagatt gtatgtgagg atcatcatct taaaagtgga ggtaggttct agaattctta   8460
taaataatga aattaacatg gaggctgaca tttgagacag agggaagtct ttcattaagt   8520
gcagactaca aggagttaat aagcaagatg aacacacaat atacagatcc agctcttatc   8580
actaagttaa ttttttaagt aaatgaaagt atttgcaaaa ataattacca attaaggaca   8640
tagttgcctg aaggtttaag aatacaggaa aagtcattaa ctcttcaatg tggttgactt   8700
cctgtactta aaaaatgtga gtgtaaagaa aacgcaatgc tgaagttaaa tattatgggg   8760
atgttataaa attacctcta agagtgttct ttccagcaag ttttggggaa gctatattat   8820
ttcccttatt cctggtttta tgttagtgta tagaaaatgc tagacatttc ctcaatgtat   8880
gtttgttgtt ctacttccta aataaagcta cttttaaaac aggtttggct gcttcttgaa   8940
agatagtgtt acaggaacct tgccaaaagt acgtcgagca ggtgcaattt ctggacattc   9000
```

-continued

```
cttaaagcag tgtggtcatc aaataagtgg taagctgcga atttcttagc tacatttgag   9060
ttaatattga atctacctta gaacagcttt tgctaaaagt ctgtactgct acagcctttg   9120
ggaaggaatc actcataaag atagaagatg ggcagtatt ctggacacaa aagagggacc   9180
catattcatc tggacacttc tgttgtcttt atcaatcgac acgtatttaa tgagcctcta   9240
ttatttatga ggttagcact caagtgtaag atttgcagaa aatgaatcca aataatcgtg   9300
tctccttgtt tccagataag aatttttaag aaaacacgag ggaacatctc tctcaggttc   9360
acgtgagggt aatttttata tcagtgattc tcaactggca gtgatttttg tctcttccat   9420
taggggacat ttgacaatgt ctggagacac ttttggttgc tatgactagg gagggcgtta   9480
ttagcattta ctaagtagag gccagaatgc ctctctcatt tactaagaag aggccagaac   9540
gttcgaatgc tgctgcccaa ccttctacaa ggcacagagc agtcctccac agcaaataat   9600
cttctggccc aaaatgtcaa cagtgctgac atcaagaaac tctgatatac cattaggccc   9660
aaactgaaga actgggttct gcaaatcttg ctaagaataa tacttcttaa aggaaacttg   9720
aggactagga tgctagagaa ctttgatttt acatctgaag ctactgatgt cttgggaaat   9780
aatttccaac actatcctaa taaatttaag acaaatgaac tatttctcaa acatgactgg   9840
gactgatcag aaagtgagaa gtgctgaaaa gattcaactg atgggttgtc ggaatcttaa   9900
aatagctgtg ctgtgattct atgtgtgact atacatcata actattttat ttgtattatg   9960
cacaattaat tttgtaggtt caaatttcag atgtttttaa atttgtcatc ctttcctccc  10020
tcattgatat caccccttcg atacatacac actttgagcc tgctgtttgc atgttaacca  10080
gttatcaaag gatggcaaag cgttcgttat gaatatgggc ctgacttagc cagtgtaata  10140
agtgtagtct acctgaggtg gggtacattt cctgttttat aagaccaatg tgtatgttca  10200
tctaatttgg tataaagtat tcaaggaagt gctgtttcca attgttgtat cttatagcaa  10260
aatttaaaga aaaagtaaca ttgtgccttc cccaatattc ctgttattgt taatgtattc  10320
taaaactcag tgttactcac ttagcttgct tttaatgttt ttttctaact tcatcatctt  10380
aaagtgaaaa attgttccca agtacataaa atctctactt tcaggaacaa ttctagtcga  10440
aagcatttag agctttcaca tgaacactta caaagttgtt atttgtgaga gtcccatccc  10500
aactcttagc ctactctttt ctcacacgca gaaaaattgg aaagagattt catttcgacc  10560
gtctgcaaat tcctgtgttt aagaaccact gtgaataatc cacctcccta cccaattccc  10620
aattcgacat gcagttttcc tgacagtttg tatgttttct gtctttccca cccttaaatt  10680
tagttttatg acttcaacca cacttcttag gagtggaaag ttacctgtaa tagattatgg  10740
tttattccac ataatcttgg ggaataaaac tttaaaaaag tttatggttt agacttctgg  10800
tttacattac ttccttaacc aaaagtctaa ctaagaaatt tgaatattta aaaaaaaaaa  10860
gagcctaatt ttgcttcctt gtctgtgaaa agaattatct atatcttttg catgtaagac  10920
aaatctcagt gaaaagggtg cttaaataga agttaacact attttaaagc aagaatggaa  10980
gtggcttcat catgcataaa caacaactct ccacattttg taacgattga tccagatgca  11040
atttgtagtc agacaggaga agttgaaagc agagaaagaa cactgggaga tagagaagct  11100
ccttcattca atgcaaaagg tcaaaggcac atcagtttct ttaataatgc aaacctcagc  11160
acacatgatc agtgtcctca ttattattgc cttgtttatt tcccactgct cactgttaat  11220
ttcaacgtga aatttacctg tattgctgca tgcatcttgc agtttaagaa gcgaagtaac  11280
ccaatttcca agctagtgct ttcaggaaaa tactggattg tatttacttc gagcagagtt  11340
```

```
tgataattta tggacatcat aaaaatttta aatcccttaa ttaatatagc aattgccaaa  11400
actgggctgt tatccttcta aactaccggc ccaaatggta gtgggatcct tctaaactac  11460
cagcccaaat ggtagtgggt atctaatcta cctctagaaa gaaaatggac tgtgtttgct  11520
ctatttcctt tttcttgtac agcttgccac cgagacattt ataaaggaat tgatatgaga  11580
ggagtcaatt ttaatgtatc taaggttagc agtgttgaag aatgccaaaa aaggtgcacc  11640
aataacattc gctgccaatt tttttcatat gccacacaaa catttcacaa tgcagagtac  11700
cggtgagtac aattcatggt gtttgttctt tatattagtg cccccaggat ttcactgtat  11760
tcttcacaac ctcttttgtt cccaaactaa aaaccaaaca gggcttttac tcctaaccac  11820
tttccttatt tacttactct attttatatt tttatcttct tttttttttt tttttgaga  11880
tggagtctcg cgtgttgccc aggctggagt gcagtggctc aatctcggct cactgcaacc  11940
tgtgcttcct ggcttcaagc aatcctcctt cctcagcctc ccatgtagct aggactacag  12000
gcgcccacca ccacacctag ctaattttta tgtttttact agagacgggg ttttaccatg  12060
ttgctcaggc tggtctggaa ctcctgatct cgtgatccac ccacctgggc ctcccaaagc  12120
gctgggatta caggcatgag ccactgctcc cggcccttca ttttaaagtt aaataattca  12180
tttaatttca tttgtttctc tactcttttc ctctggcagg taattgtacc ccatcttcaa  12240
agcctggcat cctcttccac cacttctcca aaggctgatt ctttcaggtc tttcctcaga  12300
taccgtcccc tccaaagggc catttctgag cattctcttt taagccacat tcagctctgt  12360
ttatttcatt cgtagagcta atcacaattt gattttaact tgtgaatttc tttccttatt  12420
tttaaatctc gtttttgttt gcatagatgt atggggtaca agtgtaattt tgttaccttg  12480
gtgtattgta cagtggtaaa gtctgggctt ttggtatatc catcactgga gtcacgtaca  12540
ttgtacccac taagcaattt gtcatcacct gccccttcc cacctctcta tcgccttccc  12600
agtctctact gtcgatcact ccatgctctt ctcaattgtg gtgtcatttt tcctgaagcg  12660
aaatttcggt gtcattgttt ctgaagtcat tttctgacgt ctgtgtcatt ttttgctttc  12720
ctgaagtgaa ttttggtgtc atttttcctg aagttccatt tgccccacgc ataggcctta  12780
cttgtagaat gagggtttag tgtcatggtg tctcctgcct cattctcacc ccaactttcc  12840
cttgacccct ttgcgaggag aaggatgtcc atttgattaa taatgcaaac ccctaaccca  12900
ctcattatca gcatcattgt tttttccact gtccgtttga atactaaatg ttacctggac  12960
tgctacctcc gcctcaaagt gcaggaagca aagtcacctc ttttcttccc attcaggaac  13020
acttgcctct taaagcacag tcccggagga acgcctacca ctataaaggt gctgaataac  13080
gtggaatctg gattctcact gaagccctgt gccctttcag aaattggtaa ttgtaggacc  13140
acttcacctt gtgattgtag taggcggaat aggacccccc agagatgtcc ctgtgcggag  13200
ccccggtacc tgtgcgtgtg ttcccatagc tggcaaaagc gtttctatca atgggattca  13260
gttaaggact ttgagatggg gagtttactc tggatttcct cgatgggccc aatgtactca  13320
caggattggg tgctcacaag gctaataaga aaaagggaga ggcagaaggg tcagaggcag  13380
agagaggttt gaaggtgtta cactgctggc tttgaagatg aaggtccatg agccaaggaa  13440
tgcaagtggc ctctagaagt tgaaaagggc gaggaaacag tttccctgtg gagcatcctg  13500
gaggaacaag ccctgctgat gtcttgattt tagcccagta agacccaatc tctagaatgg  13560
taagataata aatttttgtt gtttttaacc actgagtttg tggttatgcc cctatagcag  13620
cagttatagg aaactagtac agtgatattg ttataggtac aatgatattg tagcaaaact  13680
gtaaggacct tccttggttg tgtccctatc tagggaaatg actctaccgg ggggagggaa  13740
```

```
ataacattct gtcgtgtcac acataaaggt aatttcaatg gaattgtcca gaaaattgcc  13800
atgacattcc acctcattta gcgtatcagg atgttaacga caagatgtta ctgaaaccaa  13860
atcccttact gccagttctc cgcagtagtg ggtgctggct ctgtgcctgg ccctgtattg  13920
ggtgctgggc taggatttcc ctgtggaaga ttgggaaggt tggttacaag gtgtctattt  13980
tcctgtctcc tctttgtgac agcacacctt ctccacggtg cgtgccaggt tcacgtgtac  14040
tgatgatgtg attttaacgt tcatattatt tttttccggg agagtttttg aaggctgcca  14100
ggaggcagga ctcgatgcaa gcatgctcca ttctgtaccc agcactgttg ctggaaggat  14160
ttgctgcact tacccaggga acaggcaagc tcatgccgtg gttctgggct gtcacagctg  14220
ctgtccacac ctgggagagc accctggatg gctcatctct gtacttgctt tcttgttaaa  14280
ttgcagtgag ttcacatgtg atttaatctg atcaaatggc ctttacagac tggtaaaaat  14340
ctggctgttt caggcagtgt tttgagctgc taaaggcatg gcttttcact gagtacgtgt  14400
tccccgttcc tcagggaaca cccagtagct acgtgcctcc tcaacctgga gtagggctgt  14460
ctcctggcct cactgcccag atgagattca taagttaggg atcatctgta gtcatcacta  14520
caggtttgtc cttagtttca ccatggattt ttctaatttt acaaacaaaa cccctaaggc  14580
tcctagaagg agggcagaag tgaaggtgct tgggggtcat atagctgatg agctgaacga  14640
gaacttgacc cttgggtcac acagatttca cattgctcac tccccatttt gatttttttaa 14700
tggatttaat ggtgttttaa agtctcctgc ctctcaactc atataaattc atcatattta  14760
cagatttcct tctcttgcgg tccatcttcc tgcatagatc ttgacagatg tcagggtaat  14820
cacatcttcc cagttaattt aacaaaaccg tttgcaattc tgatatggga aatctaccat  14880
atgacttatt aatttatcaa ttgaggtgat aaacatattt ttcaagccaa aagtaggaga  14940
acataaactg gaaaaaaaag ttttttttatt ttttatttt ttatttttat cacctctggg  15000
gaagaaaatc tgataaatga acctggttga tgaaattgca attagtggga gcaacatcat  15060
ggtttctgtt ctgagaataa ccagatggta tacttgaaat agagaatgtc ctagaaatca  15120
actggttgct tggccaaaat atctataaat agtgcccgac atattagata ggaaaagcaa  15180
agtaaaagca attttaatag gttaggacat tgggctgaag tattgcatat atttaatgtc  15240
acgtgcatct gtgtgaagag accaccaaac aggctttgtg tgagcaataa agctttttaa  15300
tcacctgggt gcaggaaggc tgagtccaaa aagagagtca gggaagcgag atagggggtgg 15360
ggccatttta caggatttgg gtaggtaacg gaaaattaca gtcaaagggg ttgttctctg  15420
gtgggcaggg gtgggggtca caaggtgctc agtgggagag cttctgagcc aggagaagga  15480
atttcacaag gtaatgtcat cagttaaggc aggaaccgac tattttcact tcttttgtca  15540
ttcttcagtt acttcaggcc atctggatgt atgtgttcag gcttaggccc agaggcctga  15600
cattcctgtc ttctcatatt aataagaaaa ataaaatgaa ataggagtaa agtgttgggg  15660
tggcaaaaat tttggaggtg gtatggagag ataacgggca atgtttctca gggctgcttc  15720
gagcaggatt aggggtggcg tgggaaccta gagtgggaga gattaagctg aagaaagatt  15780
ttgtggtaaa ggttgatatt gtggggttgt tagtgggagc atttgtcgta tagaatgatt  15840
ggtgatagcc tggatatggt tttgtatgaa ttgagaaact aaacagaaga cataaggtct  15900
gaataagaga aggagaaaaa caggtattaa aggactaaga attgggagga cccaggacat  15960
ctaattagag agtgcctgag gggttcaac ataattagtt gcttggttgc tgagtttttg  16020
ggctctatcc ttgacagagt cctccttctt aagttggagg ctgagcttgg tgaggtgtgt  16080
```

-continued

```
ttttaaaaga ccattagtcc tttctacctt tcctgaagat tgaggagagt aaggagtatg  16140
aaggttttac tgactactaa gagcctgaga aactgcttgg gtgatttgac taataaaggc  16200
cagtccatta tcagattgta tagaggtggg aagtccaaac caaggaatta tgtcttacag  16260
aagggaagaa atgaccacgg tggccttctc agaccctgtg ggaaaggcct ctacccatcc  16320
agtgaaagtg tctgcccaga ccaagaggta ttttagtttc ctgactcggg gcatgtgagt  16380
aaagtcaatt taccagtcct ctgcagggac aaatccccaa gcttgatgtg tagggaaggg  16440
agggggcctg aacaatcctt gaggagtagt agaatagcag atggaatact gagaagtgat  16500
ttccttgggg atagatttcc acaatggaaa ggaaaagagg ggttttaaga ggcaggctag  16560
tggcttgtaa cttacatgga agaggttacg aaatgatgac agaatagaat gggcctgtga  16620
ggctggaagg agatattttc cttggtccaa gaactatttg ccttgtgtgg gaagagattg  16680
ataggtggaa gtttcaatgt gggagtagat gggagtgacc gattagaggg aggaaaaact  16740
ggccgtgagg gacagaagtt ggaatgctag ctgcttttat aactacctta tcagcatggg  16800
tgttgccttg agcaatggga tctgatgcct tttgatggcc cttgcagtga atgactccag  16860
cttcctttgg acgtaaagtg gccttgagaa gagtttttat taaagaggca ttaatgatgg  16920
aggacccttg cagagtgagg aaacctcttt cagcccatat aacagcatag tggtgcagga  16980
tatggaaggc atatttagag tcagtgtaaa tattgatgca tagtaccttt gcaagagtga  17040
ggacctgagt taaggcaatg agtttggctt gctgagaggt aagttaaggc aatgagtttg  17100
gcttgctgag aggtagtgga ggggtgcaga gtggtagcct caatgataga tgtagaagat  17160
attatagcat accctgcctt tgctggtggg tggagattag gcctggtgga actgccatca  17220
ataaaccaag tgtgattagg gtaaggaata ggaaagacag aagtatgggg aaatggagtg  17280
gatgtcaggt ggatcagaga gatacagtca tggggatggg ggccagccta aaacagtaag  17340
gtcaagttgt ttctacagaa agcnnnnnnn nnnnnnnnnn nnnnnnnnnn nnnnnnnnnn  17400
nnnnnnnnnn nnnnnnnnnn nnnnnnnnnn nnnnnnnnnn nnnnnnnnnn nnnnnnnnnn  17460
nnnnnnnnnn nnnnnnnnnn nnnnnnnnnn nnnnnnnnnn nnnnnnnnnn nnnnnnnnnn  17520
nnnnnnnnnn nnnnnnnnnn nnnnnnnnnn nnnnnnnnnn nnnnnnnnnn nnnnnnnnnn  17580
nnnnnnnnnn nnnnnnnnnn nnnnnnnnnn nnnnnnnnnn nnnnnnnnnn nnnnnnnnnn  17640
nnnnnnnnnn nnnnnnnnnn nnnnnnnnnn nnnnnnnnnn nnnnnnnnnn nnnnnnnnnn  17700
nnnnnnnnnn nnnnnnnnnn nnnnnnnnnn nnnnnnnnnn nnnnnnnnnn nnnnnnnnnn  17760
nnnnnnnnnn nnnnnnnnnn nnnnnnnnnn nnnnnnnnnn nnnnnnnnnn nnnnnnnnnn  17820
nnnnnnnnnn nnnnnnnnnn nnnnnnnnnn nnnnnnnnnn nnnnnnnnnn nnnnnnnnnn  17880
nnnnnnnnnn nnnnnnnnnn nnnnnnnnnn nnnnnnnnnn nnnnnnnnnn nnnnnnnnnn  17940
nnnnnnnnnn nnnnnnnnnn nnnnnnnnnn nnnnnnnnnn nnnnnnnnnn nnnnnnnnnn  18000
nnnnnnnnnn nnnnnnnnnn nnnnnnnnnn nnnnnnnnnn nnnnnnnnnn nnnnnnnnnn  18060
nnnnnnnnnn nnnnnnnnnn nnnnnnnnnn nnnnnnnnnn nnnnnnnnnn nnnnnnnnnn  18120
nnnnnnnnnn nnnnnnnnnn nnnnnnnnnn nnnnnnnnnn nnnnnnnnnn nnnnnnnnnn  18180
nnnnnnnnnn nnnnnnnnnn nnnnnnnnnn nnnnnnnnnn nnnnnnnnnn nnnnnnnnnn  18240
nnnnnnnnnn nnnnnnnnnn nnnnnnnnnn nnnnnnnnnn nnnnnnnnnn nnnnnnnnnn  18300
nnnnnnnnnn nnctggcgag gagcagcctg gggaggaggg gagaggtcag atgggtccat  18360
agaaaaggaa gattggaaag actcagcaac gcttggggtt gggattgagg ggacaggcgg  18420
gagggaaaga aggaagattt gggatgagtt gcattgggaa caaagactag ggagggactg  18480
```

atgtgtaaaa gactgcctgg acatcaggca gctcagacca tttgcccatt ttacaacaag 18540
aattatctag atcttgtagg atggaaaaat caaaagtgcc gttttctggc tatttggaac 18600
cattgtcaag tttgtattgg ggttaagcgg cattgcagaa gaaaataagg cgttttggtt 18660
ttaggtcagg tgtgagttga agaggtttta agttcttgag aacataggct gagggagaag 18720
aaggaggagt ggagggtgga aagttgccta tagtgaatga ggcaagccca gagaaaagag 18780
agggtagaga cacggagaga aggggtcagg gtgcttgccc cccaggaaag tggtgcttgc 18840
cactaagggt gaaggatcaa ggcaggcatc cctaaggtga tcagacacct ctgaaacatg 18900
ggcgcataat caagcaggtg tccctgtagt gattaaatgc caagggaaga ctgtcttccc 18960
gagtccatga ctggtgccag agttttgggt tcacagataa aacgcgtctc ctctgtctct 19020
accagaaaat gaaatgaatt gaaattaaga gaagggagag attgaaggat ggcgccaaga 19080
ttaaaaggag aaagaggttg agggatagtg agagagattg gataagagag taaaaagagg 19140
ccgtttaccc aatttaaaat tggtgagatg ttccttgggc tggttggtct gaggaccaga 19200
ggtcataggt ggatctttct cacagagcaa agagcaggag gacaggggat tgatctccca 19260
agggaggtcc cccaatccgt gtcacggcac caaatgtcat gtgcacccgt gtgaagagac 19320
cactaaacag gctttgtgtg agcaataaag ctttttaatc acctgggtgc aggtgggctg 19380
agtcagaaaa gagagtcagt gaagggagat aggggtgggc cgttttatag gatttgggtg 19440
ggtaatagaa aattatagtc aaaggggttg ttctctgatg ggcagggttg gagctcacaa 19500
ggtgctcagt gggtgagctt ctgagccagg agaaggaatt tcataaggtg atgtcatcag 19560
ttaaggcagg aaccggccat tttcacttct tttgtcattc ttcacttact tcaggccatc 19620
tggatgtatg cgtgcaggct tgggcccaga gacctgacat ttaacatgaa taaatgtgaa 19680
gttcttagaa tcatacatac acattggaaa agatggggtt taatagcact ttataaggag 19740
acttgaagaa tgtttgagaa tccaccatga agctgctgaa aatatcaaga aaatttaatt 19800
cttatgtata taaataatgt gtctgtttta catgaattcc ctctatcaag tttggtattt 19860
taatatagca tatattattt tttcatagta gatttaaaat ttttgatgta taatttagat 19920
aacataaaat taaccctttg aaagtgtaca actcagtggt ttttagtata tccacctgat 19980
ttcacaagaa tcaccactat ctagttccag aacattttta ttaccactga agaaagactg 20040
tatccattgg cagtctttct ccattgccta ctcctccaat cccctgacaa ccactaatct 20100
actttctatg tctgtggact tgactcttcg ggacatttta cataaatgca atcatgcaat 20160
gcagcacatt ttgcatctag ctttttttcat ctggagtgtt ttcaaggctc attcatattc 20220
tagcatatat cggtactttg ttcctattta ggactaaata gtattctatt atatgaataa 20280
accatatttt gtttatatac ttagtttgat gaacatttga gttgtttctg gatttttttt 20340
tttttttttt ttttgcctct tatgaataat gctgcaatgg acagcagttt ttgtgtaggc 20400
atacatttta aattatctta tgtatatact taggattaaa attgttggat catacagtaa 20460
ctccatgttt aactttttga ggaagtgtca aactgttttt gagagcagct acacaatttt 20520
acattcttac cagcaacaac tgagtgcttc aatctctcta caaccttaac aacacttgtt 20580
attgtctttt ttattattgc ctttctaggc agtgtgaagt ggtgtctcac tgtggttttg 20640
atatgtattt ccctaatgac taataatgtt gtgtatcttt tcatatgctt attatcaatt 20700
tgaataaatt ctttggggaa atctctgttt aaatccttta gccattaaaa ataattgggt 20760
tattttgttt tcattgttga gttgtatgaa ctctttatat actctggata ctacactctt 20820

-continued

```
gtaacatata ttattggcaa atttctgtg catctgcagg tcatcttttc actttagtga  20880
tggtgttctc tgaagcgcaa aagtttttaa acttgatgaa atacagtctg gctttattct  20940
tgcatgtgct ttacctaaaa tgccaaaacc taattcatgg ttatgaagat tttgtgtat  21000
gatttgttct tagaggttta tagttttagc tcttacattt aggcatttga tgcattttaa  21060
attaaatttt gtatatggtg taaagtagga atccaactta attcttgtat gtggatattc  21120
agttattcca ttgtcttgaa actcttttca aaatcaattt tctataaatg taagagttta  21180
tttttagacc atcagttcta tcccattgac ctgtatgtct gtcctaatgc cagttacaca  21240
cagtcttgat taccataact tcgtagtaag ttttgaactc agacagtctg agtgctttta  21300
ttttgttctt tttcaagatt aatttggtta ttccggatct tttgcatttc catatgaatt  21360
gtaggttggt tgtcaatttc tgcaaccaga aggcagcagg attttgacag agagggcatt  21420
gaatctgtag accaatgagt atcaatagaa ttatgtgtta tcaaatttag taaactacgt  21480
aaacgatagg aacacagcta aaataaaact aagatataag atcgtattaa tgtaatgtta  21540
ataaaagtag attgtctccc attctaattt taatgggcac aaggcatttt tgttaatcac  21600
ttcttattaa ataatttttt ataatattca ggaaaataca acaacaaaaa acccttacat  21660
tccaaaggcc tcagagtcag agtaatagaa ggaaaacgta aacacatgct gagtaatgca  21720
aacatttggc aacggtggtg actggagctg ggagcacagc ttttatttct ctgacatagg  21780
agtttgcccc ttagagttgg accagttttg ccttcctcta aatgacaaac agtttggagg  21840
tattttaaag gacgttttgt cacttaggat gtttagtacc atgaataata taaatagtca  21900
taattcctta attacgatga caaaatacaa gcgaatttag catcgtgtgg tttcctaagg  21960
aacatctctc tctgagttca caggttgtca catgaacatc ttccagcatc ttgccttctc  22020
ggatgtggat gttgccagag ttctcgcccc agatgctttt gtgtgtcgaa ccatctgcac  22080
ctatcatccc agctgcctct tctttacgtt ctatacgaat gcatggaaga tcgagtcaca  22140
aaggcgagta tgcatggcta gcacttgctg ctgtactttc atcaatttta ttttagagtc  22200
tgagttttta aaagtttcct tcatttccct caaaacactt ggacctgcag tttaagtagg  22260
tacttttctg ccaggtgcag attagttaag agattagcag acttctctgc ctgtcttctc  22320
ttactttaaa acacatgtta ccagctgggt gcggtggctc ccacctgtaa tcccagcaca  22380
ttgggaggcc gaggcgggtg gatcacgagg tcaggagatg gagaccatcc tggctaacac  22440
ggtgaaaccc cgtctctact aaaaatacac aaaattagcc gggcgaggtg gcggcgcctg  22500
tagtcccagc tcctcgggag gctgaggcag gagaatggcg ggaacccggg gggcggagct  22560
tgcagggagc caagatggcg ccgctcactc cagcctgggt gactgagcga gactccgtct  22620
caaacaaaaa aacaaaaaca aacaaacaaa aaaaaacacg ttaccattga atccaggaag  22680
caatagccat gagaacaaag aaggatctga cgcctttgaa tgaagattca aaacacgatc  22740
ttcacgtttt gtattagctt ggagtaaaag ccactccctg gcagaatatc ccttaagctt  22800
gttgcctctt ccctttgttt cagaaactag agctctgttt attctgatca aggctctgtc  22860
ccactctctt tatctcagat aacccaccct cttctacaca cagcatggag ctaagagaag  22920
ggtgcctagt tatggaatat catcagcagc ataaactccc agaatttctt ctttgatttt  22980
tttgtttgtt tgtttttcca gttagaaggt ggaacttcgt cactgtcctc tcttcaggtt  23040
gtctgtgcct attagtttc tccagaggga gatgtggttt gatttacatt taatctctgc  23100
aatttattag agtcctgtag tcggatttac ttggaagaga gtttcccaaa agaataaaat  23160
ttgccaactt cctttttggg tgtgagctgc ttttgtattt gcctaatgcc tttaatgcaa  23220
```

```
acttcttnnn nnnnnnnnnn nnnnnnnnnn nnnnnnnnnn nnnnnnnnnn nnnnnnnnnn  23280
nnnnnnnnnn nnnnnnnnnn nnnnnnnnnn nnnnnnnnnn nnnnnnnnnn nnnnnnnnnn  23340
nnnnnnnnnn nnnnnnnnnn nnnnnnnnnn nnnnnnnnnn nnnnnnnnnn nnnnnnnnnn  23400
nnnnnnnnnn nnnnnnnnnn nnnnnnnnnn nnnnnnnnnn nnnnnnnnnn nnnnnnnnnn  23460
nnnnnnnnnn nnnnnnnnnn nnnnnnnnnn nnnnnnnnnn nnnnnnnnnn nnnnnnnnnn  23520
nnnnnnnnnn nnnnnnnnnn nnnnnnnnnn nnnnnnnnnn nnnnnnnnnn nnnnnnnnnn  23580
nnnnnnnnnn nnnnnnnnnn nnnnnnnnna gaactttacc tggtaatgtg attcaataat  23640
aatattacat aaaacgtaac atatttcatg acttaacagc aacagtgttg aaacaatcca  23700
caaggtaaca gaaacttttg taaatgtcgt tcattgcttt tctcatttgg tatcttttca  23760
tgtttataat tgacacagaa ccctgccatt ctaaaattta cccgggagtt gactttggag  23820
gagaagaatt gaatgtgact ttcgttaaag gagtgaatgt ttgccaagag acttgtacaa  23880
agatgattcg ctgtcagttt ttcacttact ctttactccc agaagactgt aaggaggaga  23940
agtaagggac attttatttt tcatgatcat ttcatatcct ttttccccta gtgaaggctt  24000
actctttcta ctgttcattt catctaggtg taagtgtttc ttaagattat cttcggatgg  24060
ttctccaact aggattacat atgggacaca agggagctct ggttactctt tgagattgtg  24120
taacactggg gacagctctg gtgagtaacc tcactttttc atggaactgt aagggatgtc  24180
tgtcatgttg atagtgtgct tagtcttaag gaattatatg tcttgttctc cttggttaga  24240
agggactttg attcacttct aatttcaacc attagcatca acactcttgt ttcagtctgc  24300
acaacaaaaa caagctcacg cattgttgga ggaacaaact cttcttgggg agagtggccc  24360
tggcaagtga gcctgcaggt gaagctgatg gctcagaggc acctgtgtgg agggtcactc  24420
ataggacacc agtgggtcct cactgctgcc cactgctttg atgggtaagt gttggatgca  24480
tctcatccag agtcttacct tgacttttca ttttgaaggg tctgtgatca gctgcttcac  24540
cgtcatgtga ctttatgaat agagacgtgt taaagcaggg atggtattca caacatttaa  24600
ctagcagagt ccaagcactg accagtctga ccatcataac agagtgtggt ctctgtacag  24660
gactgatggc cctgggtggg tattctccca cagaaagaga aacaaacaca atacaccact  24720
cctccaaccc accacccgcc accaatccca ccacccatcc caccacacaa cccaccaccc  24780
atcctgacac caatcccaac accaattcca ccaccaatcc caccaccacc caccaccaat  24840
ccctccacca atcccaccac cacccaccac caatcccatc accaatccca ccaccaatcc  24900
caccaccacc caccaccaat cccaccacca atcccagcac ccgtcccacc accaatccct  24960
ccaccaatcc caccaccaat cccaccacca cccaccacca cccaccacca agcccgccac  25020
caatcccagc acccatccca ccaccaatcc caccatcacc caccaccacc catcaccaat  25080
cccaccacca ataacaccac cagtcccaac gctacccacc accaatccca ccaccaatcc  25140
cagcacccat cccaccacca atcccaccac caatcccacc acccatccca ccaccaatcc  25200
caccaccaat cccaccacca ccaatcctac caccacccac caccaatccc accaccaatc  25260
ccaccaccaa tcccaccacc acccaccacc aatcccacca ccagtcccac caccacccac  25320
caccaatccc accaccaatc ccaccaccac ccactaccaa tcccaccagc agtcctacca  25380
ccaatccctc caccaatccc accaccaccc accaccaatc ccaccaccac ccaccactaa  25440
tcccaccacc aatcccacca gcaatcccac cagcaataaa tcaaagactt atttctcagg  25500
cccatagaaa tgttacttct tgctttttga ttaataaata tactaataat aatttttaaa  25560
```

-continued

```
agtgagagtt ttgtactccg tatatttcaa catatgtaat ttgatctatt tcagttttat  25620
tggtcaaata gtagacatgt taggtaagtc ttaaaacact gaggttttgg agttagacaa  25680
aacatggctt gagtgataac tttgctgctt attagaggtg tggccctagg agatttgtaa  25740
atctctctga gctttatttt atctaaaaga taaataataa tagtacctaa tttgtaaggt  25800
tattgggagg attaagtgac acatttaaaa tgcttagtac tatatgtcga acatgaacac  25860
tgctcaacaa atgtaaacta tgatttctat attcaataag aagtgtagaa atggacaaag  25920
catatgaaaa agcaaaagaa atactagaag acacttgatt tttctaaaaa ataaacacaa  25980
agtatttttg ttttagtgaa attcatgctt agatgctgtg tactaggatt gaacatacag  26040
ccgccaaaat atagcagttg gtggtacatg tgggtggagc aagacccctc caccttgtca  26100
ccgtgaaggg gctccgccat acatgccctt gcatgtggtt taaaggtggt tggcctggaa  26160
gaaaaggccc aagatgggaa acagtaggtg tctttttttac taaatgtact ccaatttgag  26220
accaggaatt ttcattcttg aaggctcagt attgtaagtt tataagagat aatagacata  26280
aaagtacgat gatttcatta aaaaaaggct cctttgcacg tgatatctcc gttatttttt  26340
ctagaatatt gtgcacacat gccttgcacc acttggtgat gataaagatt tctagatctt  26400
tgcacagaat aaggctttgc tttagatcat aattttggat gtacttagta tgtattcatc  26460
ttttaaagaa tcaatttaaa ttttcatact ttcatatata tatacacaca cacatacaca  26520
aacacacgca cacactttat tttaatattt tatttattta tttattgaga tggaatctca  26580
ctctgtcacc caggctggag tgcagtggca ggatctcggc tcactgcagc ctccgcctcc  26640
caggttcaag cgagtctcct gcctcatcct cccaaatttt tgtattttca gtagagacgg  26700
ggtttcacca tgttggtcag gctggcctta aactcctggc ctcaagtgat ccacccgcct  26760
cggcctcccg aagtgctggg attacaggtg tgagccactg tgcccggccg tatagagata  26820
ttttaaacaa cactgaagtc ctcctactct gcctaattag aagagcattg aaagatcagt  26880
ctgacttctt gatagttctg aatttaatgg agcaatgagg tgcagctttg gtgaatgagc  26940
ttaatttttc catgataaat tgctagtctc ttcccactac agtgtctctc aaaaatggga  27000
cagcaacatt ctttgtgttt tcacttgcag taagtaagca tgatacaatt acataaatgt  27060
acacttctca gtttgttaaa tagaatcttc agagattcac gtctgccgct attggtgatg  27120
aaaaatgacc cgtaggagga attaggtagg agaaaatatg tcctatgtag tatttccttc  27180
ccagttctct ttgaaagaga gtgataggaa aaaggaacaa tattgaagga aggccttccc  27240
agtttcaaat aggttttatt tttctctcct aggcttccct taccggatgt ttggcgcatt  27300
tatagtggca ttttaaatct gtcagacatt acaaaagaaa cacctttctc acaaataaaa  27360
gagatcatta ttcaccaaaa ctatagaatc tcagaaggga atcatgatat cgccttaata  27420
aaactccagg ctcctttgaa ttacactggt atgtagcgta tgtaagaagg cggatagcag  27480
aattgtgctg gatgatattt tcatatcagt ttggacaaga gggcagatct agagagactg  27540
ttgttatttt ctgaccggtg gagttgaggg aaaggtgagg gttgcatggg aagtgaagat  27600
cccacgactt gccatgaaat ctcttctacg taaagagcaa gaaacgtgaa ttagttcttt  27660
cagggaggag cacagccgcg cgcaggtgat ggaaataatg gacggaggag atgtctgtgc  27720
cgtctgagag gcaccgggct tcttttgaca agagtagcag aactgtcatt gctttgggct  27780
tagggatatt agaatgtgtg aggaccagtg ggactagata catatttcca ggtataattt  27840
gggtaggaaa gagactgatg ccgaaagaag ccctggaaag gccagaacat cgtgatcaga  27900
ggtgttgcct ttggaggttc attgctgcca ggagctgaat acccactgta tccaataaca  27960
```

-continued

```
ttaatggcca ggcatggtgg ctcacccctg taatccccac actttgggat gcccaggtgg  28020
gaggattgct tgaggtcagg agtttgagat cagcctgggc aacacagtga gaccctgtct  28080
ctacataaaa ttacaaaaaa aacaattaac tgggtgtggt ggtgtgcacc tgtagtccaa  28140
gctagtcagg aggctgagac aagaggatca tgtcagccca ggaggtcaag gctgtagtga  28200
gccaagatag tgccactgca cacaattatg tgaccttggg caagttgctt tacctctttg  28260
cacctcttaa tttcctcatc tgtaaaatga ggatgataat ttcttcctgg gtttgttgta  28320
ataatcaata cattaaagca cttcatgtct ggaacagtga agacacctgc tatgactatt  28380
aaggatagca tacacggaat aagacgcagg aacttctaaa tgcttttgac cgtagattta  28440
ggttctgagt tttaagaatg taactcagga aattgtaaca ccaaaaaggt catgtgaaaa  28500
atggtggtga caaattttct tgaatcaata gccttagaag ttgggcagaa agcaaaaaag  28560
ttattcttgg tgctactcta tagaaagaga agacagaaaa agaaaaagat gtatttttaa  28620
agtctatatc cataacttta tttgaccaaa ctctaattta aaaattatgt ttcagaattc  28680
caaaaaccaa tatgcctacc ttccaaaggt gacacaaaca caatttatac caactgttgg  28740
gtaactggat ggggcttctc gaaggaaaaa ggtacagcat gatgctttaa atattgcttc  28800
tagagtaagt cttacatgtt gagatgcatg gagtgggtcg ttttaatcgg cttctctctg  28860
aaattatatc gaacccccttt atctttccta cctatttatt ccccaatatt tattcagtta  28920
ttcttaaaaa acgtattttt gctttggctt gaaaaaaaaa ttttagggag aattttaagc  28980
atcttacttc attctaaaga tcgtttgctt gacttcgcat gaaagattgt ccccatctaa  29040
ggctgacgag cccgtgcaag accatctggt cctcagtgtt agcagcattc ccatctccca  29100
ataccatgtt ctcccttgat gctaatggcc gggagcacag gcaggcgtgt cgcctctctc  29160
tgtggccagt tcttcatctt cttcttccag gcacccttcc tgcaatctga ggaagcctag  29220
gaaccacttc tctaacaatg cttttaaatg cttaaataaa atacacagga ttacaaaaga  29280
aaccaagtga agtgcaagac agttctcaaa atactttcaa aaagtactac aataatatat  29340
atgcctcttt attaatcctc tacatagcga gttattctaa taccaaacct acttttgaaa  29400
tagtggtgag cataaatggc attttcactt atctgccaca acagaaaagg gatatgaaaa  29460
tatctgtaat ctctgttgat ggcaaagtca taggtgccac tgatactgct gtgtttgttg  29520
tctgcattcg taatcgaagg gagtggtagg cttcatctgg aggtttgtga aaacaaagac  29580
ttttttttcta cacaaattta taagccatgt gaattctttc tgaggacctt aggtttgcaa  29640
ttcctacttg tgggtatctg gagtgttcca atcgtccttg aactttttaa aaaacagacc  29700
agtctccctt tccaaaatta tgttcctgat agacactatg gagaataata tctgtgtcat  29760
tctttacaga agaaggtagc ttgccaaact ctctccatct ttcccgattc agtccttagt  29820
tcaagtgatt cacattttta gattttttac tggtaatctg agacaagaag aaattaaaag  29880
taatcttcac taagcaacga aagctcccaa cactgtcctc cccatgagag atgctcgctt  29940
gcatttactc agaaacaaaa gaccccaaga cccctctgtc gcgaaagctc ggagggcttt  30000
tcagaaacga tagggctttc aattataatt tggaatatat gaaacaaaaa aatgaaaagt  30060
gagaacttcc aggctttgga tttttgtaga tgataaatat aaaatgggat ttctgggggga  30120
ctgttaccga gatgaggggga tggaagaaga cacggaagca aggtctctgg tcagcccagg  30180
gtgctgggct tgtcccaaca ccacacaggt aataagagga cagtgcaggg ctccgtgtct  30240
ctctctctct ctctctctct gtgtgtgtgt gtgtgtgtaa cactaccttc ctaattttta  30300
```

-continued ctatttgtat tcaaagatac ggcccttata aaaaagtaca ctgctctgat tcacttgaaa 30360
acttatttcc atatttacta tttattgtgt ttcctccctc tgaagttata tattggttac 30420
ttcacaggtg aaatccaaga tattctacaa aaggtaaata ttcctttggt aacaaatgaa 30480
gaatgccaga aaagatatca agattataaa ataacccaac ggatggtctg tgctggctat 30540
aaagaagggg gaaaagatgc ttgtaaggta atgcatgaga ttatgaaaaa cacaataggc 30600
tgcttgagaa aattcacttc aaaatatatt ttccaatagc ataatttatt atagttttta 30660
aaaaaaattc agagacaaat gatctgataa atttataagc aacttttaac aaattgaata 30720
tatacaatac atatttatat tattcatgat gtatgtcaca atctatgcat gtgctaattt 30780
aagagggaca aaaatacata caataattgc actaaaatat aaaaacatta gatttctttg 30840
tcattgggat gatgatatca agatttcttt gttagattta tttaagaatt gaagagggga 30900
tacaaaaaat gcaggcacat gagatacttg gagaacttta agaaagtttg tgtgtgtgtg 30960
tgtgtgtatg tgtatgtgtg tgttgctgtg tagtggacta cagaatttta gaggtggtca 31020
cttatttgag tcccattgtc ataactttct accattttat ttttcccctg tgactcaggg 31080
agattcaggg ggtcccttag cttgcaaaca caatggaatg tggcgtttgg tgggcatcac 31140
cagctggggc gaaggctgtg cccgcaggga gcaacctggt gtctacacca aagtcgctga 31200
gtacatggac tggattttag agaaaacaca gagcagtgat ggaaacgctc ggatgcaggc 31260
gccagcatga ggagcagccc agagtcttgg cgagttttac aacctgggtt caagtcaaat 31320
tctgagcctg gggtcctca tctgcaaagc atggagagtg gcatctactt tgcatcctgt 31380
cataaggaca aaagacagtg cactcagagc tgctgaggac aatgttttgc tgaagccagc 31440
tttcagcatt cagtaactgg gagctgataa tgtgaagtcg caaccgagat ctccatgatt 31500
gtgtgtcgta aaataaaatg gtaaaagatc acaattagca agtgttttct tctggttgtg 31560
aaacagaact gaaagtaagt ggttgaggtt ctagcacagt gcctggactc cctctaattg 31620
cactacttct tctggaactc agtctatctc aaagatgtaa tttcctctcc ttgctgcacc 31680
tggttagcca ctgaaaccca cgattgtctg cttcacttgt ggcaaagagc tagcaggctt 31740
gggttctgtt ctgccgagtg gaagggagaa cacctgcgtc acacccactc ttataagaaa 31800
gagatgggtt acctgaaccc atagggtata tttgcctctt ggcctcctaa ctttgctact 31860
ggggcatgga taggagggtc caggctgcgt gtgtggagga actcgagggg ctgcagcatt 31920
gcacagcctt catggtaggc aaggaatctg ctttgcaagg ggcattagcc ctggaggctc 31980
agtggatatg ggctattgca atactaattc aaggagcatt tttaggatgg cacattggct 32040
catgcctgta attccaacaa tttgggagat cacggcaggt ggatctcttg agcctaggag 32100
ttcaagacca gcctgggcaa tgtgacaaaa ccccatctct acaaaaatta gctgggcgtg 32160
gtggtgcata cctgtaatcc cagctccccc agaagctgag gcaggaggat cacttgagtg 32220
tggctgcagt gagcagagat cgcactactg cattccagcc tggacgacag agtgagactc 32280
tgtctcaaaa aaaaaaggaa gcattgttag gtataaatta ctattattta tttatttatt 32340
tttgaaagga gtctcgctct gtcacccagg ctgcagtgca gtggcgccat ctcggctcac 32400
tgcaagctcc gcctcccagg ttcacagcat tctcctgcct cagcctcccg agtagctggg 32460
attataggtg cccgccacca cgcctggcta attttttgta tttttagtag aaacggggtt 32520
tcactgtgtt ggccaggatg gtctcgatct cctgactttg tgatccacct gccttggcct 32580
cccaaagtgc tgggattaca gacttgaacc accatgcccg gccctgttag gtataaacta 32640
tttcataaaa ttcagacttg taaatttatc atagccttta gaatggatga tagaaatcct 32700

-continued

```
tatgccacac aaattcctca tatgccaggg ctcaccataa ctgataccag ctcacttgat  32760

tcagctcagt ttaacattta cacagaattg gccatttaca aaatcttaca taagttaagt  32820

agaaaaatag aaaagtgagg ttttctgaaa gagtttgggt ttttccttca atgctcaaca  32880

acagaggtcc ccaatctttc tggcaccaga gaccagtttt gtgcaagaca ctttttccat  32940

gaaccagcgt ggtggggggg ggatgattct ggaatgattc aagtgcatga catttattgt  33000

g                                                                  33001
```

```
<210> SEQ ID NO 19
<211> LENGTH: 2218
<212> TYPE: DNA
<213> ORGANISM: Papio hamadryas

<400> SEQUENCE: 19

agaacagctc ggagaccgtt catttttaag tgacaagaga ctcacctcca agaagcaatt     60

gtgttttcag aatgatttta ttcaagcaag caacttattt catttccttg tttgctacag    120

tttcctgtgg atgtctaact caactatacg aaaacacctt cttcagaggt ggggatgtag    180

cttccatgta cacccccgaat gcccagcact gccagatgat gtgcacattc cacccaaggt    240

gtttgctatt cagttttctt ccagcaagtt ccatcaatga catggagaaa aggtttggct    300

gcttcttgaa agatagtgtt acaggaaccc tgccaaaagt acatcgagca ggtgcaattt    360

ctggacattc cttaaagcag tgtggtcatc aaataagtgc ttgccaccga gacatttata    420

aaggaattga tatgagagga gtcaatttta atgtatctaa ggttagcagc gttgaagaat    480

gccaaaaaag gtgcaccaat aacattcgct gccaattttt ttcatatgcc acacaaacat    540

ttcacaatgc agagtaccgg aacacttgcc tcttaaagca cagtcccgga ggaacaccta    600

ccactataaa ggtgctgaat aacgtggaat ctggattctc actgaagccc tgtgcccttt    660

cagaaattgg ttgtcacatg aacatcttcc agcatcttgc cttctcggat gtggatgttg    720

ccagagttct cgccccagat gcttttgtgt gtcgaaccat ctgcacctat catcccagct    780

gcctcttctt tacgttctat acgaatgcat ggaagatcga gtcacaaaga aatgtttgtt    840

ttcttaaaac atctgaaagt ggcacaccaa gttcctctac tcctcaagaa aacaccacat    900

ctggatacag ccttttaacc tgcaaaaaaa ctttacctga accctgccat tctaaaattt    960

acccgggagt tgactttgga ggagaagaat tgaatgtgac ttttgttaaa ggagtgaatg   1020

tttgccaaga gacttgtaca aagatgattc gctgtcagtt tttcacttat tctttactac   1080

cagaagactg taaggaggag aagtgtaagt gtttcttaag attatcttcg gatggttctc   1140

caactaggat tacatatggg acacaaggga gctctggtta ctctttgaga ttgtgtaaca   1200

ctggggacag ctctgtctgc acaacaaaaa caagctcacg cattgttgga ggaacaaact   1260

cttcttgggg agagtggccc tggcaggtga gcctgcaggt gaagctgatg gctcagaggc   1320

acctgtgtgg agggtcactc ataggacacc agtgggtcct cactgctgcc cactgctttg   1380

atgggcttcc cttaccggat gtttggcgca tttatagtgg cattttaaat ctgtcagaca   1440

ttacaaaaga aacacctttc tcacaaataa aagagatcat tattcaccaa aactatagaa   1500

tctcagaagg gaatcatgat atcgccttaa taaaactcca gactcctttg aattacactg   1560

aattccaaaa accaatatgc ctaccttcca aaggtgacac aaacacaatt tataccaact   1620

gttgggtaac tggatggggc ttctcgaagg aaaaaggtga aatccaagat attctacaaa   1680

aggtaaatat tcctttggta acaaatgaag aatgccagaa aagatatcaa gattataaaa   1740
```

```
taacccaacg gatggtctgt gctggctata aagaaggggg aaaagatgct tgtaagggag   1800

attcaggggg tcccttagct tgcaaacaca atggaatgtg gcgtttggtg ggcatcacca   1860

gctggggcga aggctgtgcc cgcagggagc aacctggtgt ctacaccaaa gtcgctgagt   1920

acatggactg gattttagag aaaacacaga gcagtgatgg aaatgctcgg atgcaggcgc   1980

cagcatgagg agcagcccag agtcttggcg agttttacaa cctgggttca agtcaaattc   2040

tgagcctggg ggtcctcatc tgcaaagcat ggagagtggc atctactttg catcctgtca   2100

taaggacaaa agacagtgca ctcagagctg ctgaggacaa tgttttgctg aagccagctt   2160

tcagcattca gtaactggga gctgattgat gaactacctg catttatttt atttgttt     2218


<210> SEQ ID NO 20
<211> LENGTH: 1837
<212> TYPE: DNA
<213> ORGANISM: Mus musculus
<220> FEATURE:
<221> NAME/KEY: CDS
<222> LOCATION: (92)..(1606)

<400> SEQUENCE: 20

actgattctc tgcgactgtc tgctcagtct gtcctgaagc tgcctagtga ccaagaactt     60

ggaccaggac gcagctgaca tcgctgccca g atg gcc tcc agg ctg acc cca       112
                                   Met Ala Ser Arg Leu Thr Pro
                                   1               5

ctg acc ctc ctg ctg ctg ctg ctg gct ggg gat aga gcc ttc tca gat      160
Leu Thr Leu Leu Leu Leu Leu Leu Ala Gly Asp Arg Ala Phe Ser Asp
        10                  15                  20

ccc gaa gct acc agc cac agc acc cag gat cca ctg gag gct caa gcg      208
Pro Glu Ala Thr Ser His Ser Thr Gln Asp Pro Leu Glu Ala Gln Ala
    25                  30                  35

aaa agc aga gag agc ttc cct gaa aga gat gac tcc tgg agt ccc cca      256
Lys Ser Arg Glu Ser Phe Pro Glu Arg Asp Asp Ser Trp Ser Pro Pro
40                  45                  50                  55

gag cct aca gta ctg ccc tct acc tgg cca aca acc agt gta gcc atc      304
Glu Pro Thr Val Leu Pro Ser Thr Trp Pro Thr Thr Ser Val Ala Ile
                60                  65                  70

aca ata aca aat gac acc atg ggt aaa gta gcc aac gag tcc ttc agc      352
Thr Ile Thr Asn Asp Thr Met Gly Lys Val Ala Asn Glu Ser Phe Ser
            75                  80                  85

cag cac agc cag cca gct gct cag cta ccc aca gat tct cca gga cag      400
Gln His Ser Gln Pro Ala Ala Gln Leu Pro Thr Asp Ser Pro Gly Gln
        90                  95                  100

ccc cct ctg aat tct tcc agc cag ccc tcc act gcc tca gat ctt ccc      448
Pro Pro Leu Asn Ser Ser Ser Gln Pro Ser Thr Ala Ser Asp Leu Pro
    105                 110                 115

acc cag gct act act gaa ccc ttc tgc ccg gag ccg ctt gct cag tgc      496
Thr Gln Ala Thr Thr Glu Pro Phe Cys Pro Glu Pro Leu Ala Gln Cys
120                 125                 130                 135

tct gat tca gac aga gac tcc tca gag gca aag ctc tca gag gct ttg      544
Ser Asp Ser Asp Arg Asp Ser Ser Glu Ala Lys Leu Ser Glu Ala Leu
                140                 145                 150

aca gat ttc tct gtg aag ctc tac cac gcc ttc tca gct acc aag atg      592
Thr Asp Phe Ser Val Lys Leu Tyr His Ala Phe Ser Ala Thr Lys Met
            155                 160                 165

gct aag acc aac atg gcc ttt tcc cca ttc agc att gcc agc ctc ctc      640
Ala Lys Thr Asn Met Ala Phe Ser Pro Phe Ser Ile Ala Ser Leu Leu
        170                 175                 180

aca cag gtt ctt ctt ggg gct gga gac agc acc aag agc aac ttg gag      688
Thr Gln Val Leu Leu Gly Ala Gly Asp Ser Thr Lys Ser Asn Leu Glu
```

-continued

```
    185                 190                 195

agc atc ctt tcc tac ccc aag gat ttt gcc tgt gtc cac caa gca cta      736
Ser Ile Leu Ser Tyr Pro Lys Asp Phe Ala Cys Val His Gln Ala Leu
200                 205                 210                 215

aag ggc ttt tca tcc aaa ggt gtc act tct gtg tct cag att ttc cac      784
Lys Gly Phe Ser Ser Lys Gly Val Thr Ser Val Ser Gln Ile Phe His
                220                 225                 230

agc cca gat ctg gcc ata agg gac acc tat gtg aat gca tct cag agc      832
Ser Pro Asp Leu Ala Ile Arg Asp Thr Tyr Val Asn Ala Ser Gln Ser
            235                 240                 245

ctg tat gga agc agc ccc aga gtc ctg ggc cca gac agt gct gct aac      880
Leu Tyr Gly Ser Ser Pro Arg Val Leu Gly Pro Asp Ser Ala Ala Asn
        250                 255                 260

tta gaa ctc atc aac acc tgg gtg gct gag aac acc aac cat aag atc      928
Leu Glu Leu Ile Asn Thr Trp Val Ala Glu Asn Thr Asn His Lys Ile
    265                 270                 275

cgc aag ctg ctg gac agc ctg cct tct gac acc tgc ctc gtc ctt ctc      976
Arg Lys Leu Leu Asp Ser Leu Pro Ser Asp Thr Cys Leu Val Leu Leu
280                 285                 290                 295

aat gct gtc tac ttg agt gcc aag tgg aag ata aca ttt gaa cca aaa     1024
Asn Ala Val Tyr Leu Ser Ala Lys Trp Lys Ile Thr Phe Glu Pro Lys
                300                 305                 310

aag atg atg gcg cct ttc ttc tac aaa aac tct atg att aaa gtg ccc     1072
Lys Met Met Ala Pro Phe Phe Tyr Lys Asn Ser Met Ile Lys Val Pro
            315                 320                 325

atg atg agt agc gta aag tac cct gtg gcc caa ttc gat gac cat act     1120
Met Met Ser Ser Val Lys Tyr Pro Val Ala Gln Phe Asp Asp His Thr
        330                 335                 340

ttg aag gcc aag gtg gga cag ctg cag ctc tct cac aac ctg agc ttt     1168
Leu Lys Ala Lys Val Gly Gln Leu Gln Leu Ser His Asn Leu Ser Phe
    345                 350                 355

gtg atc gtg gta ccc gtg ttc cca aag cac caa ctt aaa gat gta gaa     1216
Val Ile Val Val Pro Val Phe Pro Lys His Gln Leu Lys Asp Val Glu
360                 365                 370                 375

aag gct ctc aac ccc act gtc ttc aag gcc atc atg aag aag ctg gag     1264
Lys Ala Leu Asn Pro Thr Val Phe Lys Ala Ile Met Lys Lys Leu Glu
                380                 385                 390

ctg tcc aaa ttc ctg ccc act tac ctg acg atg cct cat ata aaa gta     1312
Leu Ser Lys Phe Leu Pro Thr Tyr Leu Thr Met Pro His Ile Lys Val
            395                 400                 405

aag agc agc caa gac atg ctg tca gtc atg gag aaa ctg gaa ttc ttt     1360
Lys Ser Ser Gln Asp Met Leu Ser Val Met Glu Lys Leu Glu Phe Phe
        410                 415                 420

gac ttc act tac gat ctc aac ctg tgc ggg ctg acc gag gac cca gat     1408
Asp Phe Thr Tyr Asp Leu Asn Leu Cys Gly Leu Thr Glu Asp Pro Asp
    425                 430                 435

ctt cag gtg tct gcc atg aaa cac gag aca gtg ctg gaa ctg aca gag     1456
Leu Gln Val Ser Ala Met Lys His Glu Thr Val Leu Glu Leu Thr Glu
440                 445                 450                 455

tca ggg gtg gaa gca gct gca gcc tct gcc atc tcc ttt ggc cga agc     1504
Ser Gly Val Glu Ala Ala Ala Ala Ser Ala Ile Ser Phe Gly Arg Ser
                460                 465                 470

tta ccc atc ttt gag gtg cag cga cct ttc ctc ttc ctg ctc tgg gac     1552
Leu Pro Ile Phe Glu Val Gln Arg Pro Phe Leu Phe Leu Leu Trp Asp
            475                 480                 485

cag caa cac agg ttc cca gtc ttc atg ggt cgt gta tat gac ccc agg     1600
Gln Gln His Arg Phe Pro Val Phe Met Gly Arg Val Tyr Asp Pro Arg
        490                 495                 500

ggt tga gacaggcttg ggtaaacatt gtcacccaag cttcagctcc tccggttatt      1656
```

-continued

Gly tccttgccac tgcctgcccg agccacttca agccttagga actggcagac ggaactgttt 1716 ccatccacca acccccaggg tatcaaccac ttttttgcag cttttacggt tcaaacctat 1776 caaactctac aaataaaact tgcagacatt ttcttctctc actaaaaaaa aaaaaaaaaa 1836 a 1837

<210> SEQ ID NO 21
<211> LENGTH: 21
<212> TYPE: DNA
<213> ORGANISM: Artificial sequence
<220> FEATURE:
<223> OTHER INFORMATION: Primer

<400> SEQUENCE: 21
tgcctgctgt tcagctttct c 21

<210> SEQ ID NO 22
<211> LENGTH: 21
<212> TYPE: DNA
<213> ORGANISM: Artificial sequence
<220> FEATURE:
<223> OTHER INFORMATION: Primer

<400> SEQUENCE: 22
tggcaaagtc cctgtaatgc t 21

<210> SEQ ID NO 23
<211> LENGTH: 30
<212> TYPE: DNA
<213> ORGANISM: Artificial sequence
<220> FEATURE:
<223> OTHER INFORMATION: Primer

<400> SEQUENCE: 23
cgtgactcca cccaaagaga caaataaacg 30

<210> SEQ ID NO 24
<211> LENGTH: 21
<212> TYPE: DNA
<213> ORGANISM: Artificial sequence
<220> FEATURE:
<223> OTHER INFORMATION: Primer

<400> SEQUENCE: 24
gagtccccca gagcctacag t 21

<210> SEQ ID NO 25
<211> LENGTH: 26
<212> TYPE: DNA
<213> ORGANISM: Artificial sequence
<220> FEATURE:
<223> OTHER INFORMATION: Primer

<400> SEQUENCE: 25
tgtcatttgt tattgtgatg gctaca 26

<210> SEQ ID NO 26
<211> LENGTH: 25
<212> TYPE: DNA
<213> ORGANISM: Artificial sequence
<220> FEATURE:
<223> OTHER INFORMATION: Probe

<400> SEQUENCE: 26
ctgccctcta cctggccaac aacca 25

<210> SEQ ID NO 27
<211> LENGTH: 27
<212> TYPE: DNA
<213> ORGANISM: Artificial sequence
<220> FEATURE:
<223> OTHER INFORMATION: Primer

<400> SEQUENCE: 27
acaagtgcat tttacagacc agagtac 27

<210> SEQ ID NO 28
<211> LENGTH: 22
<212> TYPE: DNA
<213> ORGANISM: Artificial sequence
<220> FEATURE:
<223> OTHER INFORMATION: Primer

<400> SEQUENCE: 28
ggttgtccgc tgactttatg ct 22

<210> SEQ ID NO 29
<211> LENGTH: 24
<212> TYPE: DNA
<213> ORGANISM: Artificial sequence
<220> FEATURE:
<223> OTHER INFORMATION: Probe

<400> SEQUENCE: 29
aagcacagtg caagcggaac accc 24

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
ggcatattgg tttttggaat 20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
aaagtggttg ataccctggg 20

<210> SEQ ID NO 42
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 42
ccttccctga aggttcctcc 20

<210> SEQ ID NO 43
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 43
gcatgggaca gagatggtgc 20